United States Patent
Johnson et al.

(10) Patent No.: US 11,820,818 B2
(45) Date of Patent: *Nov. 21, 2023

(54) MULTI-CHAIN POLYPEPTIDE-CONTAINING TRI-SPECIFIC BINDING MOLECULES

(71) Applicant: MACROGENICS, INC., Rockville, MD (US)

(72) Inventors: Leslie S. Johnson, Rockville, MD (US); Ling Huang, Rockville, MD (US); Gurunadh Reddy Chichili, Rockville, MD (US); Kalpana Shah, Rockville, MD (US); Chia-Ying Kao Lam, Rockville, MD (US); Stephen James Burke, Rockville, MD (US); Liqin Liu, Rockville, MD (US); Paul A. Moore, Rockville, MD (US); Ezio Bonvini, Rockville, MD (US); Bhaswati Barat, Rockville, MD (US)

(73) Assignee: MACROGENICS, INC., Rockville, MD (US)

( * ) Notice: Subject to any disclaimer, the term of this patent is extended or adjusted under 35 U.S.C. 154(b) by 687 days.

This patent is subject to a terminal disclaimer.

(21) Appl. No.: 16/818,893

(22) Filed: Mar. 13, 2020

(65) Prior Publication Data
US 2020/0207850 A1    Jul. 2, 2020

Related U.S. Application Data

(62) Division of application No. 15/313,741, filed as application No. PCT/US2015/033076 on May 29, 2015, now Pat. No. 10,647,768.

(60) Provisional application No. 62/107,824, filed on Jan. 26, 2015, provisional application No. 62/008,229, filed on Jun. 5, 2014, provisional application No. 62/004,571, filed on May 29, 2014.

(51) Int. Cl.
*C07K 16/28* (2006.01)
*C07K 16/30* (2006.01)

(52) U.S. Cl.
CPC .......... *C07K 16/28* (2013.01); *C07K 16/2803* (2013.01); *C07K 16/283* (2013.01); *C07K 16/2809* (2013.01); *C07K 16/2815* (2013.01); *C07K 16/2827* (2013.01); *C07K 16/2878* (2013.01); *C07K 16/30* (2013.01); *C07K 2317/31* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/73* (2013.01); *C07K 2317/92* (2013.01); *C07K 2318/20* (2013.01); *C07K 2319/00* (2013.01)

(58) Field of Classification Search
CPC .......... C07K 2317/31; C07K 2317/524; C07K 2317/526; C07K 2317/56; C07K 2317/626
USPC ............................................ 424/133.1, 135.1
See application file for complete search history.

(56) References Cited

U.S. PATENT DOCUMENTS

| | | | |
|---|---|---|---|
| 3,842,067 A | 10/1974 | Sarantakis | |
| 3,862,925 A | 1/1975 | Sarantakis et al. | |
| 3,972,859 A | 8/1976 | Fujino et al. | |
| 4,105,603 A | 8/1978 | Vale et al. | |
| 4,526,938 A | 7/1985 | Churchill et al. | |
| 4,816,567 A | 3/1989 | Cabilly et al. | |
| 4,880,078 A | 11/1989 | Inoue et al. | |
| 4,980,286 A | 12/1990 | Morgan et al. | |
| 5,128,326 A | 7/1992 | Balazs et al. | |
| 5,290,540 A | 3/1994 | Prince et al. | |
| 5,565,332 A | 10/1996 | Hoogenboom et al. | |
| 5,580,717 A | 12/1996 | Dower et al. | |
| 5,601,819 A | 2/1997 | Wong et al. | |
| 5,624,821 A | 4/1997 | Winter et al. | |
| 5,679,377 A | 10/1997 | Bernstein et al. | |
| 5,733,743 A | 3/1998 | Johnson et al. | |
| 5,807,715 A | 9/1998 | Morrison et al. | |
| 5,843,749 A | 12/1998 | Maisonpierre et al. | |

(Continued)

FOREIGN PATENT DOCUMENTS

| CN | 101802010 A | 8/2010 |
|---|---|---|
| CN | 102448985 A | 5/2012 |

(Continued)

OTHER PUBLICATIONS

Almagro & Franssen, Frontiers in Bioscience, 13:1619-33 (2008).*

(Continued)

*Primary Examiner* — Lynn A Bristol
(74) *Attorney, Agent, or Firm* — MEDLER, FERRO, WOODHOUSE & MILLS PLLC

(57) ABSTRACT

The present invention relates to Tri-Specific Binding Molecules, which are multi-chain polypeptide molecules that possess three Binding Domains and are thus capable of mediating coordinated binding to three epitopes. The Binding Domains may be selected such that the Tri-Specific Binding Molecules are capable of binding to any three different epitopes. Such epitopes may be epitopes of the same antigen or epitopes of two or three different antigens. In a preferred embodiment, one of such epitopes will be capable of binding to CD3, the second of such epitopes will be capable of binding to CD8, and the third of such epitopes will be capable of binding to an epitope of a Disease-Associated Antigen. The invention also provides a novel ROR1-binding antibody, as well as derivatives thereof and uses for such compositions.

16 Claims, 62 Drawing Sheets

Specification includes a Sequence Listing.

(56) References Cited

U.S. PATENT DOCUMENTS

| | | | |
|---|---|---|---|
| 5,855,913 | A | 1/1999 | Hanes et al. |
| 5,866,692 | A | 2/1999 | Shitara et al. |
| 5,874,064 | A | 2/1999 | Edwards et al. |
| 5,885,573 | A | 3/1999 | Bluestone et al. |
| 5,888,533 | A | 3/1999 | Dunn |
| 5,912,015 | A | 6/1999 | Bernstein et al. |
| 5,916,597 | A | 6/1999 | Lee et al. |
| 5,934,272 | A | 8/1999 | Lloyd et al. |
| 5,945,155 | A | 8/1999 | Grill et al. |
| 5,985,309 | A | 11/1999 | Edwards et al. |
| 5,985,320 | A | 11/1999 | Edwards et al. |
| 5,989,463 | A | 11/1999 | Tracy et al. |
| 5,997,867 | A | 12/1999 | Waldmann et al. |
| 6,019,968 | A | 2/2000 | Platz et al. |
| 6,054,297 | A | 4/2000 | Carter et al. |
| 6,171,586 | B1 | 1/2001 | Lam et al. |
| 6,180,377 | B1 | 1/2001 | Morgan et al. |
| 6,194,551 | B1 | 2/2001 | Idusogie et al. |
| 6,218,149 | B1 | 4/2001 | Morrison et al. |
| 6,265,150 | B1 | 7/2001 | Terstappen et al. |
| 6,331,415 | B1 | 12/2001 | Cabilly et al. |
| 6,472,511 | B1 | 10/2002 | Leung et al. |
| 6,551,592 | B2 | 4/2003 | Lindhofer et al. |
| 6,994,853 | B1 | 2/2006 | Lindhofer et al. |
| 7,148,038 | B2 | 12/2006 | Mather |
| 7,276,586 | B2 | 10/2007 | Goddard et al. |
| 7,317,091 | B2 | 1/2008 | Lazar et al. |
| 7,351,803 | B2 | 4/2008 | Johnson et al. |
| 7,405,061 | B2 | 7/2008 | Mather et al. |
| 7,569,672 | B2 | 8/2009 | Mather et al. |
| 7,572,895 | B2 | 8/2009 | Mather et al. |
| 7,572,896 | B2 | 8/2009 | Mather et al. |
| 7,585,952 | B2 | 9/2009 | D et al. |
| 7,695,936 | B2 | 4/2010 | Carter et al. |
| 8,044,178 | B2 | 10/2011 | Boghaert et al. |
| 8,277,806 | B2 | 10/2012 | Lindhofer |
| 8,394,374 | B2 | 3/2013 | Bernett et al. |
| 8,586,713 | B2 | 11/2013 | Davis et al. |
| 8,834,876 | B2 | 9/2014 | Kosaka et al. |
| 10,093,738 | B2 * | 10/2018 | Johnson ............... C07K 16/283 |
| 10,501,552 | B2 * | 12/2019 | Moore ..................... A61P 35/02 |
| 10,633,440 | B2 | 4/2020 | Bonvini et al. |
| 10,647,768 | B2 | 5/2020 | Johnson et al. |
| 2002/0028486 | A1 | 3/2002 | Morrison et al. |
| 2003/0115614 | A1 | 6/2003 | Kanda et al. |
| 2004/0058400 | A1 | 3/2004 | Holliger et al. |
| 2004/0220388 | A1 | 11/2004 | Mertens et al. |
| 2005/0079170 | A1 | 4/2005 | Le et al. |
| 2005/0175606 | A1 | 8/2005 | Huang et al. |
| 2005/0175618 | A1 | 8/2005 | Carroll et al. |
| 2005/0255110 | A1 | 11/2005 | Lindhofer et al. |
| 2006/0166291 | A1 | 7/2006 | Mather et al. |
| 2006/0172349 | A1 | 8/2006 | Mather et al. |
| 2006/0172350 | A1 | 8/2006 | Mather et al. |
| 2007/0031436 | A1 | 2/2007 | Little et al. |
| 2007/0071675 | A1 | 3/2007 | Wu et al. |
| 2007/0196363 | A1 | 8/2007 | Arathoon et al. |
| 2008/0057054 | A1 | 3/2008 | Annaert et al. |
| 2008/0271208 | A1 | 10/2008 | Cnops et al. |
| 2009/0060910 | A1 | 3/2009 | Johnson et al. |
| 2009/0117108 | A1 | 5/2009 | Wang et al. |
| 2010/0099853 | A1 | 4/2010 | Little et al. |
| 2010/0173978 | A1 | 7/2010 | D et al. |
| 2010/0174053 | A1 | 7/2010 | Johnson et al. |
| 2010/0291112 | A1 | 11/2010 | Kellner et al. |
| 2011/0020667 | A1 | 1/2011 | Deeman et al. |
| 2011/0206670 | A1 | 8/2011 | Golde et al. |
| 2012/0294874 | A1 | 11/2012 | Macary et al. |
| 2013/0189263 | A1 | 7/2013 | Little et al. |
| 2013/0251642 | A1 | 9/2013 | Rader et al. |
| 2013/0281922 | A1 | 10/2013 | Teige |
| 2013/0295098 | A1 | 11/2013 | Wu et al. |
| 2013/0295121 | A1 | 11/2013 | Johnson et al. |
| 2014/0065142 | A1 | 3/2014 | Roschke et al. |
| 2014/0099318 | A1 | 4/2014 | Huang et al. |
| 2017/0198045 | A1 | 7/2017 | Johnson et al. |
| 2017/0204176 | A1 | 7/2017 | Bonvini et al. |
| 2018/0016344 | A1 * | 1/2018 | Moore ..................... A61P 35/02 |
| 2019/0002563 | A1 | 1/2019 | Johnson et al. |
| 2019/0085075 | A1 | 3/2019 | La Motte-mohs et al. |
| 2019/0127467 | A1 * | 5/2019 | Shah .................. C07K 16/2818 |
| 2020/0062854 | A1 | 2/2020 | Liu et al. |
| 2020/0199223 | A1 | 6/2020 | Bonvini et al. |
| 2020/0231675 | A1 * | 7/2020 | Shah .................. C07K 16/2818 |
| 2021/0155694 | A1 * | 5/2021 | Bonvini ............. C07K 16/2866 |
| 2021/0171630 | A1 * | 6/2021 | Diedrich ............ C07K 16/2809 |
| 2021/0246194 | A1 * | 8/2021 | Lam ..................... C07K 16/468 |

FOREIGN PATENT DOCUMENTS

| | | |
|---|---|---|
| CN | 103154025 A | 6/2013 |
| EP | 0 403 156 A1 | 12/1990 |
| EP | 0 519 596 A1 | 12/1992 |
| EP | 0 359 096 B1 | 11/1997 |
| EP | 1 293 514 B1 | 11/2006 |
| EP | 1 736 484 A1 | 12/2006 |
| EP | 1 820 513 A1 | 8/2007 |
| EP | 1 078 004 B1 | 10/2007 |
| EP | 2 158 221 A2 | 3/2010 |
| EP | 2 186 527 A1 | 5/2010 |
| EP | 2 241 576 A1 | 10/2010 |
| EP | 2 361 936 A1 | 8/2011 |
| EP | 2 371 866 A2 | 10/2011 |
| EP | 2 376 109 A1 | 10/2011 |
| EP | 2 585 476 A2 | 5/2013 |
| EP | 2 601 216 A1 | 6/2013 |
| EP | 2 714 079 A2 | 4/2014 |
| EP | 2 840 091 A1 | 2/2015 |
| JP | 2007-535915 A | 12/2007 |
| JP | 2008-512485 A | 4/2008 |
| JP | 2009-526823 A | 7/2009 |
| JP | 2009-529578 A | 8/2009 |
| JP | 2010-246546 A | 11/2010 |
| JP | 2011-505792 A | 3/2011 |
| JP | 2011-508592 A | 3/2011 |
| JP | 2012-228248 A | 11/2012 |
| JP | 2012-528092 A | 11/2012 |
| JP | 2013-506654 A | 2/2013 |
| JP | 2013-540696 A | 11/2013 |
| RU | 94028282 A | 7/1996 |
| WO | WO 91/03493 A1 | 3/1991 |
| WO | WO 91/05548 A1 | 5/1991 |
| WO | WO 92/19244 A2 | 11/1992 |
| WO | WO 92/22583 A2 | 12/1992 |
| WO | WO 96/20698 A2 | 7/1996 |
| WO | 96/27011 A1 | 9/1996 |
| WO | WO 97/32572 A2 | 9/1997 |
| WO | WO 97/44013 A1 | 11/1997 |
| WO | WO 98/02463 A1 | 1/1998 |
| WO | WO 98/03670 A1 | 1/1998 |
| WO | WO 98/06749 A2 | 2/1998 |
| WO | WO 98/31346 A1 | 7/1998 |
| WO | WO 99/15154 A1 | 4/1999 |
| WO | WO 99/20253 A1 | 4/1999 |
| WO | WO 99/42597 A1 | 8/1999 |
| WO | WO 99/57150 A2 | 11/1999 |
| WO | WO 99/58572 A1 | 11/1999 |
| WO | WO 99/66903 A2 | 12/1999 |
| WO | WO 00/18806 A1 | 4/2000 |
| WO | WO 00/42072 A2 | 7/2000 |
| WO | WO 02/02781 A1 | 1/2002 |
| WO | WO 02/14870 A2 | 2/2002 |
| WO | WO 02/20039 A2 | 3/2002 |
| WO | WO 02/072141 A2 | 9/2002 |
| WO | WO 03/012069 A2 | 2/2003 |
| WO | WO 03/024191 A2 | 3/2003 |
| WO | WO 03/025018 A2 | 3/2003 |
| WO | WO 03/032814 A2 | 4/2003 |
| WO | WO 03/035835 A2 | 5/2003 |
| WO | WO 03/087340 A2 | 10/2003 |
| WO | 03/094859 A2 | 11/2003 |
| WO | WO 03/093443 A2 | 11/2003 |
| WO | WO 03/100033 A2 | 12/2003 |
| WO | WO 2004/043239 A2 | 5/2004 |

(56) References Cited

FOREIGN PATENT DOCUMENTS

| | | |
|---|---|---|
| WO | WO 2004/063351 A2 | 7/2004 |
| WO | WO 2005/028498 A2 | 3/2005 |
| WO | WO 2005/061547 A2 | 7/2005 |
| WO | WO 2005/070966 A2 | 8/2005 |
| WO | WO 2005/121179 A2 | 12/2005 |
| WO | WO 2006/002438 A2 | 1/2006 |
| WO | 200/6031653 A2 | 3/2006 |
| WO | WO 2006/072152 A2 | 7/2006 |
| WO | WO 2006/076584 A2 | 7/2006 |
| WO | WO 2006/083852 A2 | 8/2006 |
| WO | WO 2006/084075 A2 | 8/2006 |
| WO | WO 2006/084078 A2 | 8/2006 |
| WO | WO 2006/084092 A2 | 8/2006 |
| WO | WO 2006/084226 A2 | 8/2006 |
| WO | WO 2006/088494 A2 | 8/2006 |
| WO | WO 2006/107617 A2 | 10/2006 |
| WO | WO 2006/107786 A2 | 10/2006 |
| WO | WO 2006/113665 A2 | 10/2006 |
| WO | WO 2007/008712 A2 | 1/2007 |
| WO | WO 2007/021841 A2 | 2/2007 |
| WO | 2007/024715 A2 | 3/2007 |
| WO | WO 2007/024249 A2 | 3/2007 |
| WO | WO 2007/046893 A2 | 4/2007 |
| WO | WO 2007/075270 A2 | 7/2007 |
| WO | WO 2007/093630 A1 | 8/2007 |
| WO | WO 2007/095338 A1 | 8/2007 |
| WO | 2007/106744 A2 | 9/2007 |
| WO | WO 2007/106707 A2 | 9/2007 |
| WO | WO 2007/146968 A2 | 12/2007 |
| WO | WO 2008/003103 A2 | 1/2008 |
| WO | WO 2008/003116 A2 | 1/2008 |
| WO | WO 2008/027236 A2 | 3/2008 |
| WO | WO 2008/140603 A2 | 11/2008 |
| WO | WO 2008/145142 A1 | 12/2008 |
| WO | WO 2008/146911 A1 | 12/2008 |
| WO | WO 2008/157379 A2 | 12/2008 |
| WO | 2009/007124 A1 | 1/2009 |
| WO | WO 2009/018386 A1 | 2/2009 |
| WO | 2009/032845 A2 | 3/2009 |
| WO | 2009/081201 A2 | 7/2009 |
| WO | WO 2009/132876 A1 | 11/2009 |
| WO | WO 2010/027797 A1 | 3/2010 |
| WO | WO 2010/028795 A1 | 3/2010 |
| WO | WO 2010/028796 A1 | 3/2010 |
| WO | WO 2010/028797 A1 | 3/2010 |
| WO | WO 2010/080538 A1 | 7/2010 |
| WO | WO 2010/108127 A1 | 9/2010 |
| WO | 2010/119119 A1 | 10/2010 |
| WO | WO 2010/124188 A1 | 10/2010 |
| WO | WO 2010/136172 A1 | 12/2010 |
| WO | WO 2011/032633 A1 | 3/2011 |
| WO | WO 2011/034660 A1 | 3/2011 |
| WO | 2011/039724 A1 | 4/2011 |
| WO | WO 2011/086091 A1 | 7/2011 |
| WO | WO 2011/109400 A2 | 9/2011 |
| WO | WO 2011/133886 A2 | 10/2011 |
| WO | WO 2011/163401 A2 | 12/2011 |
| WO | WO 2012/009544 A2 | 1/2012 |
| WO | WO 2012/018687 A1 | 2/2012 |
| WO | 2012/076066 A1 | 6/2012 |
| WO | WO 2012/075158 A1 | 6/2012 |
| WO | WO 2012/088290 A2 | 6/2012 |
| WO | 2012/131527 A1 | 10/2012 |
| WO | WO 2012/156430 A1 | 11/2012 |
| WO | WO 2012/162067 A2 | 11/2012 |
| WO | WO 2012/162068 A2 | 11/2012 |
| WO | WO 2012/162561 A2 | 11/2012 |
| WO | WO 2012/162583 A1 | 11/2012 |
| WO | 2012/167067 A1 | 12/2012 |
| WO | 2013/004842 A2 | 1/2013 |
| WO | WO 2013/003652 A1 | 1/2013 |
| WO | WO 2013/006544 A1 | 1/2013 |
| WO | WO 2013/013700 A1 | 1/2013 |
| WO | 2013/041687 A1 | 3/2013 |
| WO | 2013/068874 A1 | 5/2013 |
| WO | WO 2013/070565 A1 | 5/2013 |
| WO | WO 2013/119903 A1 | 8/2013 |
| WO | WO 2013/163427 A1 | 10/2013 |
| WO | WO 2013/174873 A1 | 11/2013 |
| WO | WO 2014/022540 A1 | 2/2014 |
| WO | WO 2014/072888 A1 | 5/2014 |
| WO | WO 2014/116846 A2 | 7/2014 |
| WO | 2014/006217 A9 | 2/2015 |
| WO | WO 2015/026894 A2 | 2/2015 |
| WO | WO 2015/158636 A1 | 10/2015 |
| WO | WO 2015/184203 A1 | 12/2015 |
| WO | WO 2015/184207 A1 | 12/2015 |

OTHER PUBLICATIONS

Edwards et al., J Mol Biol 334:103-118 (2003).*
Marchalonis et al., Dev & Comp Immunol. 30:223-247 (2006).*
Lippow et al., "Computational design of antibody-affinity improvement beyond in vivo maturation," Nature Biotechnology, 25(10): 1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260):1-11 (2018).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (2017).*
Altshuler et al., "Generation of Recombinant Antibodies and Means for Increasing Their Affinity," Biochemistry (Moscow), 75(13):1584-1605 (2010).*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Extended European Search Report dated Dec. 22, 2017 in Europe Patent Application No. 15799237.1, filed on May 29, 2015, 11 pages.
Extended European Search Report dated Jan. 18, 2018 in Europe Patent Application No. 15799187.8, filed on May 29, 2015, 13 pages.
International Preliminary Report on Patentability dated Dec. 8, 2016 in International Patent Application No. PCT/US2015/033076, filed on May 29, 2015, 8 pages.
International Preliminary Report on Patentability dated Dec. 8, 2016 in International Patent Application No. PCT/US2015/033081, filed on May 29, 2015, 7 pages.
International Search Report and Written Opinion dated Oct. 26, 2015 in International Patent Application No. PCT/US2015/033076, filed on May 29, 2015, 12 pages.
International Search Report and Written Opinion dated Sep. 2, 2015 in International Patent Application No. PCT/US2015/033081, filed on May 29, 2015, 10 pages.
Office Action dated Apr. 15, 2019 in U.S. Appl. No. 15/313,741, filed Nov. 23, 2016 and published as US 2017-0198045 dated Jul. 13, 2017, 22 pages.
Office Action dated Apr. 15, 2019 in U.S. Appl. No. 15/313,765, filed Nov. 23, 2016 and published as 2017-0204176 dated Jul. 20, 2017, 23 pages.
Office Action dated Dec. 2, 2019 in U.S. Appl. No. 15/313,765, filed on Nov. 23, 2016 and published as US-2017-0204176-A1 dated Jul. 20, 2017, 9 pages.
Office Action dated Dec. 27, 2019 in U.S. Appl. No. 15/313,741, filed Nov. 23, 2016 and published as 2017-0198045 dated Jul. 13, 2017, 9 pages.

(56) References Cited

OTHER PUBLICATIONS

Office Action dated Sep. 18, 2019 in U.S. Appl. No. 15/313,741, filed Nov. 23, 2016 and published as 2017-0198045 dated Jul. 13, 2017, 11 pages.
Office Action dated Sep. 18, 2019 in U.S. Appl. No. 15/313,765, filed Nov. 23, 2016 and published as 2017-0204176 dated Jul. 20, 2017, 10 pages.
Abdulghani et al., "TRAIL Receptor Signaling and Therapeutics", Expert Opinion on Therapeutic Targets, Oct. 2010, 14(10):1091-1108.
Adenis et al., "Inhibitors of Epidermal Growth Factor Receptor and Colorectal Cancer", Bull Cancer, 2003, 90:S228-S232.
Adkins et al., "Edrecolomab (Monoclonal Antibody 17-1A)", Drugs, Oct. 1998, 56(4):619-626.
Ahmed et al., "Intercellular Trogocytosis Plays an Important Role in Modulation of Immune Responses", Cellular & Molecular Immunology, Sep. 2008, 5(4):261-269.
Ahmed et al., "Mechanisms of Cellular Communication through Intercellular Protein Transfer", Journal of Cellular and Molecular Medicine, 2011, 15(7):1458-1473.
Akcakanat et al., "Heterogeneous Expression of GAGE, NY-ESO-1, MAGE-A and SSX Proteins in Esophageal Cancer: Implications for Immunotherapy", International Journal of Cancer, Jan. 1, 2006, 118(1):123-128.
Albrecht, "Recombinant Antibodies: From the Laboratory to the Clinic", Cancer Biotherapy and Radiopharmaceuticals, 2006, 21(4):285-304.
Alegre et al., "A Non-Activating "Humanized" Anti-CD3 Monoclonal Antibody Retains Immunosuppressive Properties In Vivo", Transplantation, 1994, 57:1537-1543.
Almqvist et al., "In Vitro and in Vivo Characterization of 177Lu-Hua33: A Radioimmunoconjugate against Colorectal Cancer", Nuclear Medicine and Biology, 2006, 33(8):991-998.
Alt et al., "Novel Tetravalent and Bispecific IgG-Like Antibody Molecules Combining Single-Chain Diabodies With the Immunoglobin Gamma 1 Fc or CH3 Region", FEBS Letters, 1999, 454(1-2):90-94.
Altschul S., "Amino Acid Substitution Matrices from an Information Theoretic Perspective", Journal of Molecular Biology, 1991, 219(3):555-565.
Andera L., "Signaling Activated by the Death Receptors of the TNFR Family", Biomed Pap Med Fac Univ Palacky Olomouc Czech Repub, 2009, 153(3):173-180.
Apostolovic et al., "pH-Sensitivity of the E3/K3 Heterodimeric Coiled Coil", Biomacromolecules, Nov. 2008, 9(11):3173-3180.
Armour et al., "Recombinant Human IgG Molecules Lacking Fcgamma Receptor I Binding and Monocyte Triggering Activities", European Journal of Immunology, 1999, 29:2613-2624.
Armstrong et al., "Conformational Changes and Flexibility in T-Cell Receptor Recognition of Peptide-MHC Complexes", Biochemical Journal, Oct. 15, 2008, 415(2):183-196.
Arndt et al., "Comparison of in Vivo Selection and Rational Design of Heterodimeric Coiled Coils", Structure, 2002, 10:1235-1248.
Arndt et al., "Helix-stabilized Fv (hsFv) Antibody Fragments: Substituting the Constant Domains of a Fab Fragment for a Heterodimeric Coiled-coil Domain", Journal of Molecular Biology, Oct. 2002, 312(1):221-228.
Aruffo et al., "Molecular Cloning of A CD28 cDNA by a High-Efficiency COS Cell Expression System", Proc. Natl. Acad. Sci. (U.S.A.), 1987, 84:8573-8577.
Asano et al., "A Diabody for Cancer Immunotherapy and its Functional Enhancement by Fusion of Human Fc Domain", Abstract 3P-683, Journal of Biochemistry, 2004, 76(8):992.
Asano et al., "Domain Order of a Bispecific Diabody Dramatically Enhances Its Antitumor Activity Beyond Structural Format Conversion: The Case of the hEx3 Diabody", Protein Engineering, Design & Selection, XP55190198. ISSN: 1741-0126. DOI: 10.1093/proteinjgzt009, Mar. 6, 2013, 26(5):359-367.
Atwell et al., "Stable Heterodimers from Remodeling the Domain Interface of a Homodimer Using a Phage Display Library", Journal of Molecular Biology, 1997, 271(1):26-35.

Bachanova et al., "NK Cells in Therapy of Cancer", Critical Reviews in Oncogenesis, 2014, 19(1-2):133-141.
Baeuerle et al., "Bispecific T-Cell Engaging Antibodies for Cancer Therapy", Cancer Research, 2009, 69(12):4941-4944.
Baeuerle et al., "BiTE: A New Class of Antibodies That Recruit T Cells", Drugs of the Future, 2008, 33:137-147.
Barderas et al., "Affinity Maturation of Antibodies Assisted by In Silico Modeling", Proceedings of the National Academy of Sciences, 2008, 105(26):9029-9034.
Barderas et al., "High Expression of IL-13 Receptor α2 in Colorectal Cancer Is Associated with Invasion, Liver Metastasis, and Poor Prognosis", Cancer Research, Jun. 2012, 72(11):2780-2790.
Bargou et al., "Tumor Regression in Cancer Patients by Very Low Doses of a T Cell-Engaging Antibody", Science, 2008, 321:974-977.
Bast et al., "New Tumor Markers: CA125 and Beyond", International Journal of Gynecological Cancer, Nov.-Dec. 2005, 15(3):274-281.
Bataille et al., "The Phenotype of Normal, Reactive and Malignant Plasma Cells. Identification of "Many and Multiple Myelomas" and of New Targets for Myeloma Therapy", Haematologica, Sep. 2006, 91(9):1234-1240.
Bauer et al., "Activation of NK Cells and T Cells by NKG2D, a Receptor for Stress-Inducible MICA", Science, Jul. 1999, 285(5428):727-729.
Bedzyk et al., "Comparison of Variable Region Primary Structures Within an Anti-Fluorescein Idiotype Family", Journal of Biological Chemistry, 1989, 264(3):1565-1569.
Beier et al., "Master Switches of T-Cell Activation and Differentiation", European Respiratory Journal, Apr. 2007, 29(4):804-812.
Bhattacharya-Chatterjee et al., "Idiotype Vaccines Against Human T Cell Acute Lymphoblastic Leukemia. I. Generation and Characterization of Biologically Active Monoclonal Anti-Idiotopes", The Journal of Immunology, 1987, 139(4):1354-1360.
Bhattacharya-Chatterjee et al., "Idiotype Vaccines Against Human T Cell Leukemia. II. Generation and Characterization of a Monoclonal Idiotype Cascade (Ab1, Ab2, and Ab3)", The Journal of Immunology, Aug. 15, 1988, 141(4):1398-1403.
Bird et al., "Single-Chain Antigen-Binding Proteins", Science, 1988, 242:423-426.
Blank et al., "Absence of Programmed Death Receptor 1 Alters Thymic Development and Enhances Generation of CD4/CD8 Double-Negative TCR-Transgenic T Cells", Journal of Immunology, 2003, 171(9):4574-4581.
Blumenthal et al., "Expression Patterns of CEACAM5 and CEACAM6 In Primary and Metastatic Cancers", BMC Cancer, 2007, 7(2):15 pages.
Bodey B., "Cancer-Testis Antigens: Promising Targets for Antigen Directed Antineoplastic Immunotherapy", Expert Opinion on Biological Therapy, 2002, 2(6):577-584.
Bodhinayake et al., "Targeting a Heterogeneous Tumor: The Promise of the Interleukin-13 Receptor A2", Neurosurgery, Aug. 2014, 75(2):N18-N19.
Boghaert et al., "The Oncofetal Protein, 5T4, Is a Suitable Target for Antibody-Guided Anti-Cancer Chemotherapy with Calicheamicin", International Journal of Oncology, Jan. 2008, 32(1):221-234.
Bostrom et al., "Improving Antibody Binding Affinity and Specificity for Therapeutic Development", Therapeutic Antibodies, 2009, 525:353-376.
Boucher et al., "Protein Detection by Western Blot via Coiled-Coil Interactions", Analytical Biochemistry, Apr. 2010, 399(1):138-140.
Bozinov et al., "Decreasing Expression of the Interleukin-13 Receptor IL-13Rα2 in Treated Recurrent Malignant Gliomas", Neurol Med Chir (Tokyo), 2010, 50(8):617-621.
Brown et al., "Glioma IL13Rα2 Is Associated with Mesenchymal Signature Gene Expression and Poor Patient Prognosis", PLoS One, Oct. 18, 2013, 8(10):e77769.
Brown et al., "Trogocytosis Generates Acquired Regulatory T Cells Adding Further Complexity to the Dysfunctional Immune Response in Multiple Myeloma", Oncolmmunology, 2012, 1:1658-1660.
Brown et al., "Tumor-Specific Genetically Engineered Murine-Human Chimeric Monoclonal Antibody", Cancer Research, 1987, 47(13):3577-3583.

(56) References Cited

OTHER PUBLICATIONS

Bruggemann et al., "Comparison of the Effector Functions of Human Immunoglobulins using a Matched Set of Chimeric Antibodies", Journal of Experimental Medicine, Nov. 1987, 166(5):1351-1361.
Buchwald et al., "Long-Term, Continuous Intravenous Heparin Administration by an Implantable Infusion Pump in Ambulatory Patients with Recurrent Venous Thrombosis", Surgery, 1980, 88(4):507-516.
Bujis et al., "SPR-MS in Functional Proteomics", Briefings in Functional Genomics, 2005, 4(1):39-47.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", Journal of Cell Biology, Nov. 1990, 111:2129-2138.
Cachia et al., "Synthetic Peptide Vaccine Development: Measurement of Polyclonal Antibody Affinity and Cross-Reactivity Using a New Peptide Capture and Release System for Surface Plasmon Resonance Spectroscopy", Journal of Molecular Recognition, 2004, 17(6):540-557.
Cai et al., "Up-Regulation of Bone Marrow Stromal Protein 2 (BST2) In Breast Cancer with Bone Metastasis", BMC Cancer, 2009, 9:102.
Calin et al., "Genomics of Chronic Lymphocytic Leukemia MicroRNAs as New Players with Clinical Significance", Seminars in Oncology, May 2006, 33(2):167-173.
Call et al., "Common Themes in the Assembly and Architecture of Activating Immune Receptors", Nature Reviews Immunology, Nov. 2007, 7(11):841-850.
Cambier et al., "M19 Modulates Skeletal Muscle Differentiation and Insulin Secretion in Pancreatic β-Cells through Modulation of Respiratory Chain Activity", Plos One, Feb. 2012, 7(2):11 pages.
Cambier John C., "New Nomenclature for the Reth Motif (or ARH1/TAM/ARAM/YXXL)", Trends in Immunology, 1995, 16(2):110.
Cameron et al., "Focal Overexpression of CEACAM6 Contributes to Enhanced Tumorigenesis in Head and Neck Cancer via Suppression of Apoptosis", Molecular Cancer, Sep. 2012, 11(74):11 pages.
Canafax et al., "Monoclonal Antilymphocyte Antibody (OKT3) Treatment of Acute Renal Allograft Rejection", Pharmacotherapy, Aug. 1987, 7(4):121-124.
Cang et al., "Novel CD20 Monoclonal Antibodies for Lymphoma Therapy", Journal of Hematology & Oncology, Oct. 11, 2012, 5(64):9 pages.
Cao et al., "Bispecific Antibody Conjugates in Therapeutics", Advanced Drug Delivery Reviews, 2003, 55(2):171-197.
Carlo-Stella et al., "Targeting TRAIL Agonistic Receptors for Cancer Therapy", Clinical Cancer Research, Apr. 2007, 13(8):2313-2317.
Caron et al., "Engineered Humanized Dimeric Forms of IgG are More Effective Antibodies", Journal of Experimental Medicine, 1992, 176:1191-1195.
Carter et al., "Humanization of an Anti-p185her2 Antibody for Human Cancer Therapy", Proceedings of the National Academy of Sciences, 1992, 89:4285-4289.
Castelli et al., "T-Cell Recognition of Melanoma-Associated Antigens", Journal of Cellular Physiology, Mar. 2000, 182(3):323-331.
Castillo et al., "Newer Monoclonal Antibodies for Hematological Malignancies", Experimental Hematology, 2008, 36(7):755-768.
Castriconi et al., "Identification of 4Ig-B7-H3 as a Neuroblastoma-Associated Molecule That Exerts a Protective Role from an NK Cell-Mediated Lysis", Proc. Natl. Acad. Sci. (U.S.A.), 2004, 101(34):12640-12645.
Caumartin et al., "Intercellular Exchanges of Membrane Patches (Trogocytosis) Highlight the Next Level of Immune Plasticity", Transplant Immunology, 2006, 17(1):20-22.
Chan et al., "The Use of Antibodies in the Treatment of Infectious Diseases", Singapore Medical Journal, 2009, 50(7):663-666.
Chapin et al., "Distribution and Surfactant Association of Carcinoembryonic Cell Adhesion Molecule 6 In Human Lung", American Journal of Physiology—Lung Cellular and Molecular Physiology, Jan. 15, 2012, 302(2):L216-L225.
Chapoval et al., "B7-H3: A Costimulatory Molecule for T Cell Activation and IFN-γ Production", Nature Immunology, 2001, 2:269-274.
Chappel et al., "Identification of a Secondary FcRI Binding Site within a Genetically Engineered Human IgG Antibody", Journal of Biological Chemistry, 1993, 268(33):25124-25131.
Chappel et al., "Identification of the Fc Gamma Receptor Class I Binding Site in Human IgG Through the use of Recombinant IgG1/IgG2 Hybrid and Point-Mutated Antibodies", Proc. Natl. Acad. Sci U.S.A., 1991, 88:9036-9040.
Chaudhari et al., "Following the TRAIL to Apoptosis", Immunologic Research, 2006, 35(3):249-262.
Chen et al., "EphA2 Enhances the Proliferation and Invasion Ability of LnCap Prostate Cancer Cells", Oncology Letters, Jul. 2014, 8(1):41-46.
Chen et al., "Targeting B Lymphoma with Nanoparticles Bearing Glycan Ligands of CD22", Leukemia & Lymphoma, 2012, 53(2):208-210.
Chen et al., "The Role and Mechanisms of Double Negative Regulatory T Cells in the Suppression of Immune Responses", Cell Mol Immunol, 2004, 1:328-335.
Cheson et al., "Monoclonal Antibody Therapy for B-Cell Non-Hodgkin's Lymphoma", The New England Journal of Medicine, 2008, 359(6):613-626.
Chetty et al., "CD3: Structure, Function, and Role of Immunostaining in Clinical Practice", The Journal of Pathology, 1994, 173(4):303-307.
Chu et al., "CD79: A Review", Applied Immunohistochemistry & Molecular Morphology, 2001, 9(2):97-106.
Chu et al., "Nonviral Oncogenic Antigens and the Inflammatory Signals Driving Early Cancer Development as Targets for Cancer Immunoprevention", Clinical Cancer Research, Apr. 1, 2015, 21(7):1549-1557.
Cleek et al., "Biodegradable Polymeric Carriers for a bFGF Antibody for Cardiovascular Application", Proc Int Symp Controlled Release Bioact Mater, 1997, 24:853-854.
Clement et al., "Anti-CD8 Antibodies Can Trigger CD8+ T Cell Effector Function in the Absence of TCR Engagement and Improve Peptide-MHCI Tetramer Staining", Journal of Immunology, 2011, 187(2):654-663.
Co et al., "Chimeric and Humanized Antibodies with Specificity for the CD33 Antigen", The Journal of Immunology, 1992, 148(4):1149-1154.
Co et al., "Humanized Antibodies for Antiviral Therapy", Proceedings of the National Academy of Sciences, 1991, 88:2869-2873.
Coleman, "Epratuzumab: targeting B-cell malignancies through CD22", Clinical Cancer Research, 2003, 9(10 Pt 2):3991S-3994S.
Collins et al., "The B7 Family of Immune-Regulatory Ligands", Genome Biology, 2005, 6(6):223.1-223.7.
Comerci et al., "CD2 Promotes Human Natural Killer Cell Membrane Nanotube Formation", PLoS One, Oct. 2012, 7(10):e47664:1-12.
Coudert et al., "Altered NKG2D Function in NK Cells Induced by Chronic Exposure to NKG2D Ligand-expressing Tumor Cells", Blood, Oct. 2005, 106:1711-1717.
Cracco et al., "Immune Response in Prostate Cancer", Minerva Urologica e Nefrologica, Dec. 2005, 57(4):301-311.
Crescenzo et al., "Real-Time Monitoring of the Interactions of Two-Stranded de Novo Designed Coiled-Coils: Effect of Chain Length on the Kinetic and Thermodynamic Constants of Binding", Biochemistry, 2003, 42(6):1754-1763.
D'Acquisto et al., "CD3+CD4-CD8- (Double Negative) T Cells: Saviours or Villains of the Immune Response?", Biochemical Pharmacology, 2011, 82(4):333-340.
Dao et al., "Identification of a Human Cyclin D1-Derived Peptide that Induces Human Cytotoxic CD4 T Cells", PLoS One, Aug. 2009, 4(8):9 pages.
Daugherty et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.

(56) References Cited

OTHER PUBLICATIONS

Defranco AL, "The Complexity of Signaling Pathways Activated by the BCR", Current Opinion in Immunology, 1997, 9(3):296-308.
Deng et al., "Expression Profiling of CEACAM6 Associated with the Tumorigenesis and Progression in Gastric Adenocarcinoma", Genetics and Molecular Research, Sep. 26, 2014, 13(3):7686-7697.
Dennis et al., "Glycoprotein Glycosylation and Cancer Progression", Biochimica et Biophysica Acta, 1999, 1473(1):21-34.
Dhainaut et al., "Regulation of Immune Reactivity by Intercellular Transfer", Frontiers in Immunology, Mar. 2014, 5(112):4 pages.
Dimaio et al., "Human Papillomaviruses and Cervical Cancer", Advances in Virus Research, 2006, 66:125-159.
Dong et al., "Immune Regulation by Novel Costimulatory Molecules", Immunologic Research, 2003, 28(1):39-48.
Duncan et al., "Localization of The Binding Site for The Human High-Affinity Fc Receptor on IgG", Nature, 1988, 332:563-564.
During et al., "Controlled Release of Dopamine from a Polymeric Brain Implant: In Vivo Characterization", Annals of Neurology, 1989, 25(4):351-356.
Durrant et al., "Development of an ELISA to Detect Early Local Relapse of Colorectal Cancer", British Journal of Cancer, Oct. 1, 1989, 60(4):533-537.
Dylke et al., "Role of the Extracellular and Transmembrane Domain of Ig-Alpha/Beta in Assembly of the B Cell Antigen Receptor (BCR)", Immunology Letters, 2007, 112(1):47-57.
Eddy Sean R., "Where did the BLOSUM62 Alignment Score Matrix Come from?", Nature Biotechnology, 2004, 22:1035-1036.
Edelson et al., "Cutaneous T Cell Lymphoma: The Helping Hand of Dendritic Cells", Annals of the New York Academy of Sciences, 2001, 941:1-11.
Edelson, "Cutaneous T-Cell Lymphoma: A Model for Selective Immunotherapy", The cancer journal from Scientific American, Mar.-Apr. 1998, 4(2):62-71.
Egloff et al., "Cyclin B1 and other Cyclins as Tumor Antigens in Immunosurveillance and Immunotherapy of Cancer", Cancer Research, Jan. 1, 2006, 66(1):6-9.
Eisen et al., "Naptumomab Estafenatox: Targeted Immunotherapy with a Novel Immunotoxin", Current Oncology Reports, Feb. 2014, 16(370):6 pages.
Elkabetz et al., "Cysteines in CH1 Underlie Retention of Unassembled Ig Heavy Chains", J. Biol. Chem., 2005, 280:14402-14412.
Emmrich et al., "Synergism in the Activation of Human CD8 T Cells by Cross-Linking the T-cell Receptor Complex with the CD8 Differentiation Antigen", PNAS, Nov. 1, 1986, 83(21):8298-8302.
Estin et al., "Transfected Mouse Melanoma Lines That Express Various Levels of Human Melanoma-Associated Antigen p97", Journal of the National Cancer Institute, Apr. 1989, 81(6):445-458.
Feizi T., "Demonstration by Monoclonal Antibodies that Carbohydrate Structures of Glycoproteins and Glycolipids are Onco-Developmental Antigens", Nature, Mar. 7-13, 1985, 314(6006):53-57.
Fernandez-Rodriquez et al., "Induced Heterodimerization and Purification of Two Target Proteins by a Synthetic Coiled-Coil Tag", Protein Science, 2012, 21:511-519.
Ferran et al., "Cytokine-Related Syndrome following Injection of Anti-CD3 Monoclonal Antibody: Further Evidence for Transient In vivo T Cell Activation", European Journal of Immunology, 1990, 20(3):509-515.
Finck et al., "The Role of T-Cell Subsets in the Response to Anti-CD3 Monoclonal Antibodies", Clinical Immunology and Immunopathology, Dec. 1992, 65(3):234-241.
Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions", Journal of Molecular Biology, 2009, 388(3):541-558.
Fitzgerald et al., "Improved Tumour Targeting by Disulphide Stabilized Diabodies Expressed in Pichia pastoris", Protein Engineering, 1997, 10(10):1221-1225.

Fivash et al., "BIAcore for Macromolecular Interaction", Current Opinions in Biotechnology, 1998, 9(1):97-101.
Flesch et al., "Functions of the Fc Receptors for Immunoglobulin G", Journal of Clinical Laboratory Analysis, 2000, 14:141-156.
Foon et al., "Immune Response to the Carcinoembryonic Antigen in Patients Treated with an Anti-Idiotype Antibody Vaccine", Journal of Clinical Investigation, 1995, 96(1):334-342.
Frangione et al., "Human Lambda Light-Chain Constant Region Gene CMor Lambda: The Primary Structure of Lambda VI Bence Jones Protein Mor", PNAS, 1985, 82(10):3415-3419.
Fujisawa et al., "A Novel Role of Interleukin-13 Receptor α2 in Pancreatic Cancer Invasion and Metastasis", Cancer Research, Nov. 2009, 69(22):8678-8685.
Ganesan A, "Solid-Phase Synthesis in the Twenty-First Century", Mini-Reviews in Medicinal Chemistry, 2006, 6(1):3-10.
Gardnerova et al., "The Use of TNF Family Ligands and Receptors and Agents Which Modify their Interaction as Therapeutic Agents", Current Drug Targets, Dec. 2000, 1(4):327-364.
Garratty G., "Blood Group Antigens as Tumor Markers, Parasitic/Bacterial/Viral Receptors, and Their Association with Immunologically Important Proteins", Immunological Investigations, Jan.-Feb. 1995, 24(1-2):213-232.
Ge et al., "CD36: A Multiligand Molecule", Laboratory Hematology, 2005, 11(1):31-37.
Geraud et al., "Endothelial Transdifferentiation in Hepatocellular Carcinoma: Loss of Stabilin-2 Expression in Peri-Tumourous Liver Correlates with Increased Survival.", Liver international: official journal of the International Association for the Study of the Liver, Jun. 2013, 33(9):1428-1440.
Ghetie et al., "Anti-CD19 Inhibits the Growth of Human B-Cell Tumor Lines in Vitro and of Daudi Cells in SCID Mice by Inducing Cell Cycle Arrest", Blood, Mar. 1994, 83(5):1329-1336.
Ghosh et al., "End-To-End and End-To-Middle Interhelical Interactions: New Classes of Interacting Helix Pairs in Protein Structures", Acta Crystallogr D Biol Crystallogr., 2009, 65(Pt 10):1032-1041.
Gil et al., "Regulation of the INK4b-ARF-INK4a Tumour Suppressor Locus: All for one or one for all", Nature Reviews Molecular Cell Biology, Sep. 2006, 7(9):667-677.
Glaser et al., "Antibody Engineering by Codon-Based Mutagenesis in a Filamentous Phage Vector System", The Journal of Immunology, Dec. 15, 1992, 149(12):3903-3913.
Gooi et al., "Monoclonal Antibody Reactive with the Human Epidermal-Growth-Factor Receptor Recognizes the Blood-Group-A Antigen", Bioscience Reports, Nov. 1983, 3(11):1045-1052.
Gorman et al., "Reshaping a Therapeutic CD4 Antibody", Proceedings of the National Academy of Sciences, 1991, 88:4181-4185.
Gorny et al., "Human Monoclonal Antibodies that Neutralize HIV-1", HIV Immunology and HIV/SIV Vaccine Databases, 2003, 37-51.
Gregoire et al., "Covalent assembly of a soluble T cell receptor-peptide-major histocompatibility class I complex", PNAS, 1996, 93:7184-7189.
Greulich et al., "Functional Analysis of Receptor Tyrosine Kinase Mutations in Lung Cancer Identifies Oncogenic Extracellular Domain Mutations of ERBB2", Proceedings of the National Academy of Sciences, Sep. 4, 2012, 109(36):14476-14481.
Grigoryan et al., "Structural Specificity in Coiled-Coil Interactions", Current Opinion in Structural Biology, Aug. 2008, 18(4):477-483.
Groh et al., "Costimulation of CD8αβ T cells by NKG2D via engagement by MIC induced on virus-infected cells", Nature Immunology, Mar. 2001, 2(3):255-260.
Groneberg et al., "Nanoparticle-Based Diagnosis and Therapy", Current Cancer Drug Targets, 2006, 7(6):643-648.
Gruber et al., "Efficient Tumor Cell Lysis Mediated by a Bispecific Single Chain Antibody Expressed in *Escherichia coli*", Journal of Immunology, 1994, 152(11):5368-5374.
Gustchina et al., "Affinity Maturation by Targeted Diversification of the CDR-H2 Loop of a Monoclonal Fab Derived from a Synthetic Naïve Human Antibody Library and Directed Against the Internal

(56) References Cited

OTHER PUBLICATIONS

Trimeric Coiled-Coil of Gp41 Yields a Set of Fabs with Improved HIV-1 Neutralization Potency and Breadth", Virology, Oct. 2009, 393(1):112-119.
Guy et al., "Organization of Proximal Signal Initiation at the TCR:CD3 Complex", Immunological Reviews, Nov. 2009, 232(1):7-21.
Hackel et al., "Stability and CDR Composition Biases Enrich Binder Functionality Landscapes", Journal of Molecular Biology, Aug. 2010, 401(1):84-96.
Hakomori S., "Cancer-Associated Glycosphingolipid Antigens: their Structure, Organization, and Function", Acta Anatomica, 1998, 161(1-4):79-90.
Heath et al., "The Human A33 Antigen is a Transmembrane Glycoprotein and a Novel Member of the Immunoglobulin Superfamily", Proceedings of the National Academy of Sciences, Jan. 21, 1997, 94(2):469-474.
Hellstrom et al., "Monoclonal Antibodies to Cell Surface Antigens Shared by Chemically Induced Mouse Bladder Carcinomas", Cancer Research, May 1985, 45:2210-2218.
Hellstrom et al., "Monoclonal Mouse Antibodies Raised against Human Lung Carcinoma", Cancer Research, Aug. 1986, 46(8):3917-3923.
Henikoff et al., "Amino Acid Substitution Matrices from Protein Blocks", Proceedings of the National Academy of Sciences, Nov. 1992, 89(22):10915-10919.
Henttu et al., "cDNA coding for the entire human prostate specific antigen shows high homologies to the human tissue kallikrein genes", Biochemical and Biophysical Research Communications, Apr. 1989, 160(2):903-910.
Herlyn et al., "Monoclonal Antibody Detection of a Circulating Tumor-Associated Antigen. I. Presence of Antigen in Sera of Patients with Colorectal, Gastric, and Pancreatic Carcinoma", Journal of Clinical Immunology, Apr. 1982, 2(2):135-140.
Hilkens et al., "Cell Membrane-Associated Mucins and Their Adhesion-Modulating Property", Trends in Biochemical Sciences, Sep. 1992, 17(9):359-363.
Hillhouse et al., "A Comprehensive Review of the Phenotype and Function of Antigen-Specific Immunoregulatory Double Negative T Cells", Journal of Autoimmunity, Feb. 2013, 40:58-65.
Hoelzer D., "Targeted Therapy with Monoclonal Antibodies in Acute Lymphoblastic Leukemia", Current Opinion in Oncology, Nov. 2013, 25(6):701-706.
Hofmeyer et al., "The Contrasting Role of B7-H3", Proceedings of the National Academy of Sciences of the United States of America, Jul. 29, 2008, 105(30):10277-10278.
Hogg et al., "A Monoclonal Antibody Exhibiting Reactivity with both X-Hapten- and Lactose-Bearing Glycolipids", Tissue Antigens, Jan. 1991, 37(1):33-38.
Holliger et al., "Carcinoembryonic Antigen (CEA)-specific T-Cell Activation in Colon Carcinoma Induced by Anti-CD3xAnti-CEA Bispecific Diabodies and B7xAnti-CEA Bispecific Fusion Proteins", Cancer Research, 1999, 59(12):2909-2916.
Holliger et al., "Diabodies': Small Bivalent and Bispecific Antibody Fragments", Proceedings of the National Academy of Sciences, 1993, 90:6444-6448.
Holliger et al., "Specific Killing of Lymphoma Cells by Cytotoxic T-Cells Mediated by a Bispecific Diabody", Protein Engineering, 1996, 9(3):299-305.
Holmberg et al., "Theratope Vaccine (STn-KLH).", Expert Opinion on Biological Therapy, Sep. 2001, 1(5):881-891.
Hoo et al., "Characterization of a single-chain T-cell receptor expressed in *Escherichia coli*", PNAS USA, 1992, 89:4759-4763.
Hoon et al., "Molecular Cloning of a Human Monoclonal Antibody Reactive to Ganglioside GM3 Antigen on Human Cancers", Cancer Research, Nov. 1993, 53(21):5244-5250.
Houghten et al., "General Method for The Rapid Solid-Phase Synthesis of Large Numbers of Peptides: Specificity of Antigen-Antibody Interaction at The Level of Individual Amino Acids", Proceedings of the National Academy of Sciences, 1985, 82(15):5131-5135.
Howard et al., "Intracerebral Drug Delivery in Rats with Lesion-Induced Memory Deficits", Journal of Neurosurgery, 1989, 71(1):105-112.
Hudrisier et al., "Capture of Target Cell Membrane Components via Trogocytosis Is Triggered by a Selected Set of Surface Molecules on T or B Cells", Journal of Immunology, Mar. 15, 2007, 178(6):3637-3647.
Hutchins et al., "Improved Biodistribution, Tumor Targeting, and Reduced Immunogenicity in Mice with a Gamma 4 Variant of Campath-1H", Proc. Natl. Acad. Sci. (U.S.A.), 1995, 92:11980-11984.
Idusogie et al., "Engineered Antibodies with Increased Activity to Recruit Complement", Journal of Immunology, 2001, 166:2571-2575.
Idusogie et al., "Mapping of The C1q Binding Site on Rituxan, a Chimeric Antibody with a Human IgG1 Fc", Journal of Immunology, 2000, 164: 4178-4184.
Israeli et al., "Molecular cloning of a complementary DNA encoding a prostate-specific membrane antigen", Cancer Research, Jan. 1993, 53(2):227-230.
Jamieson et al., "The Role of the NKG2D Immunoreceptor in Immune Cell Activation and Natural Killing", Immunity, Jul. 2002, 17(1):19-29.
Jason-Moller et al., "Overview of Biacore Systems and Their Applications", Current Protocols in Protein Science, Aug. 2006, 44(1):19.13.1-19.13.14.
Jefferis et al., "Interaction Sites on Human IgG-Fc for FcgammaR: Current Models", Immunology Letters, 2002, 82:57-65.
Jefferis et al., "Modulation of Fc(Gamma)R and Human Complement Activation by IgG3-Core Oligosaccharide Interactions", Immunology Letters, 1996, 54:101-104.
Jefferis et al., "Recognition Sites on Human IgG for Fc Gamma Receptors: The Role of Glycosylation", Immunology Letters, 1995, 44:111-117.
Jennings Veronica M., "Review of Selected Adjuvants Used in Antibody Production", ILAR Journal, 1995, 37(3):119-125.
Johansson et al., "A Unique Population of Extrathymically Derived αβTCR+CD4-CD8- T Cells with Regulatory Functions Dominates the Mouse Female Genital Tract", The Journal of Immunology, Mar. 2003, 170(4):1659-1666.
Johansson et al., "Structure, Specificity, and Mode of Interaction for Bacterial Albumin-binding Modules", Journal of Biological Chemistry, Mar. 2002, 277(10):8114-8120.
Johnson et al., "Effector Cell Recruitment with Novel Fv-Based Dual-Affinity Re-Targeting Protein Leads to Potent Tumor Cytolysis and In vivo B-Cell Depletion", Journal of Molecular Biology, 2010, 399(3):436-449.
Joliot et al., "Antennapedia Homeobox Peptide Regulates Neural Morphogenesis", Proceedings of the National Academy of Sciences, 1991, 88:1864-1868.
Joly et al., "What is Trogocytosis and what is its Purpose?", Nature Immunology, Oct. 2003, 4(9):815.
Jones et al., "Replacing the Complementarity-Determining Regions in a Human Antibody with Those from a Mouse", Nature, 1986, 321:522-525.
Jung et al., "Target Cell-induced T Cell Activation with Bi- and Trispecific Antibody Fragments", European Journal of Immunology, Oct. 1, 1991, 21(10):2431-2435.
Jurcic Joseph G., "Immunotherapy for Acute Myeloid Leukemia", Current Oncology Reports, 2005, 7(5):339-346.
Karlin et al., "Methods for Assessing the Statistical Significance of Molecular Sequence Features by using General Scoring Schemes", Proceedings of the National Academy of Sciences, 1990, 87(6):2264-2268.
Karlsson R., "SPR For Molecular Interaction Analysis: A Review of Emerging Application Areas", Journal of Molecular Recognition, 2004, 17(3):151-161.
Karu et al., "Recombinant Antibody Technology", ILAR Journal, 1995, 37(3):132-141.

(56) References Cited

OTHER PUBLICATIONS

Kasaian et al., "IL-13 Antibodies Influence IL-13 Clearance in Humans by Modulating Scavenger Activity of IL-13Ra2", The Journal of Immunology, Jul. 1, 2011, 187(1):561-569.
Kawai et al., "Interferon-α enhances CD317 expression and the antitumor activity of anti-CD317 monoclonal antibody in renal cell carcinoma xenograft models", Cancer Science, Dec. 2008, 99(12):2461-2466.
Kelley et al., "In: Genetic Engineering Principles and Methods", Setlow, J.K. Ed., Plenum Press, N.Y., 1990, 12:1-19.
Kettleborough et al., "Humanization of a Mouse Monoclonal Antibody by CDR-Grafting: The Importance of Framework Residues on Loop Conformation", Protein Engineering, 1991, 4(7):773-783.
Khawli et al., "Cytokine, Chemokine, and Co-Stimulatory Fusion Proteins for the Immunotherapy of Solid Tumors", Handbook of Experimental Pharmacology, 2008, 181:291-328.
Kim et al., "Signalling Function of the B-cell Antigen Receptors", Immunological Reviews, 1993, 132:125-146.
Klein et al., "Examination of the contributions of size and avidity to the neutralization mechanisms of the anti-HIV antibodies b12 and 4E10", PNAS USA, 2009, 106:7385-7390.
Kohler et al., "Continuous Cultures of Fused Cells Secreting Antibody of Predefined Specificity", Nature, 1975, 256:495-497.
Kontermann RE., "Dual targeting strategies with bispecific antibodies", MAbs., vol. 4, No. 2, 2012, 182-197.
Korman et al., "Checkpoint Blockade in Cancer Immunotherapy", Advances in Immunology, 2007, 90:297-339.
Kounalakis et al., "Tumor Cell and Circulating Markers in Melanoma: Diagnosis, Prognosis, and Management", Current Oncology Reports, Sep. 2005, 7(5):377-382.
Krause et al., "An Insertion Mutation That Distorts Antibody Binding Site Architecture Enhances Function of a Human Antibody", mBio, Jan./Feb. 2011, 2(1):8 pages.
Kreitman,"Immunotoxins for Targeted Cancer Therapy", The AAPS Journal, Sep. 2006, 8(3):E532-E551.
Kuan et al., "Affinity-Matured Anti-Glycoprotein NMB Recombinant Immunotoxins Targeting Malignant Gliomas and Melanomas", International Journal of Cancer, Jul. 2011, 129(1):111-121.
Kügler M, "A recombinant trispecific single-chain Fv derivative directed against CD123 and CD33 mediates effective elimination of acute myeloid leukaemia cells by dual targeting", Br J Haematol. vol. 150, No. 5, (Abstract; Figures 1 and 5) Citation is not enclosed due to copyright restrictions., Jul. 16, 2010, 574-586.
Kuhns et al., "Deconstructing the Form and Function of the TCR/CD3 Complex", Immunity, Feb. 2006, 24(2):133-139.
Kurosaki et al., "Molecular Mechanisms in B Cell Antigen Receptor Signaling", Current Opinion in Immunology, 1997, 9(3):309-318.
Kurrle et al., "BMA 031—A TCR-Specific Monoclonal Antibody for Clinical Application", Transplantation Proceedings, 1989, 21(1 Pt 1):1017-1019.
Kwong et al., "Generation, Affinity Maturation, and Characterization of a Human Anti-Human NKG2D Monoclonal Antibody with Dual Antagonistic and Agonistic Activity", Journal of Molecular Biology, Dec. 2008, 384(5):1143-1156.
Lam et al., "Microencapsulation of Recombinant Humanized Monoclonal Antibody for Local Delivery", Proc Int Symp Controlled Release Bioact Mater, 1997, 24:759-760.
Langer Robert, "New Methods of Drug Delivery", Science, 1990, 249:1527-1533.
Lanier et al., "Up on the tightrope: natural killer cell activation and inhibition", Nat Immunol., 2008, 9(5):495-502.
Lazar et al., "Transforming Growth Factor A: Mutation of Aspartic Acid 47 and Leucine 48 Results in Different Biological Activities", Molec. Cell. Biol., 1988, 8:1247-1252.
Ibragimova et al., "Stability of the beta-sheet of the WW domain: A molecular dynamics simulation study", Biophysical Journal, Oct. 1999, 77(4): 2191-2198.
Lee et al., "Targeting Cyclins and Cyclin-Dependent Kinases in Cancer: Lessons from Mice, Hopes for Therapeutic Applications in Humans", Cell Cycle, Sep. 2006, 5(18):2110-2114.

Lefranc et al., "Gm, Am and Km immunoglobulin allotypes of two populations in Tunisia", Human Genetics, 1979, 50:199-211.
Lefranc et al., "Molecular Genetics of Immunoglobulin Allotype Expression", The Human IgG Subclasses: Molecular Analysis of Structure, Function and Regulation, Pergamon Press, 1990, 43-78.
Legendre et al., "Prognostic Stratification of Dukes B Colon Cancer by a Neoglycoprotein", International Journal of Oncology, Sep. 2004, 25(2):269-276.
Lemaoult et al., "Exchanges of Membrane Patches (Trogocytosis) Split Theoretical and Actual Functions of Immune Cells", Human Immunology, Apr. 2007, 68(4):240-243.
Levy et al., "Inhibition of Calcification of Bioprosthetic Heart Valves by Local Controlled-Release Diphosphonate", Science, 1985, 228(4696):190-192.
Lewis-Wambi et al., "Overexpression of CEACAM6 promotes migration and invasion of oestrogen-deprived breast cancer cells", European Journal of Cancer, Aug. 2008, 44(12):1770-1779.
Liang et al., "Integrin-Beta6-targeted Immunoliposomes 1~fediate Tumor Specific Drug Delivery and Enhance Therapeutic Efficacy in Colon Carcinoma", Clinical Cancer Research, Mar. 2015, 21(5): 14 pages.
Lin et al., "Structure-function relationships in glucagon: properties of highly purified des-His-1-, monoiodo-, and (des-Asn-28, Thr-29)(homoserine lactone-27)-glucagon", Biochemistry, Apr. 22, 1975, 14(8):1559-1563.
Lindley et al., "The Clinical Utility of Inhibiting CD28-Mediated Costimulation", Immunological Reviews, 2009, 229:307-321.
Litowski et al., "Designing Heterodimeric Two-Stranded Alpha-Helical Coiled-Coils. Effects of Hydrophobicity and Alpha-Helical Propensity on Protein Folding, Stability, and Specificity", Journal of Biological Chemistry, Oct. 4, 2002, 277(40):37272-37279.
Livingston et al., "Improved survival in stage III melanoma patients with GM2 antibodies: a randomized trial of adjuvant vaccination with GM2 ganglioside", Journal of Clinical Oncology, May 1994, 12(5):1036-1044.
Livingston et al., "Selection of GM2, Fucosyl GM1, Globo H and Polysialic Acid as Targets on Small Cell Lung Cancers for Antibody Mediated Immunotherapy", Cancer Immunology Immunotherapy, Oct. 2005, 54(10):1018-1025.
Lobuglio et al., "Mouse-Human Chimeric Monoclonal Antibody in Man: Kinetics and Immune Response", Proceedings of the National Academy of Sciences, 1989, 86:4220-4224.
Lonberg et al., "Human Antibodies from Transgenic Mice", International Reviews of Immunology, 1995, 13:65-93.
Lotem et al., "Presentation of Tumor Antigens by Dendritic Cells Genetically Modified with Viral and Nonviral Vectors", Journal of Immunotherapy, Nov.-Dec. 2006, 29(6):616-627.
Loveless et al., "Developmental Patterning of the Carbohydrate Antigen FC10.2 during Early Embryogenesis in the Chick", Development, 1990, 108(1):97-106.
Lu et al., "A Fully Human Recombinant IgG-Like Bispecific Antibody to Both the Epidermal Growth Factor Receptor and The Insulin-Like Growth Factor Receptor for Enhanced Antitumor Activity", Journal of Biological Chemistry, 2005, 280(20):19665-19672.
Lu et al., "The Effect of a Point Mutation on the Stability of IgG4 as Monitored by Analytical Ultracentrifugation", Journal of Pharmaceutical Sciences, Feb. 2008, 97(2):960-969.
Lund et al., "Human Fc Gamma RI and Fc Gamma RII Interact with Distinct but Overlapping Sites on Human IgG", Journal of Immunology, 1991, 147:2657-2662.
Lund et al., "Multiple Binding Sites on The CH2 Domain of IgG for Mouse Fc Gamma R11", Molecular Immunology, 1992, 29:53-59.
Lund et al., "Multiple Interactions of IgG with Its Core Oligosaccharide Can Modulate Recognition by Complement and Human Fc Gamma Receptor I and Influence the Synthesis of Its Oligosaccharide Chains", Journal of Immunology, 1996, 157:4963-4969.
Lund et al., "Oligosaccharide-Protein Interactions in IgG Can Modulate Recognition by Fc Gamma Receptors", The FASEB Journal, 1995, 9:115-119.
Mace et al., "Cell Biological Steps and Checkpoints in Accessing NK Cell Cytotoxicity", Immunology & Cell Biology, Mar. 2014, 92(3):245-255.

(56) References Cited

OTHER PUBLICATIONS

Maeda et al., "Construction of Reshaped Human Antibodies With HIV-Neutralizing Activity", Human Antibodies Hybridoma, 1991, 2:124-134.

Malaguarnera et al., "Serum Markers of Hepatocellular Carcinoma", Digestive Diseases and Sciences, 2010, 55(10):2744-2755.

Mallone et al., "Targeting T lymphocytes for immune monitoring and intervention in autoimmune diabetes", American Journal of Therapeutics, 2005, 12(6):534-550.

Malmborg et al., "BIAcore as a Tool in Antibody Engineering", Journal of Immunological Methods, 1995, 183:7-13.

Malmqvist et al., "Biomolecular Interaction Analysis: Affinity Biosensor Technologies for Functional Analysis of Proteins", Current Opinion in Chemical Biology, Oct. 1997, 1(3):378-383.

Malmqvist Magnus, "BIACORE: An Affinity Biosensor System for Characterization of Biomolecular Interactions", Biochemical Society Transactions, Mar. 1999, 27(2):335-340.

Maloney,"Anti-CD20 Antibody Therapy for B-Cell Lymphomas", The New England Journal of Medicine, 2012, 366:2008-2016.

Mariuzza et al., "The Structural Basis of Antigen-Antibody Recognition", Annual Review of Biophysics and Biophysical Chemistry, 1987, 16:139-159.

Maroun et al., "Distinct Roles for CD4 and CD8 as Co-Receptors in T Cell Receptor Signalling", European Journal of Immunol, 1994, 24:959-966.

Marvin et al., "Recombinant Approaches to IgG-Like Bispecific Antibodies", Acta Pharmacologica Sinica, 2005, 26:649-658.

Masuda et al., "Possible Implication of Fcγ Receptor-Mediated Trogocytosis in Susceptibility to Systemic Autoimmune Disease", Clinical and Developmental Immunology, 2013, 2013:6 pages.

Mathelin et al., "Circulating Proteinic Biomarkers and Breast Cancer", Gynecologie, obstetrique & fertilite, 2006, 34(7-8):638-646.

McIntyre et al., "Consequences of Double Negative Regulatory T Cell and Antigen Presenting Cell Interaction on Immune Response Suppression", International Immunopharmacology, May 2011, 11(5):597-603.

Mei,"Rationale of Anti-CD19 Immunotherapy: An Option to Target Autoreactive Plasma Cells in Autoimmunity", Arthritis Research & Therapy, 2012, 14(Suppl 5): S1:1-16.

Merrifield et al., "Solid Phase Synthesis", Science, 1986, 232(4748):341-347.

Messmer et al., "CD154 Gene Therapy for Human B-Cell Malignancies", Annals of the New York Academy of Sciences, 2005, 1062:51-60.

Miao et al., "EphA2 is a Mediator of Vemurafenib Resistance and a Novel Therapeutic Target in Melanoma", Cancer Discovery, Mar. 2015, 5(3):274-287.

Michalk et al., "Characterization of a Novel Single-Chain Bispecific Antibody for Retargeting of T Cells to Tumor Cells via the TCR Co-Receptor CD8", PloS One, Apr. 21, 2014, 9(4):1-8.

Miller Jeffreys., "Therapeutic applications: Natural killer cells in the clinic", Hematology, Dec. 2013, 2013(1):247-253.

Mittelman et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies", Journal of Clinical Investigation, Dec. 1990, 86(6):2136-2144.

Moller et al., "Bispecific-Monoclonal-Antibody-Directed Lysis of Ovarian Carcinoma Cells by Activated Human T Lymphocytes", Cancer Immunology, Immunotherapy, 1991, 33(4):210-216.

Montgomery et al., "Affinity Maturation and Characterization of a Human Monoclonal Antibody Against HIV-1 Gp41", mAbs, 2009, 1(5):462-474.

Moore et al., "Application of Dual Affinity Retargeting Molecules to Achieve Optimal Redirected T-Cell Killing of B-Cell Lymphoma", Blood, 2011, 117(17):4542-4551.

Muramatsu et al., "Carbohydrate Antigens Expressed on Stem Cells and Early Embryonic Cells", Glycoconjugate Journal, 2004, 21(1-2):41-45.

Muta et al., "CD30: from Basic Research to Cancer Therapy", Immunologic Research, Dec. 2013, 57(1-3):151-158.

Nakamura et al., "NK-Cell Fratricide: Dynamic Crosstalk Between NK and Cancer Cells", OncoImmunology, 2013, 2(11):e26529.

Nashan et al., "Fine Specificity of a Panel of Antibodies Against the TCR/CD3 Complex", Transplantation Proceedings, Oct. 1987, 19(5):4270-4272.

Natali et al., "Immunohistochemical Detection of Antigen in Human Primary and Metastatic Melanomas by the Monoclonal Antibody 140.240 and Its Possible Prognostic Significance", Cancer, 1987, 59(1):55-63.

Ning et al., "Intratumoral Radioimmunotherapy of a Human Colon Cancer Xenograft Using a Sustained-Release Gel", Radiotherapy and Oncology, May 1996, 39(2):179-189.

Norman Douglasj., "Mechanisms of Action and Overview of OKT3", Therapeutic Drug Monitoring, Dec. 1995, 17(6):615-620.

Notley et al., "ANTI-CD3 therapy expands the numbers of CD4+ and CDS+ Treg cells and induces sustained amelioration of collagen-induced arthritis", Arthritis & Rheumatism, 2010, 62:171-178.

O'Dwyer P., "The Present and Future of Angiogenesis-Directed Treatments of Colorectal Cancer", Oncologist, Oct. 2006, 11(9):992-998.

Olafsen et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.

Pal et al., "Targeting HER2 Epitopes", Seminars in Oncology, Aug. 2006, 33(4):386-391.

Palma et al., "Plasmacytoids Dendritic Cells are a Therapeutic Target in Anticancer Immunity", Biochimica et Biophysica Acta (BBA)—Reviews on Cancer, Dec. 2012, 1826(2):407-414.

Peeters et al., "Production of Antibodies and Antibody Fragments in Plants", Vaccine, 2001, 19:2756-2761.

Peggs et al., "Principles and Use of Anti-CTLA4 Antibody in Human Cancer Immunotherapy", Current Opinion in Immunology, 2006, 18(2):206-213.

Peipp et al., "Bispecific Antibodies Targeting Cancer Cells", Biochemical Society Transactions, 2002, 30(4):507-511.

Peltz et al., "Human FcγRIII: Cloning, expression, and identification of the chromosomal locus of two Fc receptors for IgG", Proc. Natl. Acad. Sci. (U.S.A.), Feb. 1989, 86(3):1013-1017.

Perez et al., "Isolation and Characterization of a Cdna Encoding the KS1/4 Epithelial Carcinoma Marker", Journal of Immunology, May 15, 1989, 142(10):3662-3667.

Peters et al., "Engineering an Improved IgG4 Molecule with Reduced Disulfide Bond Heterogeneity and Increased Fab Domain Thermal Stability", Journal of Biological Chemistry, Jul. 13, 2012, 287(29):24525-24533.

Poe et al., "CD22 and Siglec-G in B Cell Function and Tolerance", Trends in Immunology, 2012, 33(8):413-420.

Pollock et al., "Transgenic Milk as a Method for The Production of Recombinant Antibodies", Journal of Immunological Methods, 1999, 231:147-157.

Ponomarenko et al., "Role of K—+A light-chain constant-domain switch in the structure and functionality of a 17 reactibody", Acta Crystallographica Section D, 2014, D70:708-719.

Portoles et al., "The TCR/CD3 Complex: Opening the Gate to Successful Vaccination", Current Pharmaceutical Design, 2009, 15(28):3290-3300.

Prange et al., "Beta-Catenin Accumulation in the Progression of Human Hepatocarcinogenesis Correlates with loss of E-Cadherin and Accumulation of P53, but not with Expression of Conventional WNT-1 Target Genes", The Journal of Pathology, 2003, 201(2):250-259.

Presta et al., "Engineering Therapeutic Antibodies for Improved Function", Biochemical Society Transactions, 2002, 30(4):487-490.

Pui et al., "Characterization of Childhood Acute Leukemia with Multiple Myeloid and Lymphoid Markers at Diagnosis and at Relapse", Blood, Sep. 1991, 78(5):1327-1337.

Rabbani et al., "Expression of ROR1 in Patients with Renal Cancer—A Potential Diagnostic Marker", Iranian Biomedical Journal, Jul. 2010, 14(3):77-82.

(56) References Cited

OTHER PUBLICATIONS

Ragnhammar et al., "Effect of monoclonal antibody 17-1A and gm-CSF in patients with advanced colorectal carcinoma-long-lasting, complete remissions can be induced", International Journal of Cancer, Mar. 1993, 53(5):751-758.

Ragupathi et al., "Antibody Inducing Polyvalent Cancer Vaccines", Cancer Treatment and Research, Feb. 2005, 123:157-180.

Raufi et al., "Targeting CD19 in B-Cell Lymphoma: Emerging Role of SAR3419", Cancer Management and Research, 2013, 5:225-233.

Raulet Davidh., "Roles of The NKG2D Immunoreceptor and Its Ligands", Nature Reviews Immunology, Oct. 2003, 3:781-790.

Ravoet et al., "Molecular profiling of CD3-CD4+ T cells from patients with the lymphocytic variant of hypereosinophilic syndrome reveals targeting of growth control pathways", Blood, 2009, 114:2969-2983.

Reddy et al., "Elimination of Fc Receptor-Dependent Effector Functions of a Modified IgG4 Monoclonal Antibody to Human CD4", Journal of Immunology, 2000, 164:1925-1933.

Reff et al., "Depletion of B Cells In vivo by a Chimeric Mouse Human Monoclonal Antibody to CD20", Blood, Jan. 15, 1994, 83(2):435-445.

Renders et al., "Engineered CD3 Antibodies for Immunosuppression", Clinical & Experimental Immunology, 2003, 133(3):307-309.

Ridgway et al., "'Knobs-Into-Holes' Engineering of Antibody CH3 Domains for Heavy Chain Heterodimerization", Protein Engineering, 1996, 9(7):617-621.

Riechmann et al., "Reshaping Human Antibodies for Therapy", Nature, 1988, 332:323-327.

Riley et al., "Design and Activity of a Murine and Humanized anti-CEACAM6 scFv in the Treatment of Pancreatic Cancer", Cancer research, Mar. 2009, 69(5):1933-1940.

Rimon et al., "Gonadotropin-Induced Gene Regulation in Human Granulosa Cells Obtained from IVF Patients: Modulation of Genes Coding for Growth Factors and their Receptors and Genes Involved in Cancer and other Diseases", International Journal of Oncology, May 2004, 24(5):1325-1338.

Ritter et al., "Characterization of Posttranslational Modifications of Human A33 Antigen, a Novel Palmitoylated Surface Glycoprotein of Human Gastrointestinal Epithelium", Biochemical and Biophysical Research Communications, Jul. 30, 1997, 236(3):682-686.

Robak et al., "Anti-CD37 Antibodies for Chronic Lymphocytic Leukemia", Expert Opinion on Biological Therapy, Feb. 2014, 14(5):651-661.

Rodriquez et al., "Influence of Interleukin-15 in CD8+ Natural Killer Cells in Human Immunodeficiency Virus Type 1-Infected Chimpanzees", Journal of General Virology, Mar. 2007, 88(Pt 2):641-651.

Rosati et al., "Chronic Lymphocytic Leukaemia: A Review of the Immuno-Architecture", Current Topics in Microbiology and Immunology, 2005, 294:91-107.

Rudikoff et al., "Single Amino Acid Substitution Altering Antigen-Binding Specificity", Proceedings of the National Academy of Sciences, 1982, 79:1979-1983.

Russell S., "CD46: A Complement Regulator and Pathogen Receptor that Mediates Links Between Innate and Acquired Immune Function", Tissue Antigens, Aug. 2004, 64(2):111-118.

Saalmuller et al., "Discrimination between two subsets of porcine CDS+ cytolytic T lymphocytes by the expression of CDS antigen", Immunology, 1994, 81:578-583.

Saatian et al., "Expression of Genes for B7-H3 and Other T Cell Ligands by Nasal Epithelial Cells During Differentiation and Activation", AJP Lung Cellular and Molecular Physiology, Aug. 2004, 287(1):L217-225.

Saito et al., "Complete primary structure of a heterodimeric T-cell receptor deduced from cDNA sequences", Nature, 1984, 309:757-762.

Saleh et al., "Generation of a human anti-idiotypic antibody that mimics the GD2 antigen", The Journal of Immunology, Sep. 15, 1993, 151(6):3390-3398.

Sato et al., "Reshaping a Human Antibody to Inhibit the Interleukin 6-dependent Tumor Cell Growth", Cancer Research, 1993, 53:851-856.

Saudek et al., "A Preliminary Trial of the Programmable Implantable Medication System for Insulin Delivery", New England Journal of Medicine, Sep. 1989, 321(9):574-579.

Sayeed et al., "Aberrant Regulation of the BST2 (Tetherin) Promoter Enhances Cell Proliferation and Apoptosis Evasion in High Grade Breast Cancer Cells", PloS ONE, Jun. 2013, 8(6):e67191, 10 pages.

Schier et al., "Isolation of Picomolar Affinity Anti-C-Erbb-2 Single-Chain Fv by Molecular Evolution of the Complementarity Determining Regions in the Center of the Antibody Binding Site", Journal of Molecular Biology, 1996, 263(4):551-567.

Schoonjians et al., "Fab chains as an efficient heterodimerization scaffold for the production of recombinant bispecific and trispecific antibody derivatives", Journal of Immunology, 2000, 165(12):7050-7057.

Schwartz et al., "A Superactive Insulin: [B10-aspartic acid]insulin(human)", PNAS, 1987, 84(18):6408-6411.

Sefton et al., "Implantable Pumps", Critical Reviews in Biomedical Engineering, 1980, 14:201-240.

Sgouros et al., "Modeling and Dosimetry of Monoclonal Antibody M195 (Anti-CD33) in Acute Myelogenous Leukemia", The Journal of Nuclear Medicine, Mar. 1, 1993, 34:422-430.

Shahani et al., "Human liver sinusoidal endothelial cells but not hepatocytes contain factor VIII", Journal of Thrombosis and Haemostasis, Jan. 2014, 12(1):36-42.

Shaw et al., "Characterization of a Mouse-Human Chimeric Monoclonal Antibody (17-1A) to a Colon Cancer Tumor-Associated Antigen", Journal of Immunology, 1987, 138(12):4534-4538.

Shearman et al., "Construction, expression and characterization of humanized antibodies directed against the human α/β T cell receptor", The Journal of Immunology, Dec. 1991, 147(12):4366-4373.

Shearman et al., "Construction, expression, and biologic activity of murine/human chimeric antibodies with specificity for the human α/β T cell receptor", The Journal of Immunology, Feb. 1991, 146(3):928-935.

Shields et al., "High Resolution Mapping of the Binding Site on Human Igg1 for Fc Gamma RI, Fc Gamma RII, Fc Gamma RIII, and Fcrn and Design of Igg1 Variants with Improved Binding to the Fc Gamma R", Journal of Biological Chemistry, 2001, 276:6591-6604.

Shitara et al., "A mouse/human chimeric anti-(ganglioside GD3) antibody with enhanced antitumor activities", Cancer Immunology, Immunotherapy, Nov. 1993, 36:373-380.

Shopes Bob, "A Genetically Engineered Human IgG Mutant with Enhanced Cytolytic Activity", J. Immunol., 1992, 148:2918-2922.

Silverberg et al., "Cancer statistics, 1989", CA:A Cancer Journal for Clinicians, Jan./Feb. 1989, 39(1):3-20.

Smith-Garvin et al., "T Cell Activation", Annual Review of Immunology, 2009, 27:591-619.

Sondermann et al., "The 3.2—A Crystal Structure of The Human Igg1 Fc Fragment-Fc GammaRIII Complex", Nature, 2000, 406:267-273.

Song et al., "Antibody Mediated Lung Targeting of Long-Circulating Emulsions", PDA Journal of Pharmaceutical Science & Technology, 1996, 50(6):372-377.

St. Clair EW., "Novel Targeted Therapies for Autoimmunity", Current Opinion in Immunology, Dec. 2009, 21(6):648-657.

Staerz et al., "Hybrid Antibodies Can Target Sites for Attack by T Cells", Nature, 1985, 314:628-631.

Staudinger et al., "The Novel Immunotoxin HM1.24-ETA Induces Apoptosis in Multiple Myeloma Cells", Blood Cancer Journal, 2014, 13;4:e219.

Stavenhagen et al., "Fc Optimization of Therapeutic Antibodies Enhances Their Ability to Kill Tumor Cells In Vitro and Controls Tumor Expansion In Vivo via Low-Affinity Activating Fcgamma Receptors", Cancer Research, 2007, 67(18):8882-8890.

Steidl et al., "In Vitro Affinity Maturation of Human GM-CSF Antibodies by Targeted CDR-Diversification", Molecular Immunology, Nov. 2008, 46(1):135-144.

(56) References Cited

OTHER PUBLICATIONS

Steinkruger et al., "The d'—d—d' Vertical Triad is Less Discriminating Than the a'—a—a' Vertical Triad in the Antiparallel Coiled-coil Dimer Motif", Journal of the American Chemical Society, Feb. 2012, 134(5):2626-2633.
Stephan et al., "Selective Cloning of Cell Surface Proteins Involved in Organ Development: Epithelial Glycoprotein Is Involved in Normal Epithelial Differentiation", Endocrinology, 1999, 140:5841-5854.
Stevenson et al., "A Chimeric Antibody with Dual Fc Regions (bisFabFc) Prepared by Manipulations at the IgG Hinge", Anti-Cancer Drug Design, 1989, 3(4):219-230.
Stievano et al., "CDS+ alpha beta+ T cells that lack surface CDS antigen expression are a major lymphotactin (XCL 1) source in peripheral blood lymphocytes", Journal of Immunology, 2003, 171:4528-4538.
Straussman et al., "Kinking the Coiled Coil—Negatively Charged Residues at the Coiled-coil Interface", Journal of Molecular Biology, 2007, 366(4):1232-1242.
Sun et al., "Characterization of Mouse and Human B7-H3 Genes", Journal of Immunology, 2002, 168:6294-6297.
Sun et al., "Mechanisms Contributing to T Cell Receptor Signaling and Assembly Revealed by The Solution Structure of an Ectodomain Fragment of The CD3ε:γ Heterodimer", Cell, Jun. 29, 2001, 105(7):913-923.
Swanson SJ, "Characterization of an Immune Response", Dev Biol (Basel), 2005, 122:95-101.
Swinnen et al., "OKT3 monoclonal antibodies induce interleukin-6 and interleukin-10: a possible cause of lymphoproliferative disorders associated with transplantation", Current Opinion in Nephrology and Hypertension, Jul. 1993, 2(4):670-678.
Tailor et al., "Nucleotide Sequence of Human Prostatic Acid Phosphatase Determined from a Full-Length CDNA Clone", Nucleic Acids Research, 1990, 18(16):1 page.
Takabe et al., "Immunomagnetic exclusion of E-cadherin-positive hepatoblasts in fetal mouse liver cell cultures impairs morphogenesis and gene expression of sinusoidal endothelial cells", Journal of Anatomy, Jun. 2012, 221(3):229-239.
Takahashi M., "A Study on Clinical Significance of Oncofetal Antigen-1 in Gynecologic Tumors", Nihon Sanka Fujinka Gakkai Zasshi, Dec. 1984, 36(12):2613-2618.
Takemura et al., "Construction of a Diabody (Small Recombinant Bispecific Antibody) Using a Refolding System", Protein Engineering, 2000, 13(8):583-588.
Tanner et al., "Characterization of a Novel Cell Line Established from a Patient with Herceptin-Resistant Breast Cancer", Molecular Cancer Therapeutics, Dec. 2004, 3(12):1585-1592.
Tellez-Avila et al., "The Carcinoembryonic Antigen: about an Old Acquaintance", Journal of Clinical Research, 2005, 57(6):814-819.
Tempest et al., "Reshaping a Human Monoclonal Antibody to Inhibit Human Respiratory Syncytial Virus Infection in Vivo", Bio-Technology, 1991, 9:266-271.
Thomas et al., "Molecular Immunology Lessons from Therapeutic T-Cell Receptor Gene Transfer", Immunology, 2010, 129(2):170-177.
Thomas et al., "Monoclonal Antibody Therapy for Hairy Cell Leukemia", Hematology/Oncology Clinics of North America, Oct. 2006, 20(5):1125-1136.
Thompson et al., "Carcinoembryonic Antigen Gene Family: Molecular Biology and Clinical Perspectives", Journal of Clinical Laboratory Analysis, 1991, 5(5):344-366.
Trauth et al., "Monoclonal antibody-mediated tumor regression by induction of apoptosis", Science, Jul. 21, 1989, 245(4915):301-305.
Tripet et al., "Kinetic Analysis of the Interactions between Troponin C and the C-terminal Troponin I Regulatory Region and Validation of a New Peptide Delivery/Capture System used for Surface Plasmon Resonance", Journal of Molecular Biology, 2002, 323(2):345-362.
Troussard et al., "Hairy Cell Leukemia. What is New Forty Years after the First Description?", Hematology and Cell Therapy, Aug. 1998, 40(4):139-148.
Tutt et al., "Trispecific F(ab')3 Derivatives That Use Cooperative Signaling via the TCR/CD3 Complex and CD2 to Activate and Redirect Resting Cytotoxic T Cells", The Journal of Immunology, Jul. 1, 1991, 147(1):60-69.
Van Der Merwe et al., "Mechanisms for T Cell Receptor Triggering", Nature Reviews Immunology, Jan. 2011, 11(1):47-55.
Van Horsen et al., "TNF-α in Cancer Treatment: Molecular Insights, Antitumor Effects, and Clinical Utility", Oncologist, 2006, 11(4):397-408.
Van Regenmortel,"Improving the Quality of BIACORE-Based Affinity Measurements", Developments in Biologicals, Feb. 2003, 112:141-151.
Velázquez-Márquez et al., "Sialyl Lewis X Expression in Cervical Scrapes of Premalignant Lesions", Journal of Biosciences, Dec. 2012, 37(6):999-1004.
Verhoeyen et al., "Reshaping Human Antibodies: Grafting an Antilysozyme Activity", Science, 1988, 239:1534-1536.
Veri et al., "Monoclonal Antibodies Capable of Discriminating the Human Inhibitory Fcgamma-Receptor IIB (CD32B) From the Activating Fcgamma-Receptor IIA (CD32A): Biochemical, Biological and Functional Characterization", Immunology, 2007, 121(3):392-404.
Veri et al., "Therapeutic Control of B Cell Activation via Recruitment of Fcgamma Receptor IIb (CD32B) Inhibitory Function with a Novel Bispecific Antibody Scaffold", Arthritis & Rheumatology, 2010, 62(7):1933-1943.
Viglietta et al., "Modulating Co-Stimulation", Neurotherapeutics, 2007, 4:666-675.
Vijayasardahl et al., "The Melanoma Antigen Gp75 is the Human Homologue of the Mouse B (Brown) Locus Gene Product", Journal of Experimental Medicine, Apr. 1, 1990, 171(4):1375-1380.
Walker et al., "Activation of T Cells by Cross-Linking an Anti-CD3 Antibody with a Second Anti-T Cell Antibody: Mechanism and Subset-Specific Activation", European Journal of Immunology, Jun. 1, 1987, 17(6):873-880.
Walker,"CD22: An Inhibitory Enigma", Immunology, 2008, 123(3):314-325.
Walter et al., "Acute Myeloid Leukemia Stem Cells and CD33-Targeted Immunotherapy", Blood, Jun. 28, 2012, 119(26):6198-6208.
Wang et al., "Chimeric and humanized anti-HM1.24 antibodies mediate antibody-dependent cellular cytotoxicity against lung cancer cells", Lung Cancer, Jan. 2009, 63(1):23-31.
Wang et al., "HM1.24 (CD317) is a novel target against lung cancer for immunotherapy using anti-HM1.24 antibody", Cancer Immunology Immunotherapy, Jun. 2009, 58(6):967-976.
Watanabe et al., "The quantity of TCR signal determines positive selection and lineage commitment of T cells", Journal of Immunology, 2000, 165:6252-6261.
Weidle et al., "The Intriguing Options of Multispecific Antibody Formats for Treatment of Cancer", Cancer Genomics Proteomics, Feb. 2, 2013, 10(1):1-18.
Weinacker et al., "Role of the integrin alpha v beta 6 in cell attachment to fibronectin. Heterologous expression of intact and secreted forms of the receptor", Journal of Biological Chemistry, 1994, 269:6940-6948.
Weiss Arthur, "T Cell Antigen Receptor Signal Transduction: A Tale of Tails and Cytoplasmic Protein-Tyrosine Kinases", Cell, Apr. 23, 1993, 73(2):209-212.
WHO Drug Information, "International Nonproprietary Names for Pharmaceutical Substances (INN)", Recommended INN: List 44, 2000, 14(3):27 pages.
WHO Drug Information, "International Nonproprietary Names for Pharmaceutical Substances (INN)", Recommended INN: List 60, 2008, 22(3):30 pages.
WHO Drug Information, "International Nonproprietary Names for Pharmaceutical Substances (INN)", Recommended INN: List 61, 2009, 23(1):35 pages.
WHO Drug Information, "International Nonproprietary Names for Pharmaceutical Substances (INN)", Recommended INN: List 65, 2011, 25(1):50 pages.

(56) References Cited

OTHER PUBLICATIONS

Willemsen et al., "Selection of human antibody fragments directed against tumor T-cell epitopes for adoptive T-cell therapy", Cytometry A., Nov. 2008, 73(11):1093-1099.
Williams et al., "Biochemical and Genetic Analysis of the Oka Blood Group Antigen", Immunogenetics, 1988, 27(5):322-329.
Winter et al., "Making Antibodies by Phage Display Technology", Annual Review of Immunology, 1994, 12.433-455.
Winter et al., "Man-made Antibodies", Nature, 1991, 349:293-299.
Wolff et al., "Monoclonal Antibody Homodimers: Enhanced Antitumor Activity in Nude Mice", Cancer Research, 1993, 53:2560-2565.
Wong et al., "EpCAM and gpA33 are markers of Barrett's metaplasia", Journal of Clinical Pathology, Mar. 2006, 59(3):260-263.
Wong et al., "Rheumatoid Arthritis T Cells Produce Th1 Cytokines in Response to Stimulation with a Novel Trispecific Antibody Directed Against CD2, CD3, and CD28", Scandinavian Journal of Rheumatology, 2000, 29(5):282-287.
Woolfson et al., "The Design of Coiled-Coil Structures and Assemblies", Advances in Protein Chemistry, 2005, 70:79-112.
Wu et al., "Multimerization of a Chimeric Anti-CD20 Single Chain Fv-Fv Fusion Protein Is Mediated Through Variable Domain Exchange", Protein Engineering, 2001, 14(12):1025-1033.
Wu et al., "Receptor-Mediated In Vitro Gene Transformation by a Soluble DNA Carrier System", Journal of Biological Chemistry, 1987, 262(10):4429-4432.
Wu et al., "Stepwise In Vitro Affinity Maturation of Vitaxin, an Avβ3-Specific Humanized Mab", Proceedings of the National Academy of Sciences, May 26, 1998, 95(11):6037-6042.
Wucherpfennig et al., "Structural Biology of the T-cell Receptor: Insights into Receptor Assembly, Ligand Recognition, and Initiation of Signaling", Cold Spring Harbor Perspectives in Biology, Apr. 2010, 2(4):14 pages.
Xie et al., "A New Format of Bispecific Antibody: Highly Efficient Heterodimerization, Expression and Tumor Cell Lysis", Journal of Immunological Methods, 2005, 296:95-101.
Xu et al., "High EphA2 Protein Expression in Renal Cell Carcinoma Is Associated with a Poor Disease Outcome", Oncology Letters, Aug. 2014, 8(2):687-692.
Xu et al., "In Vitro Characterization of Five Humanized OKT3 Effector Function Variant Antibodies", Cellular Immunology, 2000, 200:16-26.
Yang et al., "Therapeutic potential and challenges of targeting receptor tyrosine kinase ROR 1 with monoclonal antibodies in B-cell malignancies", PLoS One, 2011, 6(6): e21018.
Yelton et al., "Affinity Maturation of the BR96 Anti-Carcinoma Antibody by Codon-Based Mutagenesis", Journal of Immunology, Aug. 15, 1995, 155(4):1994-2004.
Yi et al., "BST-2 Is a Potential Activator of Invasion and Migration in Tamoxifen-Resistant Breast Cancer Cells", Biochemical and Biophysical Research Communications, 2013, 435(4):685-690.
Yokota et al., "Rapid Tumor Penetration of a Single-Chain Fv and Comparison with Other Immunoglobulin Forms", Cancer Research, Jul. 1992, 52(12):3402-3408.
Youinou et al., "Pathogenic Effects of Anti-Fc Gamma Receptor IIIb (Cd16) on Polymorphonuclear Neutrophils in Non-Organ-Specific Autoimmune Diseases", Autoimmunity Reviews, Feb. 2002, 1(1-2):13-19.
Yu et al., "Coexpression of different antigenic markers on moieties that bear CA 125 determinants", Cancer Research, Jan. 15, 1991, 51(2):468-475.
Zeng et al., "A Ligand-Pseudo receptor System Based on De Novo Designed Peptides for the Generation of Adenoviral Vectors with Altered Tropism", Journal of Gene Medicine, 2008, 10(4):355-367.
Zheng et al., "A Novel Anti-CEACAM5 Monoclonal Antibody, CC4, Suppresses Colorectal Tumor Growth and Enhances NK Cells-Mediated Tumor Immunity", Plos One, e21146, Jun. 2011, 6(6):11 pages.
Zhou et al., "Constitutive Overexpression of a Novel 21 Kda Protein by Hodgkin Lymphoma and Aggressive Non-Hodgkin Lymphomas", Molecular Cancer, 2008, 7(12):11 pages.
Zhou et al., "Lung Tumorigenesis Associated with Erb-B-2 and Erb-B-3 Overexpression in Human Erb-B-3 Transgenic Mice is Enhanced by Methylnitrosourea", Oncogene, 2002, 21(57):8732-8740.
Al-Taei et al., "Overexpression and Potential Targeting of the Oncofoetal Antigen 5T4 in Malignant Pleural Mesothelioma", Lung Cancer, 2012, 77:312-318.
Kang et al., "Antibody Redesign by Chain Shuffling from Random Combinatorial Immunoglobulin Libraries", Proceedings of the National Academy of Sciences USA, Dec. 1991, 88:11120-11123.
Lamminmaki et al., "Crystal Structure of a Recombinant Anti-estradiol Fab Fragment in Complex with 17β-Estradiol", The Journal of Biological Chemistry, Jul. 12, 2001, 276(39):36687-36694.
Padlan et al., "Structure of an Antibody-Antigen Complex: Crystal Structure of the HyHEL-10 Fab-Lysozyme Complex", Proceedings of the National Academy of Sciences USA, Aug. 1989, 86:5938-5942.
Office Action dated Jul. 1, 2022 in U.S. Appl. No. 16/805,105, filed Feb. 28, 2020 and published as US-2020-0199223-A1 dated Jun. 25, 2020, 49 pages.
Akbar et al., "A Compact Vocabulary of Paratope-Epitope Interactions Enables Predictability of Antibody- Antigen Binding", Cell Reports, 2021, 34(108856):21 pages.
Almagro et al., "Humanization of Antibodies", Frontiers in Bioscience, Jan. 1, 2008, 13:1619-1633.
Altshuler et al., "Generation of Recombinant Antibodies and Means for Increasing Their Affinity", Biochemistry (Moscow), 2010, 75(13):1584-1605.
Edwards et al., "The Remarkable Flexibility of the Human Antibody Repertoire; Isolation of Over One Thousand Different Antibodies to a Single Protein, BLyS", Journal of Molecular Biology, 2003, 334(1)103-118.
Felices et al., "Novel B7-H3 Targeting Dual Nanobody NK Cell Engagers Display Robust Activity Against a Broad Spectrum of Solid and Hematologic Malignancies", Annals of Oncology, 2021, 32(7):S1433.
Hasegawa et al., "Single Amino Acid Substitution in LC-CDR1 Induces Russell Body Phenotype that Attenuates Cellular Protein Synthesis Through elF2a Phosphorylation and thereby Downregulates IgG Secretion Despite Operational Secretory Pathway Traffic", mAbs, 2017, 9(5):854-873.
Lippow et al., "Computational Design of Antibody-Affinity Improvement Beyond In vivo Maturation", Nature Biotechnology, 2007, 25(10):1171-1176.
Lo et al., "Conformational Epitope Matching and Prediction Based on Protein Surface Spiral Features", BMC Genomics, 2021, 22(2):116:1-16.
Marchalonis et al., "The Antibody Repertoire in Evolution: Chance, Selection, and Continuity", Developmental & Comparative Immunology, 2006, 30:223-247.
Marks et al., "How Repertoire Data are Changing Antibody Science", Journal of Biological Chemistry, 2020, 295(29):9823-9837.
Sulea et al., "Application of Assisted Design of Antibody and Protein Therapeutics (ADAPT) Improves Efficacy of a Clostridium Difficile Toxin a Single- Domain Antibody", Scientific Reports, 2018, 8(260):1-11.
Vajda et al., "Progress Toward Improved Understanding of Antibody Maturation", Current Opinion in Structural Biology, 2021, 67:226-231.

\* cited by examiner

- ● B7-H3 mAb 1 X CD3 mAb 2 DART™
- ▫ B7-H3 mAb 1 X CD3 mAb 2 DART™ with Fc Domain
- ▽ B7-H3 mAb 1 / CD3 mAb 2 / CD8 mAb 1 Binding Molecule
- ○ Fluorescein mAb 1 X CD3 mab 2 DART™ with Fc Domain

- ●— B7-H3 mAb 1 / CD3 mAb 2 / CD8 mAb 1 Binding Molecule
- ▼— B7-H3 mAb 1 X CD3 mAb 2 DART™
- ☐— B7-H3 mAb 1 X CD3 mAb 2 DART™ with Fc Domain

- ● B7-H3 mAb 1 X CD3 mAb 2 DART™
- ⊠ B7-H3 mAb 1 X Anti-CD3 mAb 2 DART™ with Fc Domain
- ▽ B7-H3 mAb 1 / CD3 mAb 2 / CD8 mAb 1 Binding Molecule
- ○ Fluorescein mAb 1 X CD3 mAb 2 DART™ with Fc Domain

- B7-H3 mAb 1 X CD3 mAb 2 DART™
- B7-H3 mAb 1 X CD3 mAb 2 DART™ with Fc Domain
- B7-H3 mAb 1 / CD3 mAb 2 / CD8 mAb 1 Binding Molecule
- Fluorescein mAb 1 X CD3 mAb 2 DART™ with Fc Domain ▽ B7-H3 mAb 1 / CD3 mAb 2 / CD8 mAb 1 Binding Molecule
◆ gpA33 mAb 1 CD3 mAb 2 DART™
⊠ B7-H3 mAb 1 X CD3 mAb 2 DART™ with Fc Domain
● B7-H3 mAb 1 X CD3 mAb 2 DART™
▲ B7-H3 mAb 1 X CD3 mAb 2 Fc DART™
○ Fluorescein mAb 1 X CD3 mAb 2 DART™ with Fc Domain

- B7-H3 mAb 1 / CD3 mAb 2 / CD8 mAb 1 Binding Molecule
- B7-H3 mAb 1 / CD3 mAb 2 / CD8 mAb 2 Binding Molecule
- B7-H3 mAb 1 x CD3 mAb 2 DART™ with Fc Domain
- B7-H3 mAb 1 X B7-H3 mAb 1 DART™ with Fc Domain

- B7-H3 mAb 1 / CD3 mAb 2 / CD8 mAb 1 Binding Molecule
- B7-H3 mAb 1 / CD3 mAb 2 / CD8 mAb 2 Binding Molecule
- B7-H3 mAb 1 X CD3 mAb 2 DART™

- ⊠ B7-H3 mAb 1 / CD3 mAb 2 / CD8 mAb 1 Binding Molecule
- ◇ B7-H3 mAb 1 / CD3 mAb 2 / CD8 mAb 2 Binding Molecule
- ● B7-H3 mAb 1 X CD3 mAb 2 DART$^{TM}$ with Fc Domain

- ▣ B7-H3 mAb 1 / CD3 mAb 2 / CD8 mAb 1 Binding Molecule
- ▲ CD3 mAb 2 / CD8 mAb 1 / B7-H3 mAb 1 Binding Molecule
- ▽ B7-H3 mAb 1 / CD8 mAb 1 / CD3 mAb 2 Binding Molecule
- ● B7-H3 mAb 1 X CD8 mAb 1 DART$^{TM}$ with Fc Domain
- ○ B7-H3 mAb 1 X CD3 mAb 2 DART$^{TM}$ with Fc Domain

- B7-H3 mAb 1 / CD3 mAb 2 / CD8 mAb 1 Binding Molecule
- CD3 mAb 2 / CD8 mAb 1 / B7-H3 mAb 1 Binding Molecule
- B7-H3 mAb 1 / CD8 mAb 1 / CD3 mAb 2 Binding Molecule
- B7-H3 mAb 1 X CD8 mAb 1 DART™ with Fc Domain
- B7-H3 mAb 1 X CD3 mAb 2 DART™ with Fc Domain

- B7-H3 mAb 1 / CD3 mAb 2 / CD8 mAb 1 Binding Molecule
- CD3 mAb 2 / CD8 mAb 1 / B7-H3 mAb 1 Binding Molecule
- B7-H3 mAb 1 / CD8 mAb 1 / CD3 mAb 2 Binding Molecule
- B7-H3 mAb 1 X CD8 mAb 1 DART™ with Fc Domain
- B7-H3 mAb 1 X CD3 mAb 2 DART™ with Fc Domain

- B7-H3 mAb 1 / CD3 mAb 2 / CD8 mAb 1 Binding Molecule
- CD3 mAb 2 / CD8 mAb 1 / B7-H3 mAb 1 Binding Molecule
- B7-H3 mAb 1 / CD8 mAb 1 / CD3 mAb 2 Binding Molecule
- B7-H3 mAb 1 X CD8 mAb 1 DART™ with Fc Domain
- B7-H3 mAb 1 X CD3 mAb 2 DART™ Fc Domain

- ● B7-H3 mAb 1 / CD3 mAb 2 / CD8 mAb 1 Binding Molecule
- ▲ CD3 mAb 2 / CD8 mAb 1 / B7-H3 mAb 1 Binding Molecule
- ▼ B7-H3 mAb 1 / CD8 mAB 1 / CD3 mAb 2 Binding Molecule
- ▨ B7-H3 mAb 1 X CD3 mAb 2 DART™
- △ B7-H3 mAb 1 X B7-H3 mAb 1 DART™

- ● HIV mAb 2 / CD3 mAb 2 / CD8 mAb 1 Binding Molecule
- ■ HIV mAb 1 / CD3 mAb 2 / CD8 mAb 1 Binding Molecule
- ▲ RSV mAb 1 / CD3 mAb 2 / CD8 mAb 1 Binding Molecule

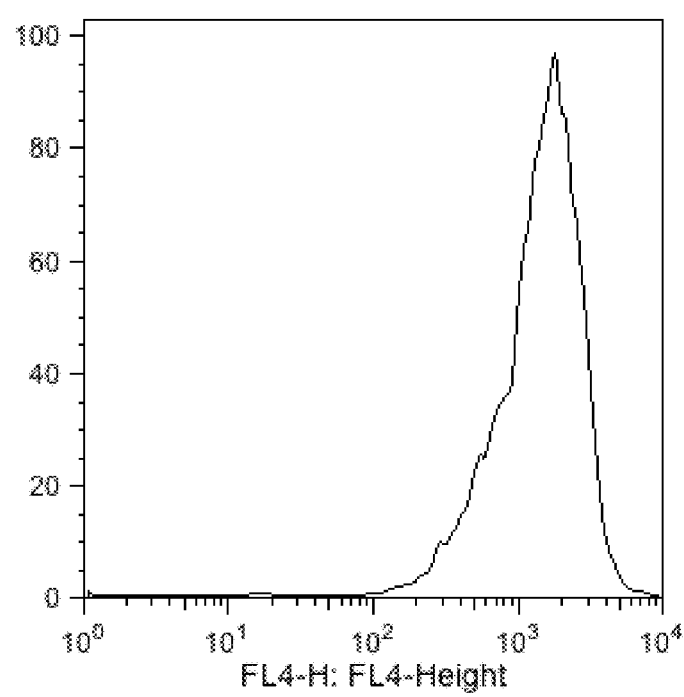
Figure 19A   Binding of HIV mAb 1 / CD3 mAb 2 / CD8 mAb 1 Binding Molecule to HIV env-Expressing HEK 293 Cells

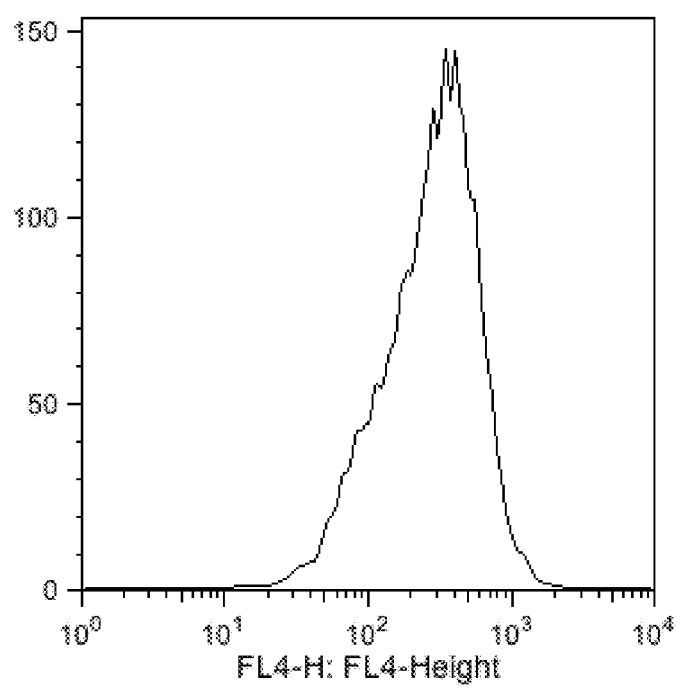
Figure 19B    Binding of HIV mAb 2 / CD3 mAb 2 / CD8 mAb 1 Binding Molecule to HIV env-Expressing HEK 293 Cells

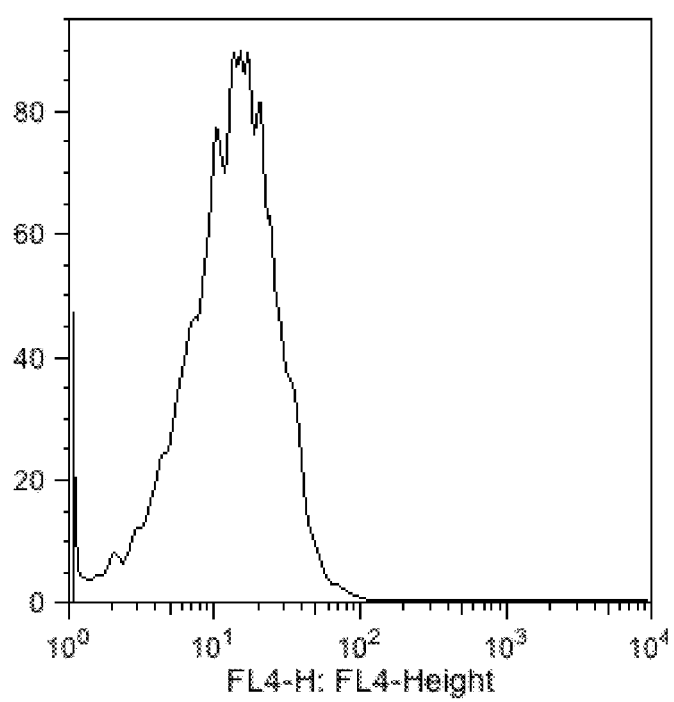
Figure 19C  Binding of RSV mAb 1 / CD3 mAb 2 / CD8 mAb 1 Binding Molecule to HIV env-Expressing HEK 293

- ● HIV mAb 1 X CD3 mAb 2 DART™
- ⊗ HIV mAb 1 X CD3 mAb 2 DART™ with Fc Domain
- ○ HIV mAb 1 / CD3 mAb 2 / CD8 mAb 1 Binding Molecule ▲ HIV mAb 2 X CD3 mAb 2 DART™
△ HIV mAb 2 X CD3 mAb 2 DART™ with Fc Domain
△ HIV mAb 2 / CD3 mAb 2 /CD8 mAb1 Binding Molecule

- ■- RSV mAb 1 X CD3 mAb 2 DART™
- ▨- RSV mAb 1 X CD3 mAb 2 DART™ with Fc Domain
- □- RSV mAb 1 / CD3 mAb 2 / CD8 mAb 1 Binding Molecule

- ● HIV mAb 1 X CD3 mAb 2 DART™ with Fc Domain
- ▼ HIV mAb 1 / CD3 mAb 2 / CD8 mAb 1 Binding Molecule
- ○ RSV mAb 1 X CD3 mAb 2 DART™ with Fc Domain
- ▽ RSV mAb 1 / CD3 mAb 2 / CD8 mAb 1 Binding Molecule

- ● HIV mAb 1 X CD3 mAb 2 DART™ with Fc Domain
- ▼ HIV mAb 1 / CD3 mAb 2 / CD8 mAb 1 Binding Molecule
- ○ RSV mAb 1 X CD3 mAb 2 DART™ with Fc Domain
- ▽ RSV mAb 1 / CD3 mAb 2 / CD8 mAb 1 Binding Molecule ■ HIV mAb 2 X CD3 mAb 2 DART™ with Fc Domain
◆ HIV- mAb 2 / CD3 mAb 2 / CD8 mAb 1 Binding Molecule
□ RSV mAb 1 X CD3 mAb 2 DART™ with Fc Domain
◇ RSV mAb 1 / CD3 mAb 2 / CD8 mAb 1 Binding Molecule -■- HIV mAb 2 X CD3 mAb 2 DART™ with Fc Domain
-◆- HIV- mAb 2 / CD3 mAb 2 / CD8 mAb 1 Binding Molecule
-□- RSV mAb 1 X CD3 mAb 2 DART™ with Fc Domain
-◇- RSV mAb 1 / CD3 mAb 2 / CD8 mAb 1 Binding Molecule

- ●  5T4 mAb 1 / CD3 mAb 2 / CD8 mAb 1 Binding Molecule
- △  5T4 mAb 1 / CD3 mAb 2 low / CD8 mAb 1 Binding Molecule
- ▼  5T4 mAb 1 / CD3 mAb 2 fast / CD8 mAb 1 Binding Molecule
- □  5T4 mAb 1 X CD3 mAb 2 DART™ with Fc Domain
- △  5T4 mAb 1 X CD3 mAb 2 Low DART™ with Fc Domain
- ▽  5T4 mAb 1 X CD3 mAb 2 Fast DART™ with Fc Domain
- ◇  5T4 mAb 1 X 5T4 mAb 1 Fc DART™

→ 5T4 mAb 1 X CD3 mAb 2 DART™ with Fc Domain
−□− 5T4 mAb 1 / CD3 mAb 2 / CD8 mAb 1 Binding Molecule
−▲− 5T4 mAb 1 / CD3 mAb 2 Low / CD8 mAb 1 Binding Molecule
−▽− 5T4 mAb 1 / CD3 mAb 2 Fast / CD8 mAb 1 Binding Molecule
−■− RSV mAb 1 / CD3 mAb 2 / CD8 mAb 1 Binding Molecule → 5T4 mAb 1 X CD3 mAb 2 DART™ with Fc Domain
□ 5T4 mAb 1 / CD3 mAb 2 / CD8 mAb 1 Binding Molecule
▲ 5T4 mAb 1 / CD3 mAb 2 Low / CD8 mAb 1 Binding Molecule
▽ 5T4 mAb 1 / CD3 mAb 2 Fast / CD8 mAb 1 Binding Molecule
■ RSV mAb 1 / CD3 mAb 2 / CD8 mAb 1 Binding Molecule Donor 1

Donor 1

Donor 1

Donor 2

Donor 2

Donor 2

SEQUENCE LISTING

```
<160> NUMBER OF SEQ ID NOS: 133

<210> SEQ ID NO 1
<211> LENGTH: 8
<212> TYPE: PRT
<213> ORGANISM: Artificial Sequence
<220> FEATURE:
<223> OTHER INFORMATION: Linker 1

<400> SEQUENCE: 1

Gly Gly Gly Ser Gly Gly Gly Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Cysteine-Containing Domain ("Linker 2")

<400> SEQUENCE: 2

Gly Gly Cys Gly Gly
1               5

<210> SEQ ID NO 3
<211> LENGTH: 28
<212> TYPE: PRT
```

```
<213> ORGANISM: Artificial Sequence
<220> FEATURE:
<223> OTHER INFORMATION: E-Coil Heterodimer-Promoting Domain

<400> SEQUENCE: 3

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 4
<211> LENGTH: 28
<212> TYPE: PRT
<213> ORGANISM: Artificial Sequence
<220> FEATURE:
<223> OTHER INFORMATION: K-Coil Heterodimer-Promoting Domain

<400> SEQUENCE: 4

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 5
<211> LENGTH: 10
<212> TYPE: PRT
<213> ORGANISM: Artificial Sequence
<220> FEATURE:
<223> OTHER INFORMATION: Cysteine-Containing Linker Peptide ("Linker 3")

<400> SEQUENCE: 5

Asp Lys Thr His Thr Cys Pro Pro Cys Pro
1               5                   10

<210> SEQ ID NO 6
<211> LENGTH: 219
<212> TYPE: PRT
<213> ORGANISM: Homo sapiens
<220> FEATURE:
<221> NAME/KEY: MISC_FEATURE
<222> LOCATION: (1)..(218)
<223> OTHER INFORMATION: Human Wild-Type IgG CH2-CH3 Domain

<400> SEQUENCE: 6

Ala Pro Ala Pro Glu Leu Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Lys Phe Asn
        35                  40                  45

Trp Tyr Val Asp Gly Val Glu Val His Asn Ala Lys Thr Lys Pro Arg
    50                  55                  60

Glu Glu Gln Tyr Asn Ser Thr Tyr Arg Val Val Ser Val Leu Thr Val
65                  70                  75                  80

Leu His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Ala Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe
    130                 135                 140
```

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
            165                 170                 175

Phe Leu Tyr Ser Lys Leu Thr Val Asp Lys Ser Arg Trp Gln Gln Gly
            180                 185                 190

Asn Val Phe Ser Cys Ser Val Met His Glu Ala Leu His Asn His Tyr
            195                 200                 205

Thr Gln Lys Ser Leu Ser Leu Ser Pro Gly Lys
    210                 215

<210> SEQ ID NO 7
<211> LENGTH: 217
<212> TYPE: PRT
<213> ORGANISM: Artificial Sequence
<220> FEATURE:
<223> OTHER INFORMATION: "Knob-Bearing" CH2-CH3 Domain

<400> SEQUENCE: 7

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 8
<211> LENGTH: 217
<212> TYPE: PRT
<213> ORGANISM: Artificial Sequence
<220> FEATURE:
<223> OTHER INFORMATION: "Hole-Bearing" IgG CH2-CH3 Domain

<400> SEQUENCE: 8

Ala Pro Glu Ala Ala Gly Gly Pro Ser Val Phe Leu Phe Pro Pro Lys

```
  1               5                  10                 15
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                      55                  60

Gln Tyr Asn Ser Thr Tyr Arg Val Val Ser Val Leu Thr Val Leu His
65                      70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
                115                 120                 125

Thr Lys Asn Gln Val Ser Leu Ser Cys Ala Val Lys Gly Phe Tyr Pro
                130                 135                 140

Ser Asp Ile Ala Val Glu Trp Glu Ser Asn Gly Gln Pro Glu Asn Asn
145                     150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
                180                 185                 190

Phe Ser Cys Ser Val Met His Glu Ala Leu His Asn Arg Tyr Thr Gln
                195                 200                 205

Lys Ser Leu Ser Leu Ser Pro Gly Lys
                210                 215

<210> SEQ ID NO 9
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 10
<211> LENGTH: 15
<212> TYPE: PRT
<213> ORGANISM: Homo sapiens
<220> FEATURE:
```

```
<221> NAME/KEY: MISC_FEATURE
<222> LOCATION: (1)..(15)
<223> OTHER INFORMATION: Human IgG1 Hinge Domain

<400> SEQUENCE: 10

Glu Pro Lys Ser Cys Asp Lys Thr His Thr Cys Pro Pro Cys Pro
1               5                   10                  15

<210> SEQ ID NO 11
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Portion of Human CL Domain

<400> SEQUENCE: 11

Phe Asn Arg Gly Glu Cys
1               5

<210> SEQ ID NO 12
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Portion of Human IgG Hinge
      Domain

<400> SEQUENCE: 12

Val Glu Pro Lys Ser Cys
1               5

<210> SEQ ID NO 13
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG1 CL Kappa Domain

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 104
<212> TYPE: PRT
<213> ORGANISM: Homo sapiens
<220> FEATURE:
```

```
<221> NAME/KEY: MISC_FEATURE
<222> LOCATION: (1)..(104)
<223> OTHER INFORMATION: Human IgG1 CL Lambda2 Domain

<400> SEQUENCE: 14

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 15
<211> LENGTH: 5
<212> TYPE: PRT
<213> ORGANISM: Artificial Sequence
<220> FEATURE:
<223> OTHER INFORMATION: Peptide Linker

<400> SEQUENCE: 15

Ala Pro Ser Ser Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Peptide Linker

<400> SEQUENCE: 16

Ala Pro Ser Ser Ser Pro Met Glu
1               5

<210> SEQ ID NO 17
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: OKT3 Anti-CD3 Antibody Light Chain Variable
      Domain

<400> SEQUENCE: 17

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
```

```
                65                  70                  75                  80
Asp Ala Ala Thr Tyr Tyr Cys Gln Gln Trp Ser Ser Asn Pro Phe Thr
                    85                  90                  95

Phe Gly Ser Gly Thr Lys Leu Glu Ile Asn Arg
                100                 105

<210> SEQ ID NO 18
<211> LENGTH: 192
<212> TYPE: PRT
<213> ORGANISM: Mus musculus
<220> FEATURE:
<221> NAME/KEY: MISC_FEATURE
<222> LOCATION: (1)..(192)
<223> OTHER INFORMATION: OKT3 Anti-CD3 Antibody Heavy Chain Variable
      Domain

<400> SEQUENCE: 18

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
        130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

<210> SEQ ID NO 19
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: M291 Anti-CD3 Antibody Light Chain Variable
      Domain

<400> SEQUENCE: 19

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Thr Tyr
            35                  40                  45
```

```
Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Asp Thr Tyr Tyr Cys Gln Gln Trp Ser Ser Asn Pro Pro Thr
                85                  90                  95

Phe Gly Ser Gly Thr Lys Leu Glu Ile Lys
            100                 105
```

<210> SEQ ID NO 20
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: M291 Anti-CD3 Antibody Heavy Chain Variable
      Domain

<400> SEQUENCE: 20

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Ile Ser Tyr
                20                  25                  30

Thr Met His Trp Val Lys Gln Arg Pro Gly Gln Gly Leu Glu Trp Ile
            35                  40                  45

Gly Tyr Ile Asn Pro Arg Ser Gly Tyr Thr His Tyr Asn Gln Lys Leu
        50                  55                  60

Lys Asp Lys Ala Thr Leu Thr Ala Asp Lys Ser Ser Ser Ala Tyr
65                  70                  75                  80

Met Gln Leu Ser Ser Leu Thr Ser Glu Asp Ser Ala Val Tyr Tyr Cys
                85                  90                  95

Ala Arg Ser Ala Tyr Tyr Asp Tyr Asp Gly Phe Ala Tyr Trp Gly Gln
                100                 105                 110

Gly Thr Leu Val Thr Val Ser Ala
            115                 120
```

<210> SEQ ID NO 21
<211> LENGTH: 130
<212> TYPE: PRT
<213> ORGANISM: Mus musculus
<220> FEATURE:
<221> NAME/KEY: MISC_FEATURE
<222> LOCATION: (1)..(130)
<223> OTHER INFORMATION: YTH12.5 Anti-CD3 Antibody Light Chain Variable
      Domain

<400> SEQUENCE: 21

```
Met Gly Trp Ser Cys Ile Ile Leu Phe Leu Val Ala Thr Ala Thr Gly
1               5                   10                  15

Val His Ser Asp Ile Gln Leu Thr Gln Pro Asn Ser Val Ser Thr Ser
                20                  25                  30

Leu Gly Ser Thr Val Lys Leu Ser Cys Thr Leu Ser Ser Gly Asn Ile
            35                  40                  45

Glu Asn Asn Tyr Val His Trp Tyr Gln Leu Tyr Glu Gly Arg Ser Pro
        50                  55                  60

Thr Thr Met Ile Tyr Asp Asp Lys Arg Pro Asp Gly Val Pro Asp
65                  70                  75                  80

Arg Phe Ser Gly Ser Ile Asp Arg Ser Ser Asn Ser Ala Phe Leu Thr
                85                  90                  95
```

Ile His Asn Val Ala Ile Glu Asp Glu Ala Ile Tyr Phe Cys His Ser
                100                 105                 110

Tyr Val Ser Ser Phe Asn Val Phe Gly Gly Gly Thr Lys Leu Thr Val
            115                 120                 125

Leu Arg
    130

<210> SEQ ID NO 22
<211> LENGTH: 138
<212> TYPE: PRT
<213> ORGANISM: Mus musculus
<220> FEATURE:
<221> NAME/KEY: MISC_FEATURE
<222> LOCATION: (1)..(138)
<223> OTHER INFORMATION: YTH12.5 Anti-CD3 Antibody Heavy Chain Variable
      Domain

<400> SEQUENCE: 22

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Pro Met Ala Trp Val Arg Gln Ala Pro Gly Lys Gly Leu
    50                  55                  60

Glu Trp Val Ser Thr Ile Ser Thr Ser Gly Arg Thr Tyr Tyr Arg
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Phe Arg Gln Tyr Ser Gly Gly Phe Asp Tyr Trp
        115                 120                 125

Gly Gln Gly Thr Leu Val Thr Val Ser Ser
    130                 135

<210> SEQ ID NO 23
<211> LENGTH: 106
<212> TYPE: PRT
<213> ORGANISM: Artificial Sequence
<220> FEATURE:
<223> OTHER INFORMATION: Humanized Anti-CD3 "mAb 1" Light Chain Variable
      Domain Variant 1

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Ser Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Humanized Anti-CD3 "mAb 1" Light Chain Variable
      Domain Variant 2

<400> SEQUENCE: 24

Asp Val Val Met Thr Gln Ser Pro Ala Ile Met Ser Ala Phe Pro Gly
1               5                   10                  15

Glu Lys Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Ser Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys
            100                 105

<210> SEQ ID NO 25
<211> LENGTH: 121
<212> TYPE: PRT
<213> ORGANISM: Artificial Sequence
<220> FEATURE:
<223> OTHER INFORMATION: Humanized Anti-CD3 "mAb 1" Heavy Chain Variable
      Domain

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ser
        115                 120

<210> SEQ ID NO 26
<211> LENGTH: 110
<212> TYPE: PRT
<213> ORGANISM: Artificial Sequence
<220> FEATURE:
<223> OTHER INFORMATION: Humanized Anti-CD3 "mAb 2" Light Chain Variable
      Domain -continued

```
<400> SEQUENCE: 26

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 27
<211> LENGTH: 125
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 28
<211> LENGTH: 125
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain D65G Variant

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
```

```
                    50                  55                  60
Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                   100                 105                 110

Ala Tyr Trp Gly Gln Gly Thr Leu Val Thr Val Ser Ser
                   115                 120                 125

<210> SEQ ID NO 29
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: OKT8 Anti-CD8 Antibody Light Chain Variable
      Domain

<400> SEQUENCE: 29

Asp Ile Val Met Thr Gln Ser Pro Ala Ser Leu Ala Val Ser Leu Gly
 1                   5                  10                  15

Gln Arg Ala Thr Ile Ser Cys Arg Ala Ser Glu Ser Val Asp Ser Tyr
                    20                  25                  30

Asp Asn Ser Leu Met His Trp Tyr Gln Gln Lys Pro Gly Gln Pro Pro
                    35                  40                  45

Lys Val Leu Ile Tyr Leu Ala Ser Asn Leu Glu Ser Gly Val Pro Ala
                50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                    85                  90                  95

Glu Asp Pro Tyr Thr Phe Gly Gly Gly Thr Lys Leu Glu Ile Lys Arg
                   100                 105                 110

<210> SEQ ID NO 30
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: OKT8 Anti-CD8 Antibody Heavy Chain Variable
      Domain

<400> SEQUENCE: 30

Gln Val Gln Leu Leu Glu Ser Gly Pro Glu Leu Leu Lys Pro Gly Ala
 1                   5                  10                  15

Ser Val Lys Met Ser Cys Lys Ala Ser Gly Tyr Thr Phe Thr Asp Tyr
                    20                  25                  30

Asn Met His Trp Val Lys Gln Ser His Gly Lys Ser Leu Glu Trp Ile
                    35                  40                  45

Gly Tyr Ile Tyr Pro Tyr Thr Gly Gly Thr Gly Tyr Asn Gln Lys Phe
                50                  55                  60

Lys Asn Lys Ala Thr Leu Thr Val Asp Ser Ser Ser Thr Ala Tyr
 65                  70                  75                  80

Met Glu Leu Arg Ser Leu Thr Ser Glu Asp Ser Ala Val Tyr Tyr Cys
                    85                  90                  95
```

```
Ala Arg Asn Phe Arg Tyr Thr Tyr Trp Tyr Phe Asp Val Trp Gly Gln
                100                 105                 110

Gly Thr Thr Val Thr Val Ser Ser
            115                 120

<210> SEQ ID NO 31
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: TRX2 Anti-CD8 Antibody Light Chain Variable
      Domain

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys
            100                 105

<210> SEQ ID NO 32
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: TRX2 Anti-CD8 Antibody Heavy Chain Variable
      Domain

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser
            115                 120

<210> SEQ ID NO 33
```

-continued

```
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: A32 Anti-HIV gp120 Antibody Light Chain
      Variable Domain

<400> SEQUENCE: 33

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu
            100                 105                 110

<210> SEQ ID NO 34
<211> LENGTH: 123
<212> TYPE: PRT
<213> ORGANISM: Mus musculus
<220> FEATURE:
<221> NAME/KEY: MISC_FEATURE
<222> LOCATION: (1)..(123)
<223> OTHER INFORMATION: A32 Anti-HIV gp120 Antibody Heavy Chain
      Variable Domain

<400> SEQUENCE: 34

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
    50                  55                  60

Leu Lys Ser Arg Ile Thr Ile Ser Gln His Thr Ser Glu Asn Gln Phe
65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Met Val Thr Val Ser Ser
        115                 120

<210> SEQ ID NO 35
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: 7B2 Anti-HIV gp41 Antibody Light Chain Variable
      Domain
```

<400> SEQUENCE: 35

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys

<210> SEQ ID NO 36
<211> LENGTH: 126
<212> TYPE: PRT
<213> ORGANISM: Mus musculus
<220> FEATURE:
<221> NAME/KEY: MISC_FEATURE
<222> LOCATION: (1)..(126)
<223> OTHER INFORMATION: 7B2 Anti-HIV gp41 Antibody Heavy Chain Variable
      Domain

<400> SEQUENCE: 36

Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
        35                  40                  45

Ala Tyr Ile Ser Lys Asn Gly Glu Tyr Ser Lys Tyr Ser Pro Ser Ser
    50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Thr Ala Val Tyr Tyr Cys
                85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser
        115                 120                 125

<210> SEQ ID NO 37
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: Palivizumab Anti-RSV Glycoprotein F Antibody
      Light Chain Variable Domain

<400> SEQUENCE: 37

Asp Ile Gln Met Thr Gln Ser Pro Ser Thr Leu Ser Ala Ser Val Gly
1               5                   10                  15

```
Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
50                      55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

<210> SEQ ID NO 38
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Palivizumab Anti-RSV Glycoprotein F Antibody
      Heavy Chain Variable Domain

<400> SEQUENCE: 38

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                      55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120
```

<210> SEQ ID NO 39
<211> LENGTH: 107
<212> TYPE: PRT
<213> ORGANISM: Artificial Sequence
<220> FEATURE:
<223> OTHER INFORMATION: "BRCA84D-5VL" Humanized Anti-B7-H3 Antibody
      Light Chain Variable Domain

<400> SEQUENCE: 39

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ala Leu Ile
        35                  40                  45

Tyr Ser Ala Ser Tyr Arg Tyr Ser Gly Val Pro Ser Arg Phe Ser Gly
50                      55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Asn Asn Tyr Pro Phe
                    85                  90                  95

Thr Phe Gly Gln Gly Thr Lys Leu Glu Ile Lys
            100                 105

<210> SEQ ID NO 40
<211> LENGTH: 122
<212> TYPE: PRT
<213> ORGANISM: Artificial Sequence
<220> FEATURE:
<223> OTHER INFORMATION: "BRCA84D-2VH" Humanized Anti-B7-H3 Antibody
      Heavy Chain Variable Domain

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Asp Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120

<210> SEQ ID NO 41
<211> LENGTH: 107
<212> TYPE: PRT
<213> ORGANISM: Artificial Sequence
<220> FEATURE:
<223> OTHER INFORMATION: "BRCA69D" Humanized Anti-B7-H3  Antibody Light
      Chain Variable Domain

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 42
<211> LENGTH: 120
<212> TYPE: PRT
```

```
<213> ORGANISM: Artificial Sequence
<220> FEATURE:
<223> OTHER INFORMATION: "BRCA69D" Humanized Anti-B7-H3 Antibody Heavy
      Chain Variable Domain

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Asp Gly Asp Thr Arg Tyr Thr Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser
        115                 120

<210> SEQ ID NO 43
<211> LENGTH: 108
<212> TYPE: PRT
<213> ORGANISM: Artificial Sequence
<220> FEATURE:
<223> OTHER INFORMATION: "PRCA157" Humanized Anti-B7-H3 Antibody Light
      Chain Variable Domain

<400> SEQUENCE: 43

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Arg Tyr Tyr Cys Gln His His Tyr Gly Thr Pro Pro
                85                  90                  95

Trp Thr Phe Gly Gly Gly Thr Asn Leu Glu Ile Lys
            100                 105

<210> SEQ ID NO 44
<211> LENGTH: 117
<212> TYPE: PRT
<213> ORGANISM: Artificial Sequence
<220> FEATURE:
<223> OTHER INFORMATION: "PRCA157" Humanized Anti-B7-H3 Antibody Heavy
      Chain Variable Domain

<400> SEQUENCE: 44

Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30
```

```
Gly Met Ser Trp Val Arg Gln Thr Pro Asp Lys Arg Leu Glu Trp Val
            35                  40                  45

Ala Thr Ile Asn Ser Gly Gly Ser Asn Thr Tyr Tyr Pro Asp Ser Leu
 50                  55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
            115

<210> SEQ ID NO 45
<211> LENGTH: 107
<212> TYPE: PRT
<213> ORGANISM: Artificial Sequence
<220> FEATURE:
<223> OTHER INFORMATION: Humanized Anti-A33 Antibody Light Chain
      Variable Domain

<400> SEQUENCE: 45

Gln Ile Val Leu Thr Gln Ser Pro Ala Ile Met Ser Ala Ser Pro Gly
 1               5                  10                  15

Glu Arg Val Thr Met Thr Cys Ser Ala Arg Ser Ser Ile Ser Phe Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Tyr Pro Leu Thr
                85                  90                  95

Phe Gly Ser Gly Thr Lys Leu Glu Leu Lys Arg
            100                 105

<210> SEQ ID NO 46
<211> LENGTH: 119
<212> TYPE: PRT
<213> ORGANISM: Artificial Sequence
<220> FEATURE:
<223> OTHER INFORMATION: Humanized Anti-A33 Antibody Heavy Chain
      Variable Domain

<400> SEQUENCE: 46

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Ser Gly Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Glu Thr Asn Tyr Asn Gly Lys Phe
 50                  55                  60

Lys Asp Lys Ala Thr Leu Thr Ala Asp Lys Ser Ser Thr Thr Ala Tyr
 65                  70                  75                  80

Met Glu Leu Ser Ser Leu Thr Ser Val Asp Ser Ala Val Tyr Phe Cys
                85                  90                  95
```

Ala Arg Ile Tyr Gly Asn Asn Val Tyr Phe Asp Val Trp Gly Ala Gly
            100                 105                 110

Thr Thr Val Thr Val Ser Ser
        115

<210> SEQ ID NO 47
<211> LENGTH: 107
<212> TYPE: PRT
<213> ORGANISM: Artificial Sequence
<220> FEATURE:
<223> OTHER INFORMATION: Humanized Anti-5T4 Antibody "mAb 1" Light Chain
      Variable Domain

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys
            100                 105

<210> SEQ ID NO 48
<211> LENGTH: 118
<212> TYPE: PRT
<213> ORGANISM: Artificial Sequence
<220> FEATURE:
<223> OTHER INFORMATION: Humanized Anti-5T4 Antibody "mAb 1" Heavy Chain
      Variable Domain

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser
        115

<210> SEQ ID NO 49
<211> LENGTH: 112
<212> TYPE: PRT
<213> ORGANISM: Artificial Sequence

```
<220> FEATURE:
<223> OTHER INFORMATION: Humanized Anti-5T4 Antibody "mAb 2" Light Chain
      Variable Domain

<400> SEQUENCE: 49

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 50
<211> LENGTH: 127
<212> TYPE: PRT
<213> ORGANISM: Artificial Sequence
<220> FEATURE:
<223> OTHER INFORMATION: Humanized Anti-5T4 Antibody "mAb 2" Heavy Chain
      Variable Domain

<400> SEQUENCE: 50

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Arg Ala Asn Tyr Asn Glu Lys Phe
50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Asn Cys
                85                  90                  95

Ala Arg Tyr Gly Pro Leu Phe Thr Thr Val Val Asp Pro Asn Ser Tyr
            100                 105                 110

Ala Met Asp Tyr Trp Gly Gln Gly Thr Ser Val Thr Val Ser Ser
        115                 120                 125

<210> SEQ ID NO 51
<211> LENGTH: 112
<212> TYPE: PRT
<213> ORGANISM: Artificial Sequence
<220> FEATURE:
<223> OTHER INFORMATION: Humanized Anti-ROR1 mAb 1 Antibody Light Chain
      Variable Domain

<400> SEQUENCE: 51

Gln Leu Val Leu Thr Gln Ser Pro Ser Ala Ser Ala Ser Leu Gly Ser
1               5                   10                  15

Ser Val Lys Leu Thr Cys Thr Leu Ser Ser Gly His Lys Thr Asp Thr
            20                  25                  30
```

```
Ile Asp Trp Tyr Gln Gln Pro Gly Lys Ala Pro Arg Tyr Leu Met
            35                  40                  45

Lys Leu Glu Gly Ser Gly Ser Tyr Asn Lys Ser Gly Val Pro Asp
 50                  55                  60

Arg Phe Gly Ser Gly Ser Ser Gly Ala Asp Arg Tyr Leu Thr Ile
 65                  70                  75                  80

Ser Ser Leu Gln Ser Glu Asp Glu Ala Asp Tyr Tyr Cys Gly Thr Asp
                 85                  90                  95

Tyr Pro Gly Asn Tyr Leu Phe Gly Gly Gly Thr Gln Leu Thr Val Leu
                100                 105                 110

<210> SEQ ID NO 52
<211> LENGTH: 121
<212> TYPE: PRT
<213> ORGANISM: Artificial Sequence
<220> FEATURE:
<223> OTHER INFORMATION: Humanized Anti-ROR1 mAb 1 Antibody Heavy Chain
      Variable Domain

<400> SEQUENCE: 52

Gln Glu Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Val Arg Gln Ala Pro Gly Lys Gly Leu Glu Trp Val
            35                  40                  45

Ala Thr Ile Tyr Pro Ser Ser Gly Lys Thr Tyr Tyr Ala Asp Ser Val
 50                  55                  60

Lys Gly Arg Phe Thr Ile Ser Ser Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Tyr Ala Asp Asp Ala Ala Leu Phe Asp Ile Trp Gly
                100                 105                 110

Gln Gly Thr Thr Val Thr Val Ser Ser
            115                 120

<210> SEQ ID NO 53
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: 2A2 Anti-ROR1 Antibody Light Chain Variable
      Domain

<400> SEQUENCE: 53

Asp Ile Val Met Thr Gln Ser Gln Lys Ile Met Ser Thr Thr Val Gly
 1               5                  10                  15

Asp Arg Val Ser Ile Thr Cys Lys Ala Ser Gln Asn Val Asp Ala Ala
                 20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
 50                  55                  60

Ser Gly Ser Gly Thr Asp Phe Thr Leu Thr Ile Ser Asn Met Gln Ser
 65                  70                  75                  80

Glu Asp Leu Ala Asp Tyr Phe Cys Gln Gln Tyr Asp Ile Tyr Pro Tyr
```

```
                    85                  90                  95

Thr Phe Gly Gly Gly Thr Lys Leu Glu Ile Lys
            100                 105

<210> SEQ ID NO 54
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: 2A2 Anti-ROR1 Antibody Heavy Chain Variable
      Domain

<400> SEQUENCE: 54

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
                20                  25                  30

Glu Met His Trp Val Ile Gln Thr Pro Val His Gly Leu Glu Trp Ile
            35                  40                  45

Gly Ala Ile Asp Pro Glu Thr Gly Gly Thr Ala Tyr Asn Gln Lys Phe
        50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 55
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: R11 Anti-ROR1 Antibody Light Chain Variable
      Domain

<400> SEQUENCE: 55

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
                20                  25                  30

Leu Ala Trp Phe Gln Gln Lys Pro Gly Gln Pro Pro Thr Leu Leu Ile
            35                  40                  45

Tyr Arg Ala Ser Asn Leu Ala Ser Gly Val Pro Ser Arg Phe Ser Gly
        50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Gly Thr Glu Val Val Val Lys
            100                 105                 110

<210> SEQ ID NO 56
<211> LENGTH: 116
```

```
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: R11 Anti-ROR1 Antibody Heavy Chain Variable
      Domain

<400> SEQUENCE: 56

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Gly Asp Phe Asn Ile Trp Gly Pro Gly Thr Leu Val
            100                 105                 110

Thr Ile Ser Ser
        115

<210> SEQ ID NO 57
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: R12 Anti-ROR1 Antibody Light Chain Variable
      Domain

<400> SEQUENCE: 57

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110

<210> SEQ ID NO 58
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: R12 Anti-ROR1 Antibody Heavy Chain Variable
      Domain
```

-continued

```
<400> SEQUENCE: 58

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 59
<211> LENGTH: 504
<212> TYPE: PRT
<213> ORGANISM: Artificial Sequence
<220> FEATURE:
<223> OTHER INFORMATION: First Polypeptide Chain of Exemplary B7-H3 mAb
      1/ CD3 mAb 2 / CD8 mAb 1 Tri-Specific Binding Molecule (VL(B7-H3
      mAb 1)-VH(CD3 mAb 2)-E-Coil-(CH2-CH3))

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220
```

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
            245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
            275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
            325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
            405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
            485                 490                 495

Ser Leu Ser Leu Ser Pro Gly Lys
            500

<210> SEQ ID NO 60
<211> LENGTH: 272
<212> TYPE: PRT
<213> ORGANISM: Artificial Sequence
<220> FEATURE:
<223> OTHER INFORMATION: Second Polypeptide Chain of Exemplary B7-H3 mAb
      1/ CD3 mAb 2 / CD8 mAb 1 Tri-Specific Binding Molecule (VL(CD3 mAb
      2)-VH(B7-H3 mAb 1)-K-Coil)

<400> SEQUENCE: 60

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
50                  55                  60

```
Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Ser Tyr Trp Met Gln Trp Val Arg Gln Ala Pro Gly
145                 150                 155                 160

Gln Gly Leu Glu Trp Met Gly Thr Ile Tyr Pro Gly Asp Gly Asp Thr
                165                 170                 175

Arg Tyr Thr Gln Lys Phe Lys Gly Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Arg Gly Ile Pro Arg Leu Trp Tyr
210                 215                 220

Phe Asp Val Trp Gly Gln Gly Thr Thr Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 61
<211> LENGTH: 448
<212> TYPE: PRT
<213> ORGANISM: Artificial Sequence
<220> FEATURE:
<223> OTHER INFORMATION: Third Polypeptide Chain of Exemplary B7-H3 mAb
      1/ CD3 mAb 2 / CD8 mAb 1 Tri-Specific Binding Molecule (Heavy
      Chain CD8 mAb 1)

<400> SEQUENCE: 61

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

Ser Gly Ala Leu Thr Ser Gly Val His Thr Phe Pro Ala Val Leu Gln
145                 150                 155                 160

Ser Ser Gly Leu Tyr Ser Leu Ser Ser Val Val Thr Val Pro Ser Ser
            165                 170                 175

Ser Leu Gly Thr Gln Thr Tyr Ile Cys Asn Val Asn His Lys Pro Ser
        180                 185                 190

Asn Thr Lys Val Asp Lys Arg Val Glu Pro Lys Ser Cys Asp Lys Thr
    195                 200                 205

His Thr Cys Pro Pro Cys Pro Ala Pro Glu Ala Ala Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
            245                 250                 255

Glu Val Lys Phe Asn Trp Tyr Val Asp Gly Val Glu Val His Asn Ala
        260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Arg Glu Glu Met Thr Lys Asn Gln Val Ser Leu Ser Cys
        340                 345                 350

Ala Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Val Ser Lys Leu Thr Val Asp Lys Ser
385                 390                 395                 400

Arg Trp Gln Gln Gly Asn Val Phe Ser Cys Ser Val Met His Glu Ala
            405                 410                 415

Leu His Asn Arg Tyr Thr Gln Lys Ser Leu Ser Leu Ser Pro Gly Lys
        420                 425                 430

435                 440                 445

<210> SEQ ID NO 62
<211> LENGTH: 214
<212> TYPE: PRT
<213> ORGANISM: Artificial Sequence
<220> FEATURE:
<223> OTHER INFORMATION: Fourth Polypeptide Chain of Exemplary B7-H3 mAb
    1/ CD3 mAb 2 / CD8 mAb 1 Tri-Specific Binding Molecule (Light
    Chain CD8 mAb 1)

<400> SEQUENCE: 62

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

```
Ser Gly Ser Gly Thr Asp Phe Thr Leu Thr Ile Ser Gly Leu Glu Pro
 65                  70                  75                  80

Glu Asp Phe Ala Met Tyr Tyr Cys Gln Gln His Asn Glu Asn Pro Leu
             85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 63
<211> LENGTH: 504
<212> TYPE: PRT
<213> ORGANISM: Artificial Sequence
<220> FEATURE:
<223> OTHER INFORMATION: First Polypeptide Chain of Exemplary B7-H3 mAb
      1/ CD3 mAb 2 / CD8 mAb 2 Tri-Specific Binding Molecule (VL(B7-H3
      mAb 1)-VH(CD3 mAb 2)-E-Coil-(CH2-CH3))

<400> SEQUENCE: 63

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Gly Asn Thr Leu Pro Pro
             85                  90                  95

Thr Phe Gly Gly Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190
```

```
Lys Asn Ser Leu Tyr Leu Gln Met Asn Ser Leu Lys Thr Glu Asp Thr
            195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240

Gly Gly Cys Gly Gly Gly Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
            275                 280                 285

Pro Glu Ala Ala Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
            370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 64
<211> LENGTH: 272
<212> TYPE: PRT
<213> ORGANISM: Artificial Sequence
<220> FEATURE:
<223> OTHER INFORMATION: Second Polypeptide Chain of Exemplary B7-H3 mAb
      1/ CD3 mAb 2 / CD8 mAb 2 Tri-Specific Binding Molecule (VL(CD3 mAb
      2)-VH(B7-H3 mAb 1)-K-Coil)

<400> SEQUENCE: 64

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
```

```
               35                  40                  45
Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Gln Val Gln Leu Val Gln Ser Gly Ala Glu
            115                 120                 125

Val Lys Lys Pro Gly Ala Ser Val Lys Val Ser Cys Lys Ala Ser Gly
        130                 135                 140

Tyr Thr Phe Thr Ser Tyr Trp Met Gln Trp Val Arg Gln Ala Pro Gly
145                 150                 155                 160

Gln Gly Leu Glu Trp Met Gly Thr Ile Tyr Pro Gly Asp Gly Asp Thr
                165                 170                 175

Arg Tyr Thr Gln Lys Phe Lys Gly Arg Val Thr Ile Thr Ala Asp Lys
                180                 185                 190

Ser Thr Ser Thr Ala Tyr Met Glu Leu Ser Ser Leu Arg Ser Glu Asp
            195                 200                 205

Thr Ala Val Tyr Tyr Cys Ala Arg Arg Gly Ile Pro Arg Leu Trp Tyr
        210                 215                 220

Phe Asp Val Trp Gly Gln Gly Thr Thr Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
                260                 265                 270

<210> SEQ ID NO 65
<211> LENGTH: 451
<212> TYPE: PRT
<213> ORGANISM: Artificial Sequence
<220> FEATURE:
<223> OTHER INFORMATION: Third Polypeptide Chain of Exemplary B7-H3 mAb
      1/ CD3 mAb 2 / CD8 mAb 2 Tri-Specific Binding Molecule (Heavy
      Chain CD8 mAb 2)

<400> SEQUENCE: 65

Gln Val Gln Leu Val Glu Ser Gly Gly Gly Val Val Gln Pro Gly Arg
  1                   5                  10                  15

Ser Leu Arg Leu Ser Cys Ala Ala Ser Gly Phe Thr Phe Ser Asp Phe
                 20                  25                  30

Gly Met Asn Trp Val Arg Gln Ala Pro Gly Lys Gly Leu Glu Trp Val
             35                  40                  45

Ala Leu Ile Tyr Tyr Asp Gly Ser Asn Lys Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro His Tyr Asp Gly Tyr Tyr His Phe Phe Asp Ser Trp Gly
                100                 105                 110

Gln Gly Thr Leu Val Thr Val Ser Ser Ala Ser Thr Lys Gly Pro Ser
            115                 120                 125
```

-continued

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Tyr Thr Gln Lys Ser Leu Ser Leu Ser
        435                 440                 445

Pro Gly Lys
    450

<210> SEQ ID NO 66
<211> LENGTH: 213
<212> TYPE: PRT
<213> ORGANISM: Artificial Sequence
<220> FEATURE:
<223> OTHER INFORMATION: Fourth Polypeptide Chain of Exemplary B7-H3 mAb
      1/ CD3 mAb 2 / CD8 mAb 2 Tri-Specific Binding Molecule (Light
      Chain CD8 mAb 2)

<400> SEQUENCE: 66

Asp Ile Gln Met Thr Gln Ser Pro Ser Ser Leu Ser Ala Ser Val Gly
1               5                   10                  15

```
Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
         35                  40                  45

Tyr Asn Thr Asp Ile Leu His Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 67
<211> LENGTH: 504
<212> TYPE: PRT
<213> ORGANISM: Artificial Sequence
<220> FEATURE:
<223> OTHER INFORMATION: First Polypeptide Chain of Exemplary CD3 mAb
      2 / CD8 mAb 1 / B7-H3 mAb 1 Tri-Specific Binding Molecule (VL(CD3
      mAb 2)-VH(CD8 mAb 1)-E-Coil-(CH2-CH3))

<400> SEQUENCE: 67

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                 85                  90                  95

Thr Phe Gly Ala Gly Thr Lys Leu Glu Leu Arg Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
```

```
145                 150                 155                 160
Glu Trp Val Gly Arg Ile Arg Ser Lys Tyr Asn Asn Tyr Ala Thr Tyr
                165                 170                 175
Tyr Ala Asp Ser Val Lys Gly Arg Phe Thr Ile Ser Arg Asp Asp Ser
                180                 185                 190
Lys Asn Ser Leu Tyr Leu Gln Met Asn Ser Leu Lys Thr Glu Asp Thr
                195                 200                 205
Ala Val Tyr Tyr Cys Val Arg His Gly Asn Phe Gly Asn Ser Tyr Val
                210                 215                 220
Ser Trp Phe Ala Tyr Trp Gly Gln Gly Thr Leu Val Thr Val Ser Ser
225                 230                 235                 240
Gly Gly Cys Gly Gly Gly Glu Val Ala Ala Leu Glu Lys Glu Val Ala
                245                 250                 255
Ala Leu Glu Lys Glu Val Ala Ala Leu Glu Lys Glu Val Ala Ala Leu
                260                 265                 270
Glu Lys Gly Gly Gly Asp Lys Thr His Thr Cys Pro Pro Cys Pro Ala
                275                 280                 285
Pro Glu Ala Ala Gly Gly Pro Ser Val Phe Leu Phe Pro Pro Lys Pro
                290                 295                 300
Lys Asp Thr Leu Met Ile Ser Arg Thr Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
                340                 345                 350
Tyr Asn Ser Thr Tyr Arg Val Val Ser Val Leu Thr Val Leu His Gln
                355                 360                 365
Asp Trp Leu Asn Gly Lys Glu Tyr Lys Cys Lys Val Ser Asn Lys Ala
                370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Glu Glu Met Thr
                405                 410                 415
Lys Asn Gln Val Ser Leu Trp Cys Leu Val Lys Gly Phe Tyr Pro Ser
                420                 425                 430
Asp Ile Ala Val Glu Trp Glu Ser Asn Gly Gln Pro Glu Asn Asn Tyr
                435                 440                 445
Lys Thr Thr Pro Pro Val Leu Asp Ser Asp Gly Ser Phe Phe Leu Tyr
450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys
                500

<210> SEQ ID NO 68
<211> LENGTH: 270
<212> TYPE: PRT
<213> ORGANISM: Artificial Sequence
<220> FEATURE:
<223> OTHER INFORMATION: Second Polypeptide Chain of Exemplary CD3 mAb
      2 / CD8 mAb 1 / B7-H3 mAb 1 Tri-Specific Binding Molecule (VL(CD8
      mAb 1)-VH(CD3 mAb 2)-K-Coil)

<400> SEQUENCE: 68
```

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65              70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Gln Gln Ser Gly Ala Glu
        115                 120                 125

Leu Val Lys Pro Gly Ala Ser Val Lys Leu Ser Cys Thr Ala Ser Gly
    130                 135                 140

Phe Asn Ile Lys Asp Thr Tyr Ile His Phe Val Arg Gln Arg Pro Glu
145                 150                 155                 160

Gln Gly Leu Glu Trp Ile Gly Arg Ile Asp Pro Ala Asn Asp Asn Thr
                165                 170                 175

Leu Tyr Ala Ser Lys Phe Gln Gly Lys Ala Thr Ile Thr Ala Asp Thr
            180                 185                 190

Ser Ser Asn Thr Ala Tyr Met His Leu Cys Ser Leu Thr Ser Gly Asp
        195                 200                 205

Thr Ala Val Tyr Tyr Cys Gly Arg Gly Tyr Gly Tyr Tyr Val Phe Asp
    210                 215                 220

His Trp Gly Gln Gly Thr Thr Leu Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 69
<211> LENGTH: 450
<212> TYPE: PRT
<213> ORGANISM: Artificial Sequence
<220> FEATURE:
<223> OTHER INFORMATION: Third Polypeptide Chain of Exemplary CD3 mAb
      2 / CD8 mAb 1 / B7-H3 mAb 1 Tri-Specific Binding Molecule Heavy
      Chain B7-H3 mAb 1)

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Asp Gly Asp Thr Arg Tyr Thr Gln Lys Phe
    50                  55                  60

Lys Gly Arg Val Thr Ile Thr Ala Asp Lys Ser Thr Ser Thr Ala Tyr
65              70                  75                  80
```

```
Met Glu Leu Ser Ser Leu Arg Ser Glu Asp Thr Ala Val Tyr Tyr Cys
                85                  90                  95

Ala Arg Arg Gly Ile Pro Arg Leu Trp Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Tyr Thr Gln Lys Ser Leu Ser Leu Ser Pro
            435                 440                 445

Gly Lys
    450

<210> SEQ ID NO 70
<211> LENGTH: 214
<212> TYPE: PRT
<213> ORGANISM: Artificial Sequence
<220> FEATURE:
<223> OTHER INFORMATION: Fourth Polypeptide Chain of Exemplary CD3 mAb
```

2 / CD8 mAb 1 / B7-H3 mAb 1 Tri-Specific Binding Molecule (Light
   Chain B7-H3 mAb 1)

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 499
<212> TYPE: PRT
<213> ORGANISM: Artificial Sequence
<220> FEATURE:
<223> OTHER INFORMATION: First Polypeptide Chain of Exemplary B7-H3 mAb
    1/ CD8 mAb 1 / CD3 mAb 2 Tri-Specific Binding Molecule (VL(B7-H3
    mAb 1)-VH(CD8 mAb 1)-E-Coil-(CH2-CH3))

<400> SEQUENCE: 71

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Gly Gly Gly Ser Gly
            100                 105                 110

```
Gly Gly Gly Gln Val Gln Leu Val Gln Ser Gly Ala Glu Val Lys Lys
            115                 120                 125
Pro Gly Ala Ser Val Lys Val Ser Cys Lys Ala Ser Gly Tyr Thr Phe
    130                 135                 140
Thr Ser Tyr Trp Met Gln Trp Val Arg Gln Ala Pro Gly Gln Gly Leu
145                 150                 155                 160
Glu Trp Met Gly Thr Ile Tyr Pro Gly Asp Gly Asp Thr Arg Tyr Thr
                165                 170                 175
Gln Lys Phe Lys Gly Arg Val Thr Ile Thr Ala Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Arg Arg Gly Ile Pro Arg Leu Trp Tyr Phe Asp Val
210                 215                 220
Trp Gly Gln Gly Thr Thr Val Thr Val Ser Ser Gly Gly Cys Gly Gly
225                 230                 235                 240
Gly Glu Val Ala Ala Leu Glu Lys Glu Val Ala Ala Leu Glu Lys Glu
                245                 250                 255
Val Ala Ala Leu Glu Lys Glu Val Ala Ala Leu Glu Lys Gly Gly Gly
            260                 265                 270
Asp Lys Thr His Thr Cys Pro Pro Cys Pro Ala Pro Glu Ala Ala Gly
        275                 280                 285
Gly Pro Ser Val Phe Leu Phe Pro Pro Lys Pro Lys Asp Thr Leu Met
    290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Pro Ile
370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Glu Glu Met Thr Lys Asn Gln Val Ser
                405                 410                 415
Leu Trp Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
Val Leu Asp Ser Asp Gly Ser Phe Phe Leu Tyr Ser Lys Leu Thr Val
450                 455                 460
Asp Lys Ser Arg Trp Gln Gln Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Pro Gly Lys

<210> SEQ ID NO 72
<211> LENGTH: 267
<212> TYPE: PRT
```

<213> ORGANISM: Artificial Sequence
<220> FEATURE:
<223> OTHER INFORMATION: Second Polypeptide Chain of Exemplary B7-H3 mAb
    1/ CD8 mAb 1 / CD3 mAb 2 Tri-Specific Binding Molecule (VL(CD8 mAb
    1)-VH(B7-H3 mAb1)-K-Coil)

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys Gly Gly Gly Ser Gly
            100                 105                 110

Gly Gly Gly Glu Val Gln Leu Gln Gln Ser Gly Ala Glu Leu Val Lys
        115                 120                 125

Pro Gly Ala Ser Val Lys Leu Ser Cys Thr Ala Ser Gly Phe Asn Ile
130                 135                 140

Lys Asp Thr Tyr Ile His Phe Val Arg Gln Arg Pro Glu Gln Gly Leu
145                 150                 155                 160

Glu Trp Ile Gly Arg Ile Asp Pro Ala Asn Asp Asn Thr Leu Tyr Ala
                165                 170                 175

Ser Lys Phe Gln Gly Lys Ala Thr Ile Thr Ala Asp Thr Ser Ser Asn
            180                 185                 190

Thr Ala Tyr Met His Leu Cys Ser Leu Thr Ser Gly Asp Thr Ala Val
        195                 200                 205

Tyr Tyr Cys Gly Arg Gly Tyr Gly Tyr Tyr Val Phe Asp His Trp Gly
210                 215                 220

Gln Gly Thr Thr Leu Thr Val Ser Ser Gly Gly Cys Gly Gly Gly Lys
225                 230                 235                 240

Val Ala Ala Leu Lys Glu Lys Val Ala Ala Leu Lys Glu Lys Val Ala
                245                 250                 255

Ala Leu Lys Glu Lys Val Ala Ala Leu Lys Glu
            260                 265
```

<210> SEQ ID NO 73
<211> LENGTH: 455
<212> TYPE: PRT
<213> ORGANISM: Artificial Sequence
<220> FEATURE:
<223> OTHER INFORMATION: Third Polypeptide Chain of Exemplary B7-H3 mAb
    1/ CD8 mAb 1 / CD3 mAb 2 Tri-Specific Binding Molecule (Heavy
    Chain CD3 mAb 2)

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45
```

```
Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn Arg Tyr Thr Gln Lys Ser
        435                 440                 445

Leu Ser Leu Ser Pro Gly Lys
    450                 455
```

<210> SEQ ID NO 74
<211> LENGTH: 217
<212> TYPE: PRT
<213> ORGANISM: Artificial Sequence
<220> FEATURE:
<223> OTHER INFORMATION: Fourth Polypeptide Chain of Exemplary B7-H3 mAb
      1/ CD8 mAb 1 / CD3 mAb 2 Tri-Specific Binding Molecule (Light
      Chain CD3 mAb 2)

<400> SEQUENCE: 74

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 75
<211> LENGTH: 509
<212> TYPE: PRT
<213> ORGANISM: Artificial Sequence
<220> FEATURE:
<223> OTHER INFORMATION: First Polypeptide Chain of Exemplary 5T4 mAb
      2 / CD3 mAb 2 / CD8 mAb 1 Tri--Specific Binding Molecule (VL(5T4
      mAb 2)-VH(CD3 mAb 2)-E-Coil-(CH2-CH3))

<400> SEQUENCE: 75

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
            65                  70                  75                  80
Ser Arg Val Glu Ala Glu Asp Leu Gly Val Tyr Tyr Cys Phe Gln Gly
                    85                  90                  95

Ser His Val Pro Phe Thr Phe Gly Ser Gly Thr Lys Leu Glu Ile Lys
                100                 105                 110

Gly Gly Gly Ser Gly Gly Gly Gly Glu Val Gln Leu Val Glu Ser Gly
                115                 120                 125

Gly Gly Leu Val Gln Pro Gly Gly Ser Leu Arg Leu Ser Cys Ala Ala
            130                 135                 140

Ser Gly Phe Thr Phe Ser Thr Tyr Ala Met Asn Trp Val Arg Gln Ala
145                 150                 155                 160

Pro Gly Lys Gly Leu Glu Trp Val Gly Arg Ile Arg Ser Lys Tyr Asn
                165                 170                 175

Asn Tyr Ala Thr Tyr Tyr Ala Asp Ser Val Lys Gly Arg Phe Thr Ile
                180                 185                 190

Ser Arg Asp Asp Ser Lys Asn Ser Leu Tyr Leu Gln Met Asn Ser Leu
            195                 200                 205

Lys Thr Glu Asp Thr Ala Val Tyr Tyr Cys Val Arg His Gly Asn Phe
210                 215                 220

Gly Asn Ser Tyr Val Ser Trp Phe Ala Tyr Trp Gly Gln Gly Thr Leu
225                 230                 235                 240

Val Thr Val Ser Ser Gly Gly Cys Gly Gly Glu Val Ala Ala Leu
                245                 250                 255

Glu Lys Glu Val Ala Ala Leu Glu Lys Glu Val Ala Ala Leu Glu Lys
                260                 265                 270

Glu Val Ala Ala Leu Glu Lys Gly Gly Gly Asp Lys Thr His Thr Cys
            275                 280                 285

Pro Pro Cys Pro Ala Pro Glu Ala Ala Gly Gly Pro Ser Val Phe Leu
            290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
                340                 345                 350

Pro Arg Glu Glu Gln Tyr Asn Ser Thr Tyr Arg Val Val Ser Val Leu
            355                 360                 365

Thr Val Leu His Gln Asp Trp Leu Asn Gly Lys Glu Tyr Lys Cys Lys
370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Glu Glu Met Thr Lys Asn Gln Val Ser Leu Trp Cys Leu Val Lys
                420                 425                 430

Gly Phe Tyr Pro Ser Asp Ile Ala Val Glu Trp Glu Ser Asn Gly Gln
            435                 440                 445

Pro Glu Asn Asn Tyr Lys Thr Thr Pro Pro Val Leu Asp Ser Asp Gly
            450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495
```

-continued

```
His Tyr Thr Gln Lys Ser Leu Ser Leu Ser Pro Gly Lys
            500                 505

<210> SEQ ID NO 76
<211> LENGTH: 279
<212> TYPE: PRT
<213> ORGANISM: Artificial Sequence
<220> FEATURE:
<223> OTHER INFORMATION: Second Polypeptide Chain of Exemplary 5T4 mAb
      2 / CD3 mAb 2 / CD8 mAb 1 Tri--Specific Binding Molecule (VL(CD3
      mAb 2)-VH(5T4 mAb 2)-K-Coil)

<400> SEQUENCE: 76

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Gln Pro Gly Ala Glu
        115                 120                 125

Leu Val Lys Pro Gly Ala Ser Val Lys Met Ser Cys Lys Ala Ser Gly
    130                 135                 140

Tyr Thr Phe Thr Ser Tyr Trp Ile Thr Trp Val Lys Gln Arg Pro Gly
145                 150                 155                 160

Gln Gly Leu Glu Trp Ile Gly Asp Ile Tyr Pro Gly Ser Gly Arg Ala
                165                 170                 175

Asn Tyr Asn Glu Lys Phe Lys Ser Lys Ala Thr Leu Thr Val Asp Thr
            180                 185                 190

Ser Ser Ser Thr Ala Tyr Met Gln Leu Ser Ser Leu Thr Ser Glu Asp
        195                 200                 205

Ser Ala Val Tyr Asn Cys Ala Arg Tyr Gly Pro Leu Phe Thr Thr Val
    210                 215                 220

Val Asp Pro Asn Ser Tyr Ala Met Asp Tyr Trp Gly Gln Gly Thr Ser
225                 230                 235                 240

Val Thr Val Ser Ser Gly Gly Cys Gly Gly Gly Lys Val Ala Ala Leu
                245                 250                 255

Lys Glu Lys Val Ala Ala Leu Lys Glu Lys Val Ala Ala Leu Lys Glu
            260                 265                 270

Lys Val Ala Ala Leu Lys Glu
        275

<210> SEQ ID NO 77
<211> LENGTH: 448
<212> TYPE: PRT
<213> ORGANISM: Artificial Sequence
<220> FEATURE:
<223> OTHER INFORMATION: Third Polypeptide Chain of Exemplary 5T4 mAb
      2 / CD3 mAb 2 / CD8 mAb 1 Tri--Specific Binding Molecule (Heavy
      Chain CD8 mAb 1)
```

<400> SEQUENCE: 77

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
```

```
                    405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445

<210> SEQ ID NO 78
<211> LENGTH: 214
<212> TYPE: PRT
<213> ORGANISM: Artificial Sequence
<220> FEATURE:
<223> OTHER INFORMATION: Fourth Polypeptide Chain of Exemplary 5T4 mAb
      2 / CD3 mAb 2 / CD8 mAb 1 Tri--Specific Binding Molecule (Light
      Chain CD8 mAb 1)

<400> SEQUENCE: 78

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 509
<212> TYPE: PRT
<213> ORGANISM: Artificial Sequence
<220> FEATURE:
<223> OTHER INFORMATION: First Polypeptide Chain of Exemplary 5T4 mAb
      2 / CD3 mAb 2 / CD8 mAb 2 Tri--Specific Binding Molecule (VL(5T4
      mAb 2)-VH(CD3 mAb 2)-E-Coil-(CH2-CH3))

<400> SEQUENCE: 79

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30
```

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
                100                 105                 110

Gly Gly Gly Ser Gly Gly Gly Gly Glu Val Gln Leu Val Glu Ser Gly
                115                 120                 125

Gly Gly Leu Val Gln Pro Gly Gly Ser Leu Arg Leu Ser Cys Ala Ala
            130                 135                 140

Ser Gly Phe Thr Phe Ser Thr Tyr Ala Met Asn Trp Val Arg Gln Ala
145                 150                 155                 160

Pro Gly Lys Gly Leu Glu Trp Val Gly Arg Ile Arg Ser Lys Tyr Asn
                165                 170                 175

Asn Tyr Ala Thr Tyr Tyr Ala Asp Ser Val Lys Gly Arg Phe Thr Ile
            180                 185                 190

Ser Arg Asp Asp Ser Lys Asn Ser Leu Tyr Leu Gln Met Asn Ser Leu
            195                 200                 205

Lys Thr Glu Asp Thr Ala Val Tyr Tyr Cys Val Arg His Gly Asn Phe
            210                 215                 220

Gly Asn Ser Tyr Val Ser Trp Phe Ala Tyr Trp Gly Gln Gly Thr Leu
225                 230                 235                 240

Val Thr Val Ser Ser Gly Gly Cys Gly Gly Gly Glu Val Ala Ala Leu
                245                 250                 255

Glu Lys Glu Val Ala Ala Leu Glu Lys Glu Val Ala Ala Leu Glu Lys
            260                 265                 270

Glu Val Ala Ala Leu Glu Lys Gly Gly Gly Asp Lys Thr His Thr Cys
            275                 280                 285

Pro Pro Cys Pro Ala Pro Glu Ala Ala Gly Gly Pro Ser Val Phe Leu
            290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
            340                 345                 350

Pro Arg Glu Glu Gln Tyr Asn Ser Thr Tyr Arg Val Val Ser Val Leu
            355                 360                 365

Thr Val Leu His Gln Asp Trp Leu Asn Gly Lys Glu Tyr Lys Cys Lys
            370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Glu Glu Met Thr Lys Asn Gln Val Ser Leu Trp Cys Leu Val Lys
            420                 425                 430

Gly Phe Tyr Pro Ser Asp Ile Ala Val Glu Trp Glu Ser Asn Gly Gln
            435                 440                 445

```
Pro Glu Asn Asn Tyr Lys Thr Thr Pro Pro Val Leu Asp Ser Asp Gly
    450                 455                 460
Ser Phe Phe Leu Tyr Ser Lys Leu Thr Val Asp Lys Ser Arg Trp Gln
465                 470                 475                 480
Gln Gly Asn Val Phe Ser Cys Ser Val Met His Glu Ala Leu His Asn
                485                 490                 495
His Tyr Thr Gln Lys Ser Leu Ser Leu Ser Pro Gly Lys
            500                 505
```

<210> SEQ ID NO 80
<211> LENGTH: 279
<212> TYPE: PRT
<213> ORGANISM: Artificial Sequence
<220> FEATURE:
<223> OTHER INFORMATION: Second Polypeptide Chain of Exemplary 5T4 mAb
      2 / CD3 mAb 2 / CD8 mAb 2 Tri--Specific Binding Molecule (VL(CD3
      mAb 2)-VH(5T4 mAb 2)-K-Coil)

<400> SEQUENCE: 80

```
Gln Ala Val Val Thr Gln Glu Pro Ser Leu Thr Val Ser Pro Gly Gly
1               5                   10                  15
Thr Val Thr Leu Thr Cys Arg Ser Ser Thr Gly Ala Val Thr Thr Ser
            20                  25                  30
Asn Tyr Ala Asn Trp Val Gln Gln Lys Pro Gly Gln Ala Pro Arg Gly
        35                  40                  45
Leu Ile Gly Gly Thr Asn Lys Arg Ala Pro Trp Thr Pro Ala Arg Phe
    50                  55                  60
Ser Gly Ser Leu Leu Gly Gly Lys Ala Ala Leu Thr Ile Thr Gly Ala
65                  70                  75                  80
Gln Ala Glu Asp Glu Ala Asp Tyr Tyr Cys Ala Leu Trp Tyr Ser Asn
                85                  90                  95
Leu Trp Val Phe Gly Gly Gly Thr Lys Leu Thr Val Leu Gly Gly Gly
            100                 105                 110
Gly Ser Gly Gly Gly Gly Gln Val Gln Leu Gln Gln Pro Gly Ala Glu
        115                 120                 125
Leu Val Lys Pro Gly Ala Ser Val Lys Met Ser Cys Lys Ala Ser Gly
    130                 135                 140
Tyr Thr Phe Thr Ser Tyr Trp Ile Thr Trp Val Lys Gln Arg Pro Gly
145                 150                 155                 160
Gln Gly Leu Glu Trp Ile Gly Asp Ile Tyr Pro Gly Ser Gly Arg Ala
                165                 170                 175
Asn Tyr Asn Glu Lys Phe Lys Ser Lys Ala Thr Leu Thr Val Asp Thr
            180                 185                 190
Ser Ser Ser Thr Ala Tyr Met Gln Leu Ser Ser Leu Thr Ser Glu Asp
        195                 200                 205
Ser Ala Val Tyr Asn Cys Ala Arg Tyr Gly Pro Leu Phe Thr Thr Val
    210                 215                 220
Val Asp Pro Asn Ser Tyr Ala Met Asp Tyr Trp Gly Gln Gly Thr Ser
225                 230                 235                 240
Val Thr Val Ser Ser Gly Gly Cys Gly Gly Gly Lys Val Ala Ala Leu
                245                 250                 255
Lys Glu Lys Val Ala Ala Leu Lys Glu Lys Val Ala Ala Leu Lys Glu
            260                 265                 270
Lys Val Ala Ala Leu Lys Glu
        275
```

-continued

<210> SEQ ID NO 81
<211> LENGTH: 451
<212> TYPE: PRT
<213> ORGANISM: Artificial Sequence
<220> FEATURE:
<223> OTHER INFORMATION: Third Polypeptide Chain of Exemplary 5T4 mAb
    2 / CD3 mAb 2 / CD8 mAb 2 Tri--Specific Binding Molecule (Heavy
    Chain CD8 mAb 2)

<400> SEQUENCE: 81

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

```
Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Tyr Thr Gln Lys Ser Leu Ser Leu Ser
        435                 440                 445

Pro Gly Lys
    450

<210> SEQ ID NO 82
<211> LENGTH: 213
<212> TYPE: PRT
<213> ORGANISM: Artificial Sequence
<220> FEATURE:
<223> OTHER INFORMATION: Fourth Polypeptide Chain of Exemplary 5T4 mAb
      2 / CD3 mAb 2 / CD8 mAb 2 Tri--Specific Binding Molecule (Light
      Chain CD8 mAb 2)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 83
<211> LENGTH: 510
<212> TYPE: PRT
<213> ORGANISM: Artificial Sequence
<220> FEATURE:
```

<223> OTHER INFORMATION: First Polypeptide Chain of Exemplary ROR1 mAb
1 / CD3 mAb 2 / CD8 mAb 1 Tri--Specific Binding Molecule (VL(ROR1
mAb 1)-VH(CD3 mAb 2)-E-Coil-(CH2-CH3))

<400> SEQUENCE: 83

```
Gln Leu Val Leu Thr Gln Ser Pro Ser Ala Ser Ala Ser Leu Gly Ser
1               5                   10                  15

Ser Val Lys Leu Thr Cys Thr Leu Ser Ser Gly His Lys Thr Asp Thr
            20                  25                  30

Ile Asp Trp Tyr Gln Gln Pro Gly Lys Ala Pro Arg Tyr Leu Met
        35                  40                  45

Lys Leu Glu Gly Ser Gly Ser Tyr Asn Lys Ser Gly Val Pro Asp
50                  55                  60

Arg Phe Gly Ser Gly Ser Ser Gly Ala Asp Arg Tyr Leu Thr Ile
65                  70                  75                  80

Ser Ser Leu Gln Ser Glu Asp Glu Ala Asp Tyr Tyr Cys Gly Thr Asp
                85                  90                  95

Tyr Pro Gly Asn Tyr Leu Phe Gly Gly Gly Thr Gln Leu Thr Val Leu
                100                 105                 110

Gly Gly Gly Gly Ser Gly Gly Gly Glu Val Gln Leu Val Glu Ser
            115                 120                 125

Gly Gly Gly Leu Val Gln Pro Gly Gly Ser Leu Arg Leu Ser Cys Ala
130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Gly Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
210                 215                 220

Phe Gly Asn Ser Tyr Val Ser Trp Phe Ala Tyr Trp Gly Gln Gly Thr
225                 230                 235                 240

Leu Val Thr Val Ser Ser Gly Cys Gly Gly Glu Val Ala Ala
                245                 250                 255

Leu Glu Lys Glu Val Ala Ala Leu Glu Lys Glu Val Ala Ala Leu Glu
                260                 265                 270

Lys Glu Val Ala Ala Leu Glu Lys Gly Gly Gly Asp Lys Thr His Thr
            275                 280                 285

Cys Pro Pro Cys Pro Ala Pro Glu Ala Ala Gly Gly Pro Ser Val Phe
290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
370                 375                 380

Lys Val Ser Asn Lys Ala Leu Pro Ala Pro Ile Glu Lys Thr Ile Ser
```

```
                385                 390                 395                 400
Lys Ala Lys Gly Gln Pro Arg Glu Pro Gln Val Tyr Thr Leu Pro Pro
                    405                 410                 415

Ser Arg Glu Glu Met Thr Lys Asn Gln Val Ser Leu Trp Cys Leu Val
                    420                 425                 430

Lys Gly Phe Tyr Pro Ser Asp Ile Ala Val Glu Trp Glu Ser Asn Gly
                    435                 440                 445

Gln Pro Glu Asn Asn Tyr Lys Thr Thr Pro Pro Val Leu Asp Ser Asp
                450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                    485                 490                 495

Asn His Tyr Thr Gln Lys Ser Leu Ser Leu Ser Pro Gly Lys
                500                 505                 510

<210> SEQ ID NO 84
<211> LENGTH: 273
<212> TYPE: PRT
<213> ORGANISM: Artificial Sequence
<220> FEATURE:
<223> OTHER INFORMATION: Second Polypeptide Chain of Exemplary ROR1 mAb
      1 / CD3 mAb 2 / CD8 mAb 1 Tri--Specific Binding Molecule (VL(CD3
      mAb 2)-VH(ROR1 mAb 1)-K-Coil)

<400> SEQUENCE: 84

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
                35                  40                  45

Leu Ile Gly Gly Thr Asn Lys Arg Ala Pro Trp Thr Pro Ala Arg Phe
            50                  55                  60

Ser Gly Ser Leu Leu Gly Gly Lys Ala Ala Leu Thr Ile Thr Gly Ala
65              70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Gln Glu Gln Leu Val Glu Ser Gly Gly Gly
            115                 120                 125

Leu Val Gln Pro Gly Gly Ser Leu Arg Leu Ser Cys Ala Ala Ser Gly
            130                 135                 140

Phe Thr Phe Ser Asp Tyr Tyr Met Ser Trp Val Arg Gln Ala Pro Gly
145                 150                 155                 160

Lys Gly Leu Glu Trp Val Ala Thr Ile Tyr Pro Ser Ser Gly Lys Thr
                165                 170                 175

Tyr Tyr Ala Asp Ser Val Lys Gly Arg Phe Thr Ile Ser Ser Asp Asn
                180                 185                 190

Ala Lys Asn Ser Leu Tyr Leu Gln Met Asn Ser Leu Arg Ala Glu Asp
            195                 200                 205

Thr Ala Val Tyr Tyr Cys Ala Arg Asp Ser Tyr Ala Asp Asp Ala Ala
        210                 215                 220

Leu Phe Asp Ile Trp Gly Gln Gly Thr Thr Val Thr Val Ser Ser Gly
225                 230                 235                 240
```

```
Gly Cys Gly Gly Gly Lys Val Ala Ala Leu Lys Glu Lys Val Ala Ala
                245                 250                 255

Leu Lys Glu Lys Val Ala Ala Leu Glu Lys Val Ala Ala Leu Lys
        260                 265                 270

Glu

<210> SEQ ID NO 85
<211> LENGTH: 447
<212> TYPE: PRT
<213> ORGANISM: Artificial Sequence
<220> FEATURE:
<223> OTHER INFORMATION: Third Polypeptide Chain of Exemplary ROR1 mAb
      1 / CD3 mAb 2 / CD8 mAb 1 Tri--Specific Binding Molecule (Heavy
      Chain CD8 mAb 1)

<400> SEQUENCE: 85

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
            305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Ser Cys
                355                 360                 365

Ala Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Arg Tyr Thr Gln Lys Ser Leu Ser Leu Ser Pro Gly
                435                 440                 445

<210> SEQ ID NO 86
<211> LENGTH: 214
<212> TYPE: PRT
<213> ORGANISM: Artificial Sequence
<220> FEATURE:
<223> OTHER INFORMATION: Fourth Polypeptide Chain of Exemplary ROR1 mAb
      1 / CD3 mAb 2 / CD8 mAb 1 Tri--Specific Binding Molecule (Light
      Chain CD8 mAb 1)

<400> SEQUENCE: 86

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
                20                  25                  30

Leu Ala Trp Tyr Gln Glu Lys Pro Gly Lys Thr Asn Lys Leu Leu Ile
                35                  40                  45

Tyr Ser Gly Ser Thr Leu Gln Ser Gly Ile Pro Ser Arg Phe Ser Gly
            50                  55                  60

Ser Gly Ser Gly Thr Asp Phe Thr Leu Thr Ile Ser Gly Leu Glu Pro
65              70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 87
<211> LENGTH: 510
<212> TYPE: PRT
<213> ORGANISM: Artificial Sequence
<220> FEATURE:
<223> OTHER INFORMATION: First Polypeptide Chain of Exemplary ROR1 mAb
1 / CD3 mAb 2 / CD8 mAb 2 Tri--Specific Binding Molecule (VL(ROR1
mAb 1)-VH(CD3 mAb 2)-E-Coil-(CH2-CH3))

<400> SEQUENCE: 87

```
Gln Leu Val Leu Thr Gln Ser Pro Ser Ala Ser Ala Ser Leu Gly Ser
1               5                   10                  15

Ser Val Lys Leu Thr Cys Thr Leu Ser Ser Gly His Lys Thr Asp Thr
            20                  25                  30

Ile Asp Trp Tyr Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Gly Ser Gly Ser Ser Gly Ala Asp Arg Tyr Leu Thr Ile
65                  70                  75                  80

Ser Ser Leu Gln Ser Glu Asp Glu Ala Asp Tyr Tyr Cys Gly Thr Asp
                85                  90                  95

Tyr Pro Gly Asn Tyr Leu Phe Gly Gly Gly Thr Gln Leu Thr Val Leu
            100                 105                 110

Gly Gly Gly Gly Ser Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Gly Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Cys Gly Gly Glu Val Ala Ala
                245                 250                 255

Leu Glu Lys Glu Val Ala Ala Leu Glu Lys Glu Val Ala Ala Leu Glu
            260                 265                 270

Lys Glu Val Ala Ala Leu Glu Lys Gly Gly Gly Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350
```

Lys Pro Arg Glu Glu Gln Tyr Asn Ser Thr Tyr Arg Val Val Ser Val
355 360 365

Leu Thr Val Leu His Gln Asp Trp Leu Asn Gly Lys Glu Tyr Lys Cys
370 375 380

Lys Val Ser Asn Lys Ala Leu Pro Ala Pro Ile Glu Lys Thr Ile Ser
385 390 395 400

Lys Ala Lys Gly Gln Pro Arg Glu Pro Gln Val Tyr Thr Leu Pro Pro
405 410 415

Ser Arg Glu Glu Met Thr Lys Asn Gln Val Ser Leu Trp Cys Leu Val
420 425 430

Lys Gly Phe Tyr Pro Ser Asp Ile Ala Val Glu Trp Glu Ser Asn Gly
435 440 445

Gln Pro Glu Asn Asn Tyr Lys Thr Thr Pro Pro Val Leu Asp Ser Asp
450 455 460

Gly Ser Phe Phe Leu Tyr Ser Lys Leu Thr Val Asp Lys Ser Arg Trp
465 470 475 480

Gln Gln Gly Asn Val Phe Ser Cys Ser Val Met His Glu Ala Leu His
485 490 495

Asn His Tyr Thr Gln Lys Ser Leu Ser Leu Ser Pro Gly Lys
500 505 510

<210> SEQ ID NO 88
<211> LENGTH: 273
<212> TYPE: PRT
<213> ORGANISM: Artificial Sequence
<220> FEATURE:
<223> OTHER INFORMATION: Second Polypeptide Chain of Exemplary ROR1 mAb
 1 / CD3 mAb 2 / CD8 mAb 2 Tri--Specific Binding Molecule (VL(CD3
 mAb 2)-VH(ROR1 mAb 1)-K-Coil)

<400> SEQUENCE: 88

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Trp Thr Pro Ala Arg Phe
50 55 60

Ser Gly Ser Leu Leu Gly Gly Lys Ala Ala Leu Thr Ile Thr Gly Ala
65 70 75 80

Gln Ala Glu Asp Glu Ala Asp Tyr Tyr Cys Ala Leu Trp Tyr Ser Asn
85 90 95

Leu Trp Val Phe Gly Gly Gly Thr Lys Leu Thr Val Leu Gly Gly Gly
100 105 110

Gly Ser Gly Gly Gly Gly Gln Glu Gln Leu Val Glu Ser Gly Gly Gly
115 120 125

Leu Val Gln Pro Gly Gly Ser Leu Arg Leu Ser Cys Ala Ala Ser Gly
130 135 140

Phe Thr Phe Ser Asp Tyr Tyr Met Ser Trp Val Arg Gln Ala Pro Gly
145 150 155 160

Lys Gly Leu Glu Trp Val Ala Thr Ile Tyr Pro Ser Ser Gly Lys Thr
165 170 175

Tyr Tyr Ala Asp Ser Val Lys Gly Arg Phe Thr Ile Ser Ser Asp Asn
180 185 190

Ala Lys Asn Ser Leu Tyr Leu Gln Met Asn Ser Leu Arg Ala Glu Asp 195                 200                 205
Thr Ala Val Tyr Tyr Cys Ala Arg Asp Ser Tyr Ala Asp Ala Ala
    210                 215                 220

Leu Phe Asp Ile Trp Gly Gln Gly Thr Thr Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu

<210> SEQ ID NO 89
<211> LENGTH: 451
<212> TYPE: PRT
<213> ORGANISM: Artificial Sequence
<220> FEATURE:
<223> OTHER INFORMATION: Third Polypeptide Chain of Exemplary ROR1 mAb
      1 / CD3 mAb 2 / CD8 mAb 2 Tri--Specific Binding Molecule (Heavy
      Chain CD8 mAb 2)

<400> SEQUENCE: 89

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

```
Glu Asp Pro Glu Val Lys Phe Asn Trp Tyr Val Asp Gly Val Glu Val
            275                 280                 285

His Asn Ala Lys Thr Lys Pro Arg Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Tyr Thr Gln Lys Ser Leu Ser Leu Ser
            435                 440                 445

Pro Gly Lys
    450

<210> SEQ ID NO 90
<211> LENGTH: 213
<212> TYPE: PRT
<213> ORGANISM: Artificial Sequence
<220> FEATURE:
<223> OTHER INFORMATION: Fourth Polypeptide Chain of Exemplary ROR1 mAb
      1 / CD3 mAb 2 / CD8 mAb 2 Tri--Specific Binding Molecule (Light
      Chain CD8 mAb 2)

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Tyr Gln Tyr Asn Asn Gly Tyr Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                    165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 91
<211> LENGTH: 509
<212> TYPE: PRT
<213> ORGANISM: Artificial Sequence
<220> FEATURE:
<223> OTHER INFORMATION: First Polypeptide Chain of Exemplary HIV mAb
      1 / CD3 mAb 2 / CD8 mAb 1 Tri--Specific Binding Molecule (VL(HIV
      mAb 1)-VH(CD3 mAb 2)-E-Coil-(CH2-CH3))

<400> SEQUENCE: 91

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Gly Arg Phe Thr
            180                 185                 190

Ile Ser Arg Asp Asp Ser Lys Asn Ser Leu Tyr Leu Gln Met Asn Ser
        195                 200                 205

Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Ala Ser Thr Lys Gly Glu Val Ala Ala Cys
                245                 250                 255

Glu Lys Glu Val Ala Ala Leu Glu Lys Glu Val Ala Ala Leu Glu Lys
            260                 265                 270

Glu Val Ala Ala Leu Glu Lys Gly Gly Gly Asp Lys Thr His Thr Cys
        275                 280                 285

Pro Pro Cys Pro Ala Pro Glu Ala Ala Gly Gly Pro Ser Val Phe Leu
    290                 295                 300
```

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
            325                 330                 335

Phe Asn Trp Tyr Val Asp Gly Val Glu Val His Asn Ala Lys Thr Lys
                340                 345                 350

Pro Arg Glu Glu Gln Tyr Asn Ser Thr Tyr Arg Val Val Ser Val Leu
            355                 360                 365

Thr Val Leu His Gln Asp Trp Leu Asn Gly Lys Glu Tyr Lys Cys Lys
370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
            405                 410                 415

Arg Glu Glu Met Thr Lys Asn Gln Val Ser Leu Trp Cys Leu Val Lys
            420                 425                 430

Gly Phe Tyr Pro Ser Asp Ile Ala Val Glu Trp Glu Ser Asn Gly Gln
            435                 440                 445

Pro Glu Asn Asn Tyr Lys Thr Thr Pro Pro Val Leu Asp Ser Asp Gly
450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
            485                 490                 495

His Tyr Thr Gln Lys Ser Leu Ser Leu Ser Pro Gly Lys
            500                 505

<210> SEQ ID NO 92
<211> LENGTH: 277
<212> TYPE: PRT
<213> ORGANISM: Artificial Sequence
<220> FEATURE:
<223> OTHER INFORMATION: Second Polypeptide Chain of Exemplary HIV mAb
      1 / CD3 mAb 2 / CD8 mAb 1 Tri--Specific Binding Molecule (VL(CD3
      mAb 2)-VH(HIV mAb 1)-K-Coil)

<400> SEQUENCE: 92

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Gly Gly
        115                 120                 125

Val Phe Lys Pro Gly Gly Ser Leu Arg Leu Ser Cys Glu Ala Ser Gly
    130                 135                 140

```
Phe Thr Phe Thr Glu Tyr Tyr Met Thr Trp Val Arg Gln Ala Pro Gly
145                 150                 155                 160

Lys Gly Leu Glu Trp Leu Ala Tyr Ile Ser Lys Asn Gly Glu Tyr Ser
                165                 170                 175

Lys Tyr Ser Pro Ser Ser Asn Gly Arg Phe Thr Ile Ser Arg Asp Asn
            180                 185                 190

Ala Lys Asn Ser Val Phe Leu Gln Leu Asp Arg Leu Ser Ala Asp Asp
    195                 200                 205

Thr Ala Val Tyr Tyr Cys Ala Arg Ala Asp Gly Leu Thr Tyr Phe Ser
210                 215                 220

Glu Leu Leu Gln Tyr Ile Phe Asp Leu Trp Gly Gln Gly Ala Arg Val
225                 230                 235                 240

Thr Val Ser Ser Ala Ser Thr Lys Gly Lys Val Ala Ala Cys Lys Glu
                245                 250                 255

Lys Val Ala Ala Leu Lys Glu Lys Val Ala Ala Leu Lys Glu Lys Val
            260                 265                 270

Ala Ala Leu Lys Glu
            275

<210> SEQ ID NO 93
<211> LENGTH: 447
<212> TYPE: PRT
<213> ORGANISM: Artificial Sequence
<220> FEATURE:
<223> OTHER INFORMATION: Third Polypeptide Chain of Exemplary HIV mAb
      1 / CD3 mAb 2 / CD8 mAb 1 Tri--Specific Binding Molecule (Heavy
      Chain CD8 mAb 1)

<400> SEQUENCE: 93

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Ile His Phe Val Arg Gln Arg Pro Glu Gln Gly Leu Glu Trp Ile
            35                  40                  45

Gly Arg Ile Asp Pro Ala Asn Asp Asn Thr Leu Tyr Ala Ser Lys Phe
50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
```

```
                210                 215                 220
His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Ser Cys
                355                 360                 365

Ala Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Arg Tyr Thr Gln Lys Ser Leu Ser Leu Ser Pro Gly
                435                 440                 445

<210> SEQ ID NO 94
<211> LENGTH: 214
<212> TYPE: PRT
<213> ORGANISM: Artificial Sequence
<220> FEATURE:
<223> OTHER INFORMATION: Fourth Polypeptide Chain of Exemplary HIV mAb
      1 / CD3 mAb 2 / CD8 mAb 1 Tri--Specific Binding Molecule (Light
      Chain CD8 mAb 1)

<400> SEQUENCE: 94

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
                20                  25                  30

Leu Ala Trp Tyr Gln Glu Lys Pro Gly Lys Thr Asn Lys Leu Leu Ile
                35                  40                  45

Tyr Ser Gly Ser Thr Leu Gln Ser Gly Ile Pro Ser Arg Phe Ser Gly
                50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Arg Thr Val Ala Ala
                100                 105                 110

Pro Ser Val Phe Ile Phe Pro Pro Ser Asp Glu Gln Leu Lys Ser Gly
                115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 95
<211> LENGTH: 506
<212> TYPE: PRT
<213> ORGANISM: Artificial Sequence
<220> FEATURE:
<223> OTHER INFORMATION: First Polypeptide Chain of Exemplary HIV mAb
      2 / CD3 mAb 2 / CD8 mAb 1 Tri--Specific Binding Molecule (VL(HIV
      mAb 2)-VH(CD3 mAb 2)-E-Coil-(CH2-CH3))

<400> SEQUENCE: 95

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
130                 135                 140

Phe Thr Phe Ser Thr Tyr Ala Met Asn Trp Val Arg Gln Ala Pro Gly
145                 150                 155                 160

Lys Gly Leu Glu Trp Val Gly Arg Ile Arg Ser Lys Tyr Asn Asn Tyr
                165                 170                 175

Ala Thr Tyr Tyr Ala Asp Ser Val Lys Gly Arg Phe Thr Ile Ser Arg
            180                 185                 190

Asp Asp Ser Lys Asn Ser Leu Tyr Leu Gln Met Asn Ser Leu Lys Thr
        195                 200                 205

Glu Asp Thr Ala Val Tyr Tyr Cys Val Arg His Gly Asn Phe Gly Asn
210                 215                 220

Ser Tyr Val Ser Trp Phe Ala Tyr Trp Gly Gln Gly Thr Leu Val Thr
225                 230                 235                 240

Val Ser Ser Ala Ser Thr Lys Gly Glu Val Ala Ala Cys Glu Lys Glu
                245                 250                 255
```

Val Ala Ala Leu Glu Lys Glu Val Ala Ala Leu Glu Lys Glu Val Ala
            260                 265                 270

Ala Leu Glu Lys Gly Gly Gly Asp Lys Thr His Thr Cys Pro Pro Cys
        275                 280                 285

Pro Ala Pro Glu Ala Ala Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Trp Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 96
<211> LENGTH: 274
<212> TYPE: PRT
<213> ORGANISM: Artificial Sequence
<220> FEATURE:
<223> OTHER INFORMATION: Second Polypeptide Chain of Exemplary HIV mAb
      2 / CD3 mAb 2 / CD8 mAb 1 Tri--Specific Binding Molecule (VL(CD3
      mAb 2)-VH(HIV mAb 2)-K-Coil)

<400> SEQUENCE: 96

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly

```
                    100                 105                 110
Gly Ser Gly Gly Gly Gln Val Gln Leu Gln Glu Ser Gly Pro Gly
        115                 120                 125
Leu Val Lys Pro Ser Gln Thr Leu Ser Leu Ser Cys Thr Val Ser Gly
    130                 135                 140
Gly Ser Ser Ser Gly Ala His Tyr Trp Ser Trp Ile Arg Gln Tyr
145                 150                 155                 160
Pro Gly Lys Gly Leu Glu Trp Ile Gly Tyr Ile His Tyr Ser Gly Asn
                165                 170                 175
Thr Tyr Tyr Asn Pro Ser Leu Lys Ser Arg Ile Thr Ile Ser Gln His
            180                 185                 190
Thr Ser Glu Asn Gln Phe Ser Leu Lys Leu Asn Ser Val Thr Val Ala
        195                 200                 205
Asp Thr Ala Val Tyr Tyr Cys Ala Arg Gly Thr Arg Leu Arg Thr Leu
    210                 215                 220
Arg Asn Ala Phe Asp Ile Trp Gly Gln Gly Thr Leu Val Thr Val Ser
225                 230                 235                 240
Ser Ala Ser Thr Lys Gly Lys Val Ala Ala Cys Lys Glu Lys Val Ala
                245                 250                 255
Ala Leu Lys Glu Lys Val Ala Ala Leu Lys Glu Lys Val Ala Ala Leu
            260                 265                 270
Lys Glu
```

<210> SEQ ID NO 97
<211> LENGTH: 447
<212> TYPE: PRT
<213> ORGANISM: Artificial Sequence
<220> FEATURE:
<223> OTHER INFORMATION: Third Polypeptide Chain of Exemplary HIV mAb 2 / CD3 mAb 2 / CD8 mAb 1 Tri--Specific Binding Molecule (Heavy Chain CD8 mAb 1)

<400> SEQUENCE: 97

```
Glu Val Gln Leu Gln Gln Ser Gly Ala Glu Leu Val Lys Pro Gly Ala
1               5                  10                  15
Ser Val Lys Leu Ser Cys Thr Ala Ser Gly Phe Asn Ile Lys Asp Thr
            20                  25                  30
Tyr Ile His Phe Val Arg Gln Arg Pro Glu Gln Gly Leu Glu Trp Ile
        35                  40                  45
Gly Arg Ile Asp Pro Ala Asn Asp Asn Thr Leu Tyr Ala Ser Lys Phe
    50                  55                  60
Gln Gly Lys Ala Thr Ile Thr Ala Asp Thr Ser Ser Asn Thr Ala Tyr
65                  70                  75                  80
Met His Leu Cys Ser Leu Thr Ser Gly Asp Thr Ala Val Tyr Tyr Cys
                85                  90                  95
Gly Arg Gly Tyr Gly Tyr Tyr Val Phe Asp His Trp Gly Gln Gly Thr
            100                 105                 110
Thr Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
```

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly
        435                 440                 445

<210> SEQ ID NO 98
<211> LENGTH: 214
<212> TYPE: PRT
<213> ORGANISM: Artificial Sequence
<220> FEATURE:
<223> OTHER INFORMATION: Fourth Polypeptide Chain of Exemplary HIV mAb
    2 / CD3 mAb 2 / CD8 mAb 1 Tri--Specific Binding Molecule (Light
    Chain CD8 mAb 1)

<400> SEQUENCE: 98

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu

```
                85                  90                  95

Thr Phe Gly Ala Gly Thr Lys Leu Glu Leu Arg Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 99
<211> LENGTH: 110
<212> TYPE: PRT
<213> ORGANISM: Artificial Sequence
<220> FEATURE:
<223> OTHER INFORMATION: Variable Light Chain Domain of Anti-Human CD3
      mAb 2 Low

<400> SEQUENCE: 99

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
                100                 105                 110

<210> SEQ ID NO 100
<211> LENGTH: 125
<212> TYPE: PRT
<213> ORGANISM: Artificial Sequence
<220> FEATURE:
<223> OTHER INFORMATION: Variable Heavy Chain Domain of Anti-Human CD3
      mAb 2 Low

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
```

```
                50                  55                  60
Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Thr Trp Phe
                100                 105                 110

Ala Tyr Trp Gly Gln Gly Thr Leu Val Thr Val Ser Ser
            115                 120                 125

<210> SEQ ID NO 101
<211> LENGTH: 110
<212> TYPE: PRT
<213> ORGANISM: Artificial Sequence
<220> FEATURE:
<223> OTHER INFORMATION: Variable Light Chain Domain of Anti-Human CD3
      mAb 2 Fast

<400> SEQUENCE: 101

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                 20                  25                  30

Asn Tyr Ala Asn Trp Val Gln Gln Lys Pro Gly Gln Ala Pro Arg Gly
             35                  40                  45

Leu Ile Gly Gly Thr Asn Lys Arg Ala Pro Trp Thr Pro Ala Arg Phe
         50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly
                100                 105                 110

<210> SEQ ID NO 102
<211> LENGTH: 125
<212> TYPE: PRT
<213> ORGANISM: Artificial Sequence
<220> FEATURE:
<223> OTHER INFORMATION: Variable Heavy Chain Domain of Anti-Human CD3
      mAb 2 Fast

<400> SEQUENCE: 102

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
             35                  40                  45

Gly Arg Ile Arg Ser Lys Tyr Asn Asn Tyr Ala Thr Tyr Tyr Ala Asp
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Lys Asn Phe Gly Asn Ser Tyr Val Thr Trp Phe
                100                 105                 110

Ala Tyr Trp Gly Gln Gly Thr Leu Val Thr Val Ser Ser
            115                 120                 125
```

<210> SEQ ID NO 103
<211> LENGTH: 504
<212> TYPE: PRT
<213> ORGANISM: Artificial Sequence
<220> FEATURE:
<223> OTHER INFORMATION: First Polypeptide Chain of Exemplary 5T4 mAb
1 / CD3 mAb 2 / CD8 mAb 1 Tri--Specific Binding Molecule (VL(5T4
mAb 1)-VH(CD3 mAb 2)-E-Coil-(CH2-CH3))

<400> SEQUENCE: 103

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350
```

```
Tyr Asn Ser Thr Tyr Arg Val Ser Val Leu Thr Val Leu His Gln
            355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
    450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 104
<211> LENGTH: 270
<212> TYPE: PRT
<213> ORGANISM: Artificial Sequence
<220> FEATURE:
<223> OTHER INFORMATION: Second Polypeptide Chain of Exemplary 5T4 mAb
      1 / CD3 mAb 2 / CD8 mAb 1 Tri--Specific Binding Molecule (VL(CD3
      mAb 2)-VH(5T4 mAb 1)-K-Coil)

<400> SEQUENCE: 104

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Phe Trp Met His Trp Val Arg Gln Ala Pro Gly
145                 150                 155                 160

Gln Gly Leu Glu Trp Met Gly Arg Ile Asp Pro Asn Arg Gly Gly Thr
                165                 170                 175

Glu Tyr Asn Glu Lys Ala Lys Ser Arg Val Thr Met Thr Ala Asp Lys
            180                 185                 190
```

-continued

```
Ser Thr Ser Thr Ala Tyr Met Glu Leu Ser Ser Leu Arg Ser Glu Asp
            195                 200                 205

Thr Ala Val Tyr Tyr Cys Ala Gly Gly Asn Pro Tyr Tyr Pro Met Asp
        210                 215                 220

Tyr Trp Gly Gln Gly Thr Thr Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 105
<211> LENGTH: 448
<212> TYPE: PRT
<213> ORGANISM: Artificial Sequence
<220> FEATURE:
<223> OTHER INFORMATION: Third Polypeptide Chain of Exemplary 5T4 mAb
      1 / CD3 mAb 2 / CD8 mAb 1 Tri--Specific Binding Molecule (Heavy
      Chain CD8 mAb 1)

<400> SEQUENCE: 105

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
            275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Ser Cys
            355                 360                 365
Ala Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Val Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn Arg Tyr Thr Gln Lys Ser Leu Ser Leu Ser Pro Gly Lys
        435                 440                 445

<210> SEQ ID NO 106
<211> LENGTH: 214
<212> TYPE: PRT
<213> ORGANISM: Artificial Sequence
<220> FEATURE:
<223> OTHER INFORMATION: Fourth Polypeptide Chain of Exemplary 5T4 mAb
      1 / CD3 mAb 2 / CD8 mAb 1 Tri--Specific Binding Molecule (Light
      Chain CD8 mAb 1)

<400> SEQUENCE: 106

Asp Val Gln Ile Asn Gln Ser Pro Ser Phe Leu Ala Ala Ser Pro Gly
1               5                   10                  15
Glu Thr Ile Thr Ile Asn Cys Arg Thr Ser Arg Ser Ile Ser Gln Tyr
            20                  25                  30
Leu Ala Trp Tyr Gln Glu Lys Pro Gly Lys Thr Asn Lys Leu Leu Ile
        35                  40                  45
Tyr Ser Gly Ser Thr Leu Gln Ser Gly Ile Pro Ser Arg Phe Ser Gly
    50                  55                  60
Ser Gly Ser Gly Thr Asp Phe Thr Leu Thr Ile Ser Gly Leu Glu Pro
65                  70                  75                  80
Glu Asp Phe Ala Met Tyr Tyr Cys Gln Gln His Asn Glu Asn Pro Leu
                85                  90                  95
Thr Phe Gly Ala Gly Thr Lys Leu Glu Leu Arg Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
        210

<210> SEQ ID NO 107
<211> LENGTH: 503
<212> TYPE: PRT
<213> ORGANISM: Artificial Sequence
<220> FEATURE:
<223> OTHER INFORMATION: First Polypeptide Chain of Exemplary 5T4 mAb
      1 / CD3 mAb 2 Low / CD8 mAb 1 Tri--Specific Binding Molecule
      (VL(5T4 mAb 1)-VH(CD3 mAb 2 Low)-E-Coil-(CH2-CH3))

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
            85                  90                  95

Thr Phe Gly Gln Gly Thr Lys Leu Glu Ile Lys Gly Gly Gly Ser Gly
        100                 105                 110

Gly Gly Gly Glu Val Gln Leu Val Glu Ser Gly Gly Gly Leu Val Gln
    115                 120                 125

Pro Gly Gly Ser Leu Arg Leu Ser Cys Ala Ala Ser Gly Phe Thr Phe
130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
            165                 170                 175

Tyr Ala Asp Ser Val Lys Gly Arg Phe Thr Ile Ser Arg Asp Asp Ser
        180                 185                 190

Lys Asn Ser Leu Tyr Leu Gln Met Asn Ser Leu Lys Thr Glu Asp Thr
    195                 200                 205

Ala Val Tyr Tyr Cys Val Arg His Gly Asn Phe Gly Asn Ser Tyr Val
210                 215                 220

Thr Trp Phe Ala Tyr Trp Gly Gln Gly Thr Leu Val Thr Val Ser Ser
225                 230                 235                 240

Ala Ser Thr Lys Gly Glu Val Ala Ala Cys Glu Lys Glu Val Ala Ala
            245                 250                 255

Leu Glu Lys Glu Val Ala Ala Leu Glu Lys Glu Val Ala Ala Leu Glu
        260                 265                 270

Lys Gly Gly Gly Asp Lys Thr His Thr Cys Pro Pro Cys Pro Ala Pro
    275                 280                 285

Glu Ala Ala Gly Gly Pro Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

```
Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
        340                 345                 350

Asn Ser Thr Tyr Arg Val Val Ser Val Leu Thr Val Leu His Gln Asp
    355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 108
<211> LENGTH: 269
<212> TYPE: PRT
<213> ORGANISM: Artificial Sequence
<220> FEATURE:
<223> OTHER INFORMATION: Second Polypeptide Chain of Exemplary 5T4 mAb
      1 / CD3 mAb 2 Low / CD8 mAb 1 Tri--Specific Binding Molecule
      (VL(CD3 mAb 2 Low)-VH(5T4 mAb 1)-K-Coil)

<400> SEQUENCE: 108

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Phe Trp Met His Trp Val Arg Gln Ala Pro Gly
145                 150                 155                 160

Gln Gly Leu Glu Trp Met Gly Arg Ile Asp Pro Asn Arg Gly Gly Thr
```

-continued

```
                165                 170                 175
Glu Tyr Asn Glu Lys Ala Lys Ser Arg Val Thr Met Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Gly Gly Asn Pro Tyr Tyr Pro Met Asp
    210                 215                 220

Tyr Trp Gly Gln Gly Thr Thr Val Thr Val Ser Ser Ala Ser Thr Lys
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 109
<211> LENGTH: 448
<212> TYPE: PRT
<213> ORGANISM: Artificial Sequence
<220> FEATURE:
<223> OTHER INFORMATION: Third Polypeptide Chain of Exemplary 5T4 mAb
      1 / CD3 mAb 2 Low / CD8 mAb 1 Tri--Specific Binding Molecule
      (Heavy Chain CD8 mAb 1)

<400> SEQUENCE: 109

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445

<210> SEQ ID NO 110
<211> LENGTH: 214
<212> TYPE: PRT
<213> ORGANISM: Artificial Sequence
<220> FEATURE:
<223> OTHER INFORMATION: Fourth Polypeptide Chain of Exemplary 5T4 mAb
      1 / CD3 mAb 2 Low / CD8 mAb 1 Tri--Specific Binding Molecule
      (Light Chain CD8 mAb 1)

<400> SEQUENCE: 110

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 503
<212> TYPE: PRT
<213> ORGANISM: Artificial Sequence
<220> FEATURE:
<223> OTHER INFORMATION: First Polypeptide Chain of Exemplary 5T4 mAb
      1 / CD3 mAb 2 Fast / CD8 mAb 1 Tri--Specific Binding Molecule
      (VL(5T4 mAb 1)-VH(CD3 mAb 2 Fast)-E-Coil-(CH2-CH3))

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145             150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Lys Asn Phe Gly Asn Ser Tyr Val
    210                 215                 220

Thr Trp Phe Ala Tyr Trp Gly Gln Gly Thr Leu Val Thr Val Ser Ser
225             230                 235                 240

Ala Ser Thr Lys Gly Glu Val Ala Ala Cys Glu Lys Glu Val Ala Ala
            245                 250                 255

Leu Glu Lys Glu Val Ala Ala Leu Glu Lys Glu Val Ala Ala Leu Glu
        260                 265                 270

Lys Gly Gly Gly Asp Lys Thr His Thr Cys Pro Pro Cys Pro Ala Pro
    275                 280                 285

Glu Ala Ala Gly Gly Pro Ser Val Phe Leu Phe Pro Pro Lys Pro Lys
```

```
                    290                 295                 300
Asp Thr Leu Met Ile Ser Arg Thr Pro Glu Val Thr Cys Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
        370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
                420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
        450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500

<210> SEQ ID NO 112
<211> LENGTH: 269
<212> TYPE: PRT
<213> ORGANISM: Artificial Sequence
<220> FEATURE:
<223> OTHER INFORMATION: Second Polypeptide Chain of Exemplary 5T4 mAb
      1 / CD3 mAb 2 Fast / CD8 mAb 1 Tri--Specific Binding Molecule
      (VL(CD3 mAb 2 Fast)-VH(5T4 mAb 1)-K-Coil)

<400> SEQUENCE: 112

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Gln Val Gln Leu Val Gln Ser Gly Ala Glu
            115                 120                 125

Val Lys Lys Pro Gly Ala Ser Val Lys Val Ser Cys Lys Ala Ser Gly
        130                 135                 140
```

```
Tyr Thr Phe Thr Ser Phe Trp Met His Trp Val Arg Gln Ala Pro Gly
145                 150                 155                 160

Gln Gly Leu Glu Trp Met Gly Arg Ile Asp Pro Asn Arg Gly Gly Thr
            165                 170                 175

Glu Tyr Asn Glu Lys Ala Lys Ser Arg Val Thr Met Thr Ala Asp Lys
        180                 185                 190

Ser Thr Ser Thr Ala Tyr Met Glu Leu Ser Ser Leu Arg Ser Glu Asp
    195                 200                 205

Thr Ala Val Tyr Tyr Cys Ala Gly Gly Asn Pro Tyr Tyr Pro Met Asp
210                 215                 220

Tyr Trp Gly Gln Gly Thr Thr Val Thr Val Ser Ser Ala Ser Thr Lys
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
                260                 265

<210> SEQ ID NO 113
<211> LENGTH: 448
<212> TYPE: PRT
<213> ORGANISM: Artificial Sequence
<220> FEATURE:
<223> OTHER INFORMATION: Third Polypeptide Chain of Exemplary 5T4 mAb
      1 / CD3 mAb 2 Fast / CD8 mAb 1 Tri--Specific Binding Molecule
      (Heavy Chain CD8 mAb 1)

<400> SEQUENCE: 113

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220
```

```
His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445

<210> SEQ ID NO 114
<211> LENGTH: 214
<212> TYPE: PRT
<213> ORGANISM: Artificial Sequence
<220> FEATURE:
<223> OTHER INFORMATION: Fourth Polypeptide Chain of Exemplary 5T4 mAb
      1 / CD3 mAb 2 Fast / CD8 mAb 1 Tri--Specific Binding Molecule
      (Light Chain CD8 mAb 1)

<400> SEQUENCE: 114

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 115
<211> LENGTH: 28
<212> TYPE: PRT
<213> ORGANISM: Artificial Sequence
<220> FEATURE:
<223> OTHER INFORMATION: Cysteine-Containing E-Coil Heterodimer-
      Promoting Domain

<400> SEQUENCE: 115

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 116
<211> LENGTH: 28
<212> TYPE: PRT
<213> ORGANISM: Artificial Sequence
<220> FEATURE:
<223> OTHER INFORMATION: Cysteine-Containing K-Coil Heterodimer-
      Promoting Domain

<400> SEQUENCE: 116

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 117
<211> LENGTH: 12
<212> TYPE: PRT
<213> ORGANISM: Artificial Sequence
<220> FEATURE:
<223> OTHER INFORMATION: Anti-ROR1 mAb 1 Light Chain Variable Domain
      CDRL1

<400> SEQUENCE: 117

Thr Leu Ser Ser Gly His Lys Thr Asp Thr Ile Asp
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Anti-ROR1 mAb 1 Light Chain Variable Domain
      CDRL2

<400> SEQUENCE: 118

Leu Glu Gly Ser Gly Ser Tyr
1               5
```

```
<210> SEQ ID NO 119
<211> LENGTH: 9
<212> TYPE: PRT
<213> ORGANISM: Artificial Sequence
<220> FEATURE:
<223> OTHER INFORMATION: Anti-ROR1 mAb 1 Light Chain Variable Domain
      CDRL3

<400> SEQUENCE: 119

Gly Thr Asp Tyr Pro Gly Asn Tyr Leu
1               5

<210> SEQ ID NO 120
<211> LENGTH: 10
<212> TYPE: PRT
<213> ORGANISM: Artificial Sequence
<220> FEATURE:
<223> OTHER INFORMATION: Anti-ROR1 mAb 1 Heavy Chain Variable Domain
      CDRH1

<400> SEQUENCE: 120

Gly Phe Thr Phe Ser Asp Tyr Tyr Met Ser
1               5                   10

<210> SEQ ID NO 121
<211> LENGTH: 17
<212> TYPE: PRT
<213> ORGANISM: Artificial Sequence
<220> FEATURE:
<223> OTHER INFORMATION: Anti-ROR1 mAb 1 Heavy Chain Variable Domain
      CDRH2

<400> SEQUENCE: 121

Thr Ile Tyr Pro Ser Ser Gly Lys Thr Tyr Tyr Ala Asp Ser Val Lys
1               5                   10                  15

Gly

<210> SEQ ID NO 122
<211> LENGTH: 12
<212> TYPE: PRT
<213> ORGANISM: Artificial Sequence
<220> FEATURE:
<223> OTHER INFORMATION: Anti-ROR1 mAb 1 Heavy Chain Variable Domain
      CDRH3

<400> SEQUENCE: 122

Asp Ser Tyr Ala Asp Asp Ala Ala Leu Phe Asp Ile
1               5                   10

<210> SEQ ID NO 123
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus Strain G148

<400> SEQUENCE: 123

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45
```

<210> SEQ ID NO 124
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148

<400> SEQUENCE: 124

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 125
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148

<400> SEQUENCE: 125

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 126
<211> LENGTH: 4
<212> TYPE: PRT
<213> ORGANISM: Artificial Sequence
<220> FEATURE:
<223> OTHER INFORMATION: Peptide Linker

<400> SEQUENCE: 126

Gly Gly Gly Ser
1

<210> SEQ ID NO 127
<211> LENGTH: 6
<212> TYPE: PRT
<213> ORGANISM: Artificial Sequence
<220> FEATURE:
<223> OTHER INFORMATION: Cysteine-Containing Domain

<400> SEQUENCE: 127

Ala Glu Pro Lys Ser Cys
1               5

<210> SEQ ID NO 128
<211> LENGTH: 7
<212> TYPE: PRT
<213> ORGANISM: Artificial Sequence
<220> FEATURE:
<223> OTHER INFORMATION: Cysteine-Containing Variant of Portion of Human
      CL Domain

<400> SEQUENCE: 128

Gly Phe Asn Arg Gly Glu Cys

```
1               5

<210> SEQ ID NO 129
<211> LENGTH: 15
<212> TYPE: PRT
<213> ORGANISM: Artificial Sequence
<220> FEATURE:
<223> OTHER INFORMATION: Alternative Cysteine-Containing Linker Peptide
      ("Linker 3")

<400> SEQUENCE: 129

Glu Pro Lys Ser Cys Asp Lys Thr His Thr Cys Pro Pro Cys Pro
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Alternative Cysteine-Containing Linker Peptide
      ("Linker 3")

<400> SEQUENCE: 130

Leu Glu Pro Lys Ser Ser Asp Lys Thr His Thr Cys Pro Pro Cys Pro
1               5                   10                  15

<210> SEQ ID NO 131
<211> LENGTH: 5
<212> TYPE: PRT
<213> ORGANISM: Artificial Sequence
<220> FEATURE:
<223> OTHER INFORMATION: Peptide Linker

<400> SEQUENCE: 131

Ala Ser Thr Lys Gly
1               5

<210> SEQ ID NO 132
<211> LENGTH: 6
<212> TYPE: PRT
<213> ORGANISM: Artificial Sequence
<220> FEATURE:
<223> OTHER INFORMATION: Peptide Linker

<400> SEQUENCE: 132

Leu Glu Pro Lys Ser Ser
1               5

<210> SEQ ID NO 133
<211> LENGTH: 7
<212> TYPE: PRT
<213> ORGANISM: Artificial Sequence
<220> FEATURE:
<223> OTHER INFORMATION: Variant of Cysteine-Containing Portion of Human
      IgG Hinge Domain

<400> SEQUENCE: 133

Gly Val Glu Pro Lys Ser Cys
1               5
```

MULTI-CHAIN POLYPEPTIDE-CONTAINING TRI-SPECIFIC BINDING MOLECULES

CROSS-REFERENCE TO RELATED APPLICATIONS

This patent application is a divisional application of U.S. application Ser. No. 15/313,741, filed Nov. 23, 2016, entitled MULTI-CHAIN POLYPEPTIDE-CONTAINING TRI-SPECIFIC BINDING MOLECULES, naming Leslie S. Johnson et al. as inventors, which is a a 35 U.S.C. 371 national phase patent application of International Application No. PCT/US2015/033076, filed on May 29, 2015, entitled TRI-SPECIFIC BINDING MOLECULES AND METHODS OF USE THEREOF, naming Leslie S. Johnson et al. as inventors, which claims priority to U.S. Patent Applications No. 62/008,229 (filed Jun. 5, 2014), 62/004,571 (filed May 29, 2014), and 62/107,824 (filed Jan. 26, 2015), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_0114PCT_Sequence_Listing_ST25.txt, created on 18 May 2015, and having a size of 244,021 bytes), which file is herein incorporated by reference in its entirety.

BACKGROUND OF THE INVENTION

Field of the Invention

The present invention relates to Tri-Specific Binding Molecules, which are multi-chain polypeptide molecules that possess three Binding Domains and are thus capable of mediating coordinated binding to three epitopes. The Binding Domains may be selected such that the Tri-Specific Binding Molecules are capable of binding to any three different epitopes. Such epitopes may be epitopes of the same antigen or epitopes of two or three different antigens. In a preferred embodiment, one of such epitopes will be capable of binding to CD3, the second of such epitopes will be capable of binding to CD8, and the third of such epitopes will be capable of binding to an epitope of a Disease-Associated Antigen. The invention also provides a novel ROR1-binding antibody, as well as derivatives thereof and uses for such compositions.

Description of Related Art

I. The Mammalian Immune System

The mammalian immune system serves as a defense against a variety of conditions, including, e.g., injury, infection and neoplasia. The efficiency with which humans and other mammals develop an immunological response to pathogens, foreign substances and cancer antigens rests on two characteristics: the exquisite specificity of the immune response for antigen recognition, and the immunological memory that allows for faster and more vigorous responses upon re-activation with the same antigen (Portoles, P. et al. (2009) "*The TCR/CD3 Complex: Opening the Gate to Successful Vaccination*," Current Pharmaceutical Design 15:3290-3300; Guy, C. S. et al. (2009) "*Organization of Proximal Signal Initiation at the TCR:CD3 Complex*," Immunol Rev. 232(1):7-21).

The mammalian immune system is mediated by two separate but interrelated systems: the cellular and humoral immune systems. Generally speaking, the humoral system is mediated by soluble products (antibodies or immunoglobulins) that have the ability to combine with and neutralize products recognized by the system as being foreign to the body. In contrast, the cellular immune system involves the mobilization of certain cells, termed "T cells," that serve a variety of therapeutic roles. T cells are lymphocytes that are derived from the thymus and circulate between the tissues, lymphatic system and the circulatory system. In response to the presence and recognition of foreign structures (antigens), T cells become "activated" to initiate an immune response. In many instances these foreign antigens are expressed on host cells as a result of neoplasia or infection. Although T cells do not themselves secrete antibodies, they are usually required for antibody secretion by the second class of lymphocytes, B cells (which derive from bone marrow). Critically, T cells exhibit extraordinary immunological specificity so as to be capable of discerning one antigen from another). Two types of T cells, "T helper cells" and "cytotoxic T cells," are of particular relevance.

T helper cells are characterized by their expression of the glycoprotein, CD4 (i.e., they are "CD4$^+$"). CD4$^+$ T cells are the essential organizers of most mammalian immune and autoimmune responses (Dong, C. et al. (2003) "*Immune Regulation by Novel Costimulatory Molecules*," Immunolog. Res. 28(1):39-48). The activation of CD4$^+$ T cells has been found to be mediated through co-stimulatory interactions between an antigen:major histocompability class II (MHC II) molecule complex that is arrayed on the surface of an Antigen Presenting Cell (such as a B cell, a macrophage or a dendritic cell) and a complex of two molecules, the T Cell Receptor ("TCR") and a CD3 cell-surface receptor ligand, that are arrayed on surface of a naive CD4$^+$ T cell. Activated T helper cells are capable of proliferating into Th1 cells that are capable of mediating an inflammatory response to the target cell.

Cytotoxic T cells are characterized by their expression of CD8 (i.e., they are "CD8+" as well as CD3$^+$). The activation of CD8$^+$ T cells has been found to be mediated through co-stimulatory interactions between an antigen:major histocompatibility class I (MHC I) molecule complex that is arrayed on the surface of a target cell and a complex of CD8 and the T Cell Receptor, that are arrayed on surface of the CD8$^+$ T cell. Unlike MHC II molecules, which are expressed by only certain immune system cells, MHC I molecules are very widely expressed. Thus, cytotoxic T cells are capable of binding to a wide variety of cell types. Activated cytotoxic T cells mediate cell killing through their release of the cytotoxins perforin, granzymes, and granulysin. Through the action of perforin, granzymes enter the cytoplasm of the target cell and their serine protease function triggers the caspase cascade, which is a series of cysteine proteases that eventually lead to apoptosis (programmed cell death) of targeted cells.

The T cell receptor ("TCR") is a covalently linked heterodimer of α and β chains ("TCRαβ"). These chains are class I membrane polypeptides of 259 (α) and 296 (β) amino acids in length. The CD3 molecule is a T cell co-receptor composed of five distinct polypeptide chains (a CD3 γ chain, a CD3 δ chain, two CD3 ε chains and two zeta chains). The individual polypeptide chains associate to form a complex of three dimers (εγ, εδ, ζζ) (Wucherpfennig, K. W. et al. (2010) "*Structural Biology Of The T Cell Receptor: Insights into Receptor Assembly, Ligand Recognition, And Initiation of Signaling*," Cold Spring Harb. Perspect. Biol. 2(4):a005140;

pages 1-14; Chetty, R. et al. (1994) "*CD3: Structure, Function And The Role Of Immunostaining In Clinical Practice*," J. Pathol. 173:303-307; Guy, C. S. et al. (2009) "*Organization of Proximal Signal Initiation at the TCR:CD3 Complex*," Immunol Rev. 232(1):7-21; Call, M. E. et al. (2007) "*Common Themes In The Assembly And Architecture Of Activating Immune Receptors*," Nat. Rev. Immunol. 7:841-850; Weiss, A. (1993) "*T Cell Antigen Receptor Signal Transduction: A Tale Of Tails And Cytoplasmic Protein-Tyrosine Kinases*," Cell 73:209-212). The CD3 complex associates with TCR in order to generate an activation signal in T lymphocytes. In the absence of CD3, TCRs do not assemble properly and are degraded (Thomas, S. et al. (2010) "*Molecular Immunology Lessons From Therapeutic T Cell Receptor Gene Transfer*," Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2):133-139).

The TCR and CD3 complex, along with the CD3 ζ chain zeta chain (also known as T cell receptor T3 zeta chain or CD247) comprise the TCR complex (van der Merwe, P. A. etc. (epub Dec. 3, 2010) "*Mechanisms For T Cell Receptor Triggering*," Nat. Rev. Immunol. 11:47-55; Wucherpfennig, K. W. et al. (2010) "*Structural Biology of the T cell Receptor: Insights into Receptor Assembly, Ligand Recognition, and Initiation of Signaling*," Cold Spring Harb. Perspect. Biol. 2:a005140). The complex is particularly significant since it contains a large number (ten) of immunoreceptor tyrosine-based activation motifs (ITAMs).

Two interactions are required for T cell activation (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). In the first interaction, a Cell must display the relevant target antigen bound to the cell's Major Histocompatibility Complex so that it can bind to the T cell Receptor ("TCR") of a naive T lymphocyte. In the second interaction, a ligand of the Cell must bind to a co-receptor of the T lymphocyte (Dong, C. et al. (2003) "*Immune Regulation by Novel Costimulatory Molecules*," Immunolog. Res. 28(1): 39-48; Lindley, P. S. et al. (2009) "*The Clinical Utility Of Inhibiting CD28-Mediated Costimulation*," Immunol. Rev. 229:307-321). T cells experiencing both stimulatory signals are then capable of responding to cytokines (such as Interleukin-2 and Interleukin-12). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors*," Exper. Pharmacol. 181:291-328). In pathologic states, T cells are the key players of various organ-specific autoimmune diseases, such as type I diabetes, rheumatoid arthritis, and multiple sclerosis (Dong, C. et al. (2003) "*Immune Regulation by Novel Costimulatory Molecules*," Immunolog. Res. 28(1):39-48). E The need for two signals to activate T cells such that they achieve an adaptive immune response is believed to provide a mechanism for avoiding responses to self-antigens that may be present on an Antigen Presenting Cell at locations in the system where it can be recognized by a T cell. Where contact of a T cell with a Cell results in the generation of only one of two required signals, the T cell does not become activated and an adaptive immune response does not occur.

II. Antibodies and Other Epitope-Binding Molecules

A. Antibodies

"Antibodies" are immunoglobulin molecules capable of specific binding to a target, such as a carbohydrate, polynucleotide, lipid, polypeptide, etc., through at least one antigen recognition site, located in the Variable Domain of the immunoglobulin molecule. As used herein, the term encompasses not only intact polyclonal or monoclonal antibodies, but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242. As used herein, an "antigen-binding fragment of an antibody" is a portion of an antibody that possesses an at least one antigen recognition site. As used herein, the term encompasses fragments (e.g., Fab, Fab', F(ab')2 Fv), and single-chain molecules (e.g., scFv).

Natural antibodies (such as IgG antibodies) are composed of two Light Chains complexed with two Heavy Chains. Each Light Chain contains a Variable Domain (VL) and a Constant Domain (CL). Each heavy chain contains a Variable Domain (VH), three Constant Domains (CH1, CH2 and CH3), and a Hinge Domain located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N") portion of each chain includes a variable region of about 100 to 110 or more amino acids primarily responsible for antigen recognition. The carboxy-terminal ("C") portion of each chain defines a constant region, with light chains having a single Constant Domain and heavy chains usually having three Constant Domains and a hinge region. Thus, the structure of the light chains of an IgG molecule is n-VL-CL-c and the structure of the IgG heavy chains is n-VH-CH1-H-CH2-CH3-c (where H is the hinge region, and n and c represent, respectively, the N-terminus and the C-terminus of the polypeptide).

The ability of an intact, unmodified antibody (e.g., an IgG antibody) to bind an epitope of an antigen depends upon the presence of Variable Domains on the immunoglobulin light and heavy chains (i.e., the VL Domain and VH Domain, respectively). Interaction of an antibody Light Chain and an antibody heavy chain and, in particular, interaction of its VL and VH Domains forms one of the epitope-binding sites of the antibody. The variable regions of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated CDR$_L$1 Domain, CDR$_L$2 Domain, and CDR$_L$3 Domain. Similarly, polypeptides that are (or may serve as) the first, second and third CDR of an antibody heavy chain are herein respectively designated CDR$_H$1 Domain, CDR$_H$2 Domain, and CDR$_H$3 Domain. Thus, the terms CDR$_L$1 Domain, CDR$_L$2 Domain, CDR$_L$3 Domain, CDR$_H$1 Domain, CDR$_H$2 Domain, and CDR$_H$3 Domain are directed to polypeptides that when incorporated into a protein cause that protein to be able to bind to an specific epitope regardless of whether such protein is an antibody having light and heavy chains or a diabody or a single-chain binding molecule (e.g., an scFv, a BiTe, etc.), or is another type of protein. In contrast to such antibodies, the scFv construct comprises a VL and VH Domain of an antibody contained in a single polypeptide chain wherein the Domains are separated by a flexible linker of sufficient length to allow self-assembly of the two Domains into a functional epitope-binding site. Where self-assembly of the VL and VH Domains is rendered impossible due to a linker of insufficient length (less than about 12 amino acid residues), two of the scFv constructs may interact with one another other to form a bivalent molecule in which the VL of one chain associates with the VH of the other (reviewed in Marvin et al. (2005) "*Recombinant Approaches To IgG-Like Bispecific Antibodies,*" Acta Pharmacol. Sin. 26:649-658).

In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases,*" Singapore Med. J. 50(7):663-666). Nearly 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')2 Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity,*" Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production,*" ILAR J. 37(3):119-125).

In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate a chimeric antibody, a humanized antibody, or a caninized antibody, or to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807, 715; 5,866,692; and 6,331,415.

The epitope-binding domain of such antibodies may comprise either complete Variable Domains fused onto Constant Domains or only the complementarity determining regions (CDRs) grafted onto appropriate framework regions in the Variable Domains. Antigen-binding sites may be wild-type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response,*" Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified.

Application of this approach to various antibodies has been reported by Sato, K. et al. (1993) Cancer Res 53:851-856. Riechmann, L. et al. (1988) "*Reshaping Human Antibodies for Therapy,*" Nature 332:323-327; Verhoeyen, M. et al. (1988) "*Reshaping Human Antibodies: Grafting An Antilysozyme Activity,*" Science 239:1534-1536; Kettleborough, C. A. et al. (1991) "*Humanization Of A Mouse Monoclonal Antibody By CDR-Grafting: The Importance Of Framework Residues On Loop Conformation,*" Protein Engineering 4:773-3783; Maeda, H. et al. (1991) "*Construction Of Reshaped Human Antibodies With HIV-Neutralizing Activity,*" Human Antibodies Hybridoma 2:124-134; Gorman, S. D. et al. (1991) "*Reshaping A Therapeutic CD4 Antibody,*" Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo,*" Bio/Technology 9:266-271; Co, M. S. et al. (1991) "*Humanized Antibodies For Antiviral Therapy,*" Proc. Natl. Acad. Sci. (U.S.A.) 88:2869-2873; Carter, P. et al. (1992) "*Humanization Of An Anti-p185her2 Antibody For Human Cancer Therapy,*" Proc. Natl. Acad. Sci. (U.S.A.) 89:4285-4289; and Co, M. S. et al. (1992) "*Chimeric And Humanized Antibodies With Specificity For The CD33 Antigen,*" J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

B. Bi-Specific Antibodies, Multi-Specific Diabodies and DART™ Diabodies

Natural antibodies are capable of binding to only one epitope species (i.e., they are "mono-specific"), although they may be able to bind multiple copies of that species (i.e., they may exhibit bi-valency or multi-valency). A wide variety of recombinant bi-specific antibody formats have been developed (see, e.g., PCT Publication Nos. WO 2008/003116, WO 2009/132876, WO 2008/003103, WO 2007/146968, WO 2007/146968, WO 2009/018386, WO 2012/009544, WO 2013/070565), most of which use linker peptides either to fuse the antibody core (IgA, IgD, IgE, IgG or IgM) to a further binding protein (e.g., scFv, VL VH, etc.) to, or within, the antibody core, or to fuse multiple antibody portions or to fuse (e.g. two Fab fragments or scFv) to a Heterodimerization-Promoting Domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a tri-specific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Domains have been replaced with additional VL and VH Domains, so as to form tri-valent binding molecules. PCT Publications Nos. WO 2003/025018 and WO2003012069 disclose recombinant diabodies whose individual chains contain scFv domains. PCT Publications No. WO 2013/006544 discloses multivalent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2007/075270, WO 1998/002463, WO 1992/022583 and WO 1991/003493 disclose adding additional Binding Domains or functional groups to an antibody or an antibody portion (e.g., adding a diabody to the antibody's Light Chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "'*Diabodies': Small Bivalent And Bispecific Antibody Fragments,*" Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity,*" J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications,*" Protein Eng Des Sel. 17(1):21-27; Wu, A. et al. (2001) "*Multimerization Of A Chimeric Anti-CD20 Single-chain Fv-Fv Fusion Protein Is Mediated Through Variable Domain Exchange,*" Protein Engineering 14(2):1025-1033; Asano et al. (2004) "*A Diabody For Cancer Immunotherapy And Its Functional Enhancement By Fusion Of Human Fc Domain,*" Abstract 3P-683, J. Biochem. 76(8):992; Takemura, S. et al. (2000) "*Construction Of A Diabody (Small Recombinant Bispecific Antibody) Using A Refolding System,*" Protein Eng. 13(8):583-588; Baeuerle, P. A. et al. (2009) "*Bispecific T-Cell Engaging Antibodies For Cancer Therapy,*" Cancer Res. 69(12):4941-4944).

The design of a diabody is based on the structure of single-chain Variable Domain fragments (scFv). Such molecules are made by linking light and/or Heavy Chain Variable Domains to one another via a short linking peptide. Bird et al. (1988) ("*Single-Chain Antigen-Binding Proteins,*" Science 242:423-426) describes an example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins,*" Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

U.S. Pat. No. 7,585,952 and United States Patent Publication No. 2010-0173978 concern scFv molecules that are immunospecific for ErbB2. Bi-specific T cell engagers ("BiTEs"), a type of scFv molecule has been described (WO 05/061547; Baeuerle, P et al. (2008) "*BiTE: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977). Such molecules are composed of a single polypeptide chain molecule having two Antigen-Binding Domains, one of which immunospecifically binds to a CD3 epitope and the second of which immunospecifically binds to an antigen present on the surface of a target cell.

The provision of non-mono-specific diabodies provides a significant advantage: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305).

Diabody epitope-binding domains may be directed to a surface determinant of any immune effector cell such as CD3, CD16, CD32, CD64, etc., which are expressed on T lymphocytes, Natural Killer (NK) cells or other mononuclear cells. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197).

For example, U.S. Pat. No. 6,171,586, concerns the production of bi-specific antibodies by proteolytically cleaving two antibodies to obtain their F(ab')2 fragments, reducing such fragments under conditions for preventing intermolecular disulfide bond formation, and then mixing the fragments to generate the bi-specific antibody). U.S. Pat. Nos. 6,551,592; 6,994,853 and 8,277,806 and PCT Publications Nos. WO 2012/156430, WO 2002/020039, WO 2000/018806 and WO 1998/003670 concern the production of tri-specific antibodies capable of simultaneously binding to T cells and other antigens on a tumor cell, and, via the Fc portion of the bi-specific antibody, to the Fc receptor of cells possessing such a receptor. PCT Publications Nos. WO 2000/018806, WO 1998/003670 and WO 2006/072152 concern the production of tri-specific antibodies capable of simultaneously binding to T cells and other antigens. United States Patent Publication No. 2008-0057054 discloses bi-specific conjugates specific for a binding element against amyloid beta oligomers and a binding element against transmembrane protein telencephalin. United States Patent Publication No. 2010-0291112 concerns bi-specific and tri-specific single-chain Fv molecules that specifically bind to a one (or two) tumor antigen(s) and an effector cell antigen (such as CD3, CD16 CD32, CD64, etc.).

PCT Publication Nos. WO 1999/042597 and WO 1998/006749 disclose antibody derivatives that comprise human Major Histocompatibility Complex binding domains, with or without bound MHC binding peptides. PCT Publication No. WO 02/072141 concerns multi-specific binding molecules whose on-rates (rates at which they bind to target molecules) and off-rates (rates at which they release target molecules) differ so as to preferentially bind to one target compared to their binding to the other such target molecule. Tri-specific molecules, for example molecules having a monovalent first portion which is an Anti-CD3 or anti-CD28 antibody, and a second portion comprising a divalent immune function exerting moiety which immunospecifically binds to one or more target ligands on a target diseased cell or immune cell.

U.S. Pat. No. 7,695,936 and Patent Publication 2007/0196363 concern bi-specific antibodies that are formed from the heavy chains of two antibodies, one of which possess a protuberance engineered into its heavy chain and the second of which possess a complementary cavity engineered into its heavy chain. The presence of such complementary "knobs" and "holes" is taught to preferentially form bi-specific hetero-antibodies (having one heavy chain of each such antibody) relative to mono-specific homo-antibodies that contain two heavy chains of the same antibody. Various bi-specific hetero-antibodies are proposed, including those that are immunospecific for CD3 and a tumor cell antigen. Various tri-specific hetero-antibodies are also proposed, including some that are immunospecific for CD3, CD8 and CD37 (a transmembrane protein expressed predominantly on B cells that is involved the regulation of T cell proliferation (Robak, T. et al. (2014) "*Anti-CD37Antibodies For Chronic Lymphocytic Leukemia*," Expert Opin. Biol. Ther. 14(5):651-661), however, no mechanism for their production and no disclosure of their structure is provided.

PCT Publication WO2012-162561 concerns bi-specific, tetravalent binding molecules that comprise two polypeptides, each of which comprises two diabody structures, separated by an intervening CH2-CH3 Domain. The document also concerns tetravalent binding molecules composed of four polypeptide chains in which two of the polypeptide chains contain variable light and variable heavy Domains for two antigens, and in which the other two polypeptide chains contain the complementary variable heavy and variable light Domains for the antigens and a terminal CH2-CH3 Domain. The bi-specific, tetravalent binding molecules form through the association of their respective CH2-CH3 Domains. In the four polypeptide chain construct, the "light" chains are not covalently bound to the heavy chains, thus leading to instability (see, Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672). The document discloses a third construct in which the chains are altered to provide such covalent bonding, but at the cost of eliminating their bi-specificity (i.e., the molecules are mono-specific). Molecules having specificity for CD2, CD3, CD4, CD8, CD161, a chemokine receptor, CD95, CCR5, etc. are disclosed. A bi-specific molecule capable of binding to both CD3 and CD8 is not disclosed.

However, the above advantages come at salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i.e., two polypeptide species) must be provided in order to form a non-mono-specific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (Takemura, S. et al. (2000) "*Construction Of A Diabody (Small Recombinant Bispecific Antibody) Using A Refolding System*," Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bi-specific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-mono-specific diabodies, termed DARTs™ (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond two polypeptide chains. For example, the addition of a cysteine residue to the C-terminus of such constructs has been shown to allow disulfide bonding between the polypeptide chains, stabilizing the resulting heterodimer without interfering with the binding characteristics of the bivalent molecule.

There are many DART™ embodiments. Each of the two polypeptides of the simplest DART™ embodiment comprises three Domains (FIG. 1A). The first polypeptide comprises: (i) a first domain that comprises a binding region of a Light Chain Variable Domain of the a first immunoglobulin (VL1), (ii) a second domain that comprises a binding region of a Heavy Chain Variable Domain of a second immunoglobulin (VH2), and (iii) a third domain that contains a cysteine residue (or a Cysteine-Containing Domain) and a Heterodimerization-Promoting Domain that serves to promote heterodimerization with the second polypeptide chain (FIG. 1B). The cysteine residue (or a Cysteine-Containing Domain) of the third domain serves to promote the covalent bonding of the first polypeptide chain to the second polypeptide chain of the diabody. The second polypeptide contains: (i) a complementary first domain (a VL2-containing Domain), (ii) a complementary second domain (a VH1-containing Domain) and (iii) a third domain that contains a cysteine residue (or a Cysteine-Containing Domain) and, optionally, a complementary Heterodimerization-Promoting Domain that complexes with the Heterodimerization-Promoting Domain of the first polypeptide chain in order to promote heterodimerization with the first polypeptide chain. The cysteine residue (or a Cysteine-Containing Domain) of the third domain of the second polypeptide chain serves to promote the covalent bonding of the second polypeptide chain to the first polypeptide chain of the diabody. Such molecules are stable, potent and have the ability to simultaneously bind two or more antigens. They are able to promote re-directed T cell mediated killing of cells expressing target antigens.

In one embodiment, the third domains of the first and second polypeptides each contain a cysteine residue, which serves to bind the polypeptides together via a disulfide bond. The third domain of one or both of the polypeptides may additionally possesses the sequence of a CH2-CH3 Domain, such that complexing of the diabody polypeptides forms an Fc Domain that is capable of binding to the Fc receptor of cells (such as B lymphocytes, dendritic cells, Natural Killer cells, macrophages, neutrophils, eosinophils, basophils and mast cells) (FIGS. 2A-2B).

Many variations of such molecules have been described (see, e.g., United States Patent Publications No. 2013-

0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). These Fc-bearing DARTs may comprise three polypeptide chains (e.g., FIG. 2B). The first polypeptide chain of such a diabody contains three domains: (i) a VL1-containing Domain, (ii) a VH2-containing Domain and (iii) a domain containing a cysteine residue (or a Cysteine-Containing Domain) and a Heterodimerization-Promoting Domain, and (iv) a cysteine residue (or a Cysteine-Containing Domain and a CH2-CH3 Domain. The second polypeptide chain of such DART™ contains: (i) a VL2-containing Domain, (ii) a VH1-containing Domain and (iii) a Domain that contains a cysteine residue (or a Cysteine-Containing Domain) and a Heterodimerization-Promoting Domain that promotes heterodimerization with the first polypeptide chain. The cysteine residue (or a Cysteine-Containing Domain) of the third domain of the second polypeptide chain serves to promote the covalent bonding of the second polypeptide chain to the first polypeptide chain of the diabody. The third polypeptide of such DART™ comprises a cysteine residue (or a Cysteine-Containing Domain) and a CH2-CH3 Domain. Thus, the first and second polypeptide chains of such DART™ associate together to form a VL1/VH1 binding site that is capable of binding to the epitope, as well as a VL2/VH2 binding site that is capable of binding to the second epitope. The first and second polypeptides are bonded to one another through a disulfide bond involving cysteine residues in their respective third domains. Notably, the first and third polypeptide chains complex with one another to form an Fc Domain that is stabilized via a disulfide bond. Such diabodies have enhanced potency. Such Fc-bearing DARTs™ may have either of two orientations (Table 1):

TABLE 1

| First Orientation | 3$^{rd}$ Chain | NH$_2$—CH2—CH3—COOH |
|---|---|---|
| | 1$^{st}$ Chain | NH$_2$-VL1-VH2-Cys-Heterodimer-Promoting Domain-CH2—CH3—COOH |
| | 2$^{nd}$ Chain | NH$_2$-VL2-VH1-Cys-Heterodimer-Promoting Domain-COOH |
| Second Orientation | 3$^{rd}$ Chain | NH$_2$—CH2—CH3—COOH |
| | 1$^{st}$ Chain | NH$_2$—CH2—CH3-VL1-VH2-Cys-Heterodimer-Promoting Domain-COOH |
| | 2$^{nd}$ Chain | NH$_2$-VL2-VH1-Cys-Heterodimer-Promoting Domain-COOH |

Even more complex DART™ diabodies, termed Ig-DART™ (FIGS. 3A-3B) and Fc-DART™ diabodies (FIG. 3C) have been described (WO 2012/018687). Fc-DARTs™ have four polypeptide chains. The first and third polypeptide chains of such a diabody contain three Domains: (i) a VL1-containing Domain, (ii) a VH2-containing Domain and (iii) a Domain containing a CH2-CH3 sequence. The second and fourth polypeptide of the Fc-DART™ contain: (i) a VL2-containing Domain, (ii) a VH1-containing Domain and (iii) a Domain that promotes heterodimerization and covalent bonding with the Fc-DART's™ first polypeptide chain. The third and fourth, and the first and second polypeptide chains may be the same or different so as to permit tetravalent binding that is either mono-specific, bi-specific or tetra-specific. Such more complex DART™ molecules also possess Cysteine-Containing Domains which function to form a covalently bonded complex. Fc-DART™ diabodies contain CH1 and CL Domains.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical chains each possessing a VH1, VL2, VH2, and VL2 Domain.

III. Re-Directed Killing

As discussed above, interactions between CD8, the MHC I and the T Cell Receptor lead to the activation of cytotoxic T cells and their ability to kill nearby cells. Bi-specific diabodies that bind to CD3 and to a tumor antigen may be used to co-localize cytotoxic CD8$^+$ T cells to the tumor cells, achieving a "re-directed killing" of such cells (WO 2010/080538, WO 2012/018687, WO/2012/162068, US 2010/0174053; US 2013/0295121).

However, efforts to treat cancer or infectious disease by co-localizing CD3$^+$ T cells to the locus of tumor or pathogen cells have not been fully successful. Antibodies that target CD3 bind to both CD3$^+$ CD8$^+$ cytotoxic T cells and to CD3$^+$ CD4$^+$ T helper cells, leading to the activation of both such cells. The cytokines produced by activated CD3$^+$ CD4$^+$ T helper cells, however, contribute to severe side-effects, e.g., life-threatening cytokine storms (Ferran, C. et al. (1990) "*Cytokine-Related Syndrome Following Injection Of Anti-CD3 Monoclonal Antibody: Further Evidence For Transient In Vivo T Cell Activation*," Eur. J. Immunol. 20:509-515). Additionally, such anti-CD3 antibodies bind to other cell types, including CD3$^+$ CD4$^-$ CD8$^-$ double negative T cells, etc. which express cytokines upon activation (Johansson, Martina et al. (2003) "*A Unique Population of Extrathymically Derived αβTCR$^+$CD4$^-$ CD8$^-$ T Cells with Regulatory Functions Dominates the Mouse Female Genital Tract*," J. Immunol. 170:1659-1666; Blank, C. et al. (2003) "*Absence of Programmed Death Receptor 1 Alters Thymic Development and Enhances Generation of CD4/CD8 Double-Negative TCR-Transgenic T Cells*," J. Immunol. 171:4574-4581; McIntyre, M. S. F. et al. (2011) "*Consequences Of Double Negative Regulatory T Cell And Antigen Presenting Cell Interaction On Immune Response Suppression*," Intl. Immunopharmacol. 11:597-603), and which suppress the cytotoxicity mediated by CD3$^+$ CD8$^+$ T cells (Hillhouse, E. E. (2013) "*A Comprehensive Review Of The Phenotype And Function Of Antigen-Specific Immunoregulatory Double Negative T Cells*," J. Autoimmun. 40:58-65).

It has been proposed that cytokine production associated with the administration of antibodies that target CD3 could be avoided using bi-specific antibodies that target CD8 and the tumor antigen (Michalk, I. et al. (2014) "*Characterization of a Novel Single-Chain Bispecific Antibody for Retargeting of T Cells to Tumor Cells via the TCR Co-Receptor CD8*," PLOS One 9(4):e95517, pages 1-8). Anti-CD8 antibodies have therefore been studied to determine whether they would be capable of inducing effector function when used alone. Clement, M. et al. reported that six of seven anti-human CD8 antibodies tested failed to activate CD8$^+$ T cells, but that such activation could be achieved using very high concentrations (10-100 μg/mL) of the anti-human CD8 antibody "OKT8" (Clement, M. et al. (2011) "*Anti-CD8 Antibodies Can Trigger CD8$^+$T Cell Effector Function In The Absence Of TCR Engagement And Improve Peptide-MHCI Tetramer Staining*," J. Immunol. 187(2):654-663). Cooperative binding to two CD8 molecules was required for such an effect, since OKT8 F(ab)'$_2$ fragments were found to be able to mediate the effect, whereas OKT8 Fab were found to be incapable of doing so.

Thus, despite such studies, the cytokine-mediated toxicity attending to the use of anti-CD4 or anti-CD8 antibodies has not been fully understood. Studies have revealed that the cytokine toxicity seen upon administration of anti-CD3 antibody is not eliminated by depleting CD3$^+$ CD4$^+$ T cells or by deleting CD3$^+$ CD8$^+$ T cells. Thus, both CD3$^+$ CD4$^+$ T cells and CD3$^+$ CD8$^+$ T cells contribute to the toxic effects of anti-CD3 antibodies, and relatively few cells are required to mediate the full effect (Finck, B. K. et al. (1992) "*The Role Of T-Cell Subsets In The Response To Anti-CD3 Monoclonal Antibodies*," Clin Immunol Immunopathol. 1992 December; 65(3):234-41).

Moreover, a bi-specific antibody that targets CD8 and a tumor antigen is not specific for CD3$^+$ CD8$^+$T cells and tumor cells, but rather is specific only for CD8$^+$ cells and tumor cells. In particular, the CD3$^-$ CD8$^+$ subset of Natural Killer (NK) cells would be targeted by such an antibody. Such cells, which represent a majority of NK cells are potent producers of cytokines and their activation would likely contribute to a cytokine storm. CD3$^-$ CD8$^+$ NK cells are the primary source of IFN-γ in HIV-1-infected chimpanzees (Rodriquez, A. R. et al. (2007) "*Influence Of Interleukin-15 On CD8+ Natural Killer Cells In Human Immunodeficiency Virus Type 1-Infected Chimpanzees*," J. Gen. Virol. 88:641-651).

Consequently, despite all prior advances, a need remains for improved compositions capable of more vigorously directing the body's immune system to attack cancer cells or pathogen-infected cells, especially at lower therapeutic concentrations. As described in detail below, the present invention addresses this need by providing Tri-Specific Binding Molecules that bind to: (1) an epitope of CD3, (2) an epitope of CD8, and (3) an epitope of a Disease-Associated Antigen that is expressed on a target cell (especially a cancer cell, or a pathogen-infected cell) and mediate coordinated binding of cytotoxic T cells to cells presenting the Disease-Associated Antigen.

SUMMARY OF THE INVENTION

The present invention relates to Tri-Specific Binding Molecules, which are multi-chain polypeptide molecules that possess three Binding Domains and are thus capable of mediating coordinated binding to three epitopes. The Binding Domains may be selected such that the Tri-Specific Binding Molecules are capable of binding to any three different epitopes. Such epitopes may be epitopes of the same antigen or epitopes of two or three different antigens. The invention also provides a novel ROR1-binding antibody, as well as derivatives thereof and uses for such compositions.

The present invention particularly relates to the embodiment of such Tri-Specific Binding Molecules in which the three epitopes are selected such that one or two of such epitopes are epitope(s) of an immune system cell, and especially, a cytotoxic lymphocyte immune system cell (CTL), and in which the remaining epitope(s) are epitope(s) of a Disease-Associated Antigen. Such particularly preferred Tri-Specific Binding Molecules are capable of localizing a cytotoxic lymphocyte cell to a cell that expresses a Disease-Associated Antigen, and of thereby facilitating the killing of cells that express the Disease-Associated Antigen. The Disease-Associated Antigen may be a cancer antigen, or may be an antigen that is characteristic of a pathogen (e.g., bacterial, fungal, viral or protozoan) infection. More particularly, the invention relates to such Tri-Specific Binding Molecules that are capable of mediating coordinated binding to: (1) an epitope of CD3, (2) an epitope of CD8, and (3) an epitope of a Disease-Associated Antigen. By binding to CD3 and CD8, and to the Disease-Associated Antigen, such molecules co-localize cytotoxic T cells to cells presenting the Disease-Associated Antigen, leading to the activation of such T cells and the initiation of a cytotoxic response against cells expressing the Disease-Associated Antigen.

In detail, the invention provides a Tri-Specific Binding Molecule capable of immunospecifically binding to three different epitopes, wherein the binding molecule comprises four different polypeptide chains covalently complexed together and comprises:

(I) an Antigen-Binding Domain I that is capable of immunospecifically binding to an Epitope I present on a first antigen, and an Antigen-Binding Domain II that is capable of immunospecifically binding to an Epitope II present on a second antigen, wherein the Antigen-Binding Domain I and the Antigen-Binding Domain II are both Diabody-Type Binding Domains;

(II) a Non-Diabody-Type Antigen-Binding Domain III that is capable of immunospecifically binding to an Epitope III present on a third antigen; and (III) an Fc Domain that is formed by the association of two CH2-CH3 Domains to one another.

wherein the first, second and third antigens are the same antigen, or are independently the same or different from another of the antigens.

The invention particularly concerns the embodiment of such Tri-Specific Binding Molecule, wherein one of Epitope I, Epitope II or Epitope III is an epitope of a cellular receptor.

The invention additionally concerns the embodiments of such Tri-Specific Binding Molecules, wherein one of Epitope I, Epitope II or Epitope III is an epitope of a Disease-Associated Antigen (and especially wherein the Disease-Associated Antigen is a cancer antigen that is arrayed on the surface of a cancer cell, or is a pathogen antigen that is arrayed on the surface of a pathogen or pathogen-infected cell).

The invention additionally concerns the embodiments of such Tri-Specific Binding Molecules, wherein the Fc Domain is capable of binding to an Fc Receptor arrayed on the surface of a cell.

The invention especially concerns the embodiments of such Tri-Specific Binding Molecules, wherein one of Epitope I, Epitope II or Epitope III is an epitope of CD3, a second of Epitope I, Epitope II or Epitope III is an epitope of CD8, and the third of Epitope I, Epitope II or Epitope III is an epitope of the Disease-Associated Antigen, and wherein the Antigen-Binding Domains I, II and III of the Tri-Specific Binding Molecules mediate coordinated binding of a cytotoxic T cell and a cell expressing the Disease-Associated Antigen. The invention particularly concerns the embodiments of such Tri-Specific Binding Molecules, wherein the CD3, the CD8 are arrayed on the surface of a T cell and wherein the Disease-Associated Antigen is arrayed on the surface of a cancer cell, pathogen or pathogen-infected cell, and wherein the immunospecific binding is sufficient to co-localize the CD3 and the CD8, and the Disease-Associated Antigen, thereby facilitating the activation of the CD8-arraying T cell against the Disease-Associated Antigen-arraying cell.

The invention additionally concerns the embodiments of above-described Tri-Specific Binding Molecules, wherein the Non-Diabody-Type Binding Domain III comprises the Fab-Type Binding Domain (VL$_{III}$/VH$_{III}$) that is capable of immunospecifically binding to the Epitope III, wherein the molecule comprises:

(A) a first polypeptide chain:
(I) that comprises in the N-terminus to C-terminus direction:
(1) a Light Chain Variable Domain of an immunoglobulin capable of binding to a first of the three epitopes (VL$_I$);
(2) a Heavy Chain Variable Domain of an immunoglobulin capable of binding to a second of the three epitopes (VH$_{II}$);
(3) (a) a first Cysteine-Containing Domain; and a Heterodimer-Promoting Domain; or
(b) a Cysteine-Containing Heterodimer-Promoting Domain;
(5) a second Cysteine-Containing Domain; and
(6) CH2 and CH3 Domains of an IgG;
or
(II) that comprises in the N-terminus to C-terminus direction:
(1) a first Cysteine-Containing Domain;
(2) CH2 and CH3 Domains of an IgG;
(3) a Light Chain Variable Domain of an immunoglobulin capable of binding to a first of the three epitopes (VL$_I$);
(4) a Heavy Chain Variable Domain of an immunoglobulin capable of binding to a second of the three epitopes (VH$_{II}$);
(5) (a) a second Cysteine-Containing Domain; and a Heterodimer-Promoting Domain; or
(b) a Cysteine-Containing Heterodimer-Promoting Domain;
(B) a second polypeptide chain that comprises, in the N-terminus to C-terminus direction:
(1) a Light Chain Variable Domain of an immunoglobulin capable of binding to the second of the three epitopes (VL$_{II}$);
(2) a Heavy Chain Variable Domain of an immunoglobulin capable of binding to the first of the three epitopes (VH$_I$);
(3) (a) a first Cysteine-Containing Domain; and a Heterodimer-Promoting Domain; or
(b) a Cysteine-Containing Heterodimer-Promoting Domain;
wherein the Heterodimer-Promoting Domain of the second polypeptide chain is complementary to the Heterodimer-Promoting Domain of the first polypeptide chain;
(C) a third polypeptide chain that comprises, in the N-terminus to C-terminus direction:
(1) a Heavy Chain Variable Domain of an immunoglobulin capable of binding to a third of the three epitopes (VH$_{III}$); and
(2) a CH1 Domain, a Cysteine-Containing Hinge Domain, and a CH2-CH3 Domain of an IgG;
and
(D) a fourth polypeptide chain that comprises, in the N-terminus to C-terminus direction:
(1) a Light Chain Variable Domain of an immunoglobulin capable of binding to the third of the three epitopes (VL$_{III}$); and
(2) a Cysteine-Containing Light Chain Constant Domain (CL);

wherein:
(i) the VL$_I$ and VH$_I$ Domains associate to form a Domain capable of binding the Epitope I;
(ii) the VL$_{II}$ and VH$_{II}$ Domains associate to form a Domain capable of binding the Epitope II;
(iii) the VL$_{III}$ and VH$_{III}$ Domains associate to form a Domain capable of binding the Epitope III;
(iv) the CH2-CH3 Domain of the first polypeptide chain and the CH2-CH3 Domain of the third polypeptide chain associate to form an Fc Domain;
(v) the first and second polypeptide chains are covalently bonded to one another;
(vi) the first and third polypeptide chains are covalently bonded to one another; and
(vii) the third and fourth polypeptide chains are covalently bonded to one another.

The invention additionally concerns the embodiments of above-described Tri-Specific Binding Molecules, wherein:
(A) the Heterodimer-Promoting Domain is an E-coil and the complementary Heterodimer-Promoting Domain is a K-coil; or
(B) the Heterodimer-Promoting Domain is a K-coil and the complementary Heterodimer-Promoting Domain is an E-coil.

The invention additionally concerns the embodiments of above-described Tri-Specific Binding Molecules, wherein:
(A) the CH2-CH3 Domains of the first and third polypeptide chains each have the sequence of SEQ ID NO:6, such that the Fc Domain formed from their association exhibits normal FcγR-mediated effector function; or
(B) the CH2-CH3 Domain of the first and third polypeptide chains comprise at least one amino acid substitution, relative to the sequence of SEQ ID NO:6, such that the Fc Domain formed from their association exhibits altered FcγR-mediated effector function.

The invention additionally concerns the embodiments of above-described Tri-Specific Binding Molecules, wherein the CH2-CH3 Domain of the first and third polypeptide chains differ from one another and have an amino acid sequence selected from the group consisting of SEQ ID NO:7 and SEQ ID NO:8.

The invention additionally concerns the embodiments of above-described Tri-Specific Binding Molecules, wherein:
(A) the Epitope I, Epitope II and Epitope III are, respectively, an epitope of CD3, an epitope of CD8 and an epitope of the Disease-Associated Antigen;
(B) the Epitope I, Epitope II and Epitope III are, respectively, an epitope of CD3, an epitope of the Disease-Associated Antigen and an epitope of CD8;
(C) the Epitope I, Epitope II and Epitope III are, respectively, an epitope of CD8, an epitope of CD3, and an epitope of the Disease-Associated Antigen;
(D) the Epitope I, Epitope II and Epitope III are, respectively, an epitope of CD8, an epitope of the Disease-Associated Antigen and an epitope of CD3;
(E) the Epitope I, Epitope II and Epitope III are, respectively, an epitope of the Disease-Associated Antigen, an epitope of CD3, and an epitope of CD8; or
(F) the Epitope I, Epitope II and Epitope III are, respectively, an epitope of the Disease-Associated Antigen, an epitope of CD8, and an epitope of CD3.

The invention additionally concerns the embodiments of above-described Tri-Specific Binding Molecules, wherein:
(A) the epitope of CD3 is a CD3 epitope recognized by antibody OKT3, M291, YTH12.5, CD3 mAb 1 or CD3 mAb 2; or (B) the epitope of CD8 is a CD8 epitope recognized by antibody TRX2 or OKT8.

The invention additionally concerns a pharmaceutical composition that comprises the above-described Tri-Specific Binding Molecule and a pharmaceutically acceptable carrier, excipient or diluent.

The invention additionally concerns a method of treating cancer which comprises administering an effective amount of the above-described pharmaceutical composition to an individual in need thereof, wherein the Disease-Associated Antigen is the cancer antigen.

The invention additionally concerns a method of treating a disease-associated with the presence of a pathogen which comprises administering an effective amount of the pharmaceutical composition of claim 15 to an individual in need thereof, wherein the Disease-Associated Antigen is the pathogen antigen.

The invention additionally concerns an anti-ROR1 antibody, or ROR1-binding fragment, wherein the antibody comprises:
(A) a Light Chain Variable Domain that comprises a $CDR_L1$ having the sequence of SEQ ID NO:117, a $CDR_L2$ having the sequence of SEQ ID NO:118, and a $CDR_L3$ having the sequence of SEQ ID NO:119; and
(B) a Heavy Chain Variable Domain that comprises a $CDR_H1$ having the sequence of SEQ ID NO:120, a $CDR_H2$ having the sequence of SEQ ID NO:121, and a $CDR_H3$ having the sequence of SEQ ID NO:122.

The invention additionally concerns the embodiments of such anti-ROR1 antibody or ROR1-binding fragment thereof, wherein the antibody has a Light Chain Variable Domain having the sequence of SEQ ID NO:51. The invention additionally concerns the embodiments of such anti-ROR1 antibodies or ROR1-binding fragments thereof, wherein the antibody has a Heavy Chain Variable Domain having the sequence of SEQ ID NO:52, or both a Light Chain Variable Domain having the sequence of SEQ ID NO:51 and a Heavy Chain Variable Domain having the sequence of SEQ ID NO:52.

The invention additionally concerns a diabody, BiTe or single-chain antibody that comprises the ROR1 binding fragment of any of such claims anti-ROR1 antibodies.

The invention additionally concerns a pharmaceutical composition that comprises any of the above-described anti-ROR1 antibodies or ROR1-binding fragments thereof and a pharmaceutically acceptable carrier, excipient or diluent. The invention additionally concerns a method of treating cancer which comprises administering an effective amount of such a pharmaceutical composition to an individual in need thereof.

BRIEF DESCRIPTION OF THE FIGURES

FIG. 1A shows a diagrammatic representation of the Domains of a basic DART™ diabody. FIG. 1B provides a schematic of a covalently bonded diabody composed of two polypeptide chains, each having a Heterodimer-Promoting Domain VL and VH domains that recognize the same epitope are shown using the same shading.

FIG. 3A shows an Ig diabody. FIG. 3B shows an Ig diabody, which contains E-coil and K-coil heterodimer-promoting domains. FIG. 3C, shows an Fc-DART™ diabody that contains antibody CH1 and CL domains. The notation "VL1" and "VH1" denote respectively, the Variable Light Chain Domain and Variable Heavy Chain Domain that bind the "first" epitope. Similarly, the notation "VL2" and "VH2" denote respectively, the Variable Light Chain Domain and Variable Heavy Chain Domain that bind the "second" epitope.

FIGS. 4A and 4B, respectively, illustrate schematically the Domains of preferred Tri-Specific Binding Molecules in which the Tri-Specific Binding Molecule's Non-Diabody-Type Binding Domain is a Fab-Type Binding Domain or a T cell Receptor Binding Domain. FIGS. 4C and 4D, respectively, illustrate schematically the Domains of preferred Tri-Specific Binding Molecules having different Domain orientations in which the Non-Diabody-Type Binding Domain is a Fab-Type Binding Domain or a T Cell Receptor-Type Binding Domain. FIGS. 4E-4J depict similar molecules having three polypeptide chains. The molecule may possess Hinge and CL Domains (FIGS. 4E, 4H) or may contain an alternative linker peptide (FIG. 4F, 4I). FIGS. 4K-4L depict similar molecules having five polypeptide chains.

FIG. 6A shows the results of a luciferase assay of cell lysis of JIMT-1 cells. FIG. 6B shows the results of an LDH assay of cytotoxicity of JIMT-1 cells. FIG. 6C shows the results of an LDH assay of cytotoxicity of A498 cells.

FIG. 7B: CD4/CD25 T cells; FIG. 7C: CD8/CD69 T cells; FIG. 7D: CD8/CD25 T cells).

FIG. 8B: CD4/CD25 T cells; FIG. 8C: CD8/CD69 T cells; FIG. 8D: CD8/CD25 T cells).

Figure 10A:
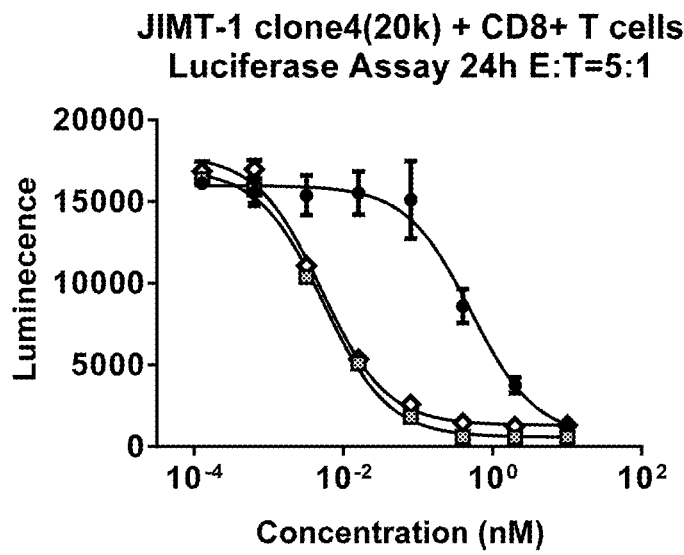
Figure 10B:
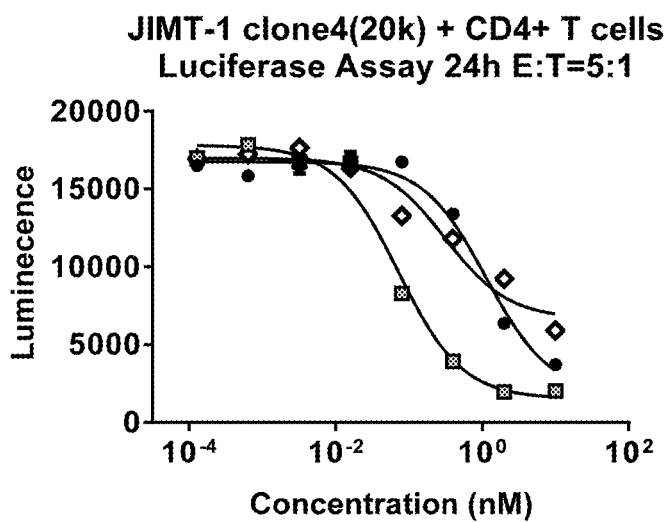
Figure 10C:
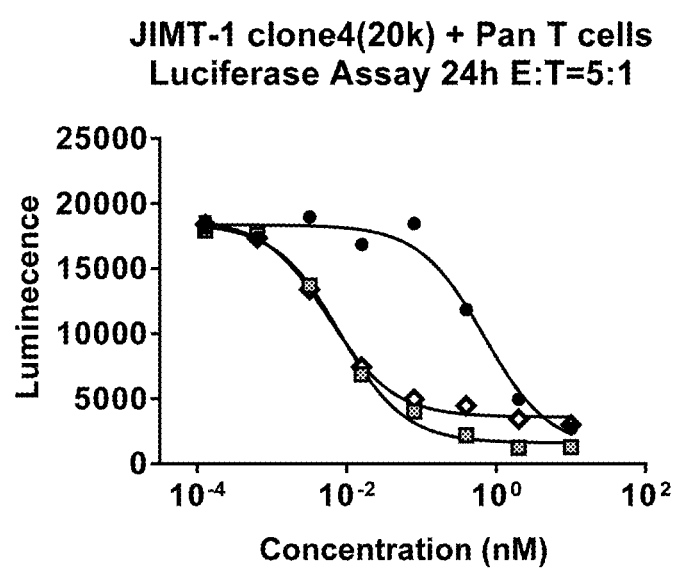

FIGS. 10A-10C show the effect of different CD8 Binding Domains on the cytotoxicity of a B7-H3 mAb 1/CD3 mAb 2/CD8 Tri-Specific Binding Molecule.

Figure 11A:
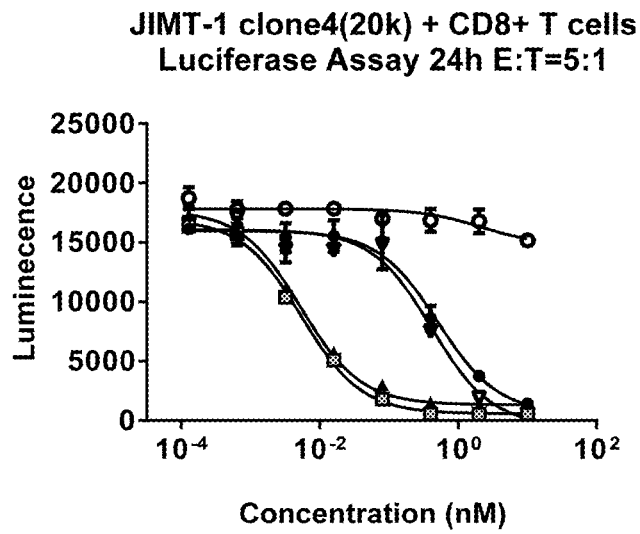
Figure 11B:
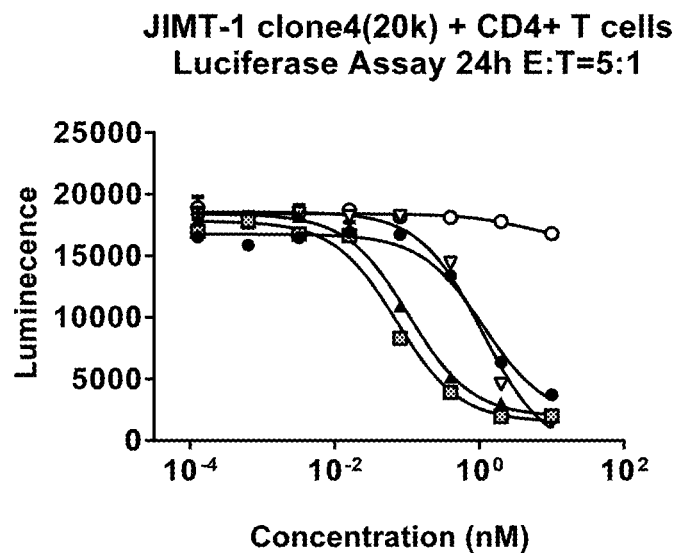
Figure 11C:
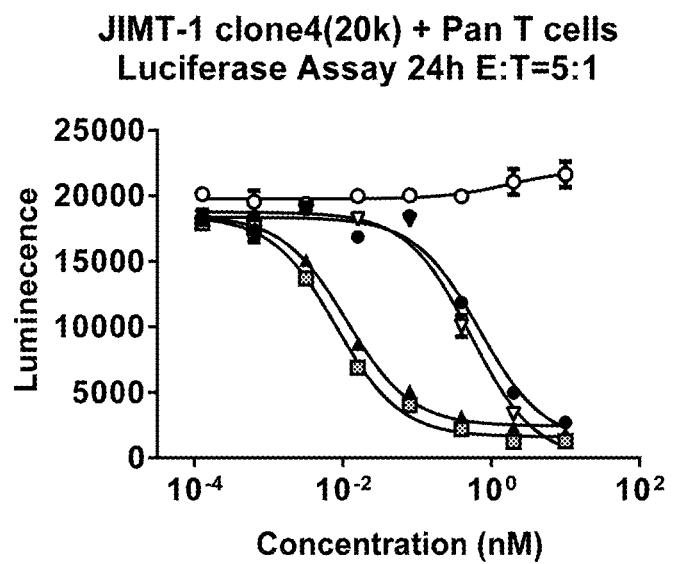

FIGS. 11A-11C demonstrate the ability to modulate the binding of the Tri-Specific Binding Molecules of the present invention by selecting Site A, Site B or Site C for the CD3 Binding Domain. The employed Tri-Specific Binding Molecules were capable of immunospecifically binding to the Disease-Associated Antigen, B7-H3. Cytotoxicity is measured using a luciferase assay.

Figure 12A:
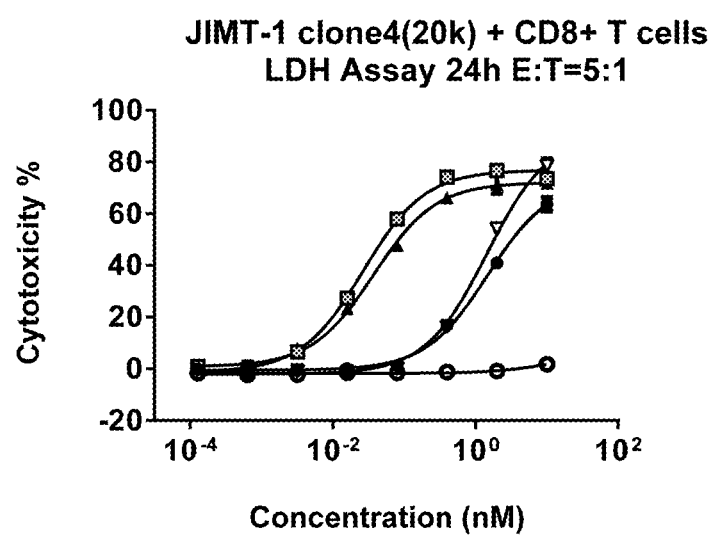
Figure 12B:
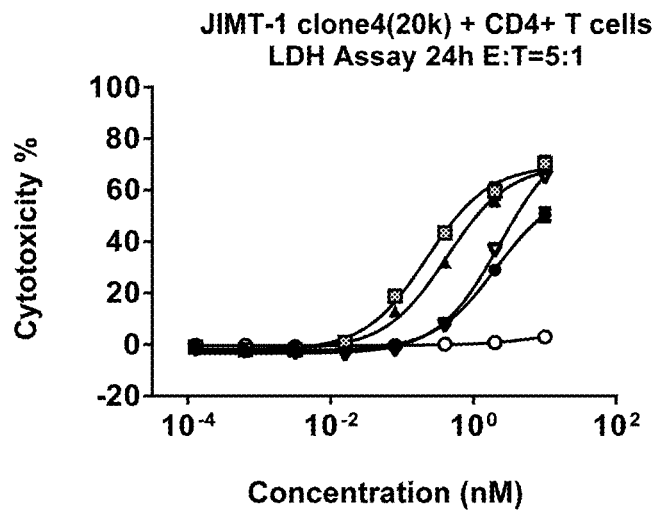
Figure 12C:
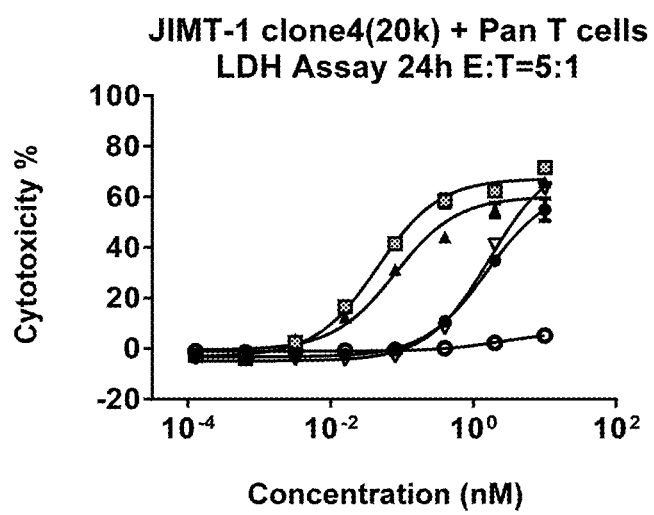
Figure 13A:
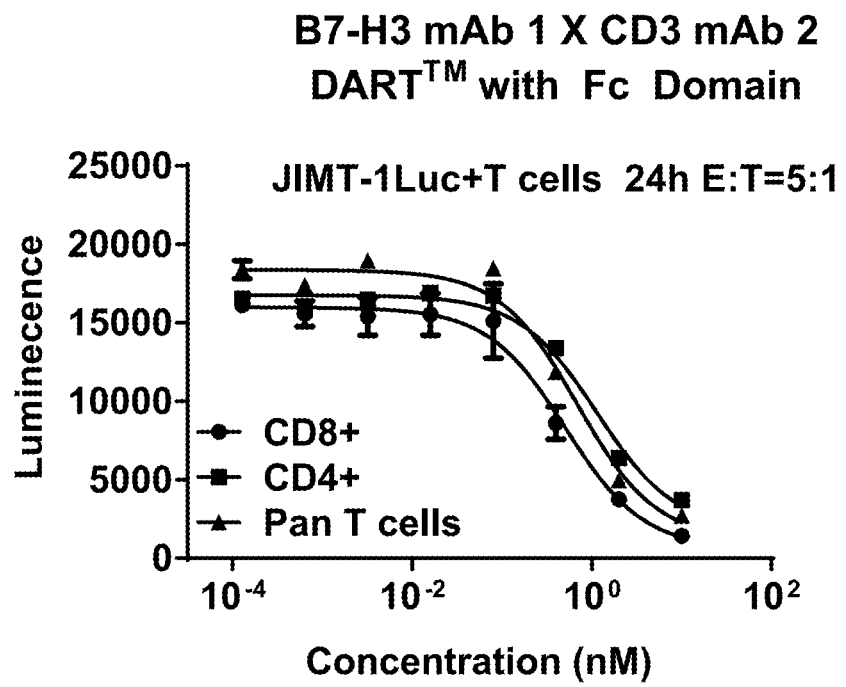
Figure 13B:
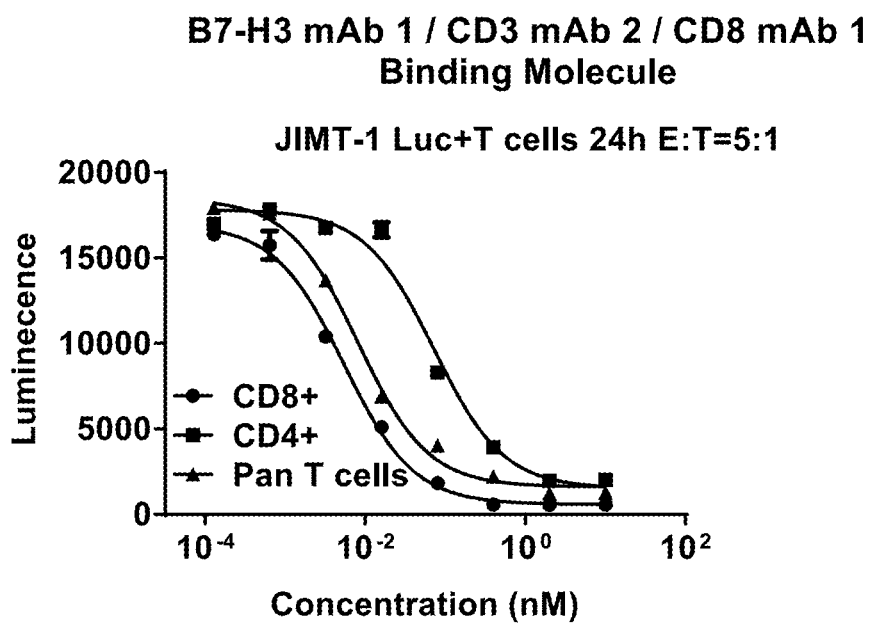
Figure 13C:
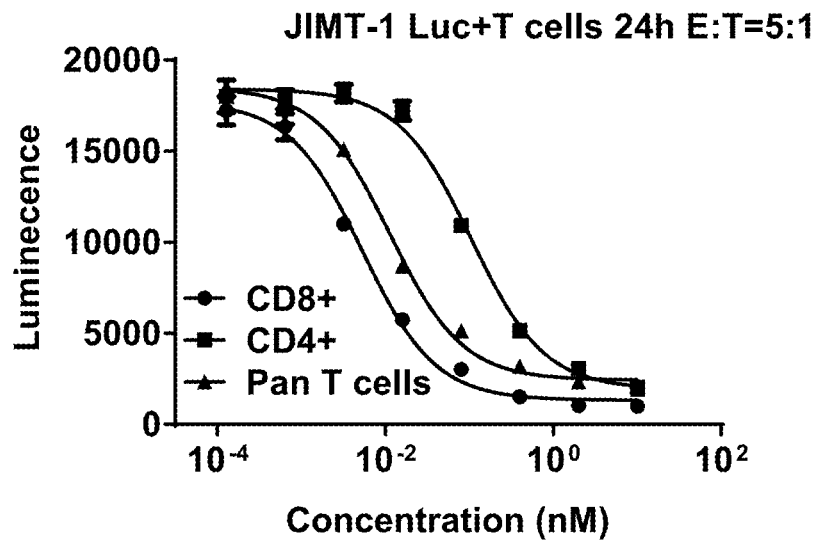
Figure 13D:
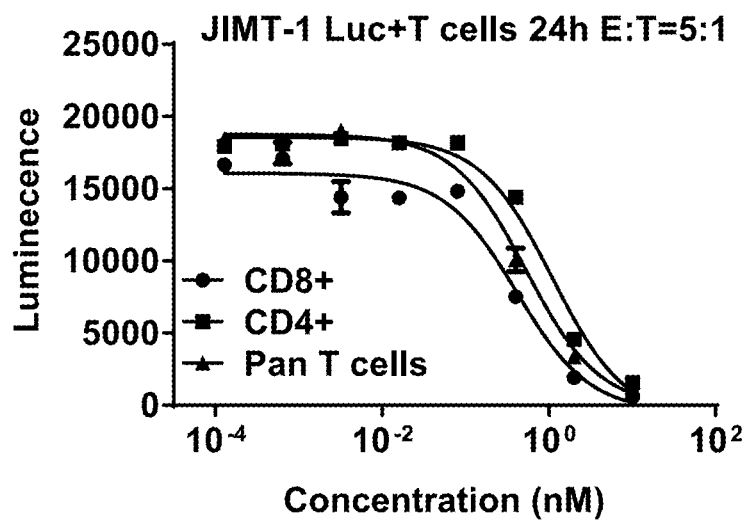
Figure 13E:
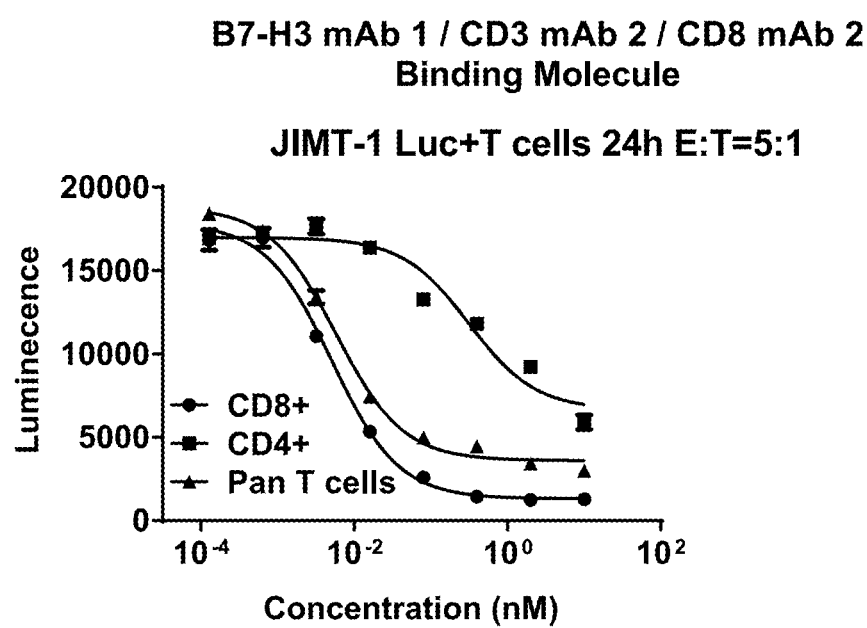

FIGS. 12A-12C demonstrate the effect of positional selection (Site A, Site B or Site C) on the cytotoxicity mediated by the Tri-Specific Binding Molecules of the present invention using an LDH assay.

FIGS. 13A-13E show the effect of positional variation on cytotoxicity using a B7-H3 mAb 1/CD3 mAb 2/CD8 mAb 1 Tri-Specific Binding Molecule, a CD3 mAb 2/CD8 mAb 1/B7-H3 mAb 1 Tri-Specific Binding Molecule and a B7-H3 mAb 1/CD8 mAb 1/CD3 mAb 2 Tri-Specific Binding Molecule. A B7-H3×CD3 DART™ with Fc Domain was used as a control.

Figure 14A:
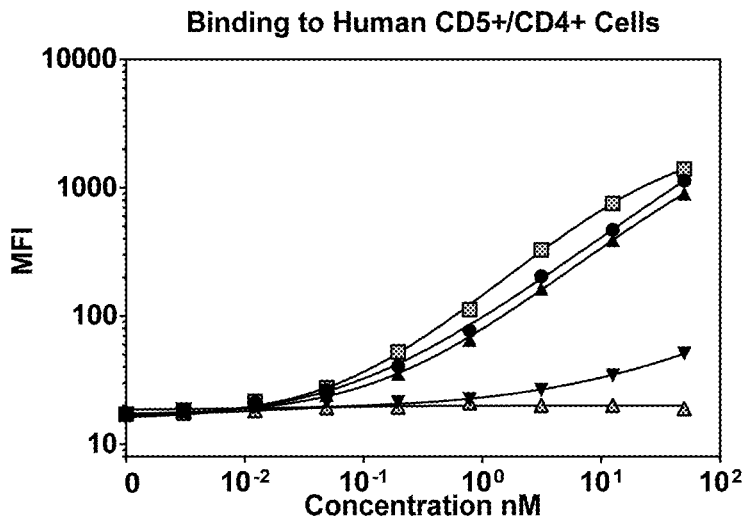
Figure 14B:
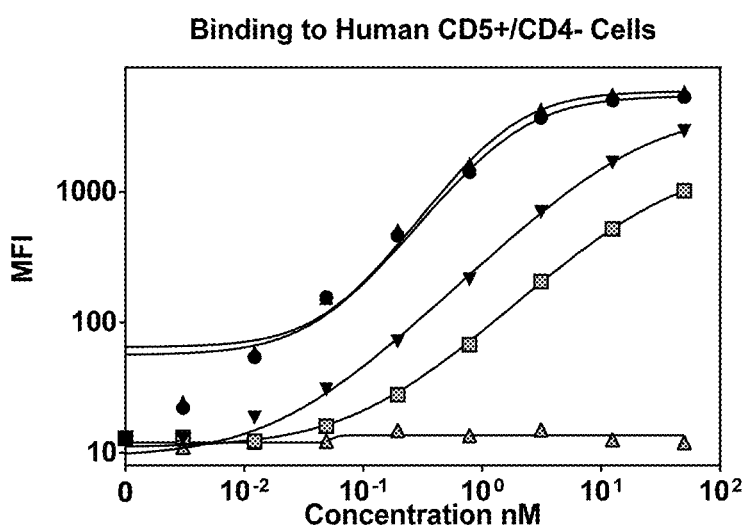

FIGS. 14A-14B, placement of the CD3 Binding Domain at Site C, greatly diminished binding to both the CD5$^+$ CD4$^+$ cells (FIG. 14A) and the CD5$^+$ CD4 cells (FIG. 14B).

Figure 15A:
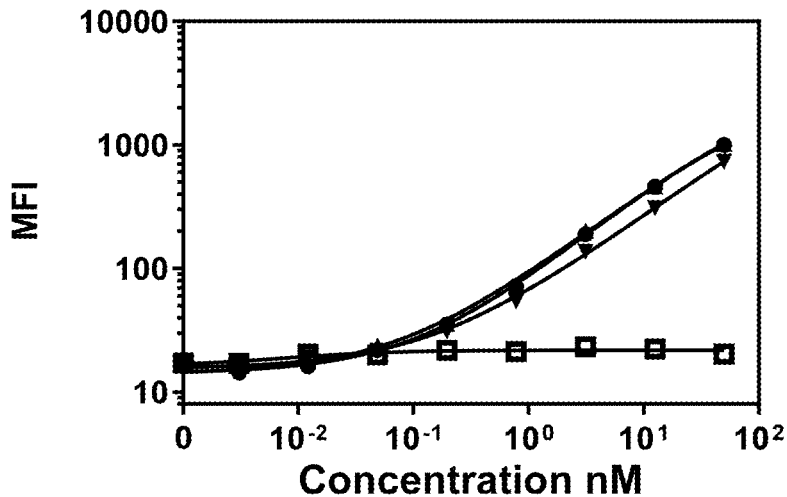
Figure 15B:
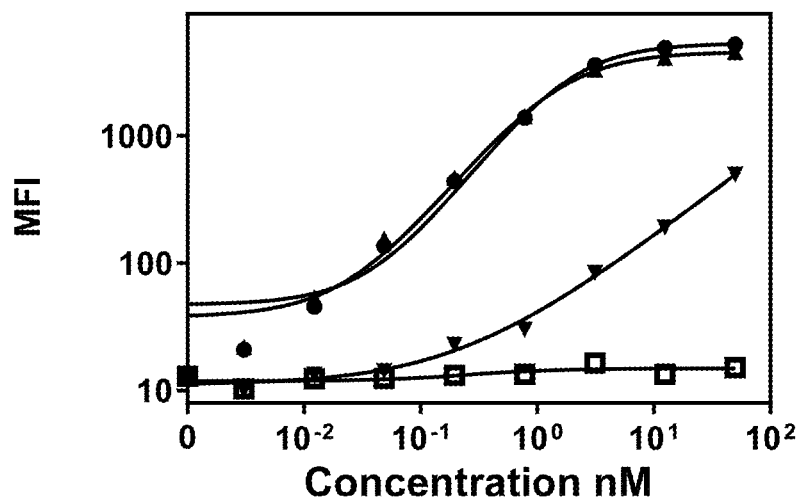

FIGS. 15A-15B show the CD5$^+$ CD4$^+$ gated (FIG. 15A) or CD5$^+$ CD4 gated (FIG. 15B) cell populations of human PMBC as a function of increasing concentration of 5T4 mAb 2/CD3 mAb 2/CD8 mAb 1 Tri-Specific Binding Molecules or 5T4 mAb2/CD3 mAb 2/CD8 mAb 2 Tri-Specific Binding Molecules. 5T4×CD3 DARTs™ (with and without Fc Domain) were used as controls.

Figure 16A:
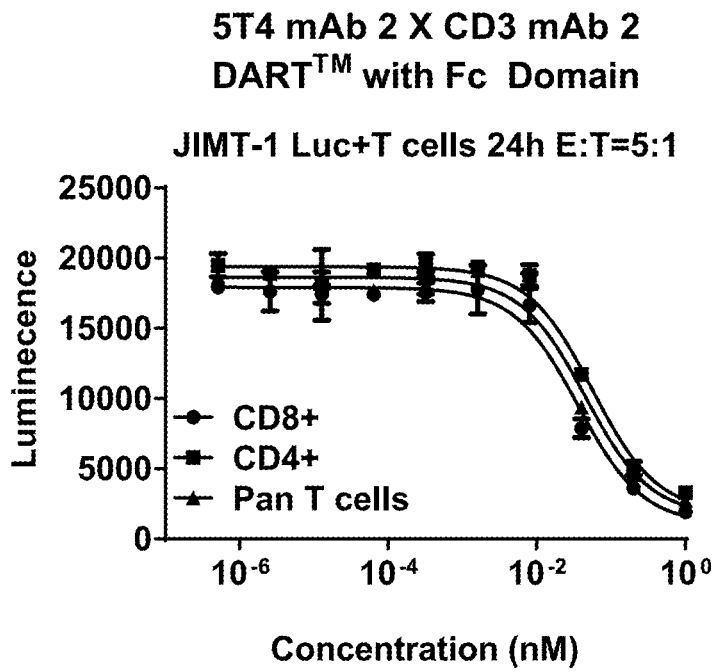
Figure 16B:
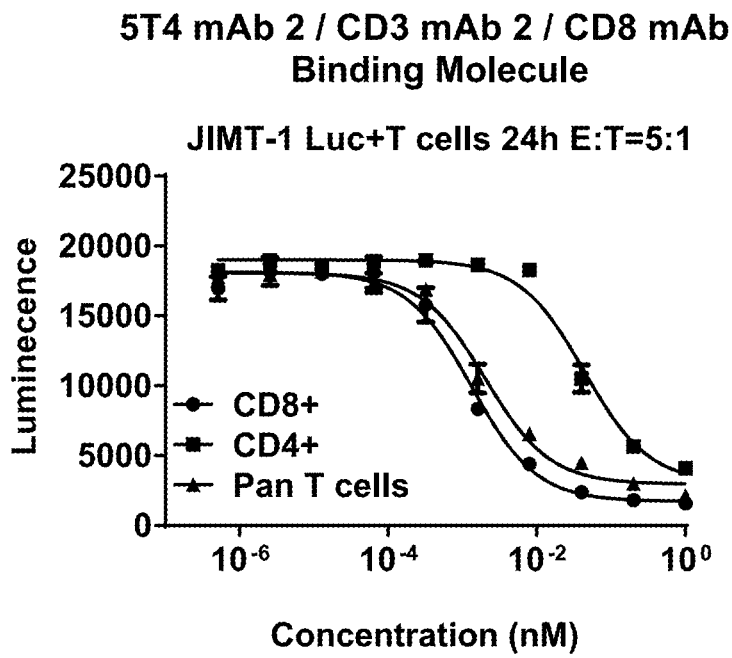
Figure 16C:
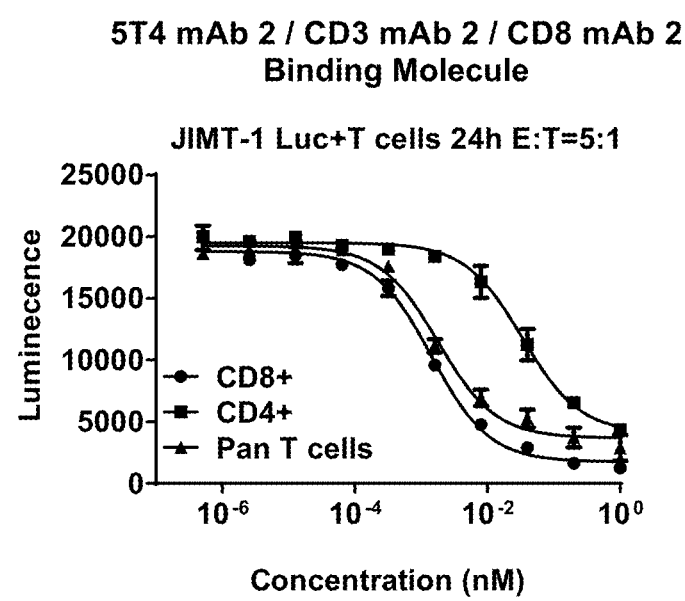

FIGS. 16A-16C show that the observed effect of positional variation on cytotoxicity was not dependent on the employed CD8 Binding Domain.

Figure 17A:
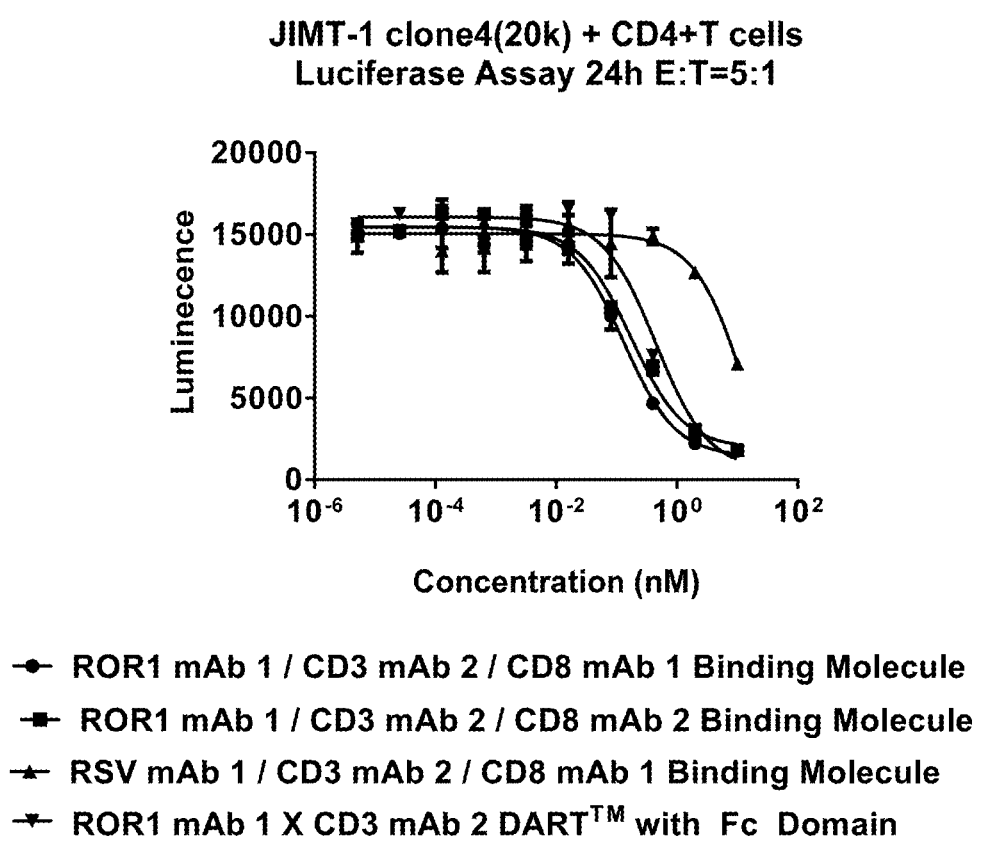
Figure 17B:
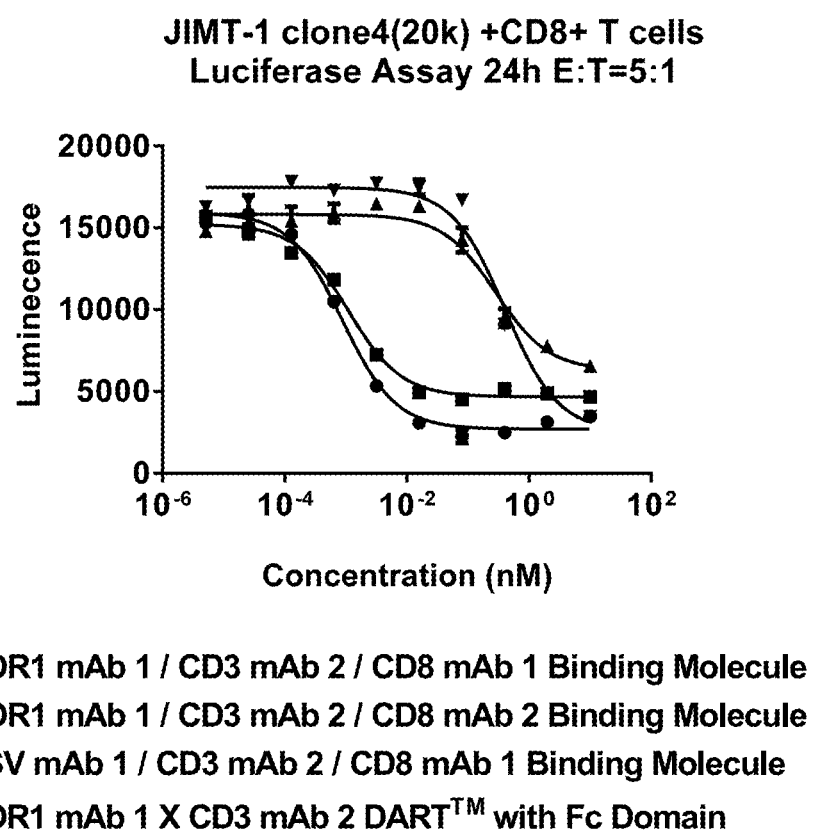
Figure 17C:
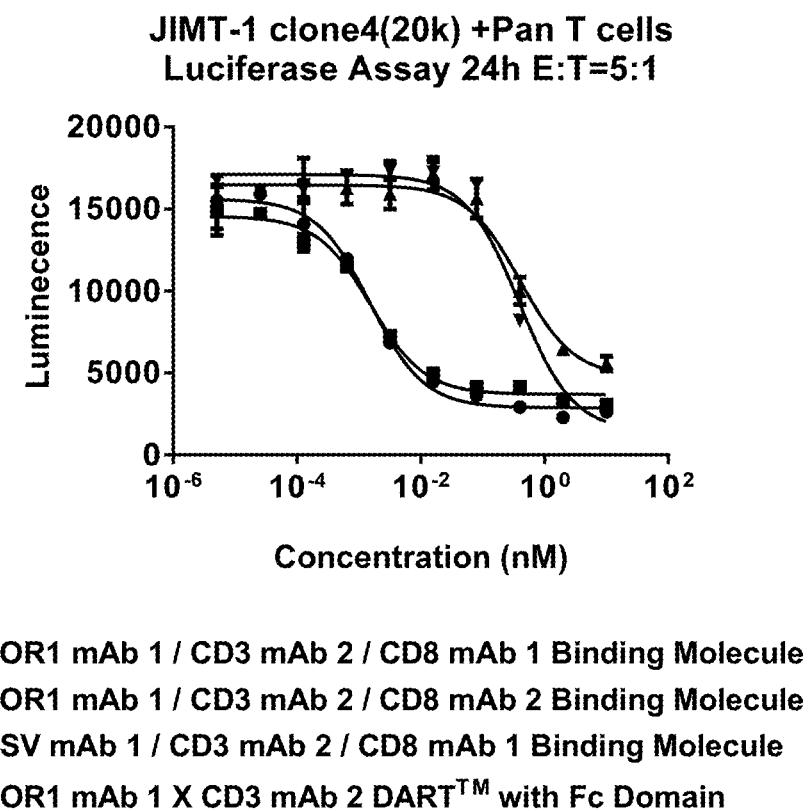

FIGS. 17A-17C demonstrate the ability of Tri-Specific Binding Molecules of the present invention to mediate the re-directed killing of target cells expressing ROR1.

Figure 18A:
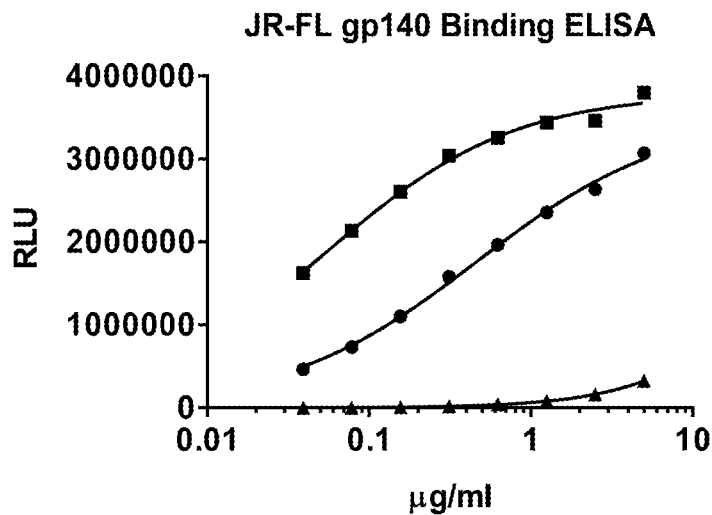
Figure 18B:
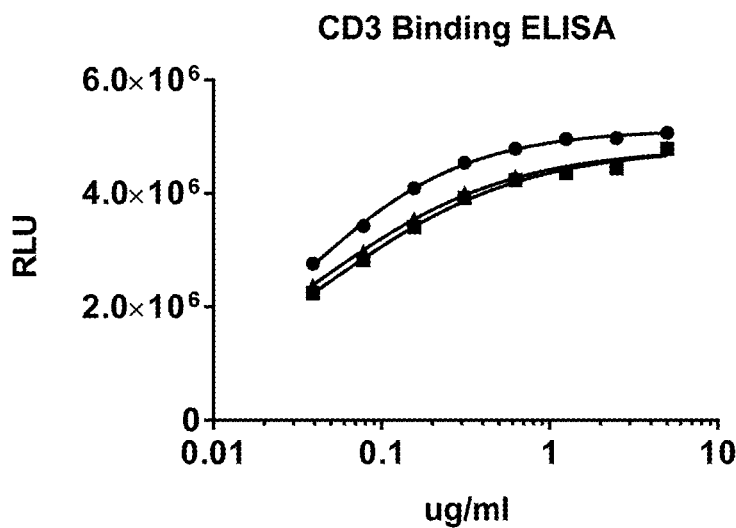
Figure 18C:
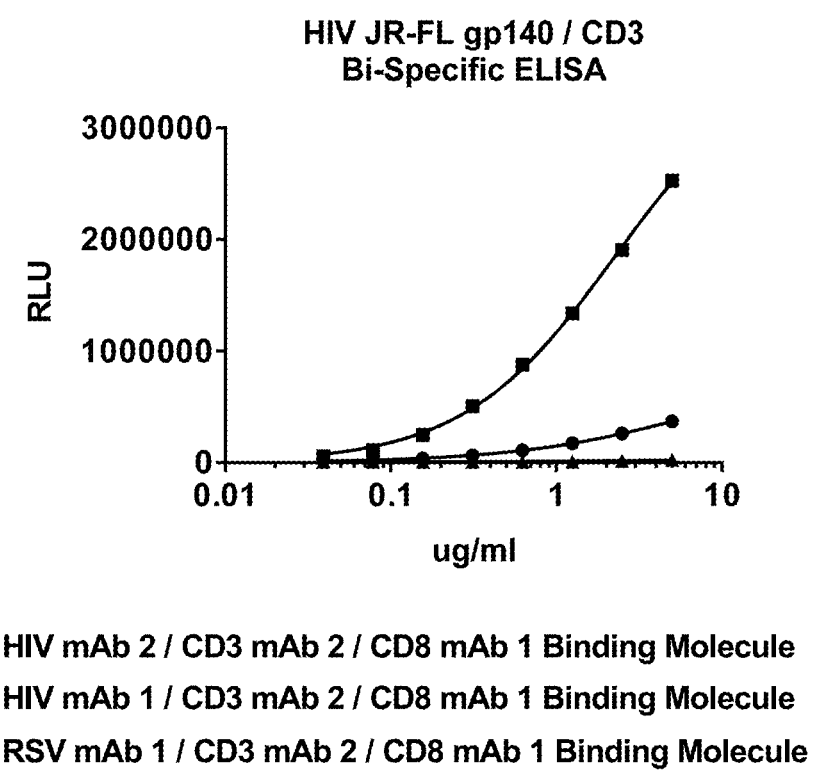

FIGS. 18A-18C show the ability of ability of HIV mAb 1/CD3 mAb 2/CD8 mAb 1 and HIV mAb 2/CD3 mAb 2/CD8 mAb 1 Tri-Specific Binding Molecules to bind to soluble, immobilized gp140 protein (FIG. 18A), human CD3 (FIG. 18B) and both gp140 protein and human CD3 (FIG. 18C).

FIGS. 19A-19C show the ability of ability of HIV mAb 1/CD3 mAb 2/CD8 mAb 1 and HIV mAb 2/CD3 mAb 2/CD8 mAb 1 Tri-Specific Binding Molecules to bind to HIV env-expressing HEK293/D375 cells in contrast to a control Tri-Specific Binding Molecule (FIG. 19C).

Figure 20A:
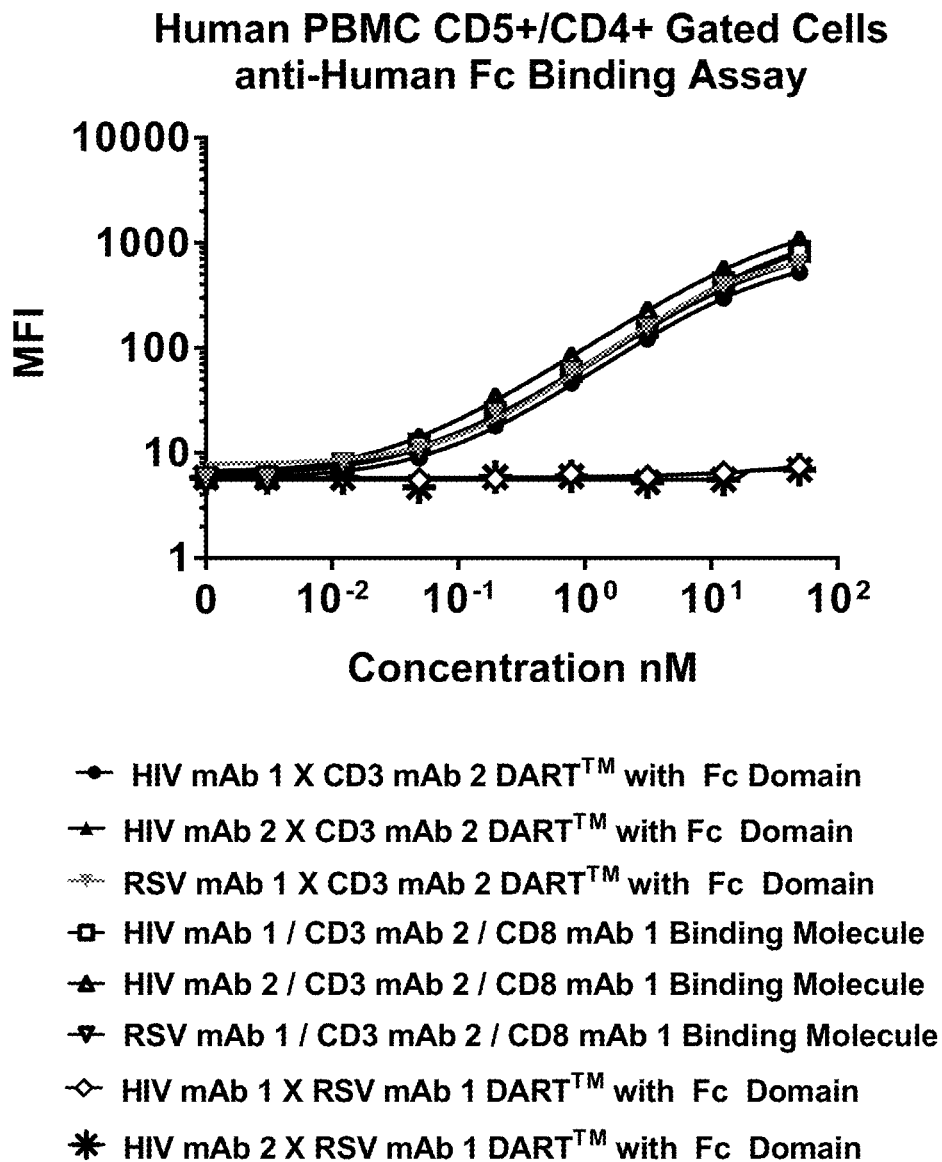
Figure 20B:
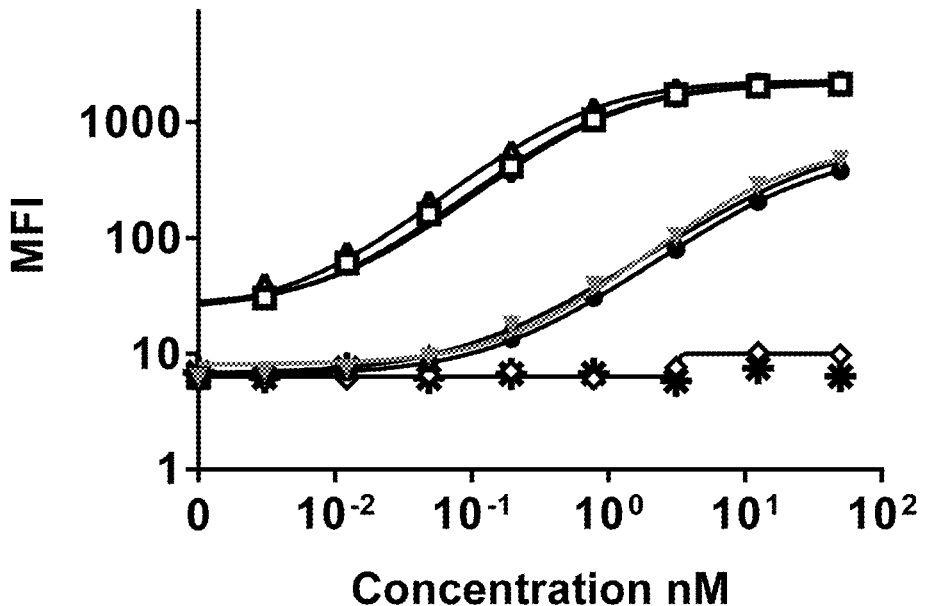

FIGS. 20A-20B show the ability of ability of HIV mAb 1/CD3 mAb 2/CD8 mAb 1 and HIV mAb 2/CD3 mAb 2/CD8 mAb 1 Tri-Specific Binding Molecules to bind to exhibit specific binding to the CD5+/CD5− cell population of human PBMCs.

Figure 21A:
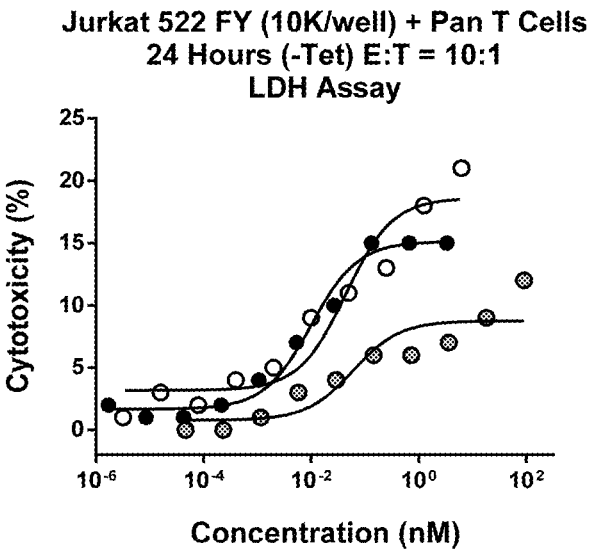
Figure 21B:
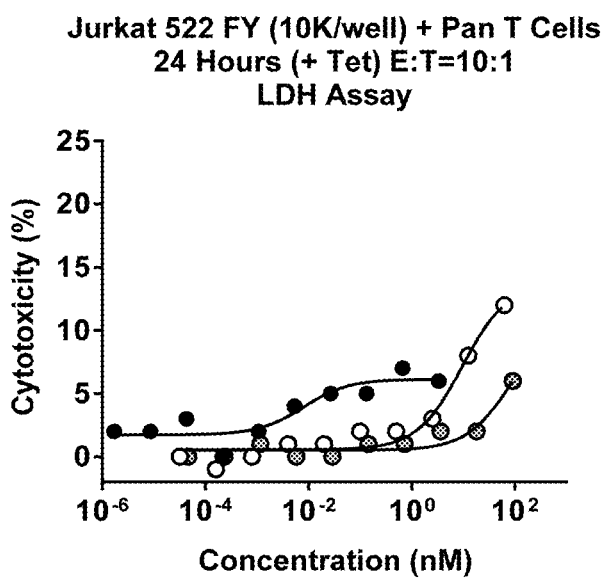
Figure 21C:
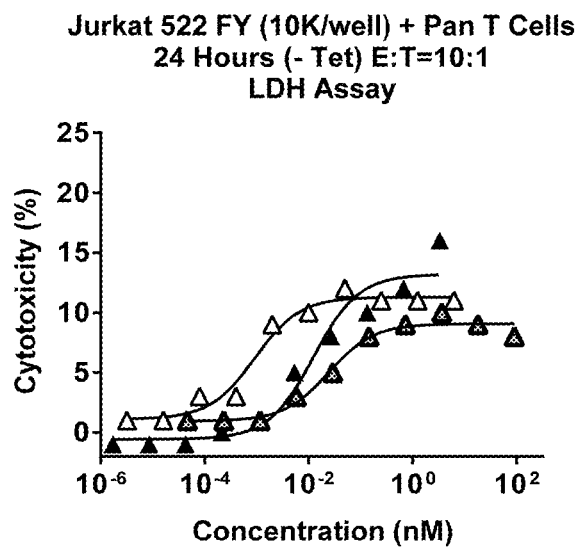
Figure 21D:
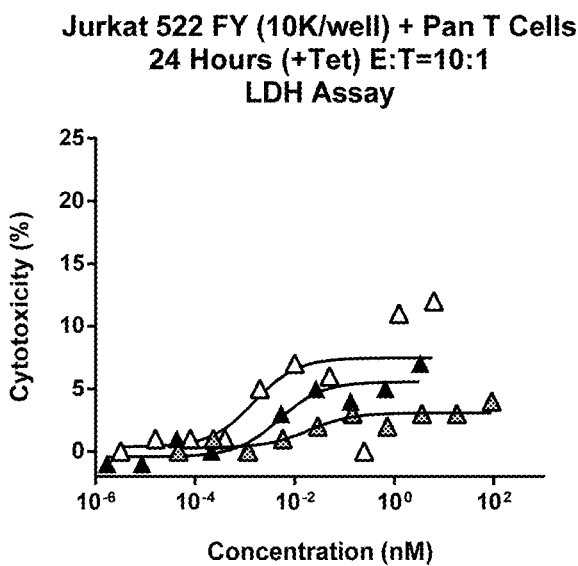
Figure 21E:
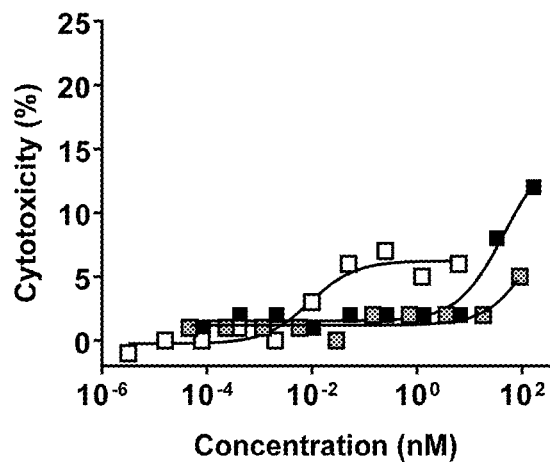
Figure 21F:
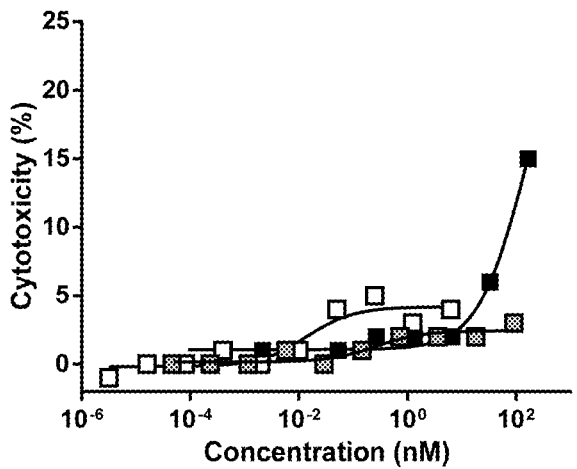

FIGS. 21A-21F show the cytotoxic activity mediated by the HIV mAb 1/CD3 mAb 2/CD8 mAb 1 or HIV mAb 2/CD3 mAb 2/CD8 mAb 1 Tri-Specific Binding Molecule on Jurkat cells in the presence or absence of tetracycline (FIGS. 21A-21B; FIGS. 21C-21D). FIGS. 21E-21F show the cytotoxic activity of a control anti-RSV antibody (Palivizumab; RSV mAb 1) Tri-Specific Binding Molecule.

Figure 22A:
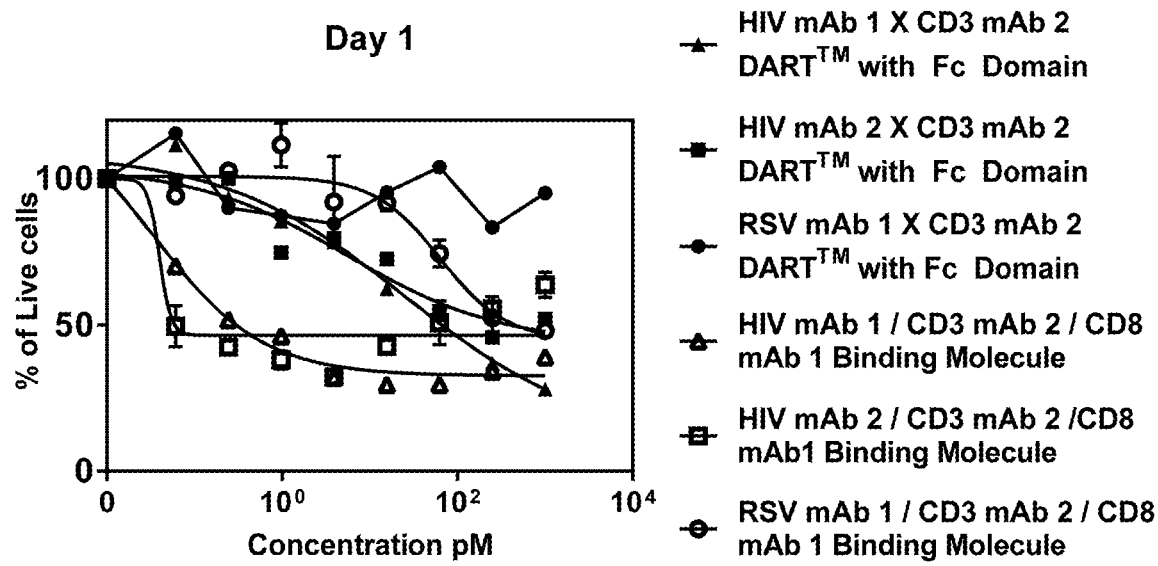
Figure 22B:
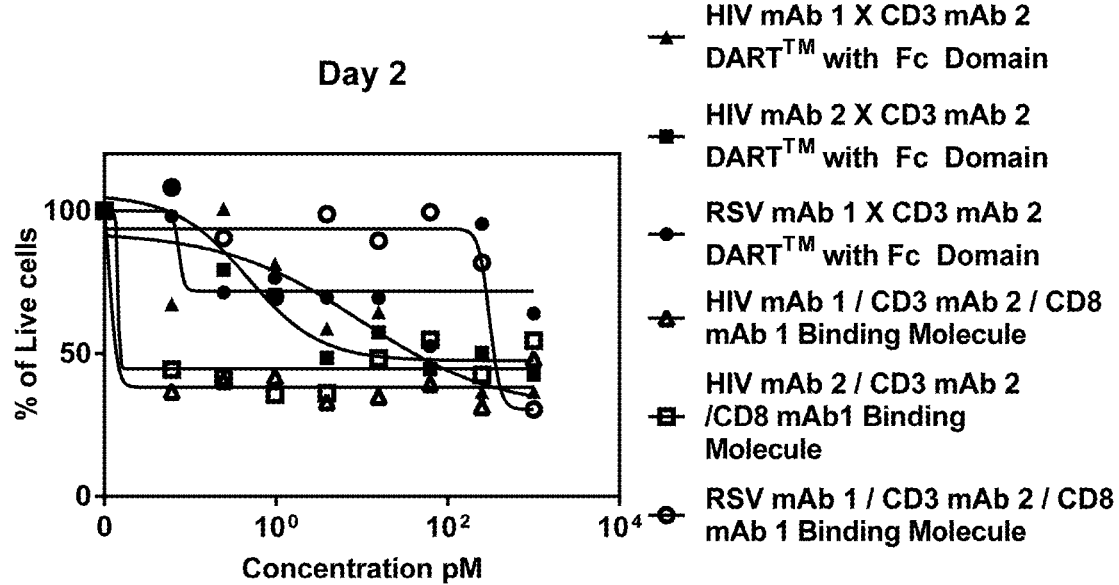

FIGS. 22A-22B show the percentage of live HIV env-expressing Jurkat 522 FY cells at one day and 2 days after incubation with purified pan T cells and HIV mAb 1/CD3 mAb 2/CD8 mAb 1 or HIV mAb 2/CD3 mAb 2/CD8 mAb 1 Tri-Specific Binding Molecules.

Figure 23A:
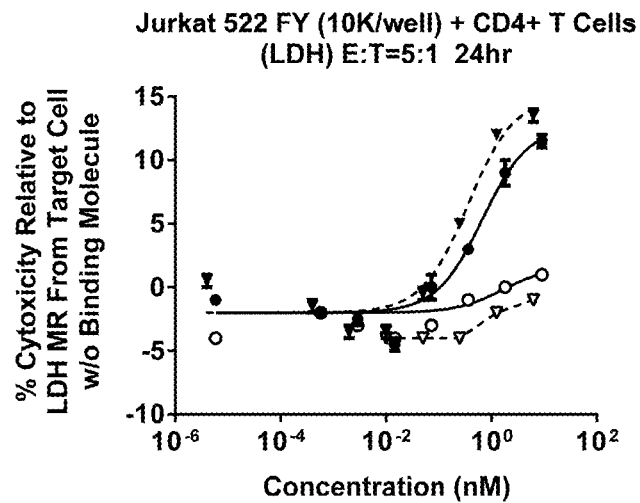
Figure 23B:
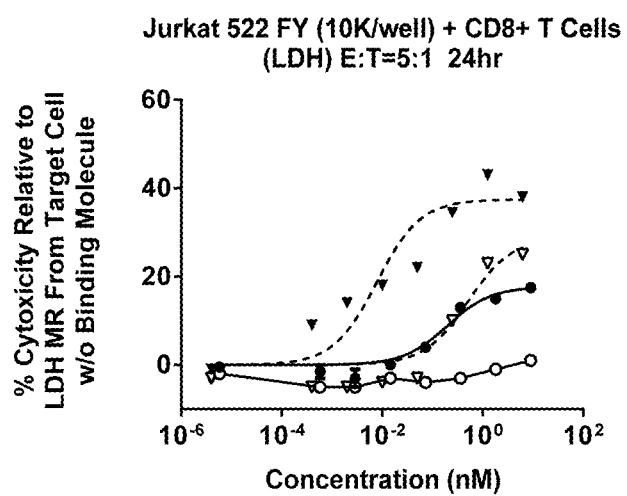
Figure 23C:
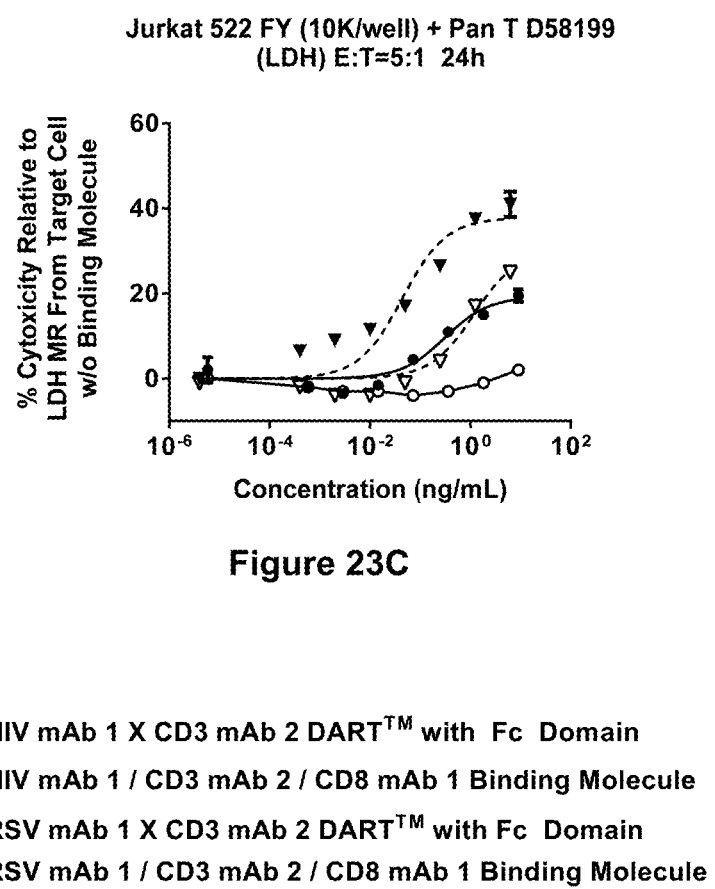

FIGS. 23A-23C show the results of an assessment of the CTL activity of the HIV mAb 1/CD3 mAb 2/CD8 mAb 1 Tri-Specific Binding Molecule on HIV env-expressing Jurkat 522 FY cells using CD4+, CD8+ or pan T cells.

Figure 24A:
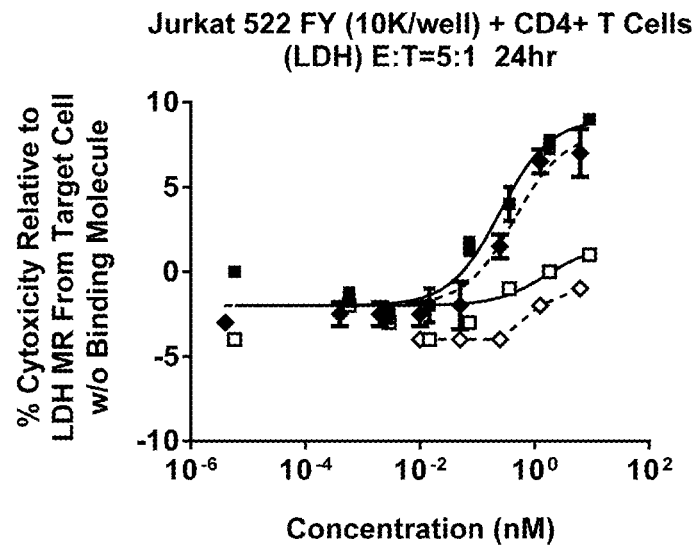
Figure 24B:
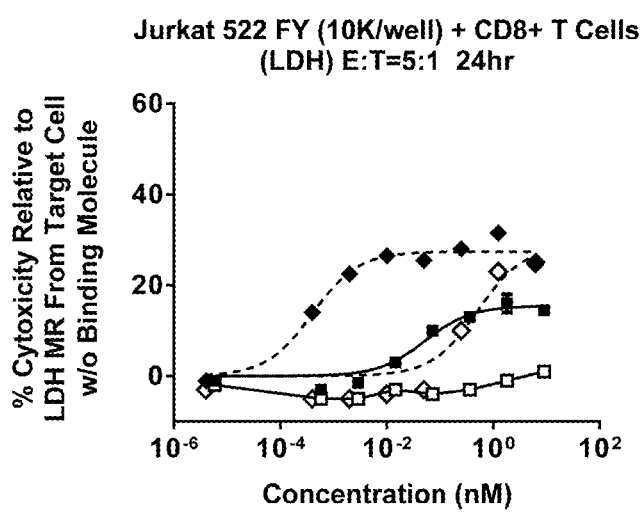
Figure 24C:
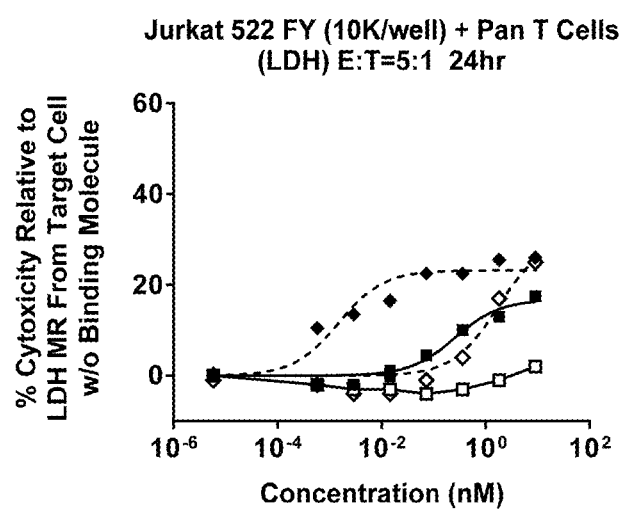

FIGS. 24A-24C show the results of an assessment of the CTL activity of the HIV mAb 2/CD3 mAb 2/CD8 mAb 1 Tri-Specific Binding Molecule on HIV env-expressing Jurkat 522 FY cells using CD4+, CD8+ or pan T cells.

Figure 25A:
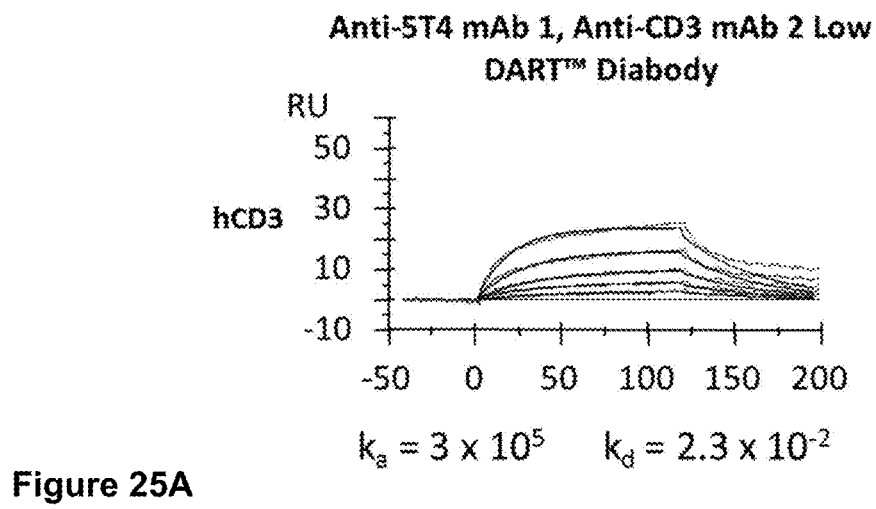
Figure 25B:
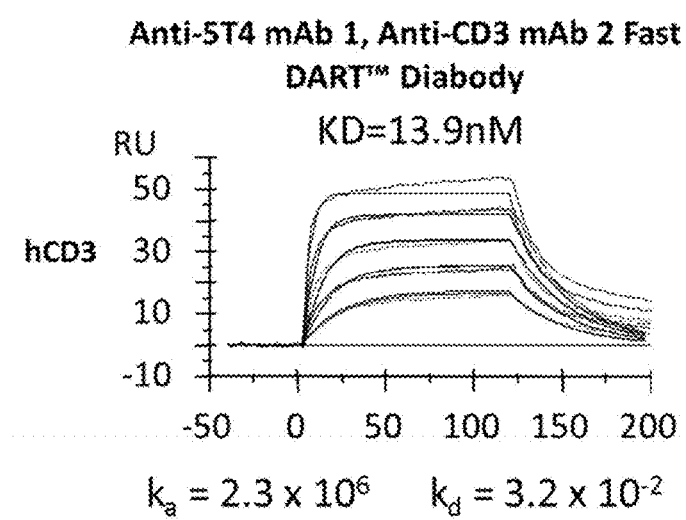
Figure 25C:
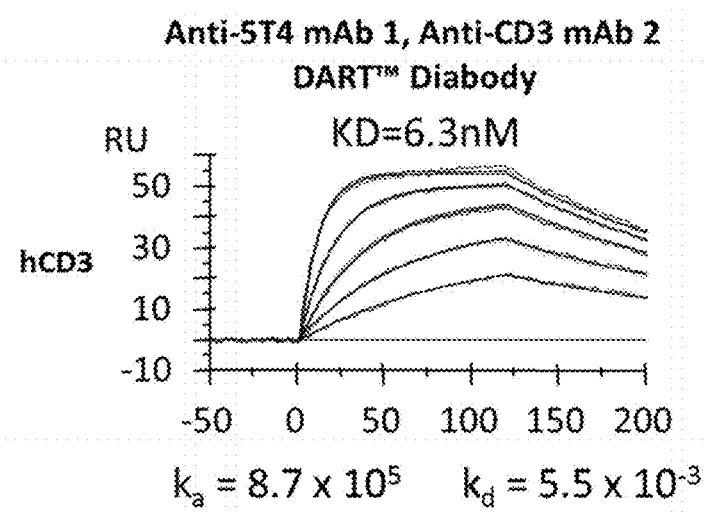

FIGS. 25A-25C show the kinetics of binding for DART™ molecules having the CD3 mAb 2 Binding Domain (FIG. 25A), and its CD3 mAb 2 Low (FIG. 25B) and CD3 mAb 2 Fast (FIG. 25C) affinity variants.

Figure 26A:
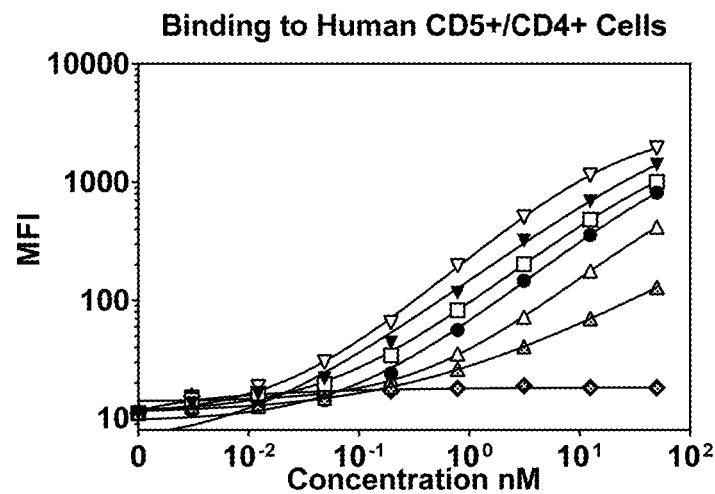
Figure 26B:
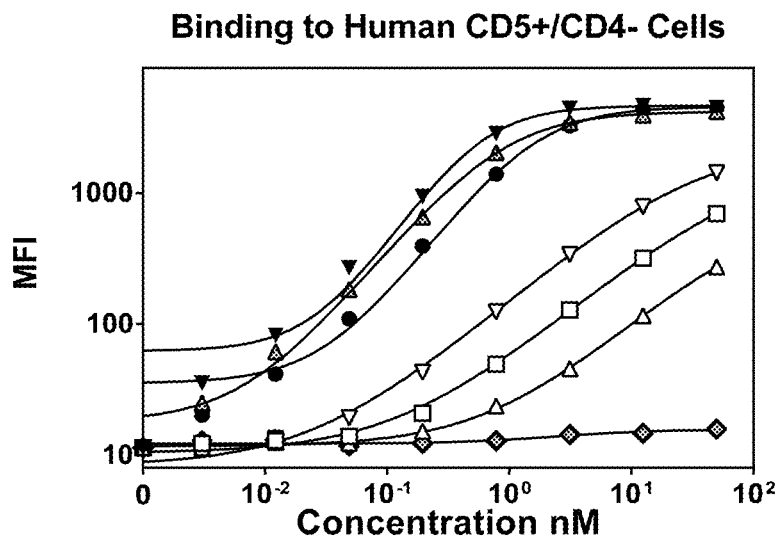

FIGS. 26A-26B show the CD5$^+$ CD4$^+$ gated (FIG. 26A) or CD5$^+$ CD4$^-$ gated (FIG. 26B) cell populations of human PMBC as a function of increasing concentration of the 5T4 mAb 1/CD3 mAb 2/CD8 mAb 1 Tri-Specific Binding Molecule, the 5T4 mAb 1/CD3 mAb 2 Low/CD8 mAb 1 Tri-Specific Binding Molecule and the 5T4 mAb 1/CD3 mAb 2 Fast/CD8 mAb 1 Tri-Specific Binding Molecule. 5T4×CD3 DARTs™ (with wild-type, Low and Fast CD3 specificities were used as controls.

Figure 27A:
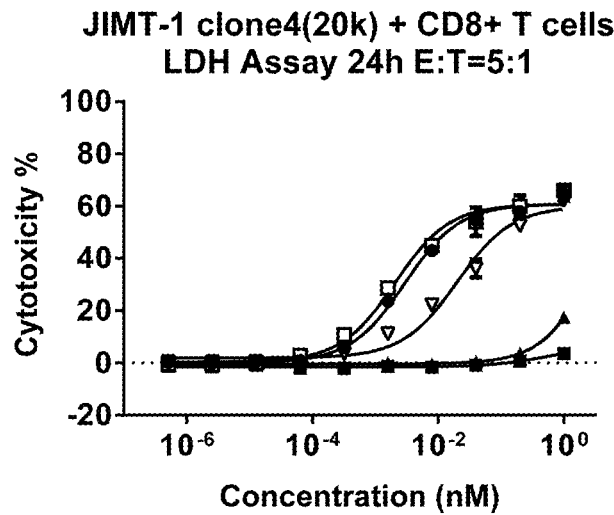
Figure 27B:
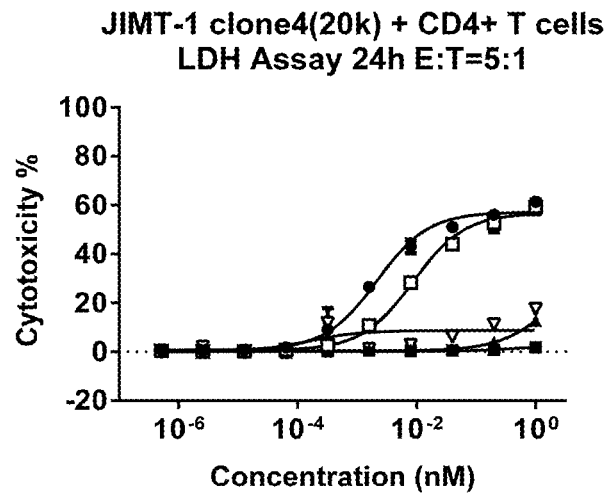
Figure 27C:
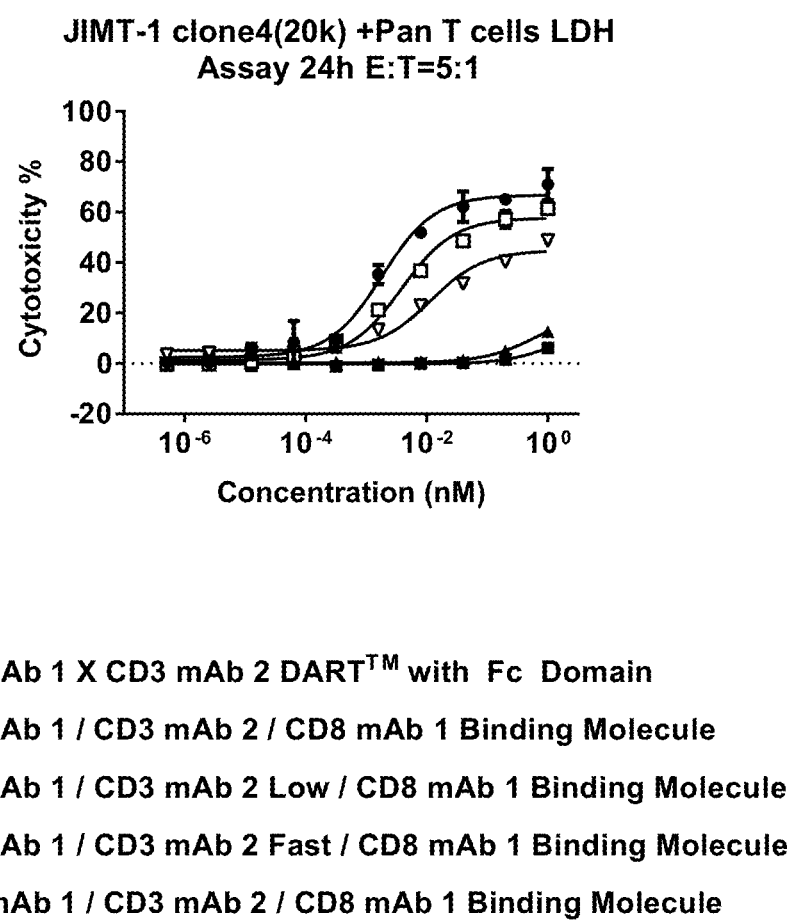
Figure 28A:
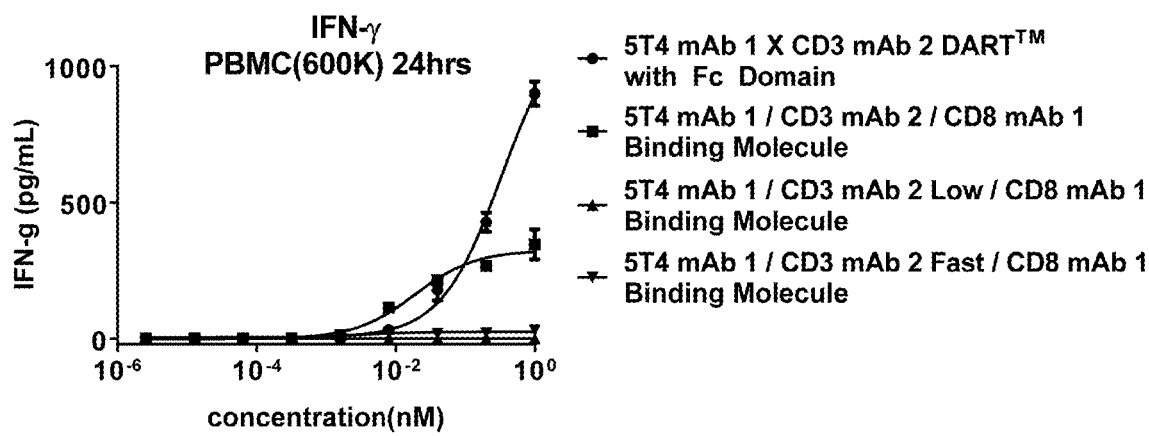
Figure 28B:
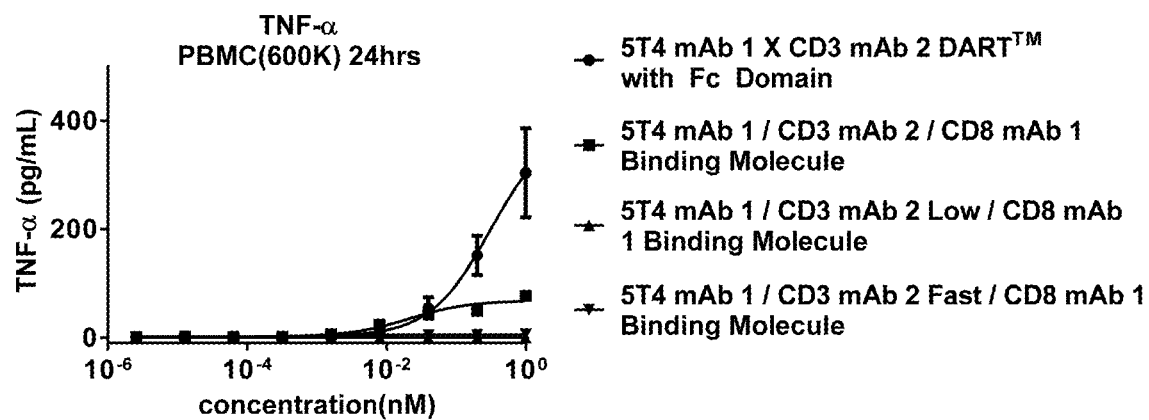
Figure 28C:
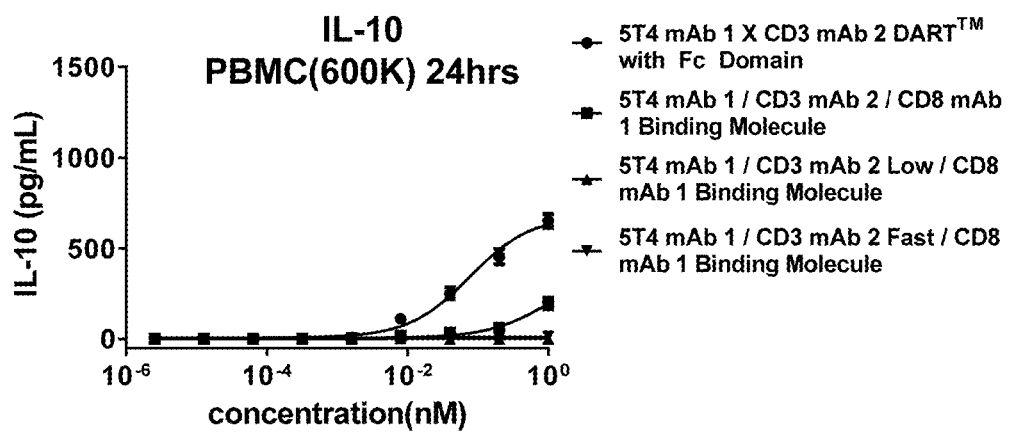
Figure 28D:
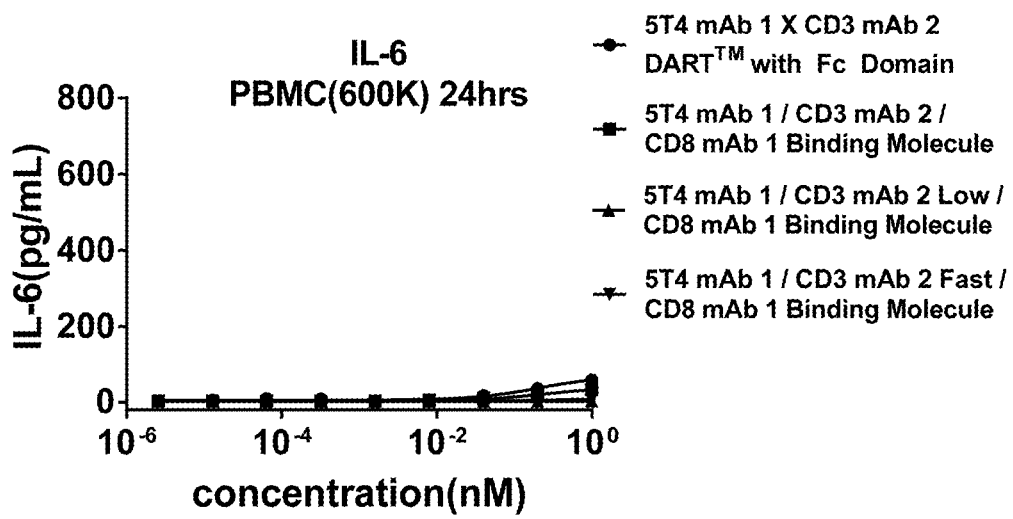
Figure 28E:
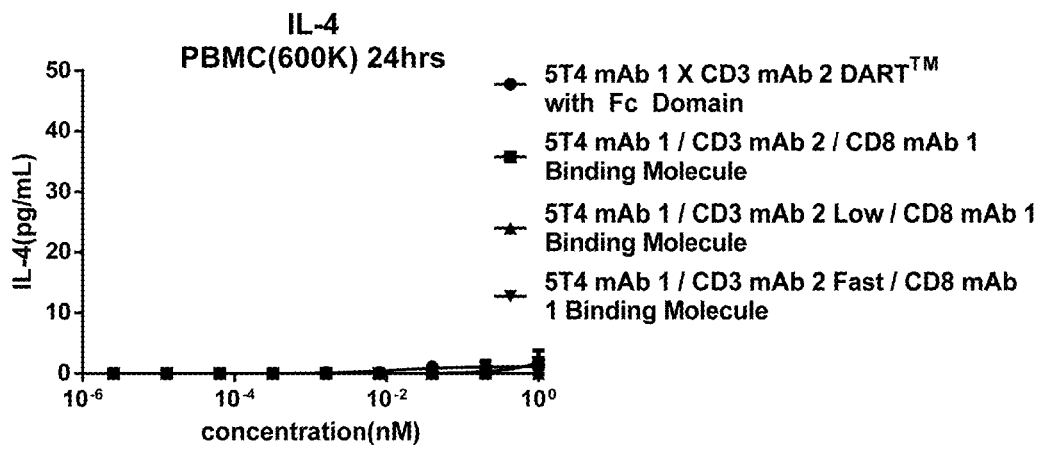
Figure 28F:
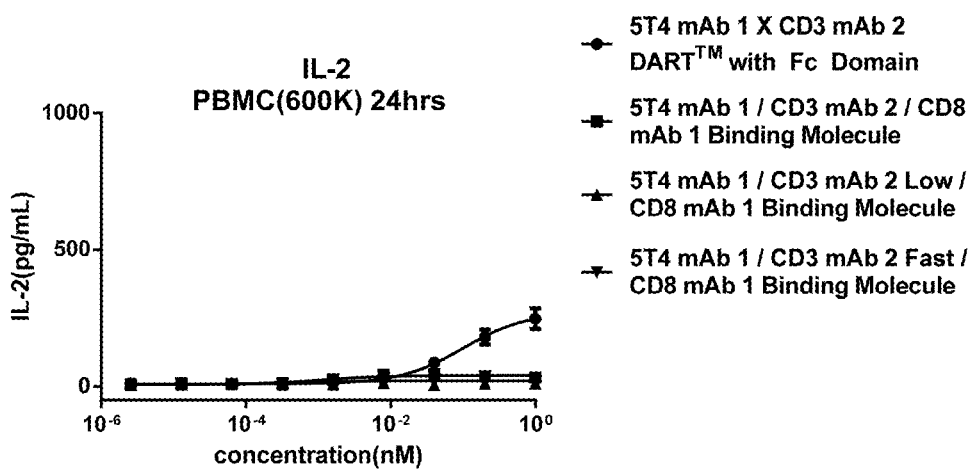
Figure 29A:
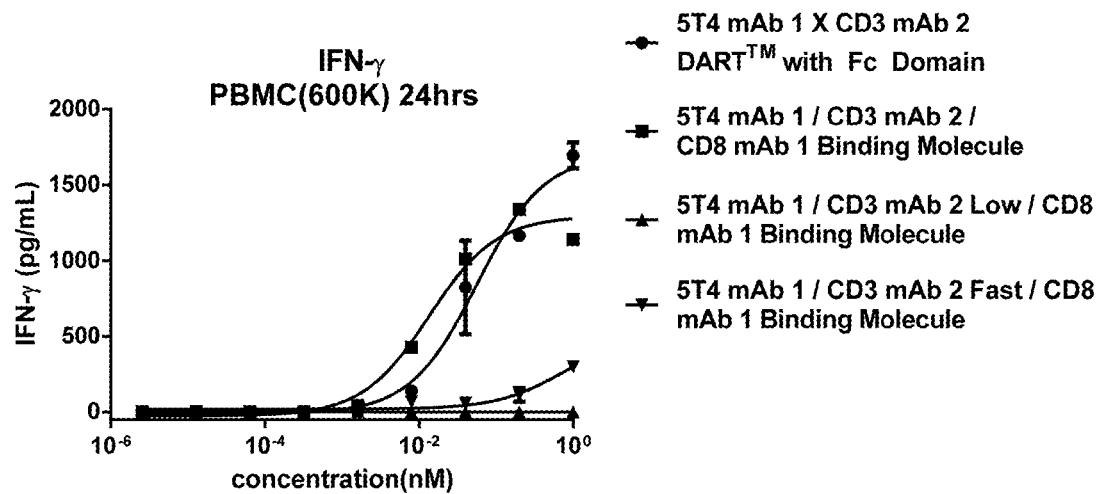
Figure 29B:
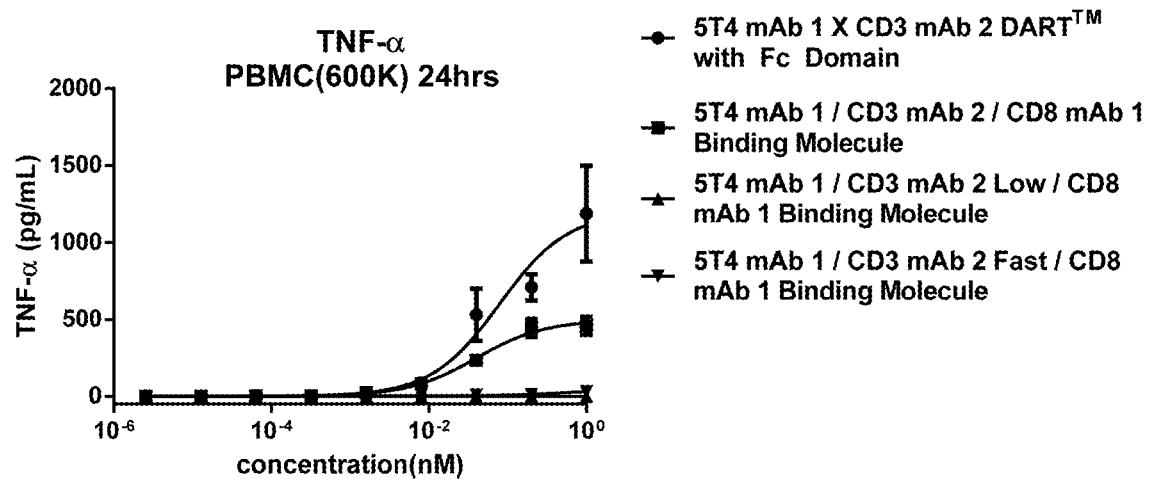
Figure 29C:
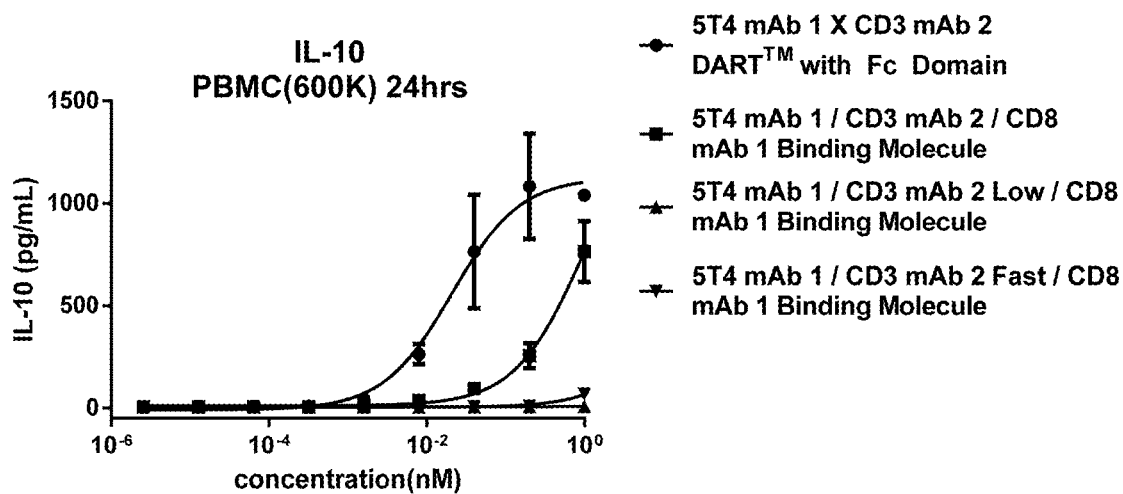
Figure 29D:
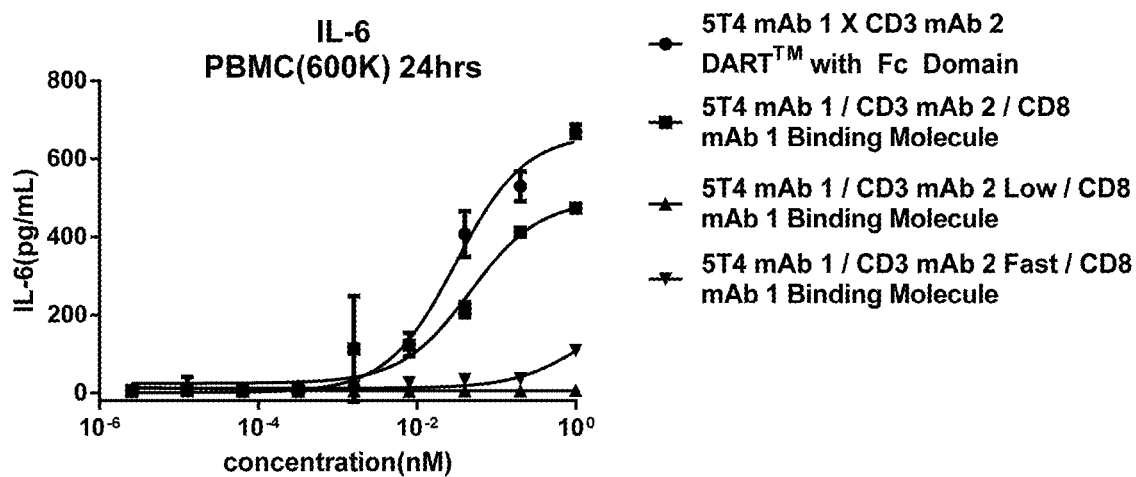
Figure 29E:
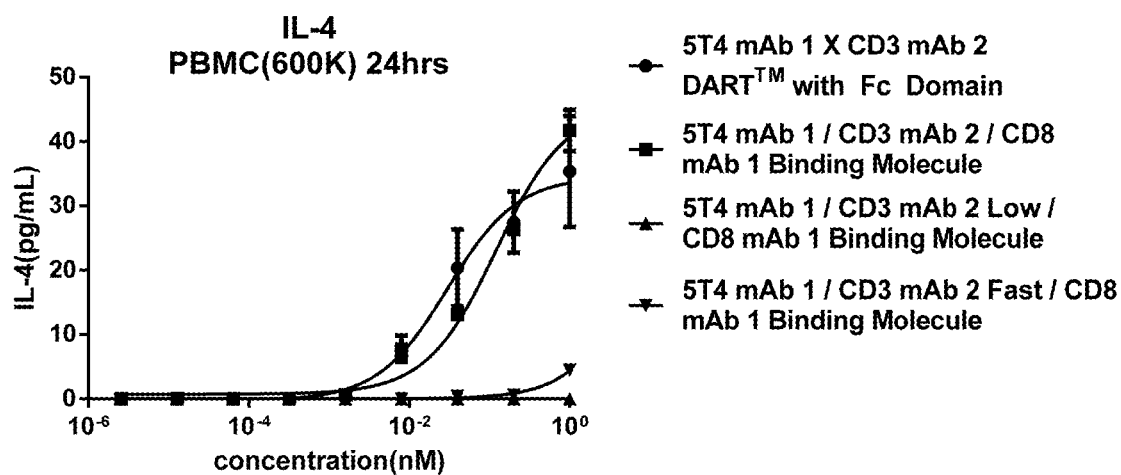
Figure 29F:
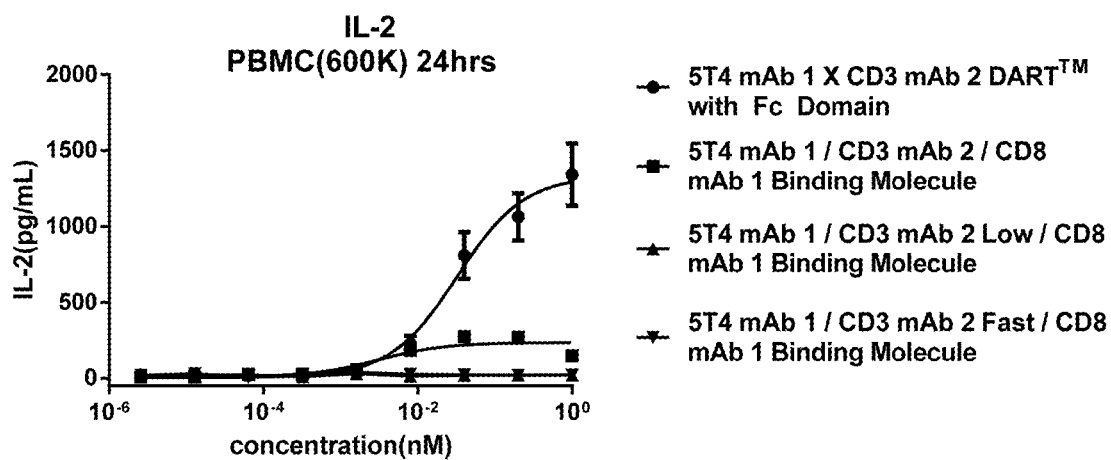

FIGS. 27A-27C show the effect of the CD3 mAb variants (CD3 mAb 2 Low and CD3 mAb 2 Fast) on the cytotoxicity of a 5T4 mAb 1/CD3 mAb 2/CD8 mAb 1 Tri-Specific Binding Molecule using an LDH assay.

FIGS. 28A-28F demonstrate the level of IFN-γ (FIG. 28A), TNF-α (FIG. 28B), IL-10 (FIG. 28C), IL-6 (FIG. 28D), IL-4 (FIG. 28E), and IL-2 (FIG. 28F) released from PBMCs from Donor 1 in the presence of increasing concentrations of 5T4 mAb 1/CD3 mAb 2/CD8 mAb 1 Tri-Specific Binding Molecule, 5T4 mAb 1/CD3 mAb 2 Low/CD8 mAb 1 Tri-Specific Binding Molecule and 5T4 mAb 1/CD3 mAb 2 Fast/CD8 mAb 1 Tri-Specific Binding Molecule.

FIGS. 29A-29F demonstrate the level of IFN-γ (FIG. 29A), TNF-α (FIG. 29B), IL-10 (FIG. 29C), IL-6 (FIG. 29D), IL-4 (FIG. 29E), and IL-2 (FIG. 29F) released from PBMCs from Donor 2 in the presence of increasing concentrations of 5T4 mAb 1/CD3 mAb 2/CD8 mAb 1 Tri-Specific Binding Molecule, 5T4 mAb 1/CD3 mAb 2 Low/CD8 mAb 1 Tri-Specific Binding Molecule and 5T4 mAb 1/CD3 mAb 2 Fast/CD8 mAb 1 Tri-Specific Binding Molecule.

DETAILED DESCRIPTION OF THE INVENTION

The present invention relates to Tri-Specific Binding Molecules, which are multi-chain polypeptide molecules that possess three Binding Domains and are thus capable of mediating coordinated binding to three epitopes. The Binding Domains may be selected such that the Tri-Specific Binding Molecules are capable of binding to any three different epitopes. Such epitopes may be epitopes of the same antigen or epitopes of two or three different antigens. The invention also provides a novel ROR1-binding antibody, as well as derivatives thereof and uses for such compositions.

I. General Techniques and General Definitions

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, MOLECULAR CLONING: A LABORATORY MANUAL, Third Edition (Sambrook et al. Eds., 2001) Cold Spring Harbor Press, Cold Spring Harbor, NY; OLIGONUCLEOTIDE SYNTHESIS: METHODS AND APPLICATIONS (Methods in Molecular Biology), Herdewijn, P., Ed., Humana Press, Totowa, NJ; OLIGONUCLEOTIDE SYNTHESIS (Gait, M. J., Ed., 1984); METHODS IN MOLECULAR BIOLOGY, Humana Press, Totowa, NJ; CELL BIOLOGY: A LABORATORY NOTEBOOK (Cellis, J. E., Ed., 1998) Academic Press, New York, NY; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, NY; CELL AND TISSUE CULTURE: LABORATORY PROCEDURES (Doyle, A. et al., Eds., 1993-8) John Wiley and Sons, Hoboken, NJ; METHODS IN ENZYMOLOGY (Academic Press, Inc.) New York, NY; WEIR'S HANDBOOK OF EXPERIMENTAL IMMUNOLOGY (Herzenberg, L. A. et al. Eds. 1997) Wiley-Blackwell Publishers, New York, NY; GENE TRANSFER VECTORS FOR MAMMALIAN CELLS (Miller, J. M. et al. Eds., 1987) Cold Spring Harbor Press, Cold Spring Harbor, NY; CURRENT PROTOCOLS IN MOLECULAR BIOLOGY (Ausubel, F. M. et al., Eds., 1987) Greene Pub. Associates, New York, NY; PCR: THE POLYMERASE CHAIN REACTION, (Mullis, K. et al., Eds., 1994) Birkhauser, Boston MA; CURRENT PROTOCOLS IN IMMUNOLOGY (Coligan, J. E. et al., eds., 1991) John Wiley and Sons, Hoboken, NJ; SHORT PROTOCOLS IN MOLECULAR BIOLOGY (John Wiley and Sons, 1999) Hoboken, NJ; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York NY); MONOCLONAL ANTIBODIES: A PRACTICAL APPROACH (Shepherd, P. et al. Eds., 2000) Oxford University Press, USA, New York NY; USING ANTIBODIES: A LABORATORY MANUAL (Harlow, E. et al. Eds., 1998) Cold Spring Harbor Laboratory Press, Cold Spring Harbor, NY; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, PA II. Preferred Tri-Specific Binding Molecules of the Present Invention A. Binding Capabilities The preferred Tri-Specific Binding Molecules of the present invention are able to coordinately and simultaneously bind to three different epitopes. Such preferred Tri-Specific Binding Molecules of the present invention comprise:

(I) a "Binding Domain I" that is capable of immunospecifically binding to an "Epitope I" present on a first antigen, and a "Binding Domain II" that is capable of immunospecifically binding to an "Epitope II" present on a second antigen, wherein said Binding Domain I and said Binding Domain II are both "Diabody-Type Binding Domains;"

(II) a "Non-Diabody-Type" "Binding Domain III" that is capable of immunospecifically binding to an "Epitope III" present on a third antigen; and (III) an Fc Domain that is formed by the complexing of two CH2-CH3 Domains to one another.

Typically, the Tri-Specific Binding Molecules of the present invention will comprise four different polypeptide chains, each having an amino terminus and a carboxyl terminus (see FIG. 4A-4D, FIG. 5A and FIG. 5B), however, the molecules may comprise fewer or greater numbers of polypeptide chains by fusing such polypeptide chains to one another (e.g., via a peptide bond) or by dividing such polypeptide chains to form additional polypeptide chains. FIGS. 4E-4J illustrate this aspect of the present invention by schematically depicting such molecules having three polypeptide chains. FIG. 4K-4L illustrate this aspect of the present invention by schematically depicting molecules having five polypeptide chains.

Although such Tri-Specific Binding Molecules are particularly preferred, the invention additionally specifically contemplates Tri-Specific Binding Molecules that comprise any combination of Binding Domains sufficient to produce a molecule having three binding specificities, of which two are binding specificities directed against Cancer Antigens, and one is a binding specificity directed against an Effector Cell Antigen. Thus, for example, the invention contemplates: a Tri-Specific Binding Molecule that comprises three Fab-Type Binding Domains, a Tri-Specific Binding Molecule that comprises one bivalent, bi-specific antibody domain (formed for example, by complexing two different light chains and two different heavy chains) and one Fab-Type Binding Domain, a Tri-Specific Binding Molecule that comprises two bivalent, bi-specific antibody domains (formed for example, by complexing four different light chains and two different heavy chains), but in which one of antibody domains has been rendered inactive, etc.

The terms "polypeptide," "polypeptide chain," and "peptide" are used interchangeably herein to refer to polymers of amino acids of any length, but especially lengths greater than 3, 5, 10, 15, 20 or 25 amino acid residues, in which two, and more preferably all, amino acid residues are joined via an amide (peptide) bond (—NH—C(O)—). The polymer may however be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The polypeptides of this invention can occur as single-chains or as complexed chains.

A "Diabody-Type Binding Domain" is the Epitope-Binding Domain of a diabody, and especially, a DART® diabody. The terms "diabody" and "DART® diabody" has been discussed above, and refers to a molecule that comprises at least two polypeptide chains that preferably complex with one another through a covalent interaction to form at least two epitope binding sites, which may recognize the same or different epitopes. Two of the polypeptide chains of a diabody or DART® diabody each comprise immunoglobulin Light Chain Variable Region and an immunoglobulin Heavy Chain Variable Region, but these regions do not interact to form an epitope binding site (i.e., they are not mutually "complementary"). Rather, the immunoglobulin Heavy Chain Variable Region of one (e.g., the first) of the diabody, or DART® diabody, chains interacts with the immunoglobulin Light Chain Variable Region of a different (e.g., the second) diabody or, DART® diabody, polypeptide chain to form an epitope binding site. Similarly, the immunoglobulin Light Chain Variable Region of one (e.g., the first) of the diabody, or DART® diabody, polypeptide chains interacts with the immunoglobulin Heavy Chain Variable Region of a different (e.g., the second) diabody, or DART® diabody, polypeptide chain to form an epitope binding site.

DART® diabody molecules are disclosed in United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; WO 2006/113665, WO 2008/157379 and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bi-specific Antibody Scaffold*," Arthritis Rheum. 62(7):1933-1943; and Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449.

Binding Domain III is preferably a "Non-Diabody-Type" Binding Domain, which is intended to denote that Binding Domain III does not have the structure of a Diabody-Type Binding Domain. Preferably, Binding Domain III is a Non-Diabody-Type Binding Domain that is a Fab-Type Binding Domain or a Receptor-Type Binding Domain. As used herein, the term "Fab-Type Binding Domain" refers to an epitope-Binding Domain that is formed by the interaction of the VL Domain of an immunoglobulin Light Chain and a complementing VH Domain of an immunoglobulin heavy chain. Fab-Type Binding Domains differ from Diabody-Type Binding Domain in that the two polypeptide chains that form a Fab-Type Binding Domain comprise only a single epitope-Binding Domain, whereas the two polypeptide chains that form a Diabody-Type Binding Domain comprise at least two epitope-Binding Domains. Thus, as used herein Fab-Type Binding Domains are distinct from Diabody-Type Binding Domain. As used herein, the term "Receptor-Type Binding Domain" refers to an epitope-binding domain of a cellular receptor that is formed by the interaction of two polypeptides. Receptor-Type Binding Domains are exemplified herein by reference to a T Cell Receptor-Type Binding Domain, which is formed from the interaction of a Variable Domain of a T Cell Receptor alpha chain and a Variable Domain of a T Cell Receptor beta chain. Such T Cell Receptor Binding Domains recognize peptides displayed in the context of MHC and are thus capable of recognizing intracellular epitopes. Although the invention is illustrated with regard to such Receptor-Type Binding Domains, it will be appreciated that Receptor-Type Binding Domains other than T Cell Receptor-Type Binding Domains may be employed, and are encompassed by the present invention. Other examples of receptors having Receptor-Type Binding Domains include the IL-2 receptor, the IL-4 receptor, the IL-7 receptor, the IL-9 receptor, the IL-15 receptor, the IL-21 the insulin receptor, and thymic stromal lymphopoietin.

The Tri-Specific Binding Molecules of the present invention are thus distinguished from tetravalent binding molecules, such as those produced from the dimerization of a bivalent antibody, and preferably possess three and not four Binding Domains. As discussed below, the trispecific molecules of the present invention may possess additional binding domains (such as an Albumin-Binding Domain, an FcγR-Binding Domain, etc.). Such additional Binding Domains are not intended to be considered or counted as being one of the three Binding Domains of the Tri-Specific Binding Molecules of the present invention.

As used herein, the terms "association" or "associating," with regard to polypeptides (e.g., one diabody polypeptide to another, an immunoglobulin Light Chain to an immunoglobulin heavy chain, one CH2-CH3 Domain to another CH2-CH3 Domain, etc.) is intended to denote a non-covalent combining of the polypeptides. The terms "complexes" or "complexing" are intended to denote a covalent combining of the polypeptides.

As used herein, Binding Domains of the Tri-Specific Binding Molecules of the invention are said to mediate "coordinated binding" if at least two of its Binding Domains and preferably all of its Binding Domains, are capable of concurrently being bound to their respective recognized epitopes or binding ligand. Such binding may be simultaneous. However, one aspect of the present invention relates to modifying the "on" and/or "off" rates with which such Binding Domains bind to their recognized epitopes. As used here, the "on rate" of binding is a measure of the affinity with which such Binding Domains recognize and initiate binding to their recognized epitopes. In contrast, the "off rate" of binding is a measure of the degree of stability of the Binding Domain:epitope complex. The "on" and/or "off" rates of binding can be modified by altering the amino acid sequence of the CDRs of a Binding Domain. As discussed below, independent of any CDR modifications, the extent of coordinated binding of the molecules of the present invention may be modulated by changing the configuration of the their Binding Domains so that a particular Binding Domain (i.e., a VLx/VHx Domain) is present as Binding Domain III or as an internal or external Diabody-Type Binding Domain relative to Binding Domain III (discussed in detail below).

The on- and off-rates of the Binding Domains of the Binding Molecules of the present invention can be readily measured by methods well-known in the art, for example by BIACORE® analysis (Jason-Moller, L. et al. (2006) "*Overview Of Biacore Systems And Their Applications*," Curr. Protoc. Protein Sci. Chapter 19:Unit 19.13; Swanson, S. J. (2005) "*Characterization Of An Immune Response*," Dev. Biol. (Basel). 122:95-101; Buijs, J. et al. (2005) "*SPR-MS In Functional Proteomics*," Brief Funct. Genomic Proteomic. 4(1):39-47; Karlsson, R. et al. (2004) "*SPR For Molecular Interaction Analysis: A Review Of Emerging Application Areas*," J. Mol. Recognit. 17(3):151-161; Van Regenmortel, M. H. (2003) "*Improving The Quality Of BIACORE-Based Affinity Measurements*," Dev. Biol. (Basel) 112:141-151; Malmqvist, M. (1999) "*BIACORE: An Affinity Biosensor System For Characterization Of Biomolecular Interactions*," Biochem. Soc. Trans. 27(2):335-340; Malmqvist, M. et al. (1997) "*Biomolecular Interaction Analysis: Affinity Biosensor Technologies For Functional Analysis Of Proteins*," Curr. Opin. Chem. Biol. 1(3):378-383; Fivash, M. et al. (1998) "*Biacore For Macromolecular Interaction*," Curr. Opin. Biotechnol. 9(1):97-101; Malmborg, A. C. et al. (1995) "*Biacore As A Tool In Antibody Engineering*," J. Immunol. Methods. 183(1):7-13). The on- and off-rates of the Binding Domains of the Binding Molecules of the present invention can be readily altered by random or directed mutagenesis of nucleic acid molecules that encode such Binding Domains, followed by the routine screening of recovered nucleic acid molecules for their ability to encode mutated proteins that exhibit such altered binding kinetics.

The Binding Domains of the Tri-Specific Binding Molecules of the present invention bind to epitopes in an "immunospecific" manner. As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "specific binding" does not necessarily require (although it can include) exclusive binding. Generally, but not necessarily, reference to binding means "specific" binding. Two molecules are said to be capable of binding to one another in a "physiospecific" manner, if such binding exhibits the specificity with which receptors bind to their respective ligands.

Thus, in their simplest embodiment, the preferred binding molecules of the present invention are at least tri-specific—being capable of mediating coordinated binding to three different epitopes. Significantly, such molecules have at least three "sites" that are capable of binding antigen: an "external" Diabody-Type Binding Domain that is located furthest from Binding Domain III, an "internal" Diabody-Type Binding Domain that is located nearest to Binding Domain III, and Binding Domain III itself. The positions of such Domains are respectively designated as Site A, Site B and Site C (FIGS. 4A-4D).

The Binding Domains that bind to Epitopes I, II and III are selected to be different from one another. However, Epitopes I, II and III may be epitopes of the same antigen, of two different antigens, or of three different antigens. Thus the Tri-Specific Binding Molecules of the present invention may be capable of coordinately binding 1, 2, or 3 different antigen molecules. The Tri-Specific Binding Molecules of the present invention may be employed with respect to any possible epitope and any possible antigen. For example, the Tri-Specific Binding Molecules of the present invention may have 1, 2, or 3 Binding Domains that bind to an epitope of an effector cell (e.g., CD2, CD3, CD16, CD19, CD20, CD22, CD32B, CD64, the B cell Receptor (BCR), the T cell Receptor (TCR), and the NKG2D Receptor), or to an epitope of a cytotoxic T cell (e.g., CD8 present on cytotoxic T cells), or to an epitope of a Disease-Associated Antigen, or any combination of such potential Binding Domains.

As used herein, a "Disease-Associated Antigen" is an antigen that is characteristically expressed on a "pathogen-infected" cell or on a "cancer cell," but characteristically not expressed on a normal cell.

As used herein, the term "pathogen-infected" cell refers to a cell that has been infected by a bacterium (e.g., *E. coli, C. difficile, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis* and *Streptococcus pneumonia*, etc.), a fungus (e.g., *Candida, Aspergillus, Cryptococcus, Coccidioides, Histoplasma, Pneumocystis,* Stachybotrys, etc.), a protozoan (Amoebozoa, Excavata, Chromalveolata, *Entamoeba, Plasmodium, Giardia, Trypanosoma, Coccidia, Besnoitia, Dicrocoelium, Leishmania,* etc.) or a virus (and especially an adenovirus, an adeno-associated virus, a B virus (macacine herpesvirus I), a BK virus, a bunyavirus, a chikungunya virus, a cocksackie virus, a coronavirus, a cytomegalovirus, an eastern equine encephalitis virus, an ebola virus, an enterovirus, an Epstein-Barr virus, a hantavirus, a hepatitis A virus, a hepatitis B virus, a hepatitis C virus, a hepatitis D virus, a hepatitis E virus, a herpes simplex virus 1, a herpes simplex virus 2, a human foamy virus, a human herpes virus 3, a human herpes virus 5, a human herpes virus 6, a human herpes virus 7, a human immunodeficiency virus, a human papillomavirus, a human β-lymphotropic virus, a human T cell leukemia virus I, a human T cell leukemia virus II, an influenza virus, a JC virus, a JEV, a Kaposi's sarcoma-associated herpesvirus, a Lassa virus, a lymphocytic choriomenengitis virus, a Marburg virus, a measles virus, a mumps virus, a Nipah virus, a norovirus, a Norwalk virus, an orthoreovirus, a parainfluenza virus, a parvovirus, a poliovirus, a rabies virus, a reovirus, a respiratory syncytial virus, rhinovirus, a Rift Valley fever virus, a rotavirus, rubella virus, a smallpox virus, a St Louis encephalitis virus, a variola major virus, a variola minor virus, a vericella-zoster virus, a West Nile virus, a western equine encephalitis virus, or a yellow fever virus).

As used herein, the term "cancer cell" refers to a malignant cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, or a uterine cancer.

Examples of antigens that are characteristically expressed by cancer cells include a "cancer antigen" such as a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkins lymphoma, or an antigen associated with chronic lymphocytic leukemia. Exemplary antigens that are characteristically expressed by cancer cells include the antigens: colon cancer antigen 19.9; gastric cancer mucin antigen 4.2; colorectal carcinoma antigen A33 (Almqvist, Y. 2006, *Nucl Med Biol.* November; 33(8):991-998); ADAM-9 (United States Patent Publication No. 2006/0172350; PCT Publication No. WO 06/084075; AFP oncofetal antigen-alpha-fetoprotein (Malaguarnera, G. et al. (2010) "*Serum markers of hepatocellular carcinoma,*" Dig. Dis. Sci. 55(10):2744-2755); ALCAM (PCT Publication No. WO 03/093443); BAGE (Bodey, B. 2002 *Expert Opin Biol Ther.* 2(6):577-84); beta-catenin (Prange W. et al. 2003 *J Pathol.* 201(2):250-9); CA125 (Bast, R. C. Jr. et al.

2005 *Int J Gynecol Cancer* 15 Suppl 3:274-81); Carboxypeptidase M (United States Patent Publication No. 2006/0166291); B1 (Egloff, A. M. et al. 2006, *Cancer Res.* 66(1):6-9); CD5 (Calin, G. A. et al. 2006 *Semin Oncol.* 33(2):167-73; CD19 (Troussard, X. et al. 1998 *Hematol Cell Ther.* 40(4):139-48); CD20 (Thomas, D. A. et al. 2006 Hematol Oncol Clin North Am. 20(5):1125-36); CD20 (Cang, S. et al. (2012) "*Novel CD20 Monoclonal Antibodies For Lymphoma Therapy,*" J. Hematol. Oncol. 5:64 pp. 1-9); CD22 (Kreitman, R. J. 2006 AAPS J. 18; 8(3):E532-51); CD23 (Rosati, S. et al. 2005 *Curr Top Microbiol Immunol.* 5; 294:91-107); CD25 (Troussard, X. et al. 1998 *Hematol Cell Ther.* 40(4):139-48); CD27 (Bataille, R. 2006 *Haematologica* 91(9):1234-40); CD28 (Bataille, R. 2006 *Haematologica* 91(9): 1234-40); CD30 (Muta, H. et al. (2013) "*CD30: From Basic Research To Cancer Therapy,*" Immunol. Res. 57(1-3):151-158); CD33 (Walter, R. B. et al. (2012) "Acute myeloid leukemia stem cells and CD33-targeted immunotherapy," Blood 119(26):6198-6208); CD36 (Ge, Y. 2005 Lab Hematol. 11(1):31-7); CD40/CD154 (Messmer, D. et al. 2005 *Ann NY Acad Sci.* 1062:51-60); CD45 (Jurcic, J. G. 2005 *Curr Oncol Rep.* 7(5):339-46); CD56 (Bataille, R. 2006 *Haematologica* 91(9):1234-40); CD46 (U.S. Pat. No. 7,148,038; PCT Publication No. WO 03/032814; Russell, S. et al. (2004) "*CD46: A Complement Regulator And Pathogen Receptor That Mediates Links Between Innate And Acquired Immune Function,*" Tissue Antigens 64(2):111-118); CD52 (Hoelzer, D. et al. (2013) "Targeted therapy with monoclonal antibodies in acute lymphoblastic leukemia," Curr. Opin. Oncol. 25(6):701-706); CD79a/CD79b (Troussard, X. et al. 1998 *Hematol Cell Ther.* 40(4):139-48; Chu, P. G. et al. 2001 Appl Immunohistochem Mol Morphol. 9(2):97-106); CD103 (Troussard, X. et al. 1998 *Hematol Cell Ther.* 40(4):139-48); CD317 (Palma, G. et al. (2012) "*Plasmacytoids Dendritic Cells Are A Therapeutic Target In Anticancer Immunity,*" Biochim. Biophys. Acta. 1826(2):407-414; CDK4 (Lee, Y. M. et al. 2006 *Cell Cycle* 5(18):2110-4); CEA (carcinoembryonic antigen; Mathelin, C. 2006 *Gynecol Obstet Fertil.* 34(7-8):638-46; Tellez-Avila, F. I. et al. 2005 *Rev Invest Clin.* 57(6):814-9); CEACAM5 and CEACAM6 (PCT Publication No. WO 2011/034660; Zheng, C. et al. (2011) "*A Novel Anti-CEACAM5 Monoclonal Antibody, CC4, Suppresses Colorectal Tumor Growth and Enhances NK Cells-Mediated Tumor Immunity,*" PLoS One 6(6):e21146, pp. 1-11); CO17-1A (Adkins, J. C. et al. (1998) "*Edrecolomab (Monoclonal Antibody 17-1A),*" Drugs 56(4):619-626; CO-43 (blood group Leb) and CO-514 (blood group Lea) (Garratty, G. (1995) "*Blood Group Antigens As Tumor Markers, Parasitic/Bacterial/Viral Receptors, And Their Association With Immunologically Important Proteins,*" Immunol. Invest. 24(1-2):213-232; CTLA-1 and CTLA-4 (Peggs, K. S. et al. 2006 Curr Opin Immunol. 18(2):206-13); Cytokeratin 8 (PCT Publication No. WO 03/024191); antigen D1.1 (Dao, T. et al. (2009) "*Identification Of A Human Cyclin D1-Derived Peptide That Induces Human Cytotoxic CD4 T Cells,*" PLoS One. 4(8):e6730); DR5 (Abdulghani, J. et al. (2010) "*TRAIL Receptor Signaling And Therapeutics,*" Expert Opin. Ther. Targets 14(10):1091-1108; Andera, L. (2009) "*Signaling Activated By The Death Receptors Of The TNFR Family,*" Biomed. Pap. Med. Fac. Univ. Palacky Olomouc Czech. Repub. 153(3):173-180; Carlo-Stella, C. et al. (2007) "*Targeting TRAIL Agonistic Receptors for Cancer Therapy,*" Clin, Cancer 13(8):2313-2317; Chaudhari, B. R. et al. (2006) "*Following the TRAIL to Apoptosis,*" Immunologic Res. 35(3):249-262); E1 series (blood group B); EGF-R (epidermal growth factor receptor; Adenis, A. et al. 2003 *Bull Cancer.* 90 Spec No:S228-32); Ephrin receptors (and in particular EphA2 (U.S. Pat. No. 7,569,672; PCT Publication No. WO 06/084226); Erb (ErbB1; ErbB3; ErbB4; Zhou, H. et al. 2002 *Oncogene* 21(57):8732-40; Rimon, E. et al. 2004 Int J Oncol. 24(5):1325-38); lung adenocarcinoma antigen F3 (Greulich, H. et al. (2012) "*Functional analysis of receptor tyrosine kinase mutations in lung cancer identifies oncogenic extracellular domain mutations of ERBB2,*" Proc. Natl. Acad. Sci. (U.S.A.) 109(36):14476-14481); antigen FC10.2 (Loveless, W. et al. (1990) "*Developmental Patterning Of The Carbohydrate Antigen FC10.2 During Early Embryogenesis In The Chick,*" Development 108(1):97-106); GAGE (GAGE-1; GAGE-2; Akcakanat, A. et al. 2006 *Int J Cancer.* 118(1):123-8); GD2/GD3/GD49/GM2/GM3 (Livingston, P. O. et al. 2005 Cancer Immunol Immunother. 54(10):1018-25); GICA 19-9 (Herlyn et al. (1982) "*Monoclonal Antibody Detection Of A Circulating Tumor-Associated Antigen. I. Presence Of Antigen In Sera Of Patients With Colorectal, Gastric, And Pancreatic Carcinoma,*" J. Clin. Immunol. 2:135-140); gp37 (human leukemia T cell antigen ((Bhattacharya-Chatterjee et al. (1988) "*Idiotype Vaccines Against Human T Cell Leukemia. II. Generation And Characterization Of A Monoclonal Idiotype Cascade (Ab1, Ab2, and Ab3),*" J. Immunol. 141:1398-1403); gp75 (melanoma antigen) (Vijayasardahl et al. (1990) "*The Melanoma Antigen Gp75 Is The Human Homologue Of The Mouse B (Brown) Locus Gene Product,*" J. Exp. Med. 171(4):1375-1380); gp100 (Lotem, M. et al. 2006 *J Immunother.* 29(6):616-27); HER-2/neu (Kumar, Pal S et al. 2006 Semin Oncol. 33(4):386-91); human B-lymphoma antigen-CD20 (Reff et al. (1994) "*Depletion Of B Cells In Vivo By A Chimeric Mouse Human Monoclonal Antibody To CD20,*" Blood 83:435-445); human milk fat globule antigen; human papillomavirus-E6/human papillomavirus-E7 (DiMaio, D. et al. 2006 *Adv Virus Res.* 66:125-59; HMW-MAA (high molecular weight melanoma antigen) (Natali et al. (1987) "*Immunohistochemical Detection Of Antigen In Human Primary And Metastatic Melanomas By The Monoclonal Antibody 140.240 And Its Possible Prognostic Significance,*" Cancer 59:55-63; Mittelman et al. (1990) "*Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies,*" J. Clin. Invest. 86:2136-2144); I antigen (differentiation antigen) (Feizi (1985) "*Demonstration By Monoclonal Antibodies That Carbohydrate Structures Of Glycoproteins And Glycolipids Are Onco-Developmental Antigens,*" Nature 314:53-57) such as I(Ma) as found in gastric adenocarcinomas; Integrin Alpha-V-Beta-6 Integrinβ6 (ITGB6) (PCT Publication No. WO 03/087340); JAM-3 (PCT Publication No. WO 06/084078); Interleukin-13 Receptor α2 (IL13Rα2) (Bodhinayake, I. et al. (2014) "*Targeting A Heterogeneous Tumor: The Promise Of The Interleukin-13 Receptor α2,*" Neurosurgery 75(2):N18-9); JAM-3 (PCT Publication No. WO 06/084078); KID3 (PCT Publication No. WO 05/028498); KID3 (PCT Publication No. WO 05/028498); KID31 (PCT Publication No. WO 06/076584); KID31 (PCT Publication No. WO 06/076584); KS 1/4 pan-carcinoma antigen (Perez et al. (1989) "*Isolation And Characterization Of A cDNA Encoding The Ks1/4 Epithelial Carcinoma Marker,*" J. Immunol. 142:3662-3667; Möller et al. (1991) "*Bispecific-Monoclonal-Antibody-Directed Lysis Of Ovarian Carcinoma Cells By Activated Human T Lymphocytes,*" Cancer Immunol. Immunother. 33(4):210-216; Ragupathi, G. 2005 *Cancer Treat Res.* 123:157-80); KS 1/4 pan-carcinoma antigen (Perez et al. (1989) "*Isolation And Characterization*

Of A cDNA Encoding The Ks1/4 Epithelial Carcinoma Marker," J. Immunol. 142:3662-3667; Möller et al. (1991) "Bispecific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); KSA (17-1A) (Ragupathi, G. 2005 Cancer Treat Res. 123:157-80); human lung carcinoma antigens L6 and L20 (Hellström et al. (1986) "Monoclonal Mouse Antibodies Raised Against Human Lung Carcinoma," Cancer Res. 46:3917-3923); LEA (Velázquez-Márquez, N. et al. (2012) "Sialyl Lewis x expression in cervical scrapes of premalignant lesions," J. Biosci. 37(6):999-1004); LUCA-2 (United States Patent Publication No. 2006/0172349; PCT Publication No. WO 06/083852); M1:22:25:8, M18, M39 (Cambier, L. et al. (2012) "M19 Modulates Skeletal Muscle Differentiation And Insulin Secretion In Pancreatic B-Cells Through Modulation Of Respiratory Chain Activity," PLoS One 7(2):e31815; Pui, C. H. et al. (1991) "Characterization of childhood acute leukemia with multiple myeloid and lymphoid markers at diagnosis and at relapse," Blood 78(5):1327-1337); MAGE (MAGE-1; MAGE-3; (Bodey, B. 2002 Expert Opin Biol Ther. 2(6):577-84); MART (Kounalakis, N. et al. 2005 Curr Oncol Rep. 7(5):377-82; Myl, MUC-1 (Mathelin, C. 2006 Gynecol Obstet Fertil. 34(7-8):638-46); MUM-1 (Castelli, C. et al. 2000 J Cell Physiol. 182(3):323-31); N-acetylglucosaminyltransferase (Dennis, J. W. 1999 Biochim Biophys Acta. 6; 1473(1):21-34); neoglycoprotein (Legendre, H. et al. (2004) "Prognostic Stratification Of Dukes B Colon Cancer By A Neoglycoprotein," Int. J. Oncol. 25(2):269-276); NS-10; OFA-1 and OFA-2 (Takahashi, M. (1984) "A Study On Clinical Significance Of Oncofetal Antigen-1 In Gynecologic Tumors," Nihon Sanka Fujinka Gakkai Zasshi. 36(12):2613-2618); Oncostatin M (Oncostatin Receptor Beta) (U.S. Pat. No. 7,572,896; PCT Publication No. WO 06/084092); p15 (Gil, J. et al. 2006 Nat Rev Mol Cell Biol. 7(9):667-77); PSA (prostate specific antigen; Cracco, C. M. et al. 2005 Minerva Urol Nefrol. 57(4):301-11); PSMA (Ragupathi, G. 2005 Cancer Treat Res. 123:157-80); PEMA (polymorphic epithelial mucin antigen) (Chu, N. J. et al. (2015) "Nonviral Oncogenic Antigens and the Inflammatory Signals Driving Early Cancer Development as Targets for Cancer Immunoprevention," Clin. Cancer Res. 21(7):1549-1557); PIPA (U.S. Pat. No. 7,405,061; PCT Publication No. WO 04/043239); prostatic acid phosphate (Tailor et al. (1990) "Nucleotide Sequence Of Human Prostatic Acid Phosphatase Determined From A Full-Length cDNA Clone," Nucl. Acids Res. 18(16):4928); R24 (Zhou, M. et al. (2008) "Constitutive Overexpression Of A Novel 21 Kda Protein By Hodgkin Lymphoma And Aggressive Non-Hodgkin Lymphomas," Mol. Cancer 7:12); ROR1 (U.S. Pat. No. 5,843,749); Rabbani, H. et al. (2010) "Expression Of ROR1 In Patients With Renal Cancer—A Potential Diagnostic Marker," Iran Biomed. J. 14(3):77-82); sphingolipids (Hakomori, S. (1998) "Cancer-Associated Glycosphingolipid Antigens: Their Structure, Organization, And Function," Acta Anat. (Basel) 161(1-4):79-90; SSEA-1, SSEA-3 and SSEA-4 (Muramatsu, T. et al. (2004) "Carbohydrate Antigens Expressed On Stem Cells And Early Embryonic Cells," Glycoconj. J. 21(1-2):41-45); sTn (Holmberg, L. A. 2001 Expert Opin Biol Ther. 1(5):881-91); T cell receptor derived peptide (Edelson (1998) "Cutaneous T-Cell Lymphoma: A Model For Selective Immunotherapy," Cancer J Sci Am. 4:62-71); TsA7 (Hogg, R. J. et al. (1991) "A monoclonal antibody exhibiting reactivity with both X-hapten-and lactose-bearing glycolipids," Tissue Antigens 37(1):33-38); TAG-72 (Yokota et al. (1992) "Rapid Tumor Penetration Of A Single-Chain Fv And Comparison With Other Immunoglobulin Forms," Cancer Res. 52:3402-3408); TL5 (blood group A) (Gooi, H. C. et al. (1983) "Monoclonal antibody reactive with the human epidermal-growth-factor receptor recognizes the blood-group-A antigen," Biosci. Rep. 3(11): 1045-1052); TNF-receptor (TNF-α receptor, TNF-β receptor; or TNF-γ receptor (van Horssen, R. et al. 2006 Oncologist. 11(4):397-408; Gardnerova, M. et al. 2000 Curr Drug Targets. 1(4):327-64); TRA-1-85 (blood group H) (Williams, B. P. et al. (1988) "Biochemical and genetic analysis of the OKa blood group antigen," Immunogenetics 27(5): 322-329); Transferrin Receptor (U.S. Pat. No. 7,572,895; PCT Publication No. WO 05/121179); TSTA tumor-specific transplantation antigen (Hellström et al. (1985) "Monoclonal Antibodies To Cell Surface Antigens Shared By Chemically Induced Mouse Bladder Carcinomas," Cancer. Res. 45:2210-2188); VEGF-R (O'Dwyer. P. J. 2006 Oncologist. 11(9):992-8); and Y hapten, Le$^y$ (Durrant, L. G. et al. (1989) "Development Of An ELISA To Detect Early Local Relapse Of Colorectal Cancer," Br. J. Cancer 60(4):533-537).

Exemplary antibodies that immunospecifically bind to an epitope of a Disease-Associated Antigen that may be used to provide the Variable Light Chain Domains, Variable Heavy Chain Domains, Antibody Light Chains or Antibody Heavy Chains of the Tri-Specific Binding Molecules of the present invention are presented in Table 2.

TABLE 2

| Antibody Name | Disease-Associated Antigen | Therapeutic Target Application |
| --- | --- | --- |
| 3F8 | Gd2 | Neuroblastoma |
| 8H9 | B7-H3 | Neuroblastoma, Sarcoma, Metastatic Brain Cancers |
| Abagovomab | CA-125 | Ovarian Cancer |
| Abciximab | CD41 | Platelet Aggregation Inhibitor |
| Actoxumab | Clostridium Difficile | Clostridium Difficile Infection |
| Adalimumab | TNF-A | Rheumatoid Arthritis, Crohn's Disease, Plaque Psoriasis, Psoriatic Arthritis, Ankylosing Spondylitis, Juvenile Idiopathic Arthritis, Hemolytic Disease Of The Newborn |
| Adecatumumab | Epcam | Prostate And Breast Cancer |
| Aducanumab | Beta-Amyloid | Alzheimer's Disease |
| Afelimomab | TNF-A | Sepsis |
| Afutuzumab | CD20 | Lymphoma |
| Alacizumab | VEGFR2 | Cancer |
| Ald518 | Il-6 | Rheumatoid Arthritis |

TABLE 2-continued

| Antibody Name | Disease-Associated Antigen | Therapeutic Target Application |
|---|---|---|
| Alemtuzumab | CD52 | Multiple Sclerosis |
| Alirocumab | NARP-1 | Hypercholesterolemia |
| Altumomab | CEA | Colorectal Cancer |
| Amatuximab | Mesothelin | Cancer |
| Anatumomab Mafenatox | TAG-72 | Non-Small Cell Lung Carcinoma |
| Anifrolumab | Interferon A/B Receptor | Systemic Lupus Erythematosus |
| Anrukinzumab | IL-13 | Cancer |
| Apolizumab | HLA-DR | Hematological Cancers |
| Arcitumomab | CEA | Gastrointestinal Cancer |
| Aselizumab | L-Selectin (CD62L) | Severely Injured Patients |
| Atinumab | RTN4 | Cancer |
| Atlizumab | IL-6 Receptor | Rheumatoid Arthritis |
| Atorolimumab | Rhesus Factor | Hemolytic Disease Of The Newborn |
| Bapineuzumab | Beta-Amyloid | Alzheimer's Disease |
| Basiliximab | CD25 | Prevention Of Organ Transplant Rejections |
| Bavituximab | Phosphatidylserine | Cancer, Viral Infections |
| Bectumomab | CD22 | Non-Hodgkin's Lymphoma (Detection) |
| Belimumab | BAFF | Non-Hodgkin Lymphoma |
| Benralizumab | CD125 | Asthma |
| Bertilimumab | CCL11 (Eotaxin-1) | Severe Allergic Disorders |
| Besilesomab | CEA-Related Antigen | Inflammatory Lesions And Metastases (Detection) |
| Bevacizumab | VEGF-A | Metastatic Cancer, Retinopathy Of Prematurity |
| Bezlotoxumab | *Clostridium difficile* | *Clostridium difficile* Infection |
| Biciromab | Fibrin II, Beta Chain | Thromboembolism (Diagnosis) |
| Bimagrumab | ACVR2B | Myostatin Inhibitor |
| Bivatuzumab | CD44 V6 | Squamous Cell Carcinoma |
| Blinatumomab | CD19 | Cancer |
| Blosozumab | SOST | Osteoporosis |
| Brentuximab | CD30 (TNFRSF8) | Hematologic Cancers |
| Briakinumab | IL-12, IL-23 | Psoriasis, Rheumatoid Arthritis, Inflammatory Bowel Diseases, Multiple Sclerosis |
| Brodalumab | IL-17 | Inflammatory Diseases |
| Canakinumab | IL-1 | Rheumatoid Arthritis |
| Cantuzumab Mertansine | Mucin Canag | Colorectal Cancer |
| Cantuzumab | MUC1 | Cancers |
| Caplacizumab | VWF | Cancers |
| Capromab | Prostatic Carcinoma Cells | Prostate Cancer (Detection) |
| Carlumab | MCP-1 | Oncology/Immune Indications |
| Catumaxomab | Epcam, CD3 | Ovarian Cancer, Malignant Ascites, Gastric Cancer |
| Cc49 | Tag-72 | Tumor Detection |
| Certolizumab | TNF-A | Crohn's Disease |
| Cetuximab | EGFR | Metastatic Colorectal Cancer And Head And Neck Cancer |
| Ch.14.18 | Undetermined | Neuroblastoma |
| Citatuzumab | Epcam | Ovarian Cancer And Other Solid Tumors |
| Cixutumumab | IGF-1 Receptor | Solid Tumors |
| Clazakizumab | *Oryctolagus Cuniculus* | Rheumatoid Arthritis |
| Clivatuzumab | MUC1 | Pancreatic Cancer |
| Conatumumab | TRAIL-R2 | Cancer |
| Concizumab | TFPI | Bleeding |
| Crenezumab | 1-40-B-Amyloid | Alzheimer's Disease |
| Cr6261 | Influenza A Hemagglutinin | Infectious Disease/Influenza A |
| Dacetuzumab | CD40 | Hematologic Cancers |
| Daclizumab | CD25 | Prevention Of Organ Transplant Rejections |
| Dalotuzumab | Insulin-Like Growth Factor I Receptor | Cancer |
| Daratumumab | CD38 | Cancer |
| Demcizumab | DLL4 | Cancer |
| Denosumab | RANKL | Osteoporosis, Bone Metastases |
| Detumomab | B-Lymphoma Cell | Lymphoma |
| Dorlimomab Aritox | Undetermined | Cancer |
| Drozitumab | DR5 | Cancer |
| Duligotumab | HER3 | Cancer |
| Dupilumab | IL4 | Atopic Diseases |
| Dusigitumab | ILGF2 | Cancer |

TABLE 2-continued

| Antibody Name | Disease-Associated Antigen | Therapeutic Target Application |
|---|---|---|
| Ecromeximab | GD3 Ganglioside | Malignant Melanoma |
| Eculizumab | C5 | Paroxysmal Nocturnal Hemoglobinuria |
| Edobacomab | Endotoxin | Sepsis Caused By Gram-Negative Bacteria |
| Edrecolomab | Epcam | Colorectal Carcinoma |
| Efalizumab | LFA-1 (CD11a) | Psoriasis (Blocks T Cell Migration) |
| Efungumab | Hsp90 | Invasive Candida Infection |
| Eldelumab | Interferon-Gamma-Induced Protein | Crohn's Disease, Ulcerative Colitis |
| Elotuzumab | SLAMF7 | Multiple Myeloma |
| Elsilimomab | IL-6 | Cancer |
| Enavatuzumab | TWEAK Receptor | Cancer |
| Enlimomab | ICAM-1 (CD54) | Cancer |
| Enokizumab | IL9 | Asthma |
| Enoticumab | DLL4 | Cancer |
| Ensituximab | 5AC | Cancer |
| Epitumomab Cituxetan | Episialin | Cancer |
| Epratuzumab | CD22 | Cancer, SLE |
| Erlizumab | ITGB2 (CD18) | Heart Attack, Stroke, Traumatic Shock |
| Ertumaxomab | HER2/Neu, CD3 | Breast Cancer |
| Etaracizumab | Integrin $A_v\beta_3$ | Melanoma, Prostate Cancer, Ovarian Cancer |
| Etrolizumab | Integrin $A_7 B_7$ | Inflammatory Bowel Disease |
| Evolocumab | PCSK9 | Hypocholesterolemia |
| Exbivirumab | Hepatitis B Surface Antigen | Hepatitis B |
| Fanolesomab | CD15 | Appendicitis (Diagnosis) |
| Faralimomab | Interferon Receptor | Cancer |
| Farletuzumab | Folate Receptor 1 | Ovarian Cancer |
| Fasinumab[51] | HNGF | Cancer |
| Fbta05 | CD20 | Chronic Lymphocytic Leukaemia |
| Felvizumab | Respiratory Syncytial Virus | Respiratory Syncytial Virus Infection |
| Fezakinumab | IL-22 | Rheumatoid Arthritis, Psoriasis |
| Ficlatuzumab | HGF | Cancer |
| Figitumumab | IGF-1 Receptor | Adrenocortical Carcinoma, Non-Small Cell Lung Carcinoma |
| Flanvotumab | TYRP1 (Glycoprotein 75) | Melanoma |
| Fontolizumab | IFN-γ | Crohn's Disease |
| Foravirumab | Rabies Virus Glycoprotein | Rabies (Prophylaxis) |
| Fresolimumab | TGF-B | Idiopathic Pulmonary Fibrosis, Focal Segmental Glomerulosclerosis, Cancer |
| Fulranumab | NGF | Pain |
| Futuximab | EGFR | Cancer |
| Galiximab | CD80 | B Cell Lymphoma |
| Ganitumab | IGF-I | Cancer |
| Gantenerumab | Beta-Amyloid | Alzheimer's Disease |
| Gavilimomab | CD147 (Basigin) | Graft-Versus-Host Disease |
| Gemtuzumab Ozogamicin | CD33 | Acute Myelogenous Leukemia |
| Gevokizumab | IL-1β | Diabetes |
| Girentuximab | Carbonic Anhydrase 9 (CA-IX) | Clear Cell Renal Cell Carcinoma[64] |
| Glembatumumab Vedotin | GPNMB | Melanoma, Breast Cancer |
| Golimumab | TNF-A | Rheumatoid Arthritis, Psoriatic Arthritis, Ankylosing Spondylitis |
| Gomiliximab | CD23 (Ige Receptor) | Allergic Asthma |
| Guselkumab | IL13 | Psoriasis |
| Ibritumomab Tiuxetan | CD20 | Non-Hodgkin's Lymphoma |
| Icrucumab | VEGFR-1 | Cancer |
| Igovomab | CA-125 | Ovarian Cancer (Diagnosis) |
| Imab362 | Cldn1 8.2 | Gastrointestinal Adenocarcinomas And Pancreatic Tumor |
| Imgatuzumab | EGFR | Cancer |
| Inclacumab | Selectin P | Cancer |
| Indatuximab Ravtansine | SDC1 | Cancer |
| Infliximab | TNF-A | Rheumatoid Arthritis, Ankylosing Spondylitis, Psoriatic Arthritis, Psoriasis, Crohn's Disease, Ulcerative Colitis |
| Intetumumab | CD51 | Solid Tumors (Prostate Cancer, Melanoma) |
| Inolimomab | CD25 (A Chain Of IL-2 Receptor) | Graft-Versus-Host Disease |

TABLE 2-continued

| Antibody Name | Disease-Associated Antigen | Therapeutic Target Application |
|---|---|---|
| Inotuzumab Ozogamicin | CD22 | Cancer |
| Ipilimumab | CD152 | Melanoma |
| Iratumumab | CD30 (TNFRSF8) | Hodgkin's Lymphoma |
| Itolizumab | CD6 | Cancer |
| Ixekizumab | IL-17A | Autoimmune Diseases |
| Keliximab | CD4 | Chronic Asthma |
| Labetuzumab | CEA | Colorectal Cancer |
| Lambrolizumab | PDCD1 | Antineoplastic Agent |
| Lampalizumab | CFD | Cancer |
| Lebrikizumab | IL-13 | Asthma |
| Lemalesomab | NCA-90 (Granulocyte Antigen) | Diagnostic Agent |
| Lerdelimumab | TGF Beta 2 | Reduction Of Scarring After Glaucoma Surgery |
| Lexatumumab | TRAIL-R2 | Cancer |
| Libivirumab | Hepatitis B Surface Antigen | Hepatitis B |
| Ligelizumab | IGHE | Cancer |
| Lintuzumab | CD33 | Cancer |
| Lirilumab | KIR2D | Cancer |
| Lodelcizumab | PCSK9 | Hypercholesterolemia |
| Lorvotuzumab | CD56 | Cancer |
| Lucatumumab | CD40 | Multiple Myeloma, Non-Hodgkin's Lymphoma, Hodgkin's Lymphoma |
| Lumiliximab | CD23 | Chronic Lymphocytic Leukemia |
| Mapatumumab | TRAIL-R1 | Cancer |
| Margetuximab | Ch4d5 | Cancer |
| Mavrilimumab | GMCSF Receptor A-Chain | Rheumatoid Arthritis |
| Matuzumab | EGFR | Colorectal, Lung And Stomach Cancer |
| Mepolizumab | IL-5 | Asthma And White Blood Cell Diseases |
| Metelimumab | TGF Beta 1 | Systemic Scleroderma |
| Milatuzumab | CD74 | Multiple Myeloma And Other Hematological Malignancies |
| Minretumomab | TAG-72 | Cancer |
| Mitumomab | GD3 Ganglioside | Small Cell Lung Carcinoma |
| Mogamulizumab | CCR4 | Cancer |
| Morolimumab | Rhesus Factor | Cancer |
| Motavizumab | Respiratory Syncytial Virus | Respiratory Syncytial Virus (Prevention) |
| Moxetumomab Pasudotox | CD22 | Cancer |
| Muromonab-CD3 | CD3 | Prevention Of Organ Transplant Rejections |
| Nacolomab Tafenatox | C242 Antigen | Colorectal Cancer |
| Namilumab | CSF2 | Cancer |
| Naptumomab Estafenatox | 5T4 | Non-Small Cell Lung Carcinoma, Renal Cell Carcinoma |
| Narnatumab | RON | Cancer |
| Natalizumab | Integrin A4 | Multiple Sclerosis, Crohn's Disease |
| Nebacumab | Endotoxin | Sepsis |
| Necitumumab | EGFR | Non-Small Cell Lung Carcinoma |
| Nerelimomab | TNF-A | Cancer |
| Nesvacumab | Angiopoietin 2 | Cancer |
| Nimotuzumab | EGFR | Squamous Cell Carcinoma, Head And Neck Cancer, Nasopharyngeal Cancer, Glioma |
| Nivolumab | Igg4 | Cancer |
| Nofetumomab Merpentan | Undetermined | Cancer |
| Ocaratuzumab | CD20 | Cancer |
| Ocrelizumab | CD20 | Rheumatoid Arthritis, Lupus Erythematosus |
| Odulimomab | LFA-1 (CD11a) | Prevention Of Organ Transplant Rejections, Immunological Diseases |
| Ofatumumab | CD20 | Chronic Lymphocytic Leukemia |
| Olaratumab | PDGF-R A | Cancer |
| Olokizumab | IL6 | Cancer |
| Onartuzumab | Human Scatter Factor Receptor Kinase | Cancer |
| Ontuxizumab | TEM1 | Cancer |
| Oportuzumab Monatox | Epcam | Cancer |
| Oregovomab | CA-125 | Ovarian Cancer |
| Orticumab | Oxldl | Cancer |
| Otlertuzumab | CD37 | Cancer |
| Oxelumab | OX-40 | Asthma |
| Ozanezumab | NOGO-A | ALS And Multiple Sclerosis |

TABLE 2-continued

| Antibody Name | Disease-Associated Antigen | Therapeutic Target Application |
|---|---|---|
| Ozoralizumab | TNF-A | Inflammation |
| Pagibaximab | Lipoteichoic Acid | Sepsis (*Staphylococcus*) |
| Palivizumab | F Protein Of Respiratory Syncytial Virus | Respiratory Syncytial Virus (Prevention) |
| Panitumumab | EGFR | Colorectal Cancer |
| Pankomab | Tumor Specific Glycosylation Of MUC1 | Ovarian Cancer |
| Panobacumab | *Pseudomonas Aeruginosa* | *Pseudomonas Aeruginosa* Infection |
| Parsatuzumab | EGFL7 | Cancer |
| Pascolizumab | IL-4 | Asthma |
| Pateclizumab | LTA | TNF |
| Patritumab | HER3 | Cancer |
| Pemtumomab | MUC1 | Cancer |
| Perakizumab | IL17A | Arthritis |
| Pertuzumab | HER2/Neu | Cancer |
| Pexelizumab | C5 | Reduction Of Side-Effects Of Cardiac Surgery |
| Pidilizumab | PD-1 | Cancer And Infectious Diseases |
| Pinatuzumab Vedotin | CD22 | Cancer |
| Pintumomab | Adenocarcinoma Antigen | Adenocarcinoma |
| Placulumab | Human TNF | Cancer |
| Polatuzumab Vedotin | CD79B | Cancer |
| Ponezumab | Human Beta-Amyloid | Alzheimer's Disease |
| Pritoxaximab | *E. Coli* Shiga Toxin Type-1 | Cancer |
| Pritumumab | Vimentin | Brain Cancer |
| Pro 140 | Ccr5 | HIV Infection |
| Quilizumab | IGHE | Cancer |
| Racotumomab | N-Glycolylneuraminic Acid | Cancer |
| Radretumab | Fibronectin Extra Domain-B | Cancer |
| Rafivirumab | Rabies Virus Glycoprotein | Rabies (Prophylaxis) |
| Ramucirumab | VEGFR2 | Solid Tumors |
| Ranibizumab | VEGF-A | Macular Degeneration (Wet Form) |
| Raxibacumab | Anthrax Toxin, Protective Antigen | Anthrax (Prophylaxis And Treatment) |
| Regavirumab | Cytomegalovirus Glycoprotein B | Cytomegalovirus Infection |
| Reslizumab | IL-5 | Inflammations Of The Airways, Skin And Gastrointestinal Tract |
| Rilotumumab | HGF | Solid Tumors |
| Rituximab | CD20 | Lymphomas, Leukemias, Some Autoimmune Disorders |
| Robatumumab | IGF-1 Receptor | Cancer |
| Roledumab | RHD | Cancer |
| Romosozumab | Sclerostin | Osteoporosis |
| Rontalizumab | IFN-α | Systemic Lupus Erythematosus |
| Rovelizumab | CD11, CD18 | Haemorrhagic Shock |
| Ruplizumab | CD154 (CD40L) | Rheumatic Diseases |
| Samalizumab | CD200 | Cancer |
| Sarilumab | IL6 | Rheumatoid Arthritis, Ankylosing Spondylitis |
| Satumomab Pendetide | TAG-72 | Cancer |
| Secukinumab | IL-17A | Uveitis, Rheumatoid Arthritis Psoriasis |
| Seribantumab | ERBB3 | Cancer |
| Setoxaximab | *E. Coli* Shiga Toxin Type-1 | Cancer |
| Sevirumab | Cytomegalovirus | Cytomegalovirus Infection |
| Sibrotuzumab | FAP | Cancer |
| Sgn-CD19a | CD19 | Acute Lymphoblastic Leukemia And B Cell Non-Hodgkin Lymphoma |
| Sgn-CD33a | CD33 | Acute Myeloid Leukemia |
| Sifalimumab | IFN-A | SLE, Dermatomyositis, Polymyositis |
| Siltuximab | IL-6 | Cancer |
| Simtuzumab | LOXL2 | Fibrosis |
| Siplizumab | CD2 | Psoriasis, Graft-Versus-Host Disease (Prevention) |

TABLE 2-continued

| Antibody Name | Disease-Associated Antigen | Therapeutic Target Application |
|---|---|---|
| Sirukumab | IL-6 | Rheumatoid Arthritis |
| Solanezumab | Beta-Amyloid | Alzheimer's Disease |
| Solitomab | Epcam | Cancer |
| Sonepcizumab | Sphingosine-1-Phosphate | Choroidal And Retinal Neovascularization |
| Sontuzumab | Episialin | Cancer |
| Stamulumab | Myostatin | Muscular Dystrophy |
| Sulesomab | NCA-90 (Granulocyte Antigen) | Osteomyelitis |
| Suvizumab | HIV-1 | Viral Infections |
| Tabalumab | BAFF | B Cell Cancers |
| Tacatuzumab Tetraxetan | Alpha-Fetoprotein | Cancer |
| Tadocizumab | Integrin AIIBβ3 | Percutaneous Coronary Intervention |
| Tanezumab | NGF | Pain |
| Taplitumomab Paptox | CD19 | Cancer |
| Tefibazumab | Clumping Factor A | *Staphylococcus Aureus* Infection |
| Telimomab | Undetermined | Cancer |
| Tenatumomab | Tenascin C | Cancer |
| Teneliximab | CD40 | Cancer |
| Teprotumumab | CD221 | Hematologic Tumors |
| Ticilimumab | CTLA-4 | Cancer |
| Tildrakizumab | IL23 | Immunologically Mediated Inflammatory Disorders |
| Tigatuzumab | TRAIL-R2 | Cancer |
| Tnx-650 | Il-13 | Hodgkin's Lymphoma |
| Tocilizumab | IL-6 Receptor | Rheumatoid Arthritis |
| Toralizumab | CD154 (CD40L) | Rheumatoid Arthritis, Lupus Nephritis |
| Tositumomab | CD20 | Follicular Lymphoma |
| Tovetumab | CD140a | Cancer |
| Tralokinumab | IL-13 | Asthma |
| Trastuzumab | HER2/Neu | Breast Cancer |
| Trbs07 | Gd2 | Melanoma |
| Tremelimumab | CTLA-4 | Cancer |
| Tucotuzumab Celmoleukin | Epcam | Cancer |
| Tuvirumab | Hepatitis B Virus | Chronic Hepatitis B |
| Ublituximab | MS4A1 | Cancer |
| Urelumab | 4-1BB | Cancer |
| Urtoxazumab | *Escherichia Coli* | Diarrhoea Caused By *E. Coli* |
| Ustekinumab | IL-12, IL-23 | Multiple Sclerosis, Psoriasis, Psoriatic Arthritis |
| Vantictumab | Frizzled Receptor | Cancer |
| Vapaliximab | AOC3 (VAP-1) | Cancer |
| Vatelizumab | ITGA2 | Cancer |
| Vedolizumab | Integrin A4β7 | Crohn's Disease, Ulcerative Colitis |
| Veltuzumab | CD20 | Non-Hodgkin's Lymphoma |
| Vepalimomab | AOC3 (VAP-1) | Inflammation |
| Vesencumab | NRP1 | Cancer |
| Volociximab | Integrin A5β1 | Solid Tumors |
| Vorsetuzumab | CD70 | Cancer |
| Votumumab | Tumor Antigen CTAA16.88 | Colorectal Tumors |
| Zalutumumab | EGFR | Squamous Cell Carcinoma Of The Head And Neck |
| Zatuximab | HER1 | Cancer |
| Ziralimumab | CD147 | Cancer |
| Zolimomab Aritox | CD5 | Systemic Lupus Erythematosus, Graft-Versus-Host Disease |

A Disease-Associated Antigen may be characteristically expressed in a pathogen-infected cell or in a cancer cells and processed and displayed on a cell surface in the context of an MHC complex, but not characteristically expressed in a normal cell. Antibodies that recognize such peptide fragments are known in the art or can be generated using well-known methods, including those described in WO 2002/014870.

The polypeptides of the Tri-Specific Binding Molecules of the present invention can be adapted to contain the Variable Light or Variable Heavy Domains (the case of the first and second polypeptide chains of such molecules) or the heavy or light chains (in the case of the third and fourth polypeptide chains of such molecules) of such antibodies. Thus, the above-described antibodies may be used to produce Tri-Specific Binding Molecules of the present invention whose Site A, Site B or Site C is capable of binding to an epitope of such Disease-Associated Antigens].

B. Preferred Structural Attributes

Typically, the Tri-Specific Binding Molecules of the present molecules will comprise four different polypeptide chains, each having an amino terminus and a carboxyl terminus (see FIGS. 4A-4D), however, the molecules may comprise fewer or greater numbers of polypeptide chains by fusing such polypeptide chains to one another (e.g., via a peptide bond) or by dividing such polypeptide chains to form additional polypeptide chains, or by associating fewer or additional polypeptide chains via disulfide bonds. FIGS. 4E-4J illustrate this aspect of the present invention by schematically depicting such molecules having three polypeptide chains. FIGS. 4K-4L illustrate this aspect of the present invention by schematically depicting molecules having five polypeptide chains.

The various immunoglobulin Domains of such molecules may be derived from immunoglobulins of any isotype or allotype including, but not limited to, IgA, IgD, IgG, IgE and IgM. In preferred embodiments, as discussed below such immunoglobulins are derived from IgG immunoglobulins. In specific embodiments, the IgG isotype used is IgG1, however IgG of other isotypes (e.g., IgG2, IgG3 or IgG4 or an allotype thereof) may be employed. When an IgG4 Fc Domain is utilized, the present invention encompasses the introduction of a stabilizing mutation such as S228P, as numbered by the EU index as set forth in Kabat (Lu et al., (2008) "*The Effect Of A Point Mutation On The Stability Of Igg4 As Monitored By Analytical Ultracentrifugation*," J. Pharmaceutical Sciences 97:960-969) to reduce the incidence of strand exchange. Other stabilizing mutations known in the art may be introduced into an IgG4 Fc Domain (Peters, P et al., (2012) "*Engineering an Improved IgG4 Molecule with Reduced Disulfide Bond Heterogeneity and Increased Fab Domain Thermal Stability*," J. Biol. Chem., 287:24525-24533; PCT Patent Publication No: WO 2008/145142). Since the N297A, L234A, L235A and D265A substitutions abolish effector function, in circumstances in which effector function is desired, these substitutions would preferably not be employed.

Figure 1A:
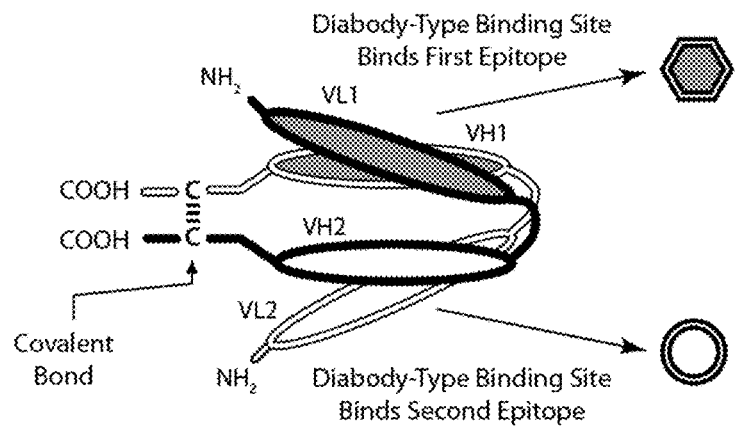
FIGS. 1A-1B show diagrammatic representation of the Domains of DART™ diabodies.
Figure 1B:
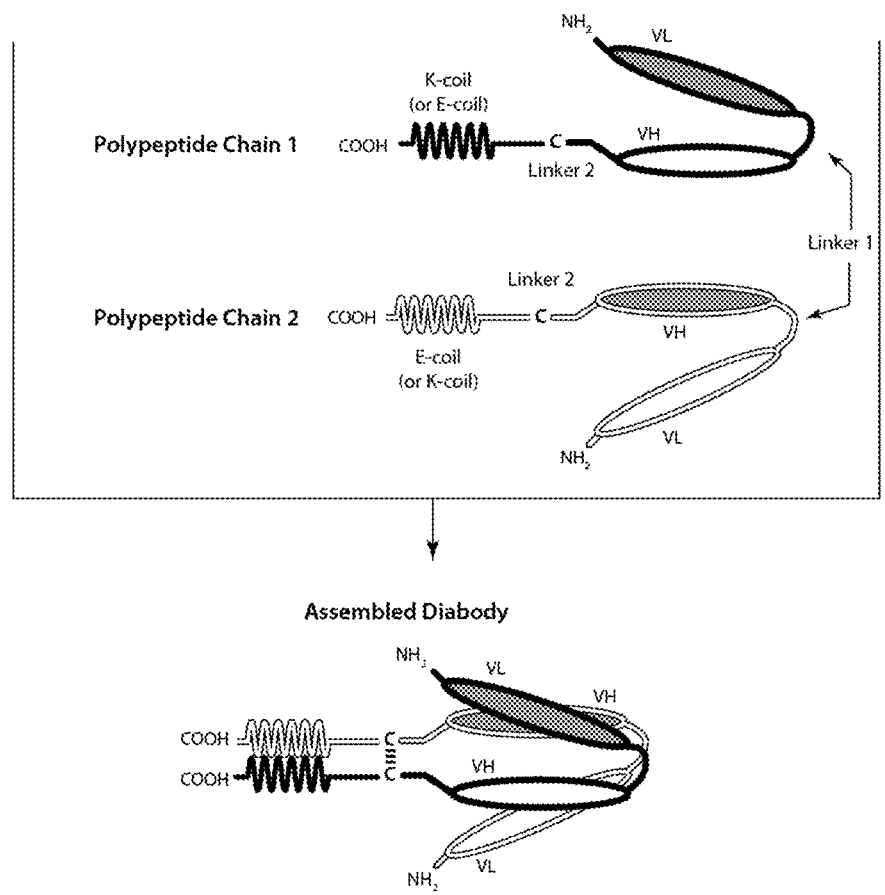
Figure 2A:
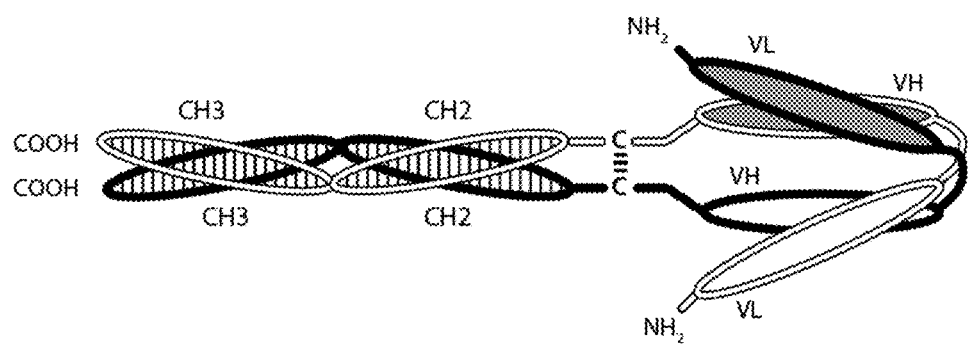
FIGS. 2A-2B provide a schematic of covalently bonded diabodies composed of two polypeptide chains, each having a CH2 and CH3 Domain (FIG. 2A) or in which only one has a CH2 and CH3 Domain (FIG. 2B), such that the associated chains form an Fc Domain that comprises all or part of a naturally occurring Fc Domain. VL and VH domains that recognize the same epitope are shown using the same shading.
Figure 2B:
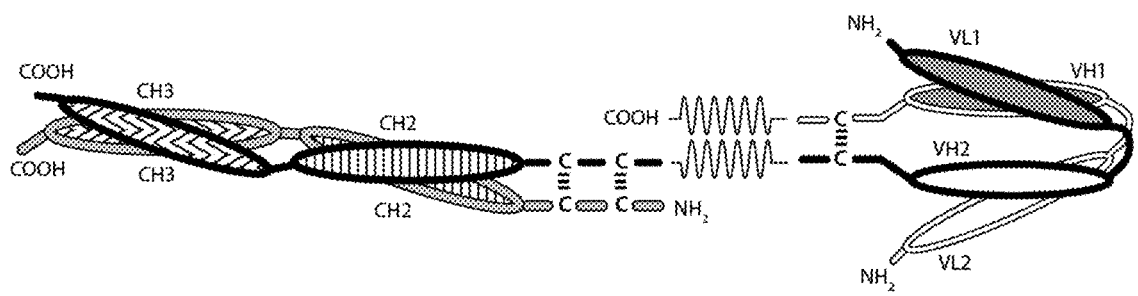
Figure 3A:
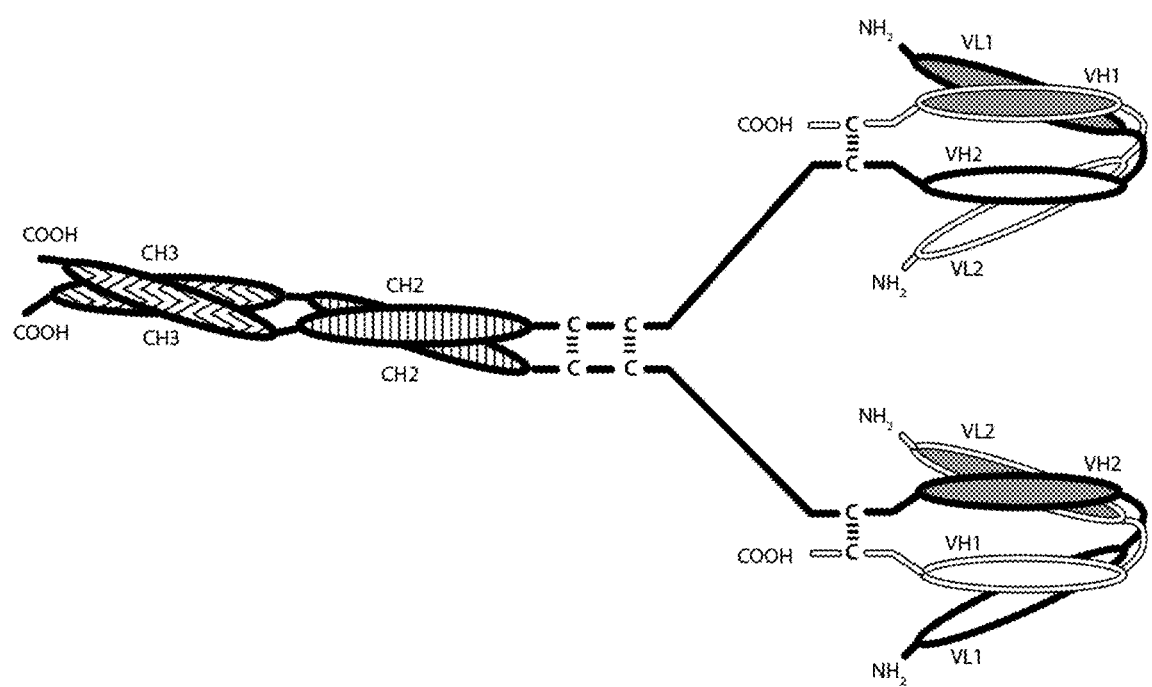
FIGS. 3A-3C provide schematics showing tetravalent diabodies composed of two pairs of polypeptide chains. The pairs are different, thus resulting in a bi-specific molecule that is bivalent with respect to each of two epitopes, in which one is an epitope of DR5 and the other is an epitope of a molecule present on the surface of an effector cell. One polypeptide of each pair possesses a CH2 and CH3 Domain, such that the associated chains form an Fc Domain that comprises all or part of a naturally occurring Fc Domain. VL and VH domains that recognize the same epitope are shown using the same shading. Only one pair of epitopes (shown with the same shading) is capable of binding to DR5.
Figure 3B:
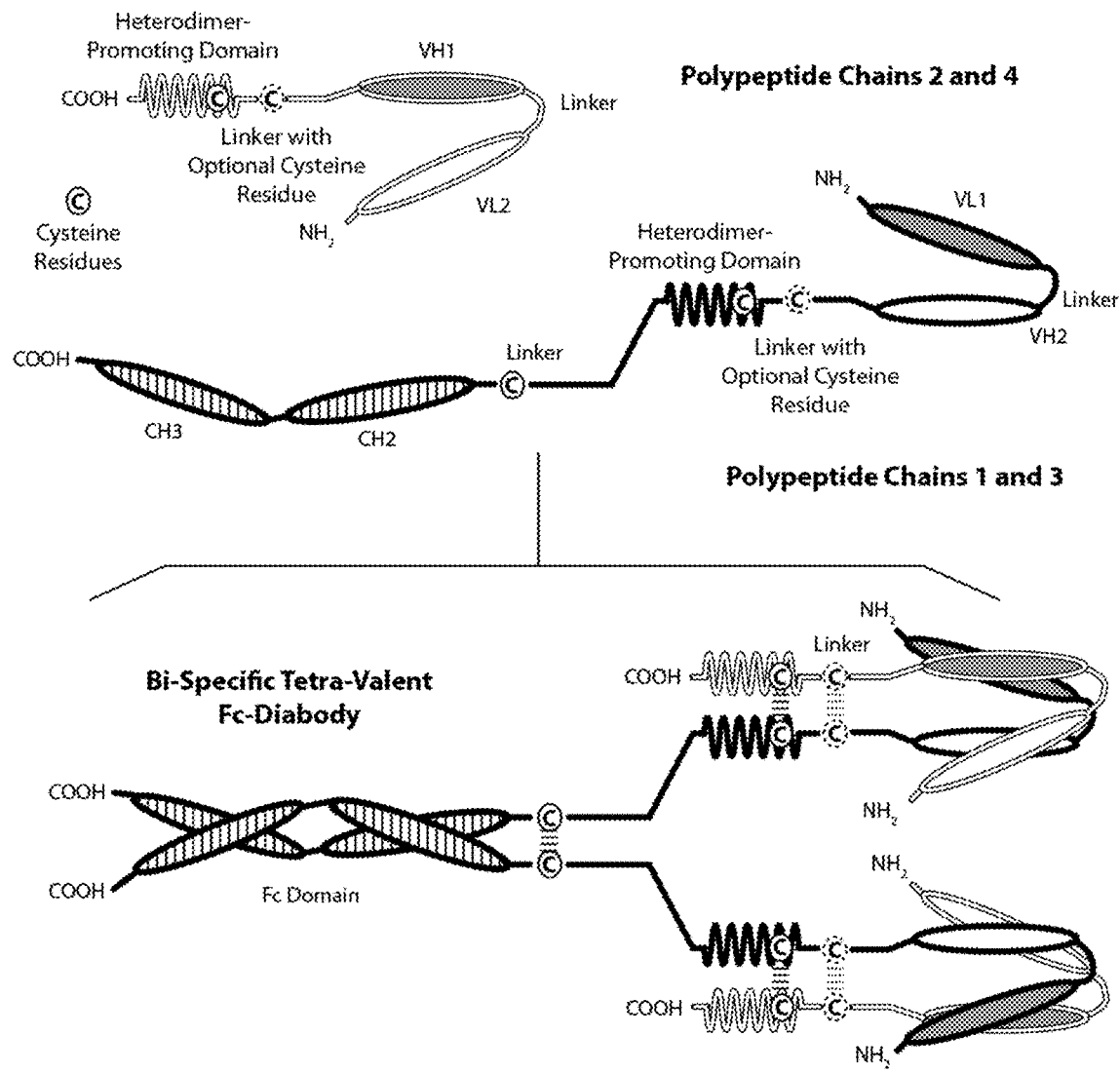
Figure 3C:
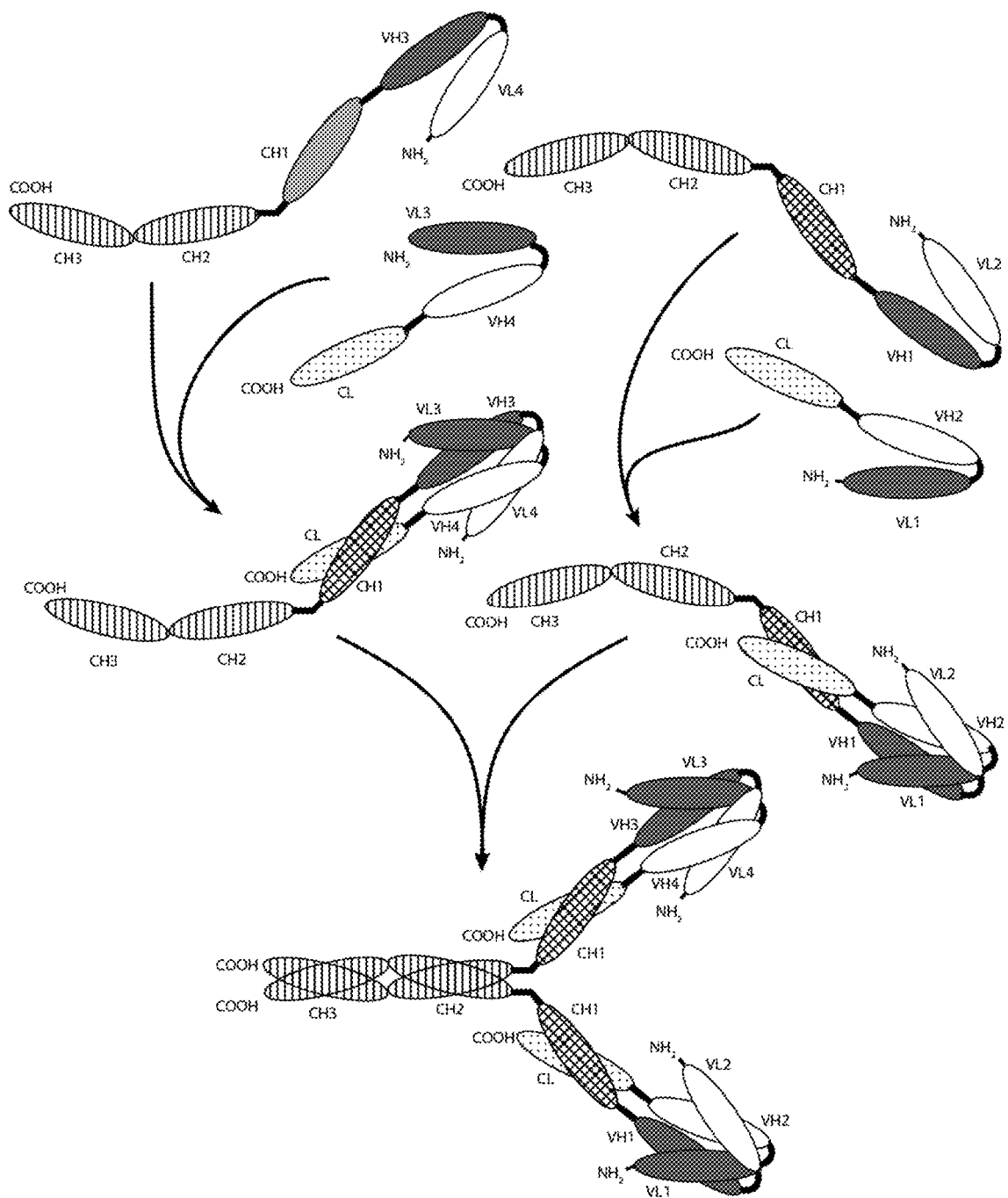
Figure 4A:
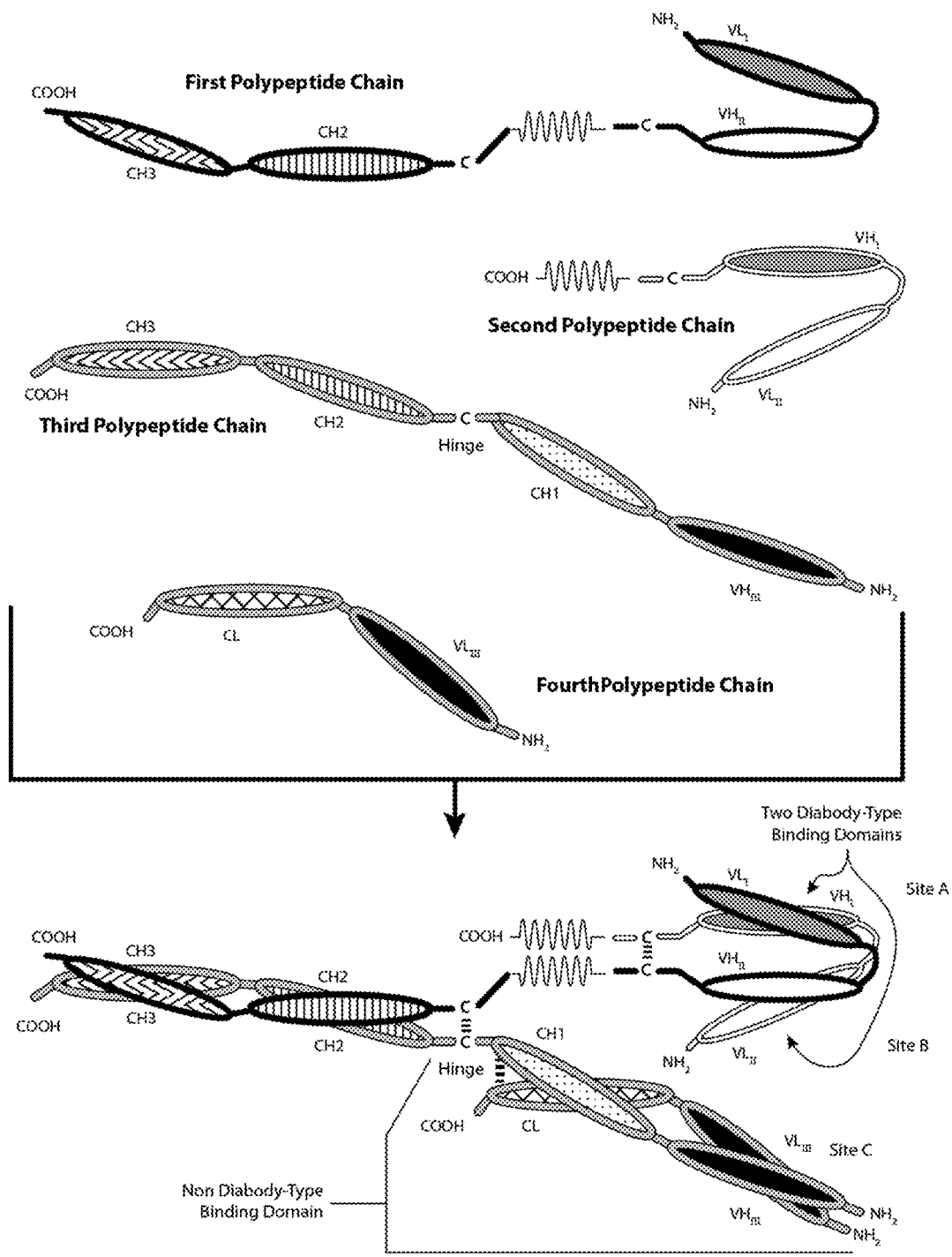
FIGS. 4A-4L provide a diagrammatic representation of the Domains of preferred Tri-Specific Binding Molecules.
Figure 4B:
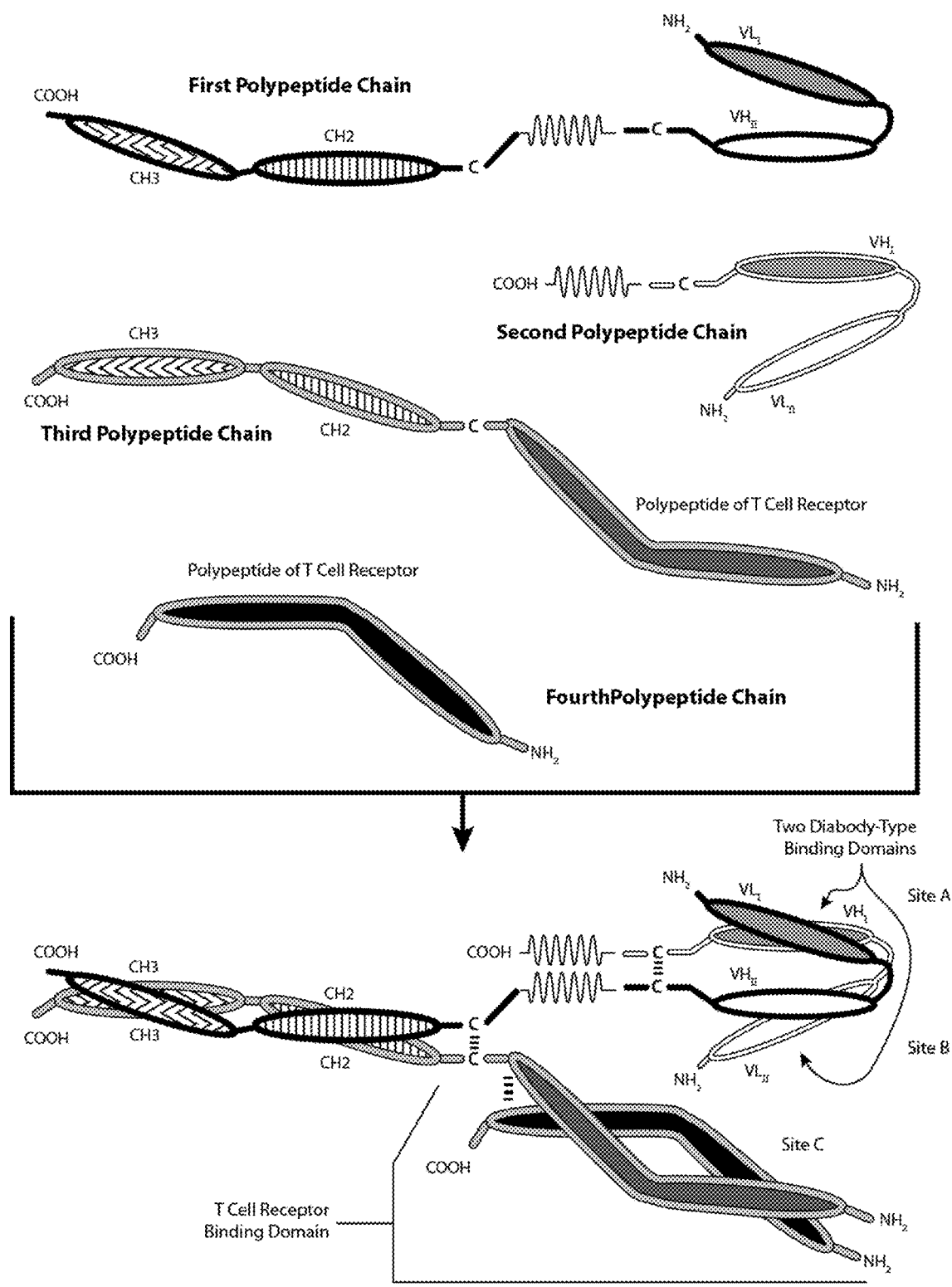
Figure 4C:
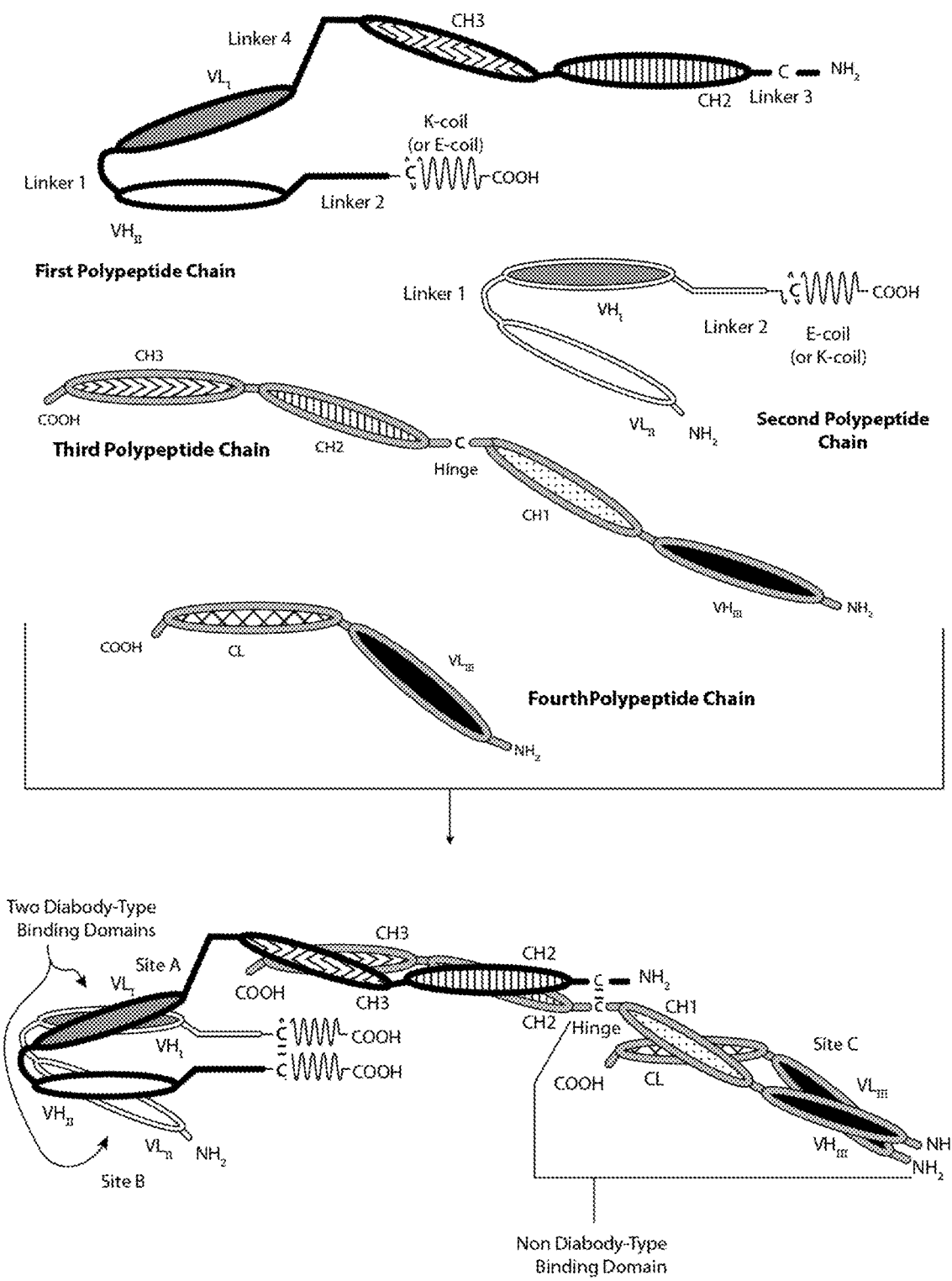
Figure 4D:
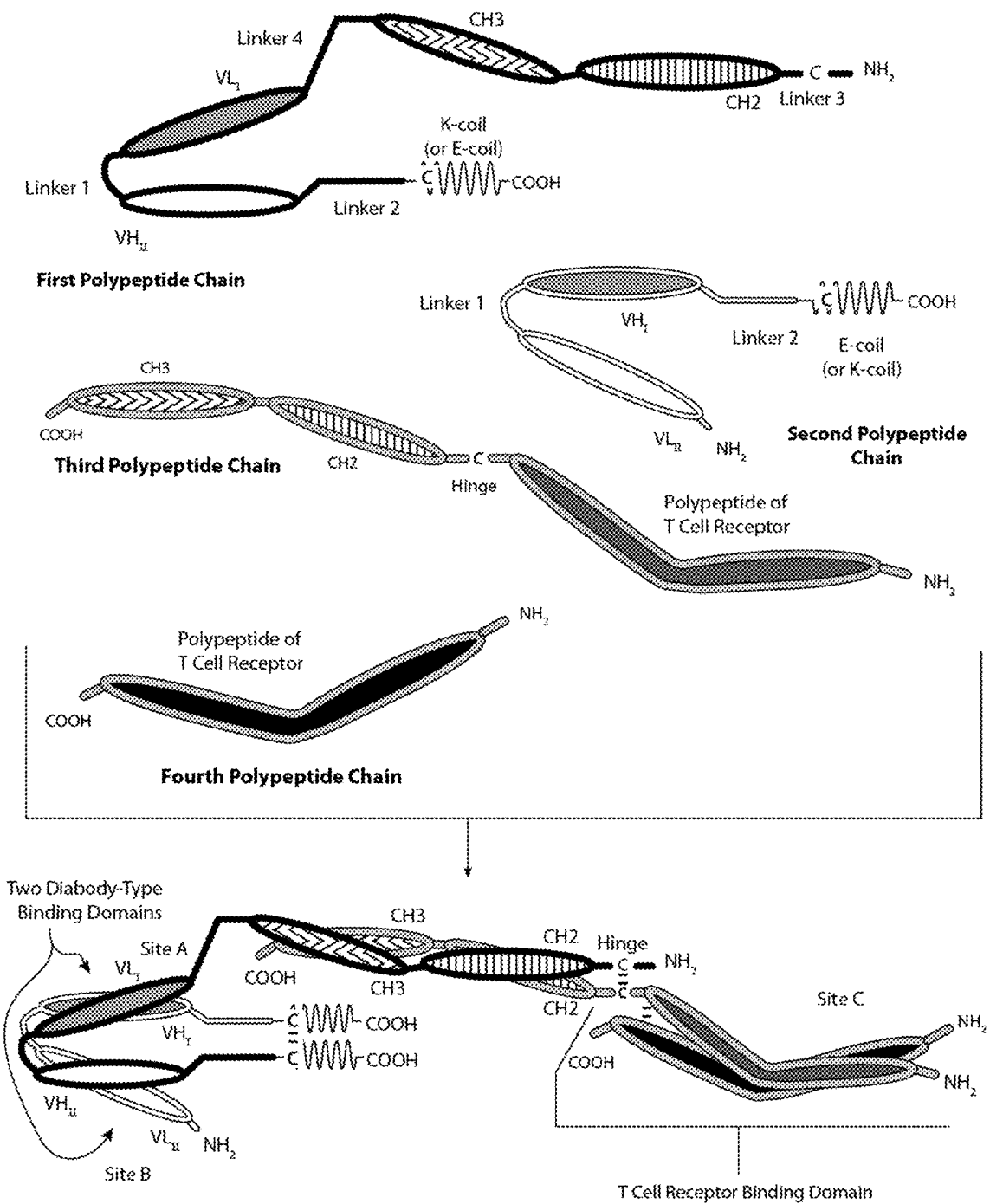
Figure 4E:
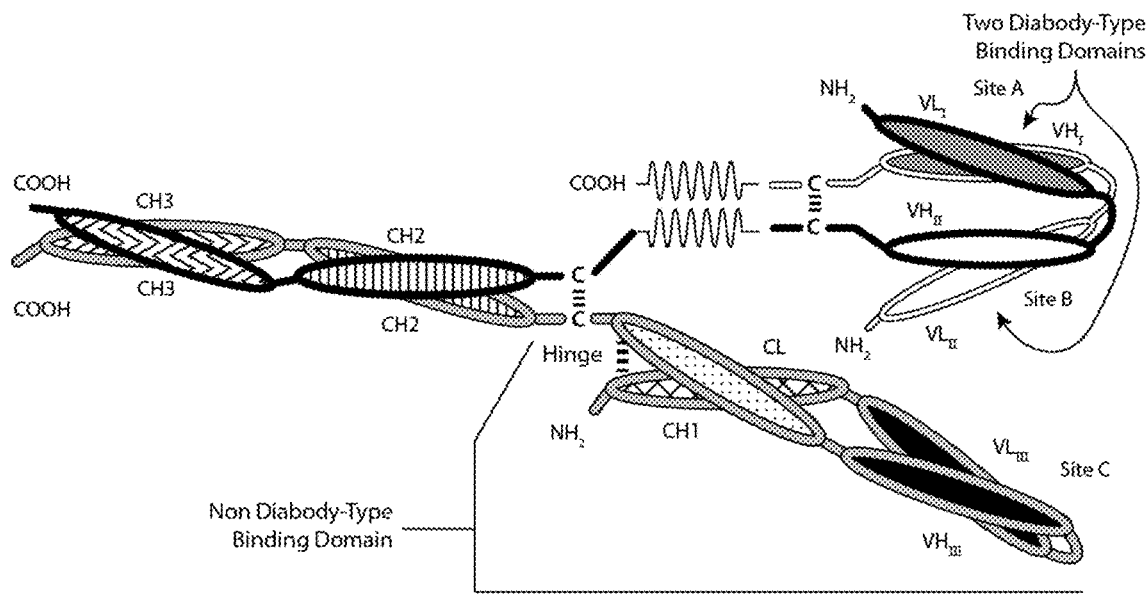
Figure 4F:
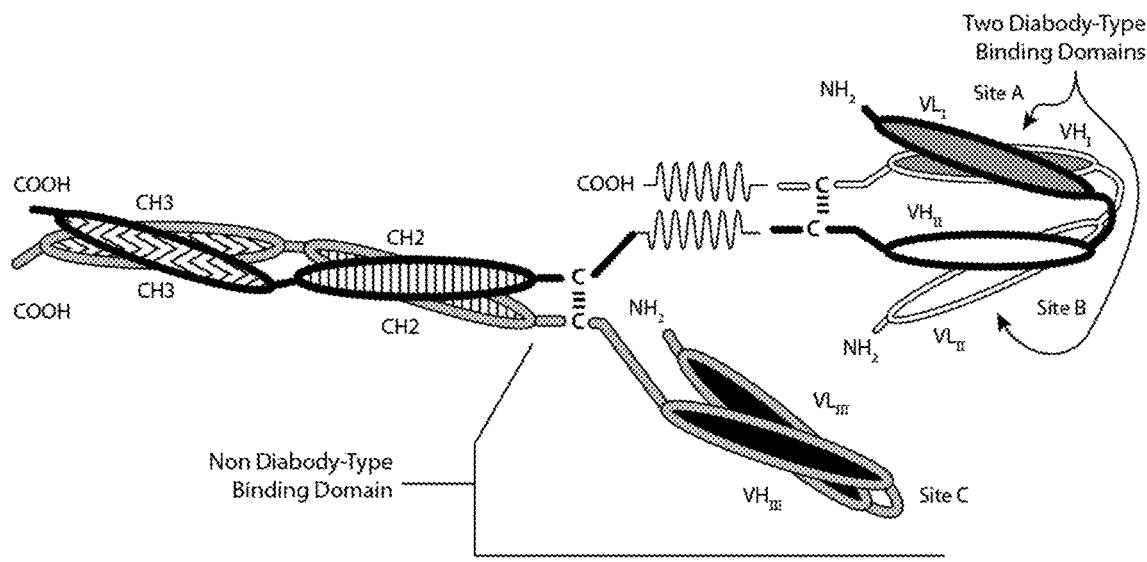
Figure 4G:
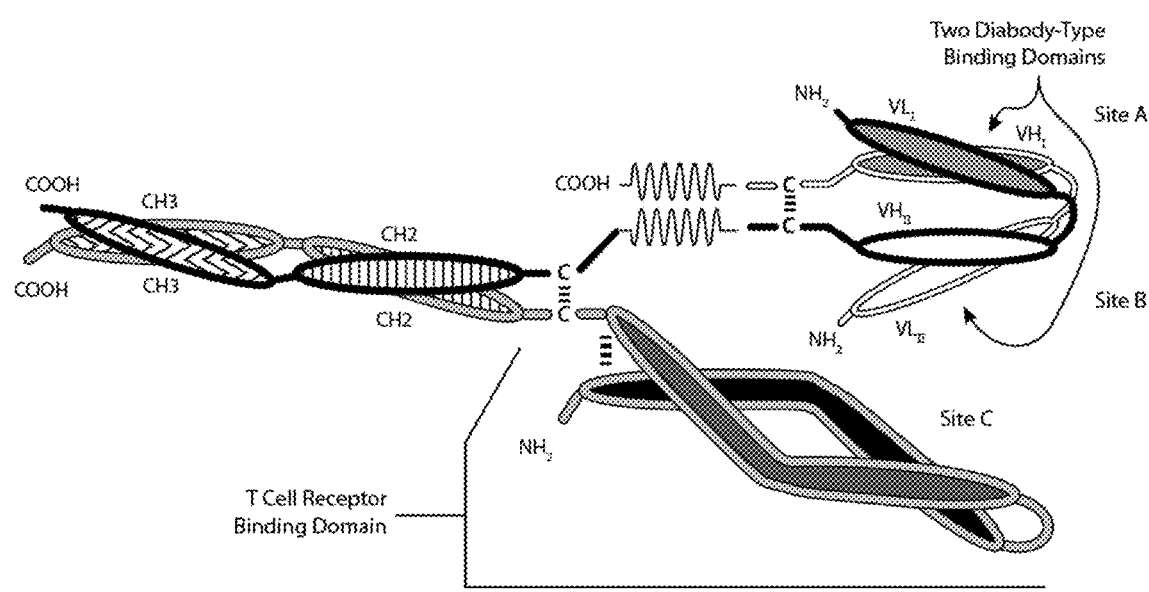
Figure 4H:
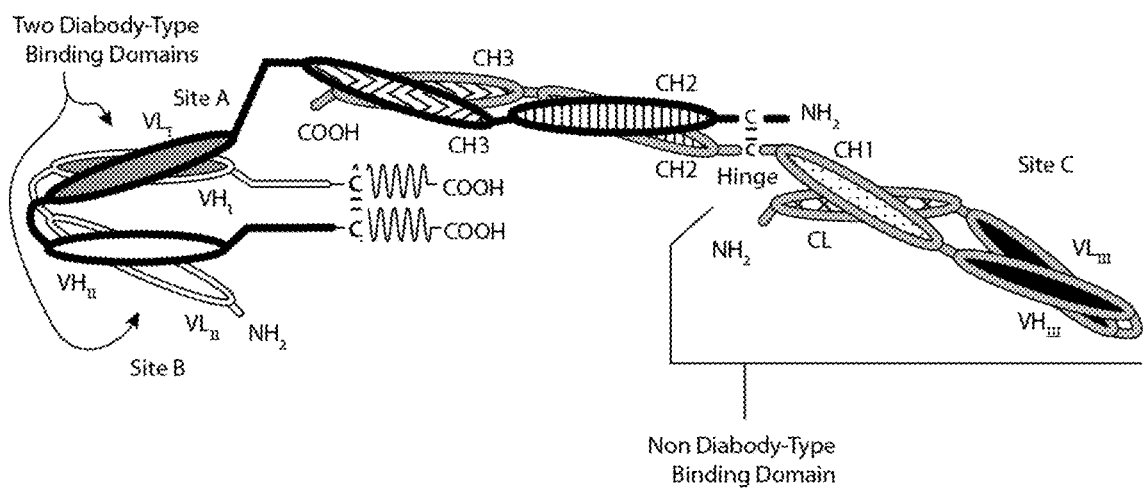
Figure 4I:
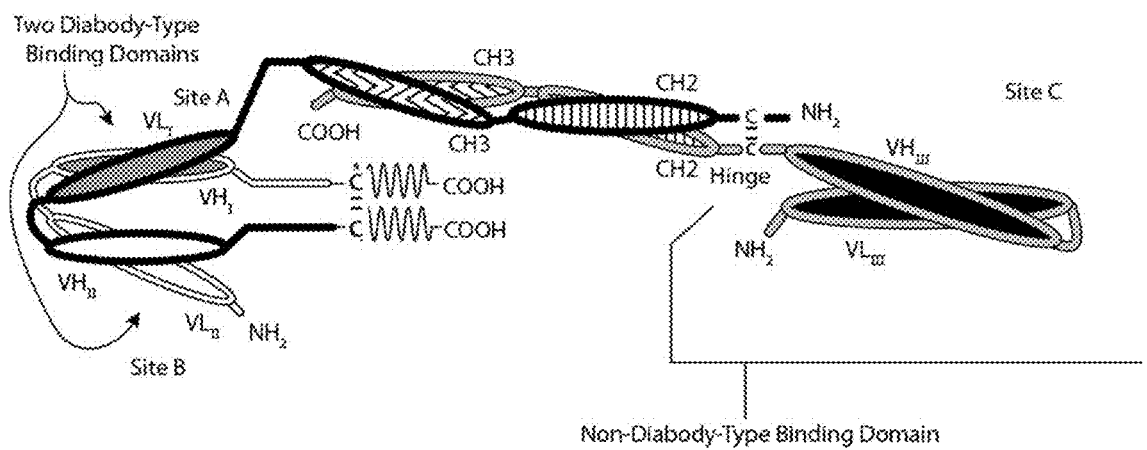
Figure 4J:
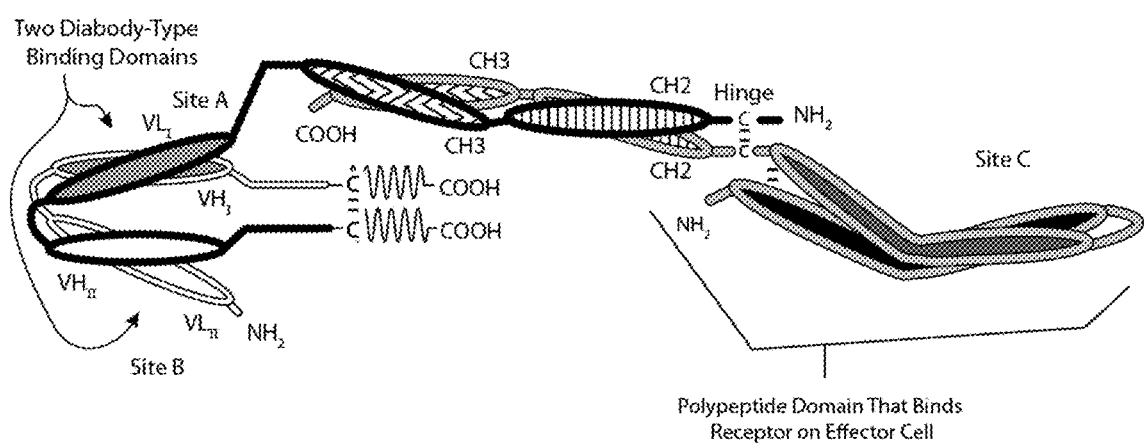
Figure 4K:
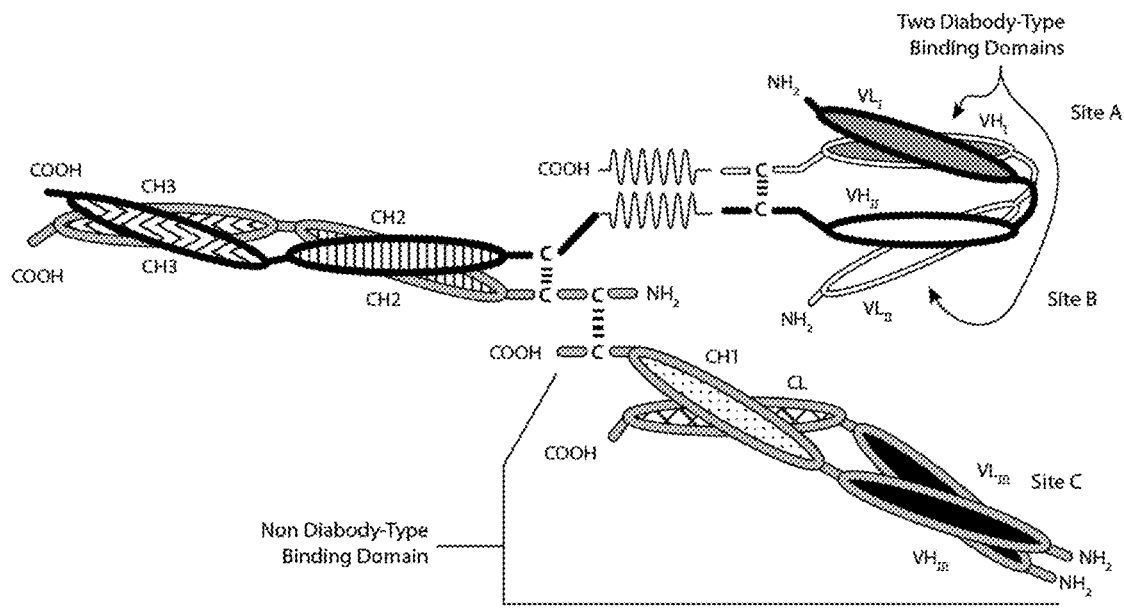
Figure 4L:
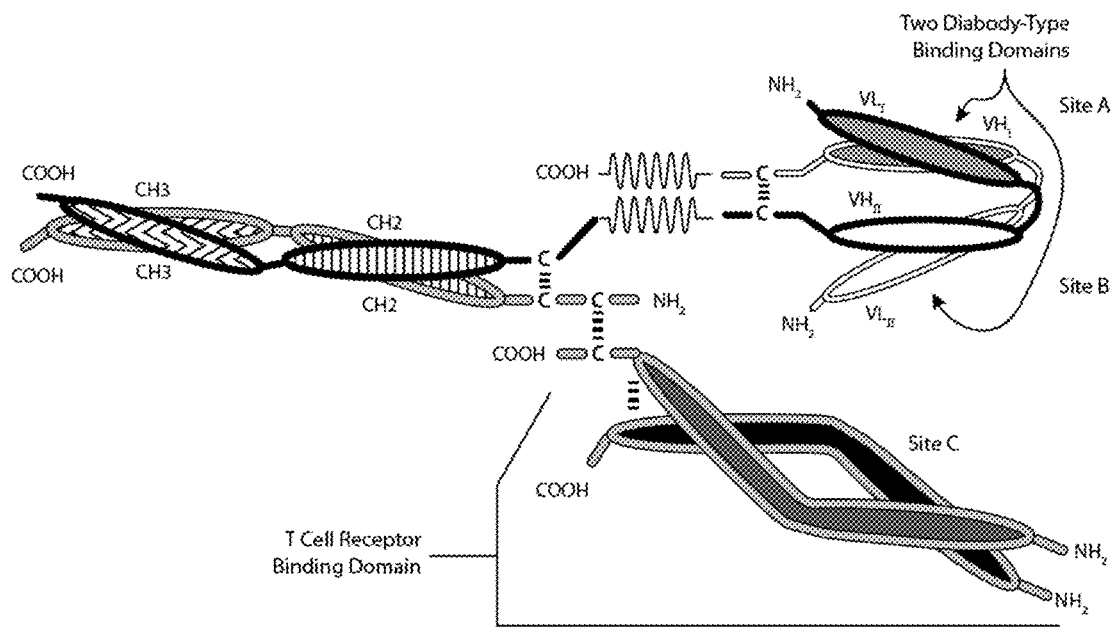

FIGS. 4A-4D provide a diagrammatic representation of the Domains of preferred Tri-Specific Binding Molecules. FIGS. 4A and 4B, respectively, illustrate schematically the Domains of preferred Tri-Specific Binding Molecules in which the Non-Diabody-Type Binding Domain is a Fab-Type Binding Domain or a Receptor-Type Binding Domain. FIGS. 4C and 4D, respectively, illustrate schematically the Domains of preferred Tri-Specific Binding Molecules having different Domain orientations in which the Non-Diabody-Type Binding Domain is a Fab-Type Binding Domain or a Receptor-Type Binding Domain.

As indicated above, one of Epitope I, Epitope II or Epitope III that is bound by the Binding Domains of such exemplary preferred Tri-Specific Binding Molecules may be an epitope of a Disease-Associated Antigen. Most preferably, the Binding Domain of such exemplary preferred Tri-Specific Binding Molecule that binds to such epitope of a Disease-Associated Antigen is a Fab-Type Binding Domain. The polypeptides of such Tri-Specific Binding Molecules of the present invention can be adapted to contain the Variable Light or Variable Heavy Domains (the case of the first and second polypeptide chains of such molecules) or the heavy or light chains (in the case of the third and fourth polypeptide chains of such molecules). Thus, such antibodies may be used to produce Tri-Specific Binding Molecules of the present invention whose Site A, Site B or Site C is capable of binding to an epitope of such Disease-Associated Antigens.

1. Preferred First Polypeptide Chain

A first polypeptide chain of a preferred Tri-Specific Binding Molecule of the present invention will comprise a Variable Light Chain Domain capable of binding to Epitope I (VL$_I$), a Variable Heavy Chain Domain capable of binding to Epitope II (VH$_{II}$), a cysteine residue or Cysteine-Containing Domain and a Heterodimer-Promoting Domain and a CH2-CH3 Domain.

Since the Variable Light Chain and Variable Heavy Chain Domains of the first polypeptide are directed toward different epitopes, they cannot associate together to form a Binding Domain that is able to bind either Epitope I or Epitope II. The Variable Light Chain and Variable Heavy Chain Domains of the first polypeptide are spaced apart from one another by an intervening linker peptide that is sufficiently short as to substantially prevent the association of these Domains. An exemplary linker, termed "Linker 1," has the sequence (SEQ ID NO:1): GGGSGGGG.

The Variable Heavy Chain Domain of the first polypeptide and the Heterodimer-Promoting Domain of that polypeptide are preferably spaced apart from one another by an intervening linker peptide that contains 1, 2, 3 or more cysteine residues. A preferred Cysteine-Containing Domain ("Linker 2") has the sequence is SEQ ID NO:2: GGCGGG. Alternatively, or additionally, a Cysteine-Containing Heterodimer-Promoting Domain, as described below, may be used.

Thus, in some embodiments, one or more cysteine residues (or Cysteine-Containing Domain, such as a cysteine-containing peptide linker) will be incorporated into the first polypeptide chain (and/or into the second, third, fourth or further polypeptide chains of the Tri-Specific Binding Molecules of the present invention) in order to covalently bond two such polypeptide chains together, whereas in equivalent embodiments such cysteine residue(s) may be incorporated into a Heterodimer-Promoting Domain, or into another domain in order to achieve the same result.

The Heterodimer-Promoting Domain of the first polypeptide and the Heterodimer-Promoting Domain of the second polypeptide are coordinately selected. The Domains differ from one another and are designed to associate with one another so as to promote the association of the first and second polypeptide chains. For example, one of the Heterodimer-Promoting Domains will be engineered to have a negative charge at pH 7, while the other of the two polypeptide chains will be engineered to have a positive charge at pH 7. The presence of such charged Domains promotes association between the first and second polypeptides, and thus fosters heterodimerization. It is immaterial which Heterodimer-Promoting Domains is provided to which chain, as long as the Domains employed on the first and second polypeptide chains differ so as to foster heterodimerization between such chains.

In a preferred embodiment, the Heterodimer-Promoting Domain of the first polypeptide chain is either an "E-coil" Domain (SEQ ID NO:3): EVAALEKEVAALEKEVAALEKEVAALEK, or a "K-coil" Domain (SEQ ID NO:4): KVAALKEKVAALKEKVAALKEKVAALKE. More preferably, the first polypeptide chain will possess an "E-coil" Domain. The first polypeptide chain may contain only a single such coil separator, or it may contain more than one such coil separators (e.g., two separators) and can be the same charge preferably of opposite charge.

In a preferred embodiment, the Heterodimer-Promoting Domain of the first polypeptide chain will comprise either four tandem "E-coil" helical domains (SEQ ID NO:3: EVAALEK-EVAALEK-EVAALEK-EVAALEK), whose glutamate residues will form a negative charge at pH 7, or four tandem "K-coil" domains (SEQ ID NO:4: KVAALKE-KVAALKE-KVAALKE-KVAALKE), whose lysine residues will form a positive charge at pH 7. The presence of such charged domains promotes association between the first and second polypeptide chains, and thus fosters heterodimerization. Especially preferred is a Heterodimer-Promoting Domain in which one of the four tandem "E-coil" helical domains of SEQ ID NO:3 or SEQ ID NO:4 has been modified to contain a cysteine residue: EVAACEK-EVAAL EK-EVAALEK-EVAALEK (SEQ ID NO:115) or in which one of the four tandem "K-coil" helical domains of SEQ ID NO:4 has been modified to contain a cysteine residue: KVAACKE-KVAALKE-KVAALKE-KVAALKE (SEQ ID NO:116). Other E-coil and K-coil Domains that may be employed in accordance with the present invention are disclosed in: Woolfson, D. N. (2005) "*The Design Of Coiled-Coil Structures And Assemblies*," Adv. Prot. Chem. 70:79-112, Straussman, R. et al. (2007) "*Kinking the Coiled Coil Negatively Charged Residues at the Coiled-coil Interface*," J. Molec. Biol. 366:1232-1242; Apostolovic, B. et al. (2008) "*pH-Sensitivity of the E3/K3 Heterodimeric Coiled Coil*," Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312: 221-228; Steinkruger, J. D. et al. (2012) "*The d'--d--d' Vertical Triad is Less Discriminating Than the a'--a--a' Vertical Triad in the Antiparallel Coiled-coil Dimer Motif*," J. Amer. Chem. Soc. 134(5):2626-2633; Ghosh, T. S. et al. (2009) "*End-To-End And End-To-Middle Interhelical Interactions: New Classes Of Interacting Helix Pairs In Protein Structures*," Acta Crystallographica D65:1032-1041; Grigoryan, G. et al. (2008) "*Structural Specificity In Coiled-Coil Interactions*," Curr. Opin. Struc. Biol. 18:477-483; Boucher, C. et al. (2010) "*Protein Detection By Western Blot Via Coiled-Coil Interactions*," Analytical Biochemistry 399: 138-140; Cachia, P. J. et al. (2004) "*Synthetic Peptide Vaccine Development: Measurement Of Polyclonal Antibody Affinity And Cross-Reactivity Using A New Peptide Capture And Release System For Surface Plasmon Resonance Spectroscopy*," J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763; Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; and Zeng, Y. et al. (2008) "*A Ligand-Pseudoreceptor System Based On de novo Designed Peptides For The Generation Of Adenoviral Vectors With Altered Tropism*," J. Gene Med. 10:355-367.

Preferably, the employed Heterodimer-Promoting Domain, and the CH2-CH3 Domain of the first polypeptide chain are spaced apart from one another by an intervening cysteine-containing linker peptide that provides improved stabilization to the Heterodimer-Promoting Domain. A preferred cysteine-containing linker peptide ("Linker 3") has the amino acid sequence (SEQ ID NO:5): DKTHTCPPCP.

The amino acid sequence of a wild-type CH2-CH3 Domain is as follows (positioning is as in the EU index as in Kabat et al. (1992) SEQUENCES OF PROTEINS OF IMMUNOLOGICAL INTEREST, National Institutes of Health Publication No. 91-3242) (SEQ ID NO:6):

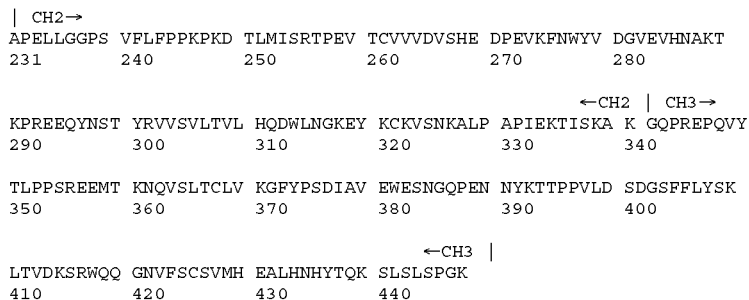

In some expression systems the C-terminal amino acid residue of the CH3 Domain may be post-translationally removed. Accordingly, the C-terminal residue of the CH3 Domain is an optional amino acid residue.

The CH2-CH3 Domain of the first polypeptide chain will preferably be modified to promote heterodimerization between the CH2-CH3 Domain of the third polypeptide chain (see below). For example, an amino acid substitution (preferably a substitution with an amino acid comprising a bulky side group forming a 'knob', e.g., tryptophan) can be introduced into the CH2 or CH3 Domain of the first polypeptide chain such that steric interference will prevent interaction with a similarly mutated Domain and will obligate the mutated Domain to pair with a Domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well-known in the art, in particular with respect to the engineering of immunoglobulin-like molecules, and are encompassed herein (see e.g., U.S. Pat. No. 7,695,936 and Patent Publication 2007/0196363, Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety. A preferred knob is created by modifying a native IgG Fc Domain to contain the modification T366W. A preferred hole is created by modifying a native IgG Fc Domain to contain the modification T366S, L368A and Y407V. To aid in purifying the Tri-Specific Binding Molecules of the present invention, the polypeptide chain containing the hole mutations additionally comprises a substitution at position 435 (H435R) to remove the Protein A binding site. Thus, homodimers of polypeptides containing the hole mutations will not bind to protein A, whereas the Tri-Specific Binding Molecules that form as a result of knob and hole containing heterodimers will retain its ability to bind protein A via the protein A binding site on the polypeptide chain containing the knob mutation.

The CH2-CH3 Domain of the first polypeptide chain will preferably be modified to reduce or abrogate binding of the Fc to Fc receptors. Such mutations are well-known in the art and include substitutions at positions 234, 235, 265 and 297 (see U.S. Pat. No. 5,624,821). Preferred substitutions include one or more of L234A and L235A, D265A and N297Q.

```
Preferably, therefore the CH2-CH3 Domain of the
first polypeptide chain will have the "knob-
bearing" sequence (SEQ ID NO: 7):
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK or the "hole-bearing" sequence with an H435R
substitution to abrogate Protein A binding
(SEQ ID NO: 8):
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

It is preferred that the first polypeptide chain will have a "knob-bearing" CH2-CH3 sequence, such as that of SEQ ID NO:7.

As will be recognized, a "hole-bearing" CH2-CH3 Domain (e.g., SEQ ID NO:8) could be employed in the first polypeptide chain, in which case, a "knob-bearing" CH2-CH3 Domain (e.g., SEQ ID NO:7) would be employed in the third polypeptide chain.

Thus, in sum, a preferred first polypeptide chain of a preferred Tri-Specific Binding Molecule of the present invention will comprise the Domains and linkers: (VL$_I$ Domain)-(Linker 1)-(VH$_{II}$ Domain)-(Cysteine-Containing Domain (Linker 2))-(E-coil Heterodimer-Promoting Domain)-(Linker 3)-(Knob-Bearing CH2-CH3 Domain) or (VL$_I$ Domain)-(Linker 1)-(VH$_{II}$ Domain)-(Linker 2)-(Cysteine-Containing E-coil Heterodimer-Promoting Domain)-(Linker 3)-(Knob-Bearing CH2-CH3 Domain or (VL$_I$ Domain)-(Linker 1)-(VH$_{II}$ Domain)-(Linker 2)-(Cysteine-Containing E-coil Heterodimer-Promoting Domain)-(Linker 3)-(Knob-Bearing CH2-CH3 Domain).

2. Preferred Second Polypeptide Chain

A second polypeptide chain of such preferred Tri-Specific Binding Molecules will comprise, in the N-terminal to C-terminal direction, a Variable Light Chain Domain capable of binding to Epitope II (VL$_{II}$), a Variable Heavy Chain Domain capable of binding to Epitope I (VH$_I$), a cysteine residue or Cysteine-Containing Domain and a Heterodimer-Promoting Domain.

Since the Variable Light Chain and Variable Heavy Chain Domains of the second polypeptide are directed toward different epitopes, they cannot associate together to form a Binding Domain that is able to bind either Epitope I or Epitope II. The Variable Light Chain and Variable Heavy Chain Domains of the second polypeptide are spaced apart from one another by an intervening linker peptide that is sufficiently short as to substantially prevent the association of these Domains. "Linker 1," having the sequence (SEQ ID NO:1): GGGSGGGG is an exemplary linker for this purpose.

As in the case of the first polypeptide chain, the Variable Heavy Chain Domain of the second polypeptide and the Heterodimer-Promoting Domain of that polypeptide are preferably spaced apart from one another by an intervening Cysteine-Containing Domain that contains 1, 2, 3 or more cysteine residues. "Linker 2," having the sequence (SEQ ID NO:2) GGCGGG is an exemplary linker for this purpose. Such cysteine residues can form disulfide bonds with cysteine residues in the cysteine-containing spacer peptide that separates the Variable Heavy Chain Domain of the first polypeptide and the Heterodimer-Promoting Domain of that polypeptide. Thus, the first and second polypeptides of the Tri-Specific Binding Molecules of the present invention are covalently bonded to one another. Alternatively, a Cysteine-Containing Heterodimer-Promoting Domain, as described above, may be used.

As discussed above, the Heterodimer-Promoting Domain of the second polypeptide chain is selected so as coordinate with the Heterodimer-Promoting Domain of the first polypeptide chain. Thus, in a preferred embodiment, the Heterodimer-Promoting Domain of the first polypeptide chain is either a "K-coil" Domain (e.g., SEQ ID NO:4 or SEQ ID NO:116) or an "E-coil" Domain (e.g., SEQ ID NO:3 or SEQ ID NO:115). Since the first polypeptide chain will preferably possess an "E-coil" Domain, the second polypeptide chain will preferably contain a "K-coil" Domain.

As the first and second polypeptide chains are polypeptide chains of a diabody, they are able to associate together to form a Domain I Binding Domain (VL$_A$/VH$_A$) that recognizes and immunospecifically binds to Epitope I, and a Domain II Binding Domain (VL$_B$/VH$_B$) that recognizes and immunospecifically binds to Epitope II.

Thus, in sum, a preferred second polypeptide chain of a preferred Tri-Specific Binding Molecule of the present invention will comprise the Domains and linkers: (VL$_1$ Domain)-(Linker 1)-(VH$_I$ Domain)-(Cysteine-Containing Domain (Linker 2))-(K-coil Heterodimer-Promoting Domain) or (VL$_{II}$ Domain)-(Linker 1)-(VH$_I$ Domain)-(Linker 2)-(Cysteine-Containing K-coil Heterodimer-Promoting Domain).

3. Preferred Third Polypeptide Chain

A third polypeptide chain of a preferred Tri-Specific Binding Molecule of the present invention is a polypeptide that comprises, in the N-terminal to C-terminal direction, a Binding Domain, a Cysteine-Containing Domain that may optionally comprise a CH1-Hinge Domain, and a CH2-CH3 Domain. The Binding Domain of the third polypeptide chain of a preferred Tri-Specific Binding Molecule of the present invention may be a Variable Heavy Chain Domain capable of binding to Epitope III (VH$_{III}$), in which case, the fourth polypeptide chain of the preferred Tri-Specific Binding Molecules of the present invention (discussed below) is a polypeptide that comprises a Variable Light Chain Domain capable of binding to Epitope III (VL$_{III}$), such that the Binding Domain is capable of immunospecific binding to an antigen possessing Epitope III. Alternatively, the Binding Domain of the third polypeptide chain of the preferred Tri-Specific Binding Molecules of the present invention may comprise a T Cell Receptor-Type Binding Domain, in which case, the fourth polypeptide chain of the preferred Tri-Specific Binding Molecules of the present invention (discussed below) is a polypeptide that comprises a complementary T Cell Receptor-Type Binding Domain, such that the interaction of two polypeptide chains forms a Binding Domain that is capable of physiospecific binding to an antigen molecule displayed in the MHC complex arrayed on the surface of a Cell. The third polypeptide chain may be isolated from naturally occurring antibodies. Alternatively, it may be constructed recombinantly. An exemplary CH1 Domain is a human IgG1 CH1 Domain having the amino acid sequence (SEQ ID NO:9):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKV
```

An exemplary Hinge Domain is a human IgG1 Hinge Domain having the amino acid sequence (SEQ ID NO:10): EPKSCDKTHTCPPCP. As will be recognized, the exemplary Hinge Domain comprises multiple cysteine residues (Elkabetz et al. (2005) "*Cysteines In CH1 Underlie Retention Of Unassembled Ig Heavy Chains*," J. Biol. Chem. 280:14402-14412) that may participate in interchain covalent bonding. Alternatively, a different Cysteine-Containing Domain may be employed (e.g., a peptide having the amino acid sequence: VEPKSC (SEQ ID NO:12), AEPKSC (SEQ ID NO:127), GVEPKSC (SEQ ID NO:133) or GGCGGG (SEQ ID NO:2)).

Although a wild-type CH2-CH3 Domain may be employed, it is preferred, as described above, to employ a modified CH2-CH3 Domain that promotes heterodimerization with the CH2-CH3 Domain of the first polypeptide chain.

Preferably, therefore the CH2-CH3 Domain of the third polypeptide chain will be a "hole-bearing" CH2-CH3 Domain whose amino acid sequence is complementary to the "knob-bearing" CH2-CH3 Domain (SEQ ID NO:7) employed in the first polypeptide. As discussed above, the hole-bearing CH2-CH3 Domain preferably should comprise a substitution at position 435 (H435R) to remove the Protein A binding site. An exemplary "hole-bearing" CH2-CH3 Domain with the H435R substitution for the third polypeptide is SEQ ID NO:8.

As will be recognized, a "knob-bearing" CH2-CH3 Domain (e.g., SEQ ID NO:7) could be employed in the third polypeptide chain, in which case, a "hole-bearing" CH2-CH3 Domain (e.g., SEQ ID NO:8) would be employed in the first polypeptide chain.

In the embodiment in which the third (and fourth) polypeptide chains of the preferred Tri-Specific Binding Molecules of the present invention each comprise a polypeptide chain of a T cell Receptor-Type Binding Domain, which recognized antigen displayed on a cell surface in the context of class I MHC. Methods are well-known in the art to produce such T cell receptor-type binding domains (e.g., US2012/0294874A1).

Thus, in sum, a third polypeptide chain of the preferred Tri-Specific Binding Molecules of the present invention will comprise the Domains and linkers: (VH$_{III}$ Domain)-(Cysteine-Containing Domain (optionally a CH1 Domain and/or a Hinge Domain)-(Hole-Bearing CH2-CH3 Domain), or (Receptor-Type Binding Domain; first or second polypeptide thereof)-(Cysteine-Containing Domain (optionally a CH1 Domain and/or a Hinge Domain)-(Hole-Bearing CH2-CH3 Domain).

4. Preferred Fourth Polypeptide Chain

A fourth polypeptide chain of the preferred Tri-Specific Binding Molecules of the present invention is either a polypeptide of a Receptor-Type Binding Domain (wherein the third and fourth polypeptide chains form a Receptor-Type Binding Domain), or more preferably, a polypeptide portion of a Light Chain of the above-indicated antibody that immunospecifically binds to Epitope III and/or which is complementary to the Binding Domain of the third polypeptide chain.

Thus, wherein the third and fourth polypeptides form a Fab-Type Binding Domain such fourth polypeptide chain comprises, in the N-terminal to C-terminal direction, a Variable Light Chain Domain capable of binding to Epitope III (VL$_{III}$), and a Cysteine-Containing Domain for promoting covalent bonding to the third polypeptide chain, or a Binding Domain and such Cysteine-Containing Domain for promoting covalent bonding to the third polypeptide chain. Such Cysteine-Containing Domain may be a CL Domain, or a cysteine-containing portion thereof, such as (SEQ ID NO:11) FNRGEC or (SEQ ID NO:128) GFNRGEC or a linker such as Linker 2 (having the sequence (SEQ ID NO:2) GGCGGG. An exemplary a Cysteine-Containing Domain that forms disulfide bonds with such Linker 2 comprises the amino acid sequence VEPKSC (SEQ ID NO:12) or a Hinge Domain.

The fourth polypeptide chain may be isolated from naturally occurring antibodies. Alternatively, it may be constructed recombinantly. An preferred CL Domain is a human IgG1 CL Kappa Domain having the amino acid sequence (SEQ ID NO:13):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG1 CL Lambda2 Domain having the amino acid sequence (SEQ ID NO:14):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

As will be noticed, the CL Domain, or other Cysteine-Containing Domain, of the fourth polypeptide chain comprises a cysteine residue that is able to covalently bond to a cysteine residue of the Cysteine-Containing Domain of the third polypeptide chain (e.g., a CH1 Domain) to thereby covalently complex the third and fourth polypeptide chains of the Tri-Specific Binding Molecules of the present invention to one another. Thus the third and fourth polypeptide chains are covalently bonded to one another.

Additionally, cysteine residues of the CH2-CH3 Domain of the first polypeptide chain can form disulfide bonds with cysteine residues of the CH2-CH3 Domain of the third polypeptide chain. Thus the first and third polypeptide chains are covalently bonded to one another.

Thus, in sum, a fourth polypeptide chain of the preferred Tri-Specific Binding Molecules of the present invention will comprise the Domains and linkers: (VL$_{III}$ Domain)-(Cysteine-Containing Domain (optionally a CL Domain), or (Receptor-Type Binding Domain; first or second polypeptide thereof)-(Cysteine-Containing Domain (optionally a CL Domain).

C. Alternative First Polypeptide Chain

In one embodiment, the orientations of the above-described Domains will be in the N-terminal to C-terminal direction. The present invention, however, also contemplates a variation thereof, wherein the orientations of the Domains of the first polypeptide chain are: NH$_2$-(Knob-Bearing CH3-CH2 Domain)-(VL$_I$ Domain)-(Linker 1)-(VH$_{II}$ Domain)-(Cysteine-Containing Domain Linker 2)-(E-coil Heterodimer-Promoting Domain). Preferably, a Cysteine-Containing Domain is present, N-terminal to such CH2-CH3 Domain. The sequence of an exemplary peptide is (SEQ ID NO:5): DKTHTCPPCP, however, alternative linkers may be employed, e.g., EPKSCDKTHTCPPCP (SEQ ID NO:129) or LEPKSSDKTHTCPPCP; SEQ ID NO:130). Preferably in this embodiment, the CH3 Domain is spaced apart from the VL$_I$ Domain by an intervening peptide linker, such as one having the amino acid sequence of (SEQ ID NO:15): APSSS, and more preferably, the amino acid sequence (SEQ ID NO:16) APSSSPME, however, alternative linkers may be employed, e.g., ASTKG (SEQ ID NO:131), LEPKSS (SEQ ID NO:132), GGC or GGG.

D. Albumin-Binding Domain

As disclosed in WO 2012/018687, in order to improve the in vivo pharmacokinetic properties of diabodies, a diabody may be modified to contain a polypeptide portion of a serum-binding protein at one or more of the termini of the diabody. Such considerations are also applicable to the Tri-Specific Binding Molecules of the present invention. Most preferably, when a polypeptide portion of a serum-binding protein is desired to be incorporated into the Tri-Specific Binding Molecules of the present invention, such polypeptide portion will be installed at the C-terminus of one of the polypeptide chains of the Tri-Specific Binding Molecule.

Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules,*" J. Biol. Chem. 277 (10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:123): LAEAKVLANR ELDKYGVSDY YKNLIDNAKS AEGVKALIDE ILAALP.

As disclosed in WO 2012/162068 (herein incorporated by reference), "deimmunized" variants of SEQ ID NO:123 have the ability to attenuate or eliminate MHC class II binding. Based on combinational mutation results, the following combinations of substitutions are considered to be preferred substitutions for forming such a deimmunized Albumin-Binding Domain: 66S/70S+71A; 66S/70S+79A; 64A/65A/71A+66S; 64A/65A/71A+66D; 64A/65A/71A+ 66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

(SEQ ID NO: 124)
LAEAKVLANR ELDKYGVSDY YKNA$_{64}$A$_{65}$NNAKT VEGVKALIA$_{79}$E

ILAALP, or the amino acid sequence:

(SEQ ID NO: 125)
LAEAKVLANR ELDKYGVSDY YKNLIS$_{66}$NAKS$_{70}$ VEGVKALIA$_{79}$E

ILAALP, are particularly preferred as such deimmunized Albumin-Binding Domains exhibit substantially wild-type binding while providing attenuated MHC class II binding. Although such Albumin-Binding Domains may be incorporated into any of the polypeptide chains of the Tri-Specific Binding Molecules of the present invention, it is preferred to position such Domain C-terminally to the E-coil (or K-coil) Domain of the first or third polypeptide chain (via a linker that intervenes between the E-coil (or K-coil) Domain and the Albumin-Binding Domain (which is preferably a deimmunized Albumin-Binding Domain)). A preferred sequence for such a linker is SEQ ID NO:126: GGGS.

E. Functionality of the Fc Domain

In one embodiment, the CH2-CH3 Domain of the first polypeptide chain and the CH2-CH3 Domain of the third polypeptide will complex to form an Fc Domain that is substantially incapable of binding to an Fc receptor (i.e., binding at less than 10% the extent of a wild-type Fc Domain. Alternatively, the Fc Domain of such molecules will be capable of binding to the Fc receptor under physiological conditions, so that such Tri-Specific Binding Molecules will be tetra-specific, capable of mediating coordinated binding to four molecules (Epitope I, Epitope II and Epitope III, and an Fc receptor). Most preferably, such molecules capable of binding to the Fc receptor will additionally mediate Fc receptor-dependent effector function.

The invention also encompasses molecules comprising variant Fc Domains comprising one or more amino acid substitutions, insertions, or deletions relative to a comparable wild-type Fc Domain. Molecules comprising variant Fc Domains normally have altered phenotypes relative to molecules comprising wild-type Fc Domains The variant phenotype may be expressed as altered serum half-life, altered stability, altered susceptibility to cellular enzymes or altered effector function as assayed in an NK dependent or macrophage dependent assay. Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors,*" Cancer Res. 57(18):8882-8890). Exemplary variants of human IgG1 Fc Domains with reduced binding to CD32B and/or increased binding to CD16A contain F243L, R292P, Y300L, V305I or P296L substitutions. These amino acid substitutions may be present in a human IgG1 Fc Domain in any combination. In one embodiment, the human IgG1 Fc Domain variant contains a F243L, R292P and Y300L substitution. In another embodiment, the human IgG1 Fc Domain variant contains a F243L, R292P, Y300L, V305I and P296L substitution. In another embodiment, the human IgG1 Fc Domain variant contains an N297Q substitution, L234A and L235A substitutions or a D265A substitution, as these mutations abolish FcR binding.

III. Exemplification of the Tri-Specific Binding Molecules of the Present Invention: Tri-Specific Binding Molecules Having Binding Domains that Bind to Epitopes of CD3 and CD8 and to an Epitope of a Disease-Antigen As stated above, the present invention particularly relates to the embodiment of Tri-Specific Binding Molecules in which the three epitopes are selected such that one or two of such epitopes are epitope(s) of an immune system cell, and especially, a cytotoxic lymphocyte immune system cell (CTL), and in which the remaining epitope(s) are epitope(s) of a Disease-Associated Antigen. In a particularly preferred embodiment of such Tri-Specific Binding Molecule, the Binding Domains of such molecule are selected such that Epitope I, Epitope II or Epitope III is an epitope of CD3, a second of Epitope I, Epitope II or Epitope III is an epitope of CD8, and the third of Epitope I, Epitope II or Epitope III is an epitope of a Disease-Associated Antigen, wherein the Binding Domains I, II and III of such Tri-Specific Binding Molecules mediate coordinated binding of a cytotoxic T cell and a cell expressing the Disease-Associated Antigen. Such Tri-Specific Binding Molecules are capable of localizing a cytotoxic lymphocyte cell to a cell that expresses a Disease-Associated Antigen, and of thereby facilitate the killing of cells that express the Disease-Associated Antigen. The Disease-Associated Antigen may be a cancer antigen, or may be an antigen that is characteristic of a pathogen (e.g., bacterial, fungal, viral or protozoan) infection. More particularly, the invention relates to such Tri-Specific Binding Molecules that are capable of mediating coordinated binding to: (1) an epitope of CD3, (2) an epitope of CD8, and (3) an epitope of a Disease-Associated Antigen. By binding to CD3 and CD8, and to the Disease-Associated Antigen, such molecules co-localize cytotoxic T cells to cells presenting the Disease-Associated Antigen, leading to the activation of such T cells and the initiation of a cytotoxic response against cells expressing the Disease-Associated Antigen.

The heavy chains of an anti-CD3 or anti-CD8 antibody may be employed as the third polypeptide chain of such exemplary Tri-Specific Binding Molecules of the present invention. Likewise, the light chains of such antibodies may be employed as the fourth polypeptide chain of the Tri-Specific Binding Molecules of the present invention. Alternatively, the Light Chain Variable Domains and/or the Heavy Chain Variable Domains of such antibodies may be combined with other immunoglobulin constant regions to achieve such third and fourth polypeptide chains. Thus, such antibodies may be used to produce Tri-Specific Binding Molecules of the present invention whose Site C is capable of binding CD3 or CD8.

Similarly, such Variable Domains can be incorporated into the Variable Domain portions of the first and third polypeptide of the Tri-Specific Binding Molecules of the present invention so as to produce Tri-Specific Binding Molecules of the present invention whose Site A is capable of binding CD3 or CD8, or whose Site B is capable of binding CD3 or CD8.

1. Exemplary Anti-CD3 Antibodies

Any of the exemplary anti-CD3 or anti-CD8 antibodies provided below may be employed to make the CD3 or CD8 Binding Domains of the Tri-Specific Binding Molecules of the present invention.

OKT3

OKT3 Light Chain Variable Domain (SEQ ID NO:17) (CDRs shown underlined):

```
QIVLTQSPAI MSASPGEKVT MTCSASSSVS YMNWYQQKSG

TSPKRWIYDT SKLASGVPAH FRGSGSGTSY SLTISGMEAE

DAATYYCQQW SSNPFTFGSG TKLEINR
```

OKT3 Heavy Chain Variable Domain (SEQ ID NO:18) (CDRs shown underlined):

```
QVQLQQSGAE LARPGASVKM SCKASGYTFT RYTMHWVKQR

PGQGLEWIGY INPSRGYTNY NQKFKDKATL TTDKSSSTAY

MQLSSLTSED SAVYYCARYY DDHYCLDYWG QGTTLTVSSA

KTTAPSVYPL APVCGDTTGS SVTLGCLVKG YFPEPVTLTW

NSGSLSSGVH TFPAVLQSDL YTLSSSVTVT SS
M291
```

M291 Light Chain Variable Domain (SEQ ID NO:19) (CDRs shown underlined):

```
DIVLTQSPAI MSASPGEKVT MTCSASSSVS YMNWYQQKSG

TSPKRWTYDT SKLASGVPAR FSGSGSGTSY SLTISSMEAE

DADTYYCQQW SSNPPTFGSG TKLEIK
```

M291 Heavy Chain Variable Domain (SEQ ID NO:20) (CDRs shown underlined):

```
QVQLQQSGAE LARPGASVKM SCKASGYTFI SYTMHWVKQR

PGQGLEWIGY INPRSGYTHY NQKLKDKATL TADKSSSSAY

MQLSSLTSED SAVYYCARSA YYDYDGFAYW GQGTLVTVSA
YTH12.5
```

YTH12.5 Light Chain Variable Domain (SEQ ID NO:21) (CDRs shown underlined):

```
MGWSCIILFL VATATGVHSD IQLTQPNSVS TSLGSTVKLS

CTLSSGNIEN NYVHWYQLYE GRSPTTMIYD DDKRPDGVPD

RFSGSIDRSS NSAFLTIHNV AIEDEAIYFC HSYVSSFNVF

GGGTKLTVLR
```

YTH12.5 Heavy Chain Variable Domain (SEQ ID NO:22) (CDRs shown underlined):

```
MGWSCIILFL VATATGVHSE VQLLESGGGL VQPGGSLRLS

CAASGFTFSS FPMAWVRQAP GKGLEWVSTI STSGGRTYYR

DSVKGRFTIS RDNSKNTLYL QMNSLRAEDT AVYYCAKFRQ

YSGGFDYWGQ GTLVTVSS
```

Humanized Anti-CD3 Antibody 1 ("CD3 mAb 1") (US2014/0099318A1)

CD3 mAb 1 Light Chain Variable Domain (SEQ ID NO:23) Variant 1 (CDRs shown underlined):

```
DIQMTQSPSS LSASVGDRVT ITCSASSSVS YMNWYQQKPG

KAPKRLIYDS SKLASGVPSR FSGSGSGTEF TLTISSLQPE

DFATYYCQQW SRNPPTFGGG TKVEIK
```

CD3 mAb 1 Light Chain Variable Domain (SEQ ID NO:24) Variant 2 (CDRs shown underlined):

```
DVVMTQSPAI MSAFPGEKVT ITCSASSSVS YMNWYQQKPG

KAPKRWIYDS SKLASGVPSR FSGSGSGTEF TLTISSLQPE

DFATYYCQQW SRNPPTFGGG TKVEIK
```

CD3 mAb 1 Heavy Chain Variable Domain (SEQ ID NO:25) Variant 1 (CDRs shown underlined):

```
QVQLVQSGAE VKKPGASVKV SCKASGYTFT RSTMHWVRQA

PGQGLEWIGY INPSSAYTNY NQKFKDRVTI TADKSTSTAY

MELSSLRSED TAVYYCASPQ VHYDYNGFPY WGQGTLVTVS S
```

Humanized Anti-CD3 Antibody 2 ("CD3 mAb 2") (US2014/0099318A1)

CD3 mAb 2 Light Chain Variable Domain (SEQ ID NO:26) (CDRs shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

CD3 mAb 2 Heavy Chain Variable Domain (SEQ ID NO:27) (CDRs shown underlined):

```
EVQLVESGGG LVQPGGSLRL SCAASGFTFS TYAMNWVRQA

PGKGLEWVGR IRSKYNNYAT YYADSVKDRF TISRDDSKNS

LYLQMNSLKT EDTAVYYCVR HGNFGNSYVS WFAYWGQGTL

VTVSS
```

CD3 mAb 2 Heavy Chain Variable Domain D65G Variant (SEQ ID NO:28) (CDRs shown underlined):

```
EVQLVESGGG LVQPGGSLRL SCAASGFTFS TYAMNWVRQA

PGKGLEWVGRIRSKYNNYAT YYADSVKGRF TISRDDSKNS

LYLQMNSLKT EDTAVYYCVR HGNFGNSYVS WFAYWGQGTL VTVSS
```

2. Exemplary Anti-CD8 Antibodies

OKT8 ("CD8 mAb 1")

OKT8 Light Chain Variable Domain (SEQ ID NO:29) (CDRs shown underlined):

```
DIVMTQSPAS LAVSLGQRAT ISCRASESVD SYDNSLMHWY

QQKPGQPPKV LIYLASNLES GVPARFSGSG SRTDFTLTID

PVEADDAATY YCQQNNEDPY TFGGGTKLEI KR
```

OKT8 Heavy Chain Variable Domain (SEQ ID NO:30) (CDRs shown underlined):

```
QVQLLESGPE LLKPGASVKM SCKASGYTFT DYNMHWVKQS

HGKSLEWIGY IYPYTGGTGY NQKFKNKATL TVDSSSSTAY

MELRSLTSED SAVYYCARNF RYTYWYFDVW GQGTTVTVSS
```

TRX2 ("CD8 mAb 2")

TRX2 Light Chain Variable Domain (SEQ ID NO:31) (CDRs shown underlined):

```
DIQMTQSPSS LSASVGDRVT ITCKGSQDIN NYLANYQQKP

GKAPKLLIYN TDILHTGVPS RFSGSGSGTD FTFTISSLQP

EDIATYYCYQ YNNGYTFGQG TKVEIK
```

TRX2 Heavy Chain Variable Domain (SEQ ID NO:32) (CDRs shown underlined):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS S
```

3. Exemplary Binding Domains that Bind to Epitopes of Disease-Associated Antigens (a) HIV Gp41

An illustrative Disease-Associated Antigen is HIV gp41. An exemplary gp41 antibody is 7B2 ("HIV mAb 1").

Amino Acid Sequence of 7B2 Light Chain Variable Domain (SEQ ID NO:35):

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIK
```

Amino Acid Sequence of 7B2 Heavy Chain Variable Domain (SEQ ID NO:36):

```
QVQLVQSGGG VFKPGGSLRL SCEASGFTFT EYYMTWVRQA

PGKGLEWLAY ISKNGEYSKY SPSSNGRFTI SRDNAKNSVF

LQLDRLSADD TAVYYCARAD GLTYFSELLQ YIFDLWGQGA RVTVSS
```

(b) HIV Gp120

A second illustrative Disease-Associated Antigen is HIV gp120. An exemplary gp120 antibody is A32 ("HIV mAb 2").

Amino Acid Sequence of A32 VL Light Chain Variable Domain (SEQ ID NO:33):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL
```

Amino Acid Sequence of A32 VH Heavy Chain Variable Domain (SEQ ID NO:34):

```
QVQLQESGPG LVKPSQTLSL SCTVSGGSSS SGAHYWSWIR

QYPGKGLEWI GYIHYSGNTY YNPSLKSRIT ISQHTSENQF

SLKLNSVTVA DTAVYYCARG TRLRTLRNAF DIWGQGTMVT VSS
```

(c) RSV Glycoprotein F

A further illustrative Disease-Associated Antigen is RSV glycoprotein F. An exemplary anti-RSV glycoprotein F antibody is palivizumab ("RSV mAb 1").

Amino Acid Sequence of Palivizumab Light Chain Variable Domain (SEQ ID NO:37):

```
DIQMTQSPST LSASVGDRVT ITCRASQSVG YMHWYQQKPG

KAPKLLIYDT SKLASGVPSR FSGSGSGTEF TLTISSLQPD

DFATYYCFQG SGYPFTFGGG TKLEIK
```

Amino Acid Sequence of palivizumab Heavy Chain Variable Domain (SEQ ID NO:38):

```
QVTLRESGPA LVKPTQTLTL TCTFSGFSLS TSGMSVGWIR

QPPGKALEWL ADIWWDDKKD YNPSLKSRLT ISKDTSKNQV

VLKVTNMDPA DTATYYCARS MITNWYFDVW GAGTTVTVSS
```

(d) B7-H3

A particularly preferred illustrative Disease-Associated Antigen is B7-H3, which is expressed on a variety of cancer cells (e.g., neuroblastomas, gastric, ovarian and non-small cell lung cancers, etc.). B7-H3 protein expression has been immunohistologically detected in tumor cell lines (Chapoval, A. et al. (2001) "*B7-H3: A Costimulatory Molecule For T Cell Activation and IFN-γ Production,*" Nature Immunol. 2:269-274; Saatian, B. et al. (2004) "*Expression Of Genes For B7-H3 And Other T Cell Ligands By Nasal Epithelial Cells During Differentiation And Activation,*" Amer. J. Physiol. Lung Cell. Mol. Physiol. 287:L217-L225; Castriconi et al. (2004) "*Identification Of 4Ig-B7-H3 As A Neuroblastoma-Associated Molecule That Exerts A Protective Role From An NK Cell-Mediated Lysis,*" Proc. Natl. Acad. Sci. (U.S.A.) 101(34): 12640-12645); Sun, M. et al. (2002) "*Characterization of Mouse and Human B7-H3 Genes,*" J. Immunol. 168:6294-6297). mRNA expression has been found in heart, kidney, testes, lung, liver, pancreas, prostate, colon, and osteoblast cells (Collins, M. et al. (2005) "*The B7 Family Of Immune-Regulatory Ligands,*" Genome Biol. 6:223.1-223.7). At the protein level, B7-H3 is found in human liver, lung, bladder, testis, prostate, breast, placenta, and lymphoid organs (Hofmeyer, K. et al. (2008) "*The Contrasting Role Of B7-H3,*" Proc. Natl. Acad. Sci. (U.S.A.) 105(30):10277-10278). Illustrative antibodies that bind to B7-H3 include humanized "BRCA84D," "BRCA69D" and "PRCA157" (WO 2011/109400). Exemplary light and heavy variable chains have the following sequences (CDRs shown underlined):

Amino Acid Sequence of exemplary humanized BRCA84D-5VL Light Chain Variable Domain (SEQ ID NO:39):

```
DIQLTQSPSF LSASVGDRVT ITCKASQNVD TNVAWYQQKP

GQAPKALIYS ASYRYSGVPS RFSGSGSGTD FTLTISSLQP

EDFATYYCQQ YNNYPFTFGQ GTKLEIK
```

Amino Acid Sequence of exemplary humanized BRCA84D-2VH Heavy Chain Variable Domain (SEQ ID NO:40):

```
EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCGRGR ENIYYGSRLD YWGQGTTVTV SS
```

Amino Acid Sequence of exemplary BRCA69D ("B7-H3 mAb 1") Light Chain Variable Domain (SEQ ID NO:41):

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIK
```

Amino Acid Sequence of exemplary BRCA69D ("B7-H3 mAb 1") Heavy Chain Variable Domain (SEQ ID NO:42):

```
QVQLVQSGAE VKKPGASVKV SCKASGYTFT SYWMQWVRQA

PGQGLEWMGT IYPGDGDTRY TQKFKGRVTI TADKSTSTAY

MELSSLRSED TAVYYCARRG IPRLWYFDVW GQGTTVTVSS
```

Amino Acid Sequence of exemplary PRCA157 Light Chain Variable Domain (SEQ ID NO:43):

```
DIQMTQSPAS LSVSVGETVT ITCRASESIY SYLAWYQQKQ

GKSPQLLVYN TKTLPEGVPS RFSGSGSGTQ FSLKINSLQP

EDFGRYYCQH HYGTPPWTFG GGTNLEIK
```

Amino Acid Sequence of exemplary PRCA157 Heavy Chain Variable Domain (SEQ ID NO:44):

```
EVQQVESGGD LVKPGGSLKL SCAASGFTFS SYGMSWVRQT

PDKRLEWVAT INSGGSNTYY PDSLKGRFTI SRDNAKNTLY

LQMRSLKSED TAMYYCARHD GGAMDYWGQG TSVTVSS
```

(e) A33 Tumor Antigen

The A33 tumor antigen is another illustrative Disease-Associated Antigen. The amino acid sequence of the Light Chain Variable Domain of an exemplary humanized anti-A33 antibody ("gpA33 mAb 1") is (SEQ ID NO:45):

```
QIVLTQSPAI MSASPGERVT MTCSARSSIS FMYWYQQKPG

SSPRLLIYDT SNLASGVPVR FSGSGSGTSY SLTISRMEAE

DAATYYCQQW SSYPLTFGSG TKLELKR
```

The amino acid sequence of the Heavy Chain Variable Domain of such exemplary humanized anti-A33 (gpA33 mAb 1) antibody is (SEQ ID NO:46):

```
QVQLQQSGPE LVKPGASVKI SCKASGYTFS GSWMNWVKQR

PGQGLEWIGR IYPGDGETNY NGKEKDKATL TADKSSTTAY

MELSSLTSVD SAVYFCARIY GNNVYFDVWG AGTTVTVSS
```

(f) 5T4 Tumor Antigen

The 5T4 tumor antigen is another illustrative Disease-Associated Antigen. The amino acid sequence of the Light Chain Variable Domain of an exemplary humanized anti-5T4 mAb 1 antibody ("5T4 mAb 1") is (SEQ ID NO:47):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIK
```

The amino acid sequence of the Heavy Chain Variable Domain of such exemplary humanized 5T4 mAb 1 is (SEQ ID NO:48):

```
QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSS
```

The amino acid sequence of the Light Chain Variable Domain of a second exemplary humanized 5T4 mAb 2 antibody ("5T4 mAb 2") is (SEQ ID NO:49):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IK
```

The amino acid sequence of the Heavy Chain Variable Domain of such second exemplary humanized 5T4 mAb 2 is (SEQ ID NO:50):

```
QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN SYAMDYWGQG

TSVTVSS
```

(g) ROR1 Antigen

The ROR1 tumor antigen is another illustrative Disease-Associated Antigen. Exemplary anti-ROR1 antibodies include antibody 2A2 (WO 2010/124188), R11 (WO 2012/075158) and R12 (WO 2012/075158).

The amino acid sequence of the Light Chain Variable Domain of the 2A2 antibody is (SEQ ID NO:53):

```
DIVMTQSQKI MSTTVGDRVS ITCKASQNVD AAVAWYQQKP

GQSPKLLIYS ASNRYTGVPD RFTGSGSGTD FTLTISNMQS

EDLADYFCQQ YDIYPYTFGG GTKLEIK
```

The amino acid sequence of the Heavy Chain Variable Domain of the 2A2 antibody is (SEQ ID NO:54):

```
QVQLQQSGAE LVRPGASVTL SCKASGYTFS DYEMHWVIQT

PVHGLEWIGA IDPETGGTAY NQKFKGKAIL TADKSSSTAY

MELRSLTSED SAVYYCTGYY DYDSFTYWGQ GTLVTVSA
```

The amino acid sequence of the Light Chain Variable Domain of the R11 antibody is (SEQ ID NO:55):

```
ELVMTQTPSS TSGAVGGTVT INCQASQSID SNLAWFQQKP

GQPPTLLIYR ASNLASGVPS RFSGSRSGTE YTLTISGVQR

EDAATYYCLG GVGNVSYRTS FGGGTEVVVK
```

The amino acid sequence of the Heavy Chain Variable Domain of the R11 antibody is (SEQ ID NO:56):

```
QSVKESEGDL VTPAGNLTLT CTASGSDIND YPISWVRQAP

GKGLEWIGFI NSGGSTWYAS WVKGRFTISR TSTTVDLKMT

SLTTDDTATY FCARGYSTYY GDFNIWGPGT LVTISS
```

The amino acid sequence of the Light Chain Variable Domain of the R12 antibody is (SEQ ID NO:57):

```
ELVLTQSPSV SAALGSPAKI TCTLSSAHKT DTIDWYQQLQ

GEAPRYLMQV QSDGSYTKRP GVPDRFSGSS SGADRYLIIP

SVQADDEADY YCGADYIGGY VFGGGTQLTV TG
```

The amino acid sequence of the Heavy Chain Variable Domain of the R12 antibody is (SEQ ID NO:58)

```
QEQLVESGGR LVTPGGSLTL SCKASGFDFS AYYMSWVRQA

PGKGLEWIAT IYPSSGKTYY ATWVNGRFTI SSDNAQNTVD

LQMNSLTAAD RATYFCARDS YADDGALFNI WGPGTLVTIS

S
```

One aspect of the present invention (discussed in detail below) is the provision of a more preferred humanized anti-ROR1 antibody ("ROR1 mAb 1"). This more preferred ROR1 mAb 1 has a Light Chain Variable Domain having the sequence (SEQ ID NO:51):

```
QLVLTQSPSA SASLGSSVKL TCTLSSGHKT DTIDWYQQQP

GKAPRYLMRL EGSGSYNKGS GVRDRFGSGS SSGADRYLTI

SSLQSEDEAD YYCGTDYPGN YLFGGGTQLT VL
```

The amino acid sequence of the Heavy Chain Variable Domain of such more preferred humanized ROR1 mAb 1 is (SEQ ID NO:52):

```
QEQLVESGGG LVQPGGSLRL SCAASGFTFS DYYMSWVRQA

PGKGLEWVAT IYPSSGKTYY ADSVKGRFTI SSDNAKNSLY

LQMNSLRAED TAVYYCARDS YADDAALFDI WGQGTTVTVS S
```

IV. Selection of Binding Site: Site A, Site B and Site C

As indicated above, the preferred Tri-Specific Binding Molecules of the present invention are at least tri-specific, having an "external" Diabody-Type Binding Domain (Site A) that is located furthest from a Binding Domain III, an "internal" Diabody-Type Binding Domain (Site B) that is located nearest to a Binding Domain III, and the Binding Domain III itself (Site C). As used herein, a description of a Tri-Specific Binding Molecule such as "X/Y/Z" indicates that the X Binding Domain is at Site A, the Y Binding Domain is at Site B and the Z Binding Domain is at Site C. For example, the Tri-Specific Binding Molecule designation "B7-H3 mAb 1/CD3 mAb 2/CD8 mAb 1" indicates the B7-H3 mAb 1 Variable Domains occupy Site A of the Tri-Specific Binding Molecule, CD3 mAb 2 Variable Domains occupy Site B and CD8 mAb 1 Variable Domains occupy Site C of the Tri-Specific Binding Molecule.

The present invention thus permits choice as to which of such Sites is to be used to bind a particular desired epitope. One factor to guide such selection, particularly with Tri-Specific Binding Molecules that bind to CD3, CD8 and a Disease-Associated Antigen, involves a consideration of the effect and desirability of trogocytosis. "Trogocytosis" is a process through which a cell can acquire a portion of a cell membrane of a contacting cell (Masuda, S. et al. (2013) "*Possible Implication Of Fc γ Receptor-Mediated Trogocytosis In Susceptibility To Systemic Autoimmune Disease*," Clin. Dev. Immunol. 2013: Article ID 345745, 6 pages); Dhainaut, M. et al. (2014) "*Regulation of Immune Reactivity by Intercellular Transfer*," Front Immunol. 5:112; Ahmed, K. A. et al. (2011) "*Mechanisms Of Cellular Communication Through Intercellular Protein Transfer*," J. Cell. Mol. Med. 15(7):1458-1473; Ahmed, K. A. et al. (2008) "*Intercellular Trogocytosis Plays An Important Role In Modulation Of Immune Responses*," Cell. Mol. Immunol. 5(4):261-269; LeMaoult, J. et al. (2007) "*Exchanges Of Membrane Patches (Trogocytosis) Split Theoretical And Actual Functions Of Immune Cells*," Hum. Immunol. 68(4):240-243; Caumartin. J. et al. (2006) "*Intercellular Exchanges Of Membrane Patches (Trogocytosis) Highlight The Next Level Of Immune Plasticity*," Transpl. Immunol. 17(1):20-22).

The acquisition of cognate MHC class I ligands by trogocytosis induces cytotoxic T lymphocytes to become "Acquired Treg" cells that mediate the killing ("fratricide") of other cytotoxic T cells, thereby contributing to the clearance of $CD8^+$ cells (D'Acquisto, F. et al. (2011) "*$CD3^+CD4^-CD8^-$ (Double Negative) T Cells: Saviours Or Villains Of The Immune Response?*" Biochem. Pharmacol. 82:333-340; Joly, E. et al. (2003) "*What Is Trogocytosis And What Is Its Purpose?*" Nat. Immunol. 4:815-; Hudrisier, D. et al. (2007) "*Capture Of Target Cell Membrane Components Via Trogocytosis Is Triggered By A Selected Set Of Surface Molecules On T Or B Cells*," J. Immunol. 178:3637-3647).

A Tri-Specific Binding Molecule of the present invention that possesses a CD3 Binding Domain as its Site C position has the attributes of an anti-CD3 antibody, and likewise such a Tri-Specific Binding Molecule that possesses a CD8 Binding Domain as its Site C position has the attributes of an anti-CD8 antibody. It has been shown that a neutrophil, monocyte or macrophage having an Fc receptor that is bound to the Fc Domain of an anti-CD8 antibody (that has bound to a CD8 molecule of a T cell) is capable of transferring the antibody and the bound CD8 molecule from the T cell to itself via trogocytosis and of then rapidly internalizing the antibody; bystander molecules, such as TCR and CD3 may also be transferred in this process (Masuda, S. et al., (2013) "*Possible Implication of Fcg Receptor-Mediated Trogocytosis in Susceptibility to Systemic Autoimmune Disease*," Clin. Develop. Immunol. 2013:Article ID 345745, 6 pages).

The structures of CD3 and CD8 differ in that CD3 lies close to the cell membrane, while CD8 extends further from the cell membrane. It is thus expected that Fc receptor trogocytosis of CD3 by an anti-CD3 antibody would be more efficient than Fc receptor trogocytosis of CD8 by an anti-CD8 antibody.

This phenomenon indicates that a Tri-Specific Binding Molecule of the present invention that binds to CD3, CD8 and a Disease-Associated Antigen whose CD3 Binding Domain is located on the Site C position will exhibit less cytotoxicity than an analogous Tri-Specific Binding Molecule in which the CD3 Binding Domain is located at Site A or at Site B. Thus, by electing to place the CD3 Binding Domain on the Site C position (as opposed to either of the Sites A or B), one may modulate the extent of cytotoxicity. Additionally, one may compound pharmaceutical compositions that contain a mixture of a "Site C" and a "Site A (or B)" CD3 in order to obtain a preferred extent of cytotoxicity.

V. Anti-ROR1 mAb 1 Antibody

As indicated above, one aspect of the present application is the provision of highly preferred humanized anti-ROR1 antibody ("ROR1 mAb 1") whose Light Chain Variable Domain has the amino acid sequence (SEQ ID NO:51):

```
QLVLTQSPSA SASLGSSVKL TCTLSSGHKT DTIDWYQQQP

GKAPRYLMKL EGSGSYNKGS GVRDRFGSGS SSGADRYLTI

SSLQSEDEAD YYCGTDYPGN YLFGGGTQLT VL
``` and whose Heavy Chain Variable Domain has the amino acid sequence (SEQ ID NO:52):

```
QEQLVESGGG LVQPGGSLRL SCAASGFTFS DYYMSWVRQA

PGKGLEWVAT IYPSSGKTYY ADSVKGRFTI SSDNAKNSLY

LQMNSLRAED TAVYYCARDS YADDAALFDI WGQGTTVTVS S
```

The sequences of CDR$_L$1, CDR$_L$2, and CDR$_L$3 of the Light Chain Variable Domain of such ROR1 mAb 1 antibody are:

```
Light Chain Variable Domain CDR_L1
(SEQ ID NO: 117):
TLSSGHKTDTID

Light Chain Variable Domain CDR_L2
(SEQ ID NO: 118):
LEGSGSY

Light Chain Variable Domain CDR_L3
(SEQ ID NO: 119):
GTDYPGNYL
```

The sequences of CDR$_H$1, CDR$_H$2, and CDR$_H$3 of the Heavy Chain Variable Domain of such ROR1 mAb 1 antibody are:

```
Heavy Chain Variable Domain CDR_H1
(SEQ ID NO: 120):
GFTFSDYYMS

Heavy Chain Variable Domain CDR_H2
(SEQ ID NO: 121):
TIYPSSGKTYYADSVKG

Heavy Chain Variable Domain CDR_H3
(SEQ ID NO: 122):
DSYADDAALFDI
```

The ROR1 mAb 1 antibody mediates increased cytotoxicity and is less immunogenic relative to prior art anti-ROR1 antibodies (e.g., anti-ROR1 antibody R12).

The invention encompasses not only such sequences, but also intact ROR1 mAb 1 antibody derivatives (including chimeric or humanized derivatives thereof) that possess 1, 2 or 3 of the CDRs of such Light Chain Variable Domain (SEQ ID NO:51, CDRs shown underlined) or 1, 2 or 3 of the CDRs of such Heavy Chain Variable Domain (SEQ ID NO:52; CDRs shown underlined), and which immunospecifically bind to ROR1. More preferably, such encompassed antibodies, chimeric antibodies and humanized antibodies will possess 1, 2 or 3 of the CDRs of such Light Chain Variable Domain (SEQ ID NO:51, CDRs shown underlined) and also 1, 2 or 3 of the CDRs of such Heavy Chain Variable Domain (SEQ ID NO:52; CDRs shown underlined), and will immunospecifically bind to ROR1. Most preferably, such encompassed antibodies, chimeric antibodies and humanized antibodies will possess all 3 of the CDRs of such Light Chain Variable Domain, and all 3 of the CDRs of such Heavy Chain Variable Domain and be capable of immunospecifically binding to ROR1.

The invention additionally encompasses fragments and derivatives of such encompassed ROR1 mAb 1 antibodies, including Fab, Fab', F(ab')2 Fv), single-chain (ScFv), "BiTEs®," "DART™" diabody molecules, mutants thereof, naturally occurring variants, and fusion proteins, all of which comprise 1, 2, or 3 of the Light Chain Variable Domain CDRs, or 1, 2, or 3 of the Heavy Chain Variable Domain CDRs, or 1, 2, or 3 of the Light Chain Variable Domain CDRs, and also 1, 2, or 3 of the Heavy Chain Variable Domain CDRs, and which are capable of immunospecifically binding to ROR1.

In a preferred embodiment, such ROR1 mAb 1 antibodies or their fragments or derivatives may have variant Fc Domains. Modification of the Fc Domain normally leads to an altered phenotype, for example altered serum half-life, altered stability, altered susceptibility to cellular enzymes or altered effector function. It may be desirable to modify the antibody of the invention with respect to effector function, so as to enhance the effectiveness of the antibody in treating cancer, for example. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor specific B cells with low levels of FcγRIIB (e.g., non-Hodgkins lymphoma, CLL, and Burkitt's lymphoma). In said embodiments, molecules of the invention with conferred or enhanced effector function activity are useful for the treatment and/or prevention of a disease, disorder or infection where an enhanced efficacy of effector function activity is desired.

In certain embodiments, such ROR1 mAb 1 antibodies or their fragments or derivatives comprise one or more modifications to the amino acids of the Fc Domain, which reduce the affinity and avidity of the Fc Domain of such molecule for one or more FcγR receptors. In other embodiments, such ROR1 mAb 1 antibodies or their fragments or derivatives may comprise one or more modifications to the amino acids of the Fc Domain that increase the affinity and avidity of the Fc Domain of such molecule for one or more FcγR receptors. In other embodiments, the molecules comprise a variant Fc Domain wherein said variant confers or mediates increased ADCC activity and/or an increased binding to FcγRIIA, relative to a molecule comprising no Fc Domain or comprising a wild-type Fc Domain. In alternate embodiments, the molecules comprise a variant Fc Domain wherein said variant confers or mediates decreased ADCC activity (or other effector function) and/or an increased binding to FcγRIIB, relative to a molecule comprising no Fc Domain or comprising a wild-type Fc Domain.

In some embodiments, the invention encompasses such ROR1 mAb 1 antibodies or their fragments or derivatives that comprise a variant Fc Domain, which variant Fc Domain does not show a detectable binding to any FcγR, relative to a comparable molecule comprising the wild-type Fc Domain. In other embodiments, the invention encompasses such ROR1 mAb 1 antibodies or their fragments or derivatives that comprise a variant Fc Domain, which variant Fc Domain only binds a single FcγR, preferably one of FcγRIIA, FcγRIIB, or FcγRIIIA.

Such ROR1 mAb 1 antibodies or their fragments or derivatives may comprise altered affinities for an activating and/or inhibitory Fcγ receptor. In one embodiment, the antibody or molecule comprises a variant Fc Domain that has increased affinity for FcγRIIB and decreased affinity for FcγRIIIA and/or FcγRIIA, relative to a comparable molecule with a wild-type Fc Domain. In another embodiment, such ROR1 mAb 1 antibodies or their fragments or derivatives may comprise a variant Fc Domain that has decreased affinity for FcγRIIB and increased affinity for FcγRIIIA and/or FcγRIIA, relative to a comparable molecule with a wild-type Fc Domain. In yet another embodiment, such ROR1 mAb 1 antibodies or their fragments or derivatives comprise a variant Fc Domain that has decreased affinity for FcγRIIB and decreased affinity for FcγRIIIA and/or FcγRIIA, relative to a comparable molecule with a wild-type Fc Domain. In still another embodiment, such ROR1 mAb 1 antibodies or their fragments or derivatives may comprise a variant Fc Domain that has unchanged affinity for FcγRIIB and decreased (or increased) affinity for FcγRIIIA and/or FcγRIIA, relative to a comparable molecule with a wild-type Fc Domain.

In certain embodiments, the invention encompasses such ROR1 mAb 1 antibodies or their fragments or derivatives that comprise a variant Fc Domain with an altered affinity for FcγRIIIA and/or FcγRIIA such that the immunoglobulin has an enhanced effector function, e.g., ADCC. Non-limiting examples of effector cell functions include ADCC, antibody dependent cellular phagocytosis (ADCP), phagocytosis, opsonization, opsonophagocytosis, cell binding, rosetting, C1q binding, and CDC.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Domain. In other embodiments of the invention, the variant Fc Domain specifically binds one or more FcRs with at least 65%, preferably at least 70%, 75%, 80%, 85%, 90%, 95%, 100%, 125%, 150%, 175%, 200%, 225%, or 250% greater affinity relative to a molecule comprising a wild-type Fc Domain. Such measurements can be in vivo or in vitro assays, and in a preferred embodiment are in vitro assays such as ELISA or surface plasmon resonance assays.

In different embodiments, such ROR1 mAb 1 antibodies or their fragments or derivatives comprise a variant Fc Domain wherein said variant agonizes at least one activity of an FcγR receptor, or antagonizes at least one activity of an FcγR receptor. In a preferred embodiment, the molecules comprise a variant that agonizes (or antagonizes) one or more activities of FcγRIIB, for example, B cell receptor-mediated signaling, activation of B cells, B cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the molecules comprise a variant that agonizes (or antagonizes) one or more activities of FcεRI, for example, mast cell activation, calcium mobilization, degranulation, cytokine production, or serotonin release.

In certain embodiments, such ROR1 mAb 1 antibodies or their fragments comprise an Fc Domain-comprising domain from two or more IgG isotypes (e.g., IgG1, IgG2, IgG3 and IgG4). The various IgG isotypes exhibit differing physical and functional properties including serum half-life, complement-fixation, FcγR binding affinities and effector function activities (e.g. ADCC, CDC, etc.) due to differences in the amino acid sequences of their hinge and/or Fc Domains, for example as described in Flesch, B. K. and Neppert, J. (1999) "Functions Of The Fc Receptors For Immunoglobulin G," J. Clin. Lab. Anal. 14:141-156; Chappel, M. S. et al. (1993) "Identification Of A Secondary Fc Gamma RI Binding Site Within A Genetically Engineered Human IgG Antibody," J. Biol. Chem. 33:25124-25131; Chappel, M. S. et al. (1991) "Identification Of The Fc Gamma Receptor Class I Binding Site In Human IgG Through The Use Of Recombinant IgG1/IgG2 Hybrid And Point-Mutated Antibodies," Proc. Natl. Acad. Sci. (U.S.A.) 88:9036-9040; Brüggemann, M. et al. (1987) "Comparison Of The Effector Functions Of Human Immunoglobulins Using A Matched Set Of Chimeric Antibodies," J. Exp. Med 166:1351-1361. This type of variant Fc Domain may be used alone, or in combination with an amino acid modification, to affect Fc-mediated effector function and/or binding activity. In combination, the amino acid modification and IgG hinge/Fc Domain may display similar functionality (e.g., increased affinity for FcγRIIA) and may act additively or, more preferably, synergistically to modify the effector functionality in the molecule of the invention, relative to a molecule of the invention comprising a wild-type Fc Domain. In other embodiments, the amino acid modification and IgG Fc Domain may display opposite functionality (e.g., increased and decreased affinity for FcγRIIA, respectively) and may act to selectively temper or reduce a specific functionality in the molecule of the invention, relative to a molecule of the invention not comprising an Fc Domain or comprising a wild-type Fc Domain of the same isotype.

In a preferred specific embodiment, such ROR1 mAb 1 antibodies or their fragments comprise a variant Fc Domain, wherein said variant Fc Domain comprises at least one amino acid modification relative to a wild-type Fc Domain, such that the molecule has an altered affinity for an FcR, provided that said variant Fc Domain does not have a substitution at positions that make a direct contact with FcγR based on crystallographic and structural analysis of Fc-FcR interactions such as those disclosed by Sondermann, P. et al. (2000) "The 3.2-A Crystal Structure Of The Human IgG1 Fc Fragment-Fc GammaRIII Complex," Nature 406:267-273. Examples of positions within the Fc Domain that make a direct contact with FcγR are amino acid residues 234-239 (Hinge Domain), amino acid residues 265-269 (B/C loop), amino acid residues 297-299 (C'/E loop), and amino acid residues 327-332 (F/G loop). In some embodiments, the molecules of the invention comprise variant Fc Domains comprise modification of at least one residue that does not make a direct contact with an FcγR based on structural and crystallographic analysis, e.g., is not within the Fc-FcγR binding site.

Variant Fc Domains are well-known in the art, and any known Fc variant may be used in the present invention to confer or modify the effector function exhibited by such ROR1 mAb 1 antibodies or their fragments comprising an Fc Domain (or portion thereof) as functionally assayed, e.g., in an NK dependent or macrophage dependent assay. For example, Fc Domain variants identified as altering effector function are disclosed in PCT Publications No. WO 04/063351; WO 06/088494; WO 07/024249; WO 06/113665; WO 07/021841; WO 07/106707; WO 2008/140603, and any suitable variant disclosed therein may be used in the present molecules.

In certain embodiments, such ROR1 mAb 1 antibodies or their fragments comprise a variant Fc Domain, having one or more amino acid modifications in one or more sites, which modification(s) alter (relative to a wild-type Fc Domain) the Ratio of Affinities of the variant Fc Domain to an activating FcγR (such as FcγRIIA or FcγRIIIA) relative to an inhibiting FcγR (such as FcγRIIB):

$$\text{Ratio of Affinities} = \frac{\text{Wild-Type to Variant Change in Affinity to } Fc\gamma R_{Activating}}{\text{Wild-Type to Variant Change in Affinity to } Fc\gamma R_{Inhibiting}}$$

Where an Fc variant has a Ratio of Affinities greater than 1, the methods of the invention have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. Where an Fc variant has a Ratio of Affinities less than 1, the methods of the invention have particular use in providing a therapeutic or prophylactic treatment of a disease or disorder, or the amelioration of a symptom thereof, where a decreased efficacy of effector cell function mediated by FcγR is desired, e.g., autoimmune or inflammatory disorders. Table 3 lists exemplary single, double, triple, quadruple and quintuple mutations by whether their Ratio of Affinities is greater than or less than 1, and more information concerning these mutations may be found in PCT Publications No. WO 04/063351; WO 06/088494; WO 07/024249; WO 06/113665; WO 07/021841; WO 07/106707; WO 2008/140603.

In a preferred embodiment, in variant Fc Domains that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Domain has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

TABLE 3

Exemplary Single and Multiple Mutations Listed by Ratio of Affinities

| Ratio | Single | Double | Triple | Quadruple | Quintuple |
|---|---|---|---|---|---|
| >1 | F243L D270E R292G R292P | F243L & R292P F243L & Y300L F243L & P396L F243L & V305I D270E & P396L R292P & Y300L R292P & V305I R292P & P396L Y300L & P396L P396L & Q419H | F243L, P247L & N421K F243L, R292P & Y300L F243L, R292P & V305I F243L, R292P & P396L F243L, Y300L & P396L P247L, D270E & N421K R255L, D270E & P396L D270E, G316D & R416G D270E, K392T & P396L D270E, P396L & Q419H V284M, R292L & K370N R292P, Y300L & P396L | L234F, F243L, R292P & Y300L L235I, F243L, R292P & Y300L L235Q, F243L, R292P & Y300L F243L, P247L, D270E & N421K F243L, R255L, D270E & P396L F243L, D270E, G316D & R416G F243L, D270E, K392T & P396L F243L, D270E, P396L & Q419H F243L, R292P, Y300L, & P396L F243L, R292P, V305I & P396L P247L, D270E, Y300L & N421K R255L, D270E, R292G & P396L R255L, D270E, Y300L & P396L D270E, G316D, P396L & R416G | L235V, F243L, R292P, Y300L & P396L L235P, F243L, R292P, Y300L & P396L F243L, R292P, V305I, Y300L & P396L |
| <1 | Y300L P396L | F243L & P396L P247L & N421K R255L & P396L R292P & V305I K392T & P396L P396L & Q419H | F243L, R292P & V305I | | |

In a specific embodiment, in variant Fc Domains, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Domains, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a different embodiment, in variant Fc Domains that bind an FcγR (via its Fc Domain) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439.

In a different embodiment, in variant Fc Domains that bind an FcγR (via its Fc Domain) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398, or 430. In a different embodiment, in variant Fc Domains that binds FcγRIIA with an enhanced affinity, any of the following residues: A255, A256, A258, A267, A268, N268, A272, A276, A280, A283, A285, A286, D286, Q286, S286, A290, S290, M301, E320, M320, Q320, R320, E322, A326, D326, E326, S326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from groups 1-105:

| Group | Variant |
|---|---|
| 1 | A330L/I332E |
| 2 | D265F/N297E/I332E |
| 3 | D265Y/N297D/I332E |
| 4 | D265Y/ N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264R |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/ I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332 E |
| 80 | S239E/V264I/I332 E |
| 81 | S239E/V264I/S298A/A330Y/I332E |
| 82 | S239N/A330L/I332E |
| 83 | S239N/A330Y/I332E |
| 84 | S239N/I332D |

| Group | Variant |
|---|---|
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/ S298A/I332E |
| 100 | Y296D/N297D/I332E |
| 101 | Y296E/N297D/I332 E |
| 102 | Y296H/N297D/I332E |
| 103 | Y296N/N297D/I332E |
| 104 | Y296Q/N297I/I332E |
| 105 | Y296T/N297D/I332E |

In one embodiment, such ROR1 mAb 1 antibodies or their fragments will comprise a variant Fc Domain having at least one modification in the Fc Domain. In certain embodiments, the variant Fc Domain comprises at least one substitution selected from the group consisting of L235V, F243L, R292P, Y300L, V305I, and P396L, wherein said numbering is that of the EU index as in Kabat. In a specific embodiment, the variant Fc Domain comprises:
 (A) at least one substitution selected from the group consisting of F243L, R292P, Y300L, V305I, and P396L;
 (B) at least two substitutions selected from the group consisting of:
  (1) F243L and P396L;
  (2) F243L and R292P; and
  (3) R292P and V305I;
 (C) at least three substitutions selected from the group consisting of:
  (1) F243L, R292P and Y300L;
  (2) F243L, R292P and V305I;
  (3) F243L, R292P and P396L; and
  (4) R292P, V305I and P396L;
 (D) at least four substitutions selected from the group consisting of:
  (1) F243L, R292P, Y300L and P396L; and
  (2) F243L, R292P, V305I and P396L; or
 (E) at least the five substitutions selected from the group consisting of:
  (1) F243L, R292P, Y300L, V305I and P396L; and
  (2) L235V, F243L, R292P, Y300L and P396L.

In another specific embodiment, the variant Fc Domain comprises substitutions of:
 (A) F243L, R292P, and Y300L;
 (B) L235V, F243L, R292P, Y300L, and P396L; or
 (C) F243L, R292P, Y300L, V305I, and P396L.

In other embodiments, such ROR1 mAb 1 antibodies or their fragments may possess any Fc variant known in the art, such as those disclosed in Jefferis, R. et al. (2002) "Interaction Sites On Human IgG-Fc For FcgammaR: Current Models," Immunol. Lett. 82:57-65; Presta, L. G. et al. (2002) "Engineering Therapeutic Antibodies For Improved Function," Biochem. Soc. Trans. 30:487-90; Idusogie, E. E. et al. (2001) "Engineered Antibodies With Increased Activity To Recruit Complement," J. Immunol. 166:2571-75; Shields, R. L. et al. (2001) "High Resolution Mapping Of The Binding Site On Human IgG1 For Fc Gamma RI, Fc Gamma RI, Fc Gamma RIII, And FcRn And Design Of IgG1 Variants With Improved Binding To The Fc gamma R," J. Biol. Chem. 276:6591-6604; Idusogie, E. E. et al. (2000) "Mapping Of The C1q Binding Site On Rituxan, A Chimeric Antibody With A Human IgG Fc," J. Immunol. 164:4178-84; Reddy, M. P. et al. (2000) "Elimination Of Fc Receptor-Dependent Effector Functions Of A Modified IgG4 Monoclonal Antibody To Human CD4," J. Immunol. 164:1925-1933; Xu, D. et al. (2000) "In Vitro Characterization of Five Humanized OKT3 Effector Function Variant Antibodies," Cell. Immunol. 200: 16-26; Armour, K. L. et al. (1999) "Recombinant human IgG Molecules Lacking Fcgamma Receptor I Binding And Monocyte Triggering Activities," Eur. J. Immunol. 29:2613-24; Jefferis, R. et al. (1996) "Modulation Of Fc(Gamma)R And Human Complement Activation By IgG3-Core Oligosaccharide Interactions," Immunol. Lett. 54:101-04; Lund, J. et al. (1996) "Multiple Interactions Of IgG With Its Core Oligosaccharide Can Modulate Recognition By Complement And Human Fc Gamma Receptor I And Influence The Synthesis Of Its Oligosaccharide Chains," J. Immunol. 157:4963-4969; Hutchins et al. (1995) "Improved Biodistribution, Tumor Targeting, And Reduced Immunogenicity In Mice With A Gamma 4 Variant Of Campath-1H," Proc. Natl. Acad. Sci. (U.S.A.) 92:11980-84; Jefferis, R. et al. (1995) "Recognition Sites On Human IgG For Fc Gamma Receptors: The Role Of Glycosylation," Immunol. Lett. 44:111-17; Lund, J. et al. (1995) "Oligosaccharide-Protein Interactions In IgG Can Modulate Recognition By Fc Gamma Receptors," FASEB J. 9:115-19; Alegre, M. L. et al. (1994) "A Non-Activating "Humanized" Anti-CD3 Monoclonal Antibody Retains Immunosuppressive Properties In Vivo," Transplantation 57:1537-1543; Lund et al. (1992) "Multiple Binding Sites On The CH2 Domain Of IgG For Mouse Fc Gamma R11," Mol. Immunol. 29:53-59; Lund et al. (1991) "Human Fc Gamma RI And Fc Gamma RI Interact With Distinct But Overlapping Sites On Human IgG," J. Immunol. 147:2657-2662; Duncan, A. R. et al. (1988) "Localization Of The Binding Site For The Human High-Affinity Fc Receptor On IgG," Nature 332:563-564; U.S. Pat. Nos. 5,624,821; 5,885,573; 6,194,551; 7,276,586; and 7,317,091; and PCT Publications WO 00/42072 and PCT WO 99/58572.

In some embodiments, such ROR1 mAb 1 antibodies or their fragments may further comprise one or more glycosylation sites, so that one or more carbohydrate moieties are covalently attached to the molecule. Preferably, such ROR1 mAb 1 antibodies or their fragments with one or more glycosylation sites and/or one or more modifications in the Fc Domain confer or have an enhanced antibody mediated effector function, e.g., enhanced ADCC activity, compared to the unmodified ROR1 mAb 1 antibodies or fragment. In some embodiments, the invention further comprises such ROR1 mAb 1 antibodies or their fragments comprising one or more modifications of amino acids that are directly or indirectly known to interact with a carbohydrate moiety of the Fc Domain, including but not limited to amino acids at positions 241, 243, 244, 245, 245, 249, 256, 258, 260, 262, 264, 265, 296, 299, and 301. Amino acids that directly or indirectly interact with a carbohydrate moiety of an Fc Domain are known in the art, see, e.g., Jefferis, R. et al. (1995) "Recognition Sites On Human IgG For Fc Gamma Receptors: The Role Of Glycosylation," Immunol. Lett. 44:111-17.

In another embodiment, the invention encompasses such ROR1 mAb 1 antibodies or their fragments that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. Such ROR1 mAb 1 antibodies or their fragments may comprise one or more glycosylation sites, including N-linked and O-linked glycosylation sites. Any glycosylation site for N-linked or O-linked glycosylation known in the art may be used in accordance with the instant invention. An exemplary N-linked glycosylation site is the amino acid sequence: Asn-X-Thr/Ser, wherein X may be any amino acid and Thr/Ser indicates a threonine or a serine. Such a site or sites may be introduced into a molecule of the invention using methods well-known in the art to which this invention pertains (see for example, IN VITRO MUTAGENESIS, RECOMBINANT DNA: A SHORT COURSE, J. D. Watson, et al. W.H. Freeman and Company, New York, 1983, chapter 8, pp. 106-116, which is incorporated herein by reference in its entirety. An exemplary method for introducing a glycosylation site into such ROR1 mAb 1 antibodies or their fragments may comprise: modifying or mutating an amino acid sequence of the molecule so that the desired Asn-X-Thr/Ser sequence is obtained, or expressing a ROR1 mAb 1 antibodies encoding nucleic acid molecule having such a sequence.

In some embodiments, the invention encompasses methods of modifying the carbohydrate content of such ROR1 mAb 1 antibodies or their fragments by adding or deleting a glycosylation site. Methods for modifying the carbohydrate content of antibodies (and molecules comprising antibody domains, e.g., Fc Domain) are well-known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of such ROR1 mAb 1 antibodies or their fragments by deleting one or more endogenous carbohydrate moieties of the molecule. In a specific embodiment, the invention encompasses shifting the glycosylation site of the Fc Domain of an antibody, by modifying positions adjacent to 297. In a specific embodiment, the invention encompasses modifying position 296 so that position 296 and not position 297 is glycosylated.

Effector function can be modified by techniques such as those described in PCT Publications No. WO 04/063351; WO 06/088494; WO 07/024249; WO 06/113665; WO 07/021841; WO 07/106707; WO 2008/140603, or by other means. For example, cysteine residue(s) may be introduced in the Fc Domain, thereby allowing interchain disulfide bond formation in this region, resulting in the generation of a homodimeric antibody that may have improved internalization capability and/or increased complement-mediated cell killing and ADCC. See Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9): 2918-2922. Homodimeric antibodies with enhanced antitumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc Domains and may thereby have enhanced complement lysis and ADCC capabilities (Stevenson, G. T. et al. (1989) "*A Chimeric Antibody With Dual Fc Domains (bisFabFc) Prepared By Manipulations At The IgG Hinge*," Anti-Cancer Drug Design 3:219-230.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 4 presents the BLOSUM62.iij substitution scores (the higher the score the more conservative the substitution and thus the more likely the substitution will not affect function). If an antigen-binding fragment comprising the resultant CDR fails to bind to ROR1, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 4

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | -1 | -2 | -2 | 0 | -1 | -1 | 0 | -2 | -1 | -1 | -1 | -1 | -2 | -1 | +1 | 0 | -3 | -2 | 0 |
| R | -1 | +5 | 0 | -2 | -3 | +1 | 0 | -2 | 0 | -3 | -2 | +2 | -1 | -3 | -2 | -1 | -1 | -3 | -2 | -3 |
| N | -2 | 0 | +6 | +1 | -3 | 0 | 0 | 0 | +1 | -3 | -3 | 0 | -2 | -3 | -2 | +1 | 0 | -4 | -2 | -3 |
| D | -2 | -2 | +1 | +6 | -3 | 0 | +2 | -1 | -1 | -3 | -4 | -1 | -3 | -3 | -1 | 0 | -1 | -4 | -3 | -3 |
| C | 0 | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0 | 0 | -3 | +5 | +2 | -2 | 0 | -3 | -2 | +1 | 0 | -3 | -1 | 0 | -1 | -2 | -1 | -2 |
| E | -1 | 0 | 0 | +2 | -4 | +2 | +5 | -2 | 0 | -3 | -3 | +1 | -2 | -3 | -1 | 0 | -1 | -3 | -2 | -2 |
| G | 0 | -2 | 0 | -1 | -3 | -2 | -2 | +6 | -2 | -4 | -4 | -2 | -3 | -3 | -2 | 0 | -2 | -2 | -3 | -3 |
| H | -2 | 0 | +1 | -1 | -3 | 0 | 0 | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0 | -3 | -2 | -1 | -3 | -1 | +3 |
| L | -1 | -2 | -3 | -4 | -1 | -2 | -3 | -4 | -3 | +2 | +4 | -2 | +2 | 0 | -3 | -2 | -1 | -2 | -1 | +1 |
| K | -1 | +2 | 0 | -1 | -3 | +1 | +1 | -2 | -1 | -3 | -2 | +5 | -1 | -3 | -1 | 0 | -1 | -3 | -2 | -2 |
| M | -1 | -1 | -2 | -3 | -1 | 0 | -2 | -3 | -2 | +1 | +2 | -1 | +5 | 0 | -2 | -1 | -1 | -1 | -1 | +1 |
| F | -2 | -3 | -3 | -3 | -2 | -3 | -3 | -3 | -1 | 0 | 0 | -3 | 0 | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0 | -1 | 0 | 0 | 0 | -1 | -2 | -2 | 0 | -1 | -2 | -1 | +4 | +1 | -3 | -2 | -2 |
| T | 0 | -1 | 0 | -1 | -1 | -1 | -1 | -2 | -2 | -1 | -1 | -1 | -1 | -2 | -1 | +1 | +5 | -2 | -2 | 0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0 | -3 | -3 | -3 | -1 | -2 | -2 | -3 | -3 | +3 | +1 | -2 | +1 | -1 | -2 | -2 | 0 | -3 | -1 | +4 |

The invention thus contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naive Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "Affinity maturation of antibodies assisted by in silico modeling," Proc. Natl. Acad. Sci. (USA) 105(26): 9029-9034. As an example, multi-well plates may be coated with a selected ROR1 mAb 1 antibody (e.g., 100 ng/well in carbonate buffer at room temperature for 2 hrs) and subsequently incubated with soluble ROR1 added at a dilution of 1/10 and incubated at room temperature for 16 hours or diluted to a concentration of 50 ng/ml in PBS-T-BSA (0.05 ml added to each well and incubated for at least 2 h at room temperature). The plate is then washed and dilutions of recombinant antibodies starting at 0.5 μg/ml in PBS-T-BSA are then added and incubated for 1 hour at room temp. Binding of recombinant antibodies to the captured antigen is then measured using, for example, an anti-human IgG-HRP conjugate and TMB substrate. After stopping color development using dilute sulfuric acid, the plate is read at 450 nM and higher affinity antibodies identified (see, e.g., U.S. Pat. No. 7,351,803).

VI. Pharmaceutical Compositions

In one embodiment, the present invention includes pharmaceutical compositions for the treatment of a cancer or disease that is characterized by the presence of a Disease-Associated Antigen. Such compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a modified diabody of the present invention, or a combination of such agents and a pharmaceutically acceptable carrier. Preferably, compositions of the invention comprise a prophylactically or therapeutically effective amount of one or more molecules of the invention and a pharmaceutically acceptable carrier. The invention also encompasses pharmaceutical compositions comprising such modified diabodies and a second therapeutic antibody that is specific for a particular disease antigen, and a pharmaceutically acceptable carrier.

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) infected cells or other diseased cells, decreasing symptoms resulting from the disease, increasing the quality of life of those suffering from the disease, decreasing the dose of other medications required to treat the disease, delaying the progression of the disease, and/or prolonging survival of companion animal recipients.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans (see, e.g., REMINGTON: THE SCIENCE AND PRACTICE OF PHARMACY (2012) Allen, Loyd V., Jr. (Ed.)$_{22nd}$ Edition, Pharmaceutical Press, London UK). The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers containing a modified diabody of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of cancer or a disease characterized by the presence of a Disease-Associated Antigen, in one or more containers. In another embodiment, a kit further comprises one or more antibodies or diabodies that bind one or more Disease-Associated Antigens. In certain embodiments, the other prophylactic or therapeutic agent is a chemotherapeutic. In other embodiments, the prophylactic or therapeutic agent is a biological or hormonal therapeutic.

VII. Methods of Producing the Tri-Specific Binding Molecules of the Present Invention The Tri-Specific Tri-Specific Binding Molecules of the present invention are most preferably produced through the recombinant expression of nucleic acid molecules that encode such polypeptides, as is well-known in the art.

Polypeptides of the invention may be conveniently prepared using solid-phase peptide synthesis (Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty-First Century*," Mini Rev. Med. Chem. 6(1):3-10).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., chimeric, humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

The antibodies or protein of interest may be subjected to sequencing by Edman degradation, which is well-known to those of skill in the art. The peptide information generated from mass spectrometry or Edman degradation can be used to design probes or primers that are used to clone the protein of interest.

An alternative method of cloning the protein of interest is by "panning" using purified proteins or portions thereof for cells expressing the antibody or protein of interest. The "panning" procedure may be conducted by obtaining a cDNA library from tissues or cells that express or over-express the desired cDNAs in a second cell type, and screening the transfected cells of the second cell type for a specific binding to the desired protein. Detailed descriptions of the methods used in cloning mammalian genes coding for cell-surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854).

cDNAs encoding antibodies, and other peptide agonists, antagonists and modulators can be obtained by reverse transcribing the mRNAs from a particular cell type according to standard methods in the art. Specifically, mRNA can be isolated using various lytic enzymes or chemical solutions according to the procedures set forth in Sambrook et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, more preferably 20-fold higher, more preferably 50-fold higher, more preferably 100-fold higher than that of the corresponding endogenous antibody or protein of interest, if present, in the host cells. Screening the host cells for a specific binding to a desired protein is preferably effected by an immunoassay or FACS. A cell over-expressing the antibody or protein of interest can be identified in this way.

Various techniques are also available which may now be employed to produce mutant peptide agonists, antagonists, and modulators which encodes for additions, deletions, or changes in amino acid sequence of the resultant protein relative to the parent peptide agonist, antagonist or modulator molecule.

The invention includes modifications to the Tri-Specific Binding Molecules of the invention that do not significantly affect their properties and variants that have enhanced or decreased activity. Modification of polypeptides is routine practice in the art. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. These polypeptides also include glycosylated and non-glycosylated polypeptides, as well as polypeptides with other post translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention also encompasses fusion proteins comprising one or more fragments or regions from the polypeptides and antibodies of this invention. In one embodiment, a fusion polypeptide is provided that comprises at least 10 contiguous amino acids of variable Light Chain region and at least 10 amino acids of variable heavy chain region. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide Domains that specifically bind to a desired viral epitope or a desired activating receptor of an immune effector cell or a protein present on the surface of an immune effector cell that expresses such an activating receptor and another amino acid sequence to which it is not attached in the native molecule, for example, a heterologous sequence or a homologous sequence from another region.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, such a polypeptide could be produced by an automated polypeptide synthesizer employing the solid-phase method.

VIII. Uses of the Compositions of the Invention

The present invention encompasses compositions, including pharmaceutical compositions, comprising the Tri-Specific Binding Molecules of the invention, polypeptides derived from such molecules, polynucleotides comprising sequences encoding such molecules or polypeptides, and other agents as described herein.

The Tri-Specific Binding Molecules of the present invention have the ability to coordinately bind to three epitopes, and thus have substantial use in diagnostics, chemical separation, and therapeutics involving such epitopes. For example, such molecules may be used as a reagent in a sandwich immunoassay.

In the embodiment in which such Tri-Specific Binding Molecules bind to an epitope of a Disease-Associated Antigen, such molecules may be used to treat the disease or condition associated with or characterized by the expression of such Disease-Associated Antigen. Thus, without limitation, pharmaceutical compositions comprising such molecules may be employed in the diagnosis or treatment of cancer, and diseases caused by a pathogen (e.g., bacterial, fungal, viral or protozoan) infection.

IX. Methods of Administration

The compositions of the present invention may be provided for the treatment, prophylaxis, and amelioration of one or more symptoms associated with a disease, disorder or infection by administering to a subject an effective amount of a pharmaceutical composition of the invention. In a preferred aspect, such compositions are substantially purified (i.e., substantially free from substances that limit its effect or produce undesired side-effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262: 4429-4432), construction of a nucleic acid as part of a retroviral or other vector, etc.

Methods of administering the Tri-Specific Binding Molecules of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the Tri-Specific Binding Molecules of the present invention may be packaged in a hermetically sealed container such as an ampoule or sachette indicating the quantity of such molecules. In one embodiment, the Tri-Specific Binding Molecules of the present invention are supplied as a dry sterilized lyophilized powder or water free concentrate in a hermetically sealed container and can be reconstituted, e.g., with water or saline to the appropriate concentration for administration to a subject. Preferably, the Tri-Specific Binding Molecules of the present invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized Tri-Specific Binding Molecules of the present invention should be stored at between 2 and 8° C. in their original container and the molecules should be administered within 12 hours, preferably within 6 hours, within 5 hours, within 3 hours, or within 1 hour after being reconstituted. In an alternative embodiment, the Tri-Specific Binding Molecules of the present invention are supplied in liquid form in a hermetically sealed container indicating the quantity and concentration of the molecule, fusion protein, or conjugated molecule. Preferably, the liquid form of the Tri-Specific Binding Molecules of the present invention is supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

As used herein, an "effective amount" of a pharmaceutical composition, in one embodiment, is an amount sufficient to effect beneficial or desired results including, without limitation, clinical results such as decreasing symptoms resulting from the disease attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages for antibody administration comprise one or more unit doses between 0.1-to 100 mg/kg/body weight.

The amount of the Tri-Specific Binding Molecule of the present invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For the Tri-Specific Binding Molecules of the present invention, the dosage administered to a patient is typically at least about 0.01 µg/kg/day, at least about 0.05 µg/kg/day, at least about 0.1 µg/kg/day, at least about 0.2 µg/kg/day, at least about 0.5 µg/kg/day, at least about 1 µg/kg/day, at least about 2 µg/kg/day, at least about 5 µg/kg/day, at least about 10 µg/kg/day, at least about 20 µg/kg/day, at least about 50 µg/kg/day, at least about 0.1 mg/kg/day, or more of the subject's body weight Preferably, the dosage administered to a patient is between about 0.01 µg/kg/day and about 0.1 mg/kg/day, more preferably, between about 0.01 µg/kg/day and about 50 µg/kg/day, more preferably, between about 0.01 µg/kg/day and about 50 µg/kg/day, more preferably, between about 0.01 µg/kg/day and about 10 µg/kg/day, more preferably, between about 0.01 µg/kg/day and about 1 µg/kg/day, more preferably, between about 0.01 µg/kg/day and about 0.5 µg/kg/day, and more preferably, between about 0.01 µg/kg/day and about 0.1 µg/kg/day of the subject's body weight. The dosage and frequency of administration of the Tri-Specific Binding Molecules of the invention may be reduced or altered by enhancing uptake and tissue penetration of the Tri-Specific Binding Molecules by modifications such as, for example, lipidation.

In another embodiment, the patient is administered a treatment regimen comprising one or more doses of such prophylactically or therapeutically effective amount of the Tri-Specific Binding Molecules encompassed by the invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the Tri-Specific Binding Molecules encompassed by the invention (for example, administering a dose on day 1, day 2, day 3 and day 4 of a given week and not administering doses of the prophylactically or therapeutically effective amount of the Tri-Specific Binding Molecules encompassed by the invention on day 5, day 6 and day 7 of the same week). Typically, there are 1, 2, 3, 4, 5, or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the Tri-Specific Binding Molecules encompassed by the invention is achieved.

In one embodiment, the dosage of the Tri-Specific Binding Molecules of the present invention administered to a patient may be calculated for use as a single agent therapy. In another embodiment the Tri-Specific Binding Molecules of the present invention are used in combination with other therapeutic compositions and the dosage administered to a patient are lower than when such Tri-Specific Binding Molecules are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "New Methods Of Drug Delivery," Science 249:1527-1533); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Florida (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ-controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, "New Methods Of Drug Delivery," Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety.

In a specific embodiment where the composition of the invention is a nucleic acid encoding a Tri-Specific Binding Molecule of the present invention, the nucleic acid can be administered in vivo to promote expression of its encoded Tri-Specific Binding Molecule, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "Antennapedia Homeobox Peptide Regulates Neural Morphogenesis," Proc. Natl. Acad. Sci. (U.S.A.) 88:1864-1868), etc. Alternatively, anucleic acid can be introduced intracellularly and incorporated within host cell DNA for expression by homologous recombination.

Treatment of a subject with a therapeutically or prophylactically effective amount of the Tri-Specific Binding Molecules of the present invention can include a single treatment or, preferably, can include a series of treatments. In a preferred example, a subject is treated with molecules of the invention one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

Having now generally described the invention, the same will be more readily understood through reference to the following Examples. Such Examples are provided by way of illustration and are not intended to be limiting of the present invention unless specified.

Example 1

Production and Properties of Exemplary Anti-CD3, Anti-CD8, Anti-B7-H3 Tri-Specific Binding Molecules In order to develop a therapeutic molecule that would exhibit greater specificity to CD8+ T cells, and more potent re-directed killing, Tri-Specific Binding Molecules were constructed having the ability to coordinately bind to CD3, to CD8 and to a Disease-Associated Antigen. The produced Tri-Specific Binding Molecule additionally possessed an Fc Domain to enhance the half-life of the Tri-Specific Binding Molecule in vivo. The general structures of the Tri-Specific Binding Molecules are shown in FIGS. 4A-4D. An exemplary Tri-Specific Binding Molecule specific for the Disease-Associated Antigen B7-H3 was constructed. The Tri-Specific Binding Molecule is termed B7-H3 mAb 1/CD3 mAb 2/CD8 mAb 1 to denote the relative positions of the Binding Domains within the Tri-Specific Binding Molecule. The B7-H3 Binding Domain occupies the Site A position, the CD3 Binding Domain occupies the Site B position and the CD8 Binding Domain occupies the Site C position (FIG. 4A). The B7-H3 mAb 1/CD3 mAb 2/CD8 mAb 1 Tri-Specific Binding Molecule was composed of four different polypeptide chains (Table 5).

TABLE 5

| Polypeptide Chain | Domains | Binding Affinity |
| --- | --- | --- |
| 1 | VL(B7-H3 mAb 1)-<br>VH(CD3 mAb 2)-<br>E-Coil-(CH2—CH3) | Light Chain:<br>B7-H3<br>Heavy Chain: CD3 |
| 2 | VL(CD3 mAb 2)-<br>VH(B7-H3 mAb 1)-<br>K-Coil | Light Chain: CD3<br>Heavy Chain:<br>B7-H3 |
| 3 | Heavy Chain CD8 mAb 1 | CD8 |
| 4 | Light Chain CD8 mAb 1 | CD8 |

The amino acid sequence of the first polypeptide chain of the B7-H3 mAb 1/CD3 mAb 2/CD8 mAb 1 Tri-Specific Binding Molecule is (SEQ ID NO:59):

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIKGGG SGGGGEVQLV

ESGGGLVQPG GSLRLSCAAS GFTFSTYAMN WVRQAPGKGL

EWVGRIRSKY NNYATYYADS VKDRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP
```

```
REPQVYTLPP SREEMTKNQV SLWCLVKGFY PSDIAVEWES

NGQPENNYKT TPPVLDSDGS FFLYSKLTVD KSRWQQGNVF

SCSVMHEALH NHYTQKSLSL SPGK
```

In the first polypeptide chain, VL(B7-H3 mAb 1) has the amino acid sequence of SEQ ID NO:41, VH(CD3 mAb 2) has the amino acid sequence of SEQ ID NO:27, E-coil has the amino acid sequence of SEQ ID NO:3 and (CH2-CH3) has the amino acid sequence of the "knob-bearing" amino acid sequence of SEQ ID NO:7.

The amino acid sequence of the second polypeptide chain of the B7-H3 mAb 1/CD3 mAb 2/CD8 mAb 1 Tri-Specific Binding Molecule is (SEQ ID NO:60):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSY WMQWVRQAPG

QGLEWMGTIY PGDGDTRYTQ KFKGRVTITA DKSTSTAYME

LSSLRSEDTA VYYCARRGIP RLWYFDVWGQ GTTVTVSSGG

CGGGKVAALK EKVAALKEKV AALKEKVAAL KE
```

In the second polypeptide chain, VL(CD3 mAb 2) has the amino acid sequence of SEQ ID NO:26, VH(B7-H3 mAb 1) has the amino acid sequence of SEQ ID NO:42, and K-coil has the amino acid sequence of SEQ ID NO:4.

The amino acid sequence of the third polypeptide chain of the B7-H3 mAb 1/CD3 mAb 2/CD8 mAb 1 Tri-Specific Binding Molecule is (SEQ ID NO:61):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

In the third polypeptide chain, the amino acid sequence of the employed CD8 mAb 1 Heavy Chain Variable Domain has the amino acid sequence of SEQ ID NO:30, a Hinge Domain, a CH1 Domain and the "hole-bearing" CH2-CH3 Domain with an H435R substitution to remove the Protein A binding site (SEQ ID NO:8).

The amino acid sequence of the fourth polypeptide chain of the B7-H3 mAb 1/CD3 mAb 2/CD8 mAb 1 Tri-Specific Binding Molecule is (SEQ ID NO:62):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

In the fourth polypeptide chain, the amino acid sequence of the employed CD8 mAb 1 Light Chain Variable Domain has the amino acid sequence of SEQ ID NO:29 and a kappa Light Chain Constant Domain.

The expressed B7H3 mAb 1/CD3 mAb 2/CD8 mAb 1 Tri-Specific Binding Molecule was loaded onto an MSA resin, washed with 10 mM NaPO$_4$ (pH6); 10 mM NaPO$_4$, 1M NaCl (pH6) and 10 mM NaPO$_4$ (pH6). Polypeptides were eluted from the resin with 50 mM glycine (pH3) and neutralized with 1M Tris (pH8). Expression was found to be 1.7 mg/L; the Tri-Specific Binding Molecule preparation was 0.6 mg/ml, having a final yield of 0.42 mg.

Figure 5A:
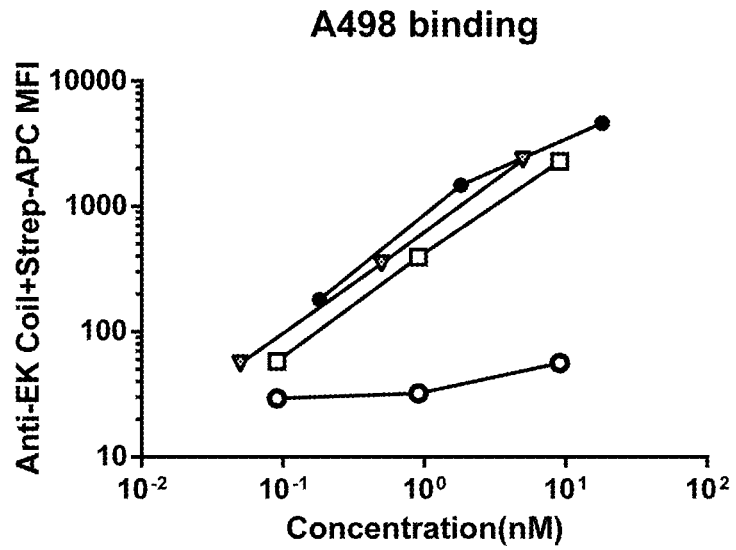
FIGS. 5A-5D show the ability of B7-H3 mAb 1/CD3 mAb 2/CD8 mAb 1 Tri-Specific Binding Molecule to bind to A498 target cells (FIG. 5A), and JIMT-1 target cells (FIG. 5B), CD5+/CD4− gated PBMCs (FIG. 5C) and CD5+/CD4+ gated PBMCs (FIG. 5D).
Figure 5B:
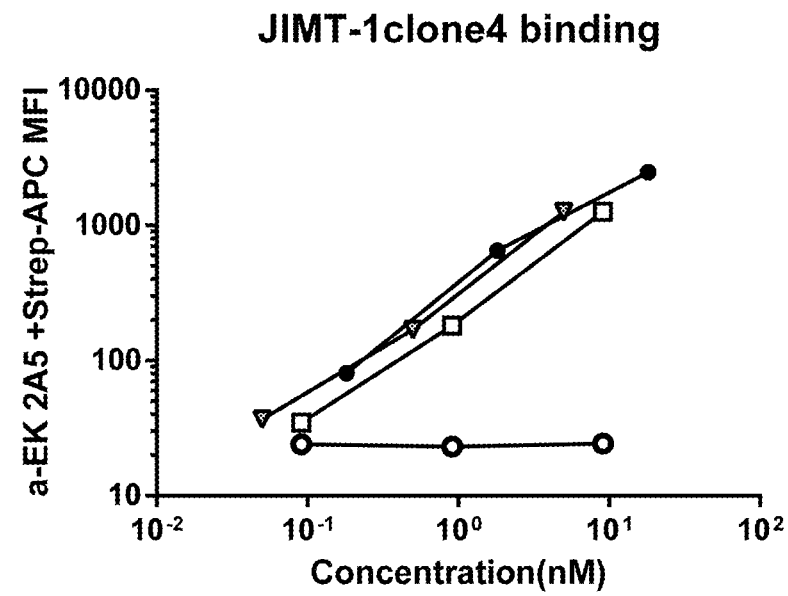
Figure 5C:
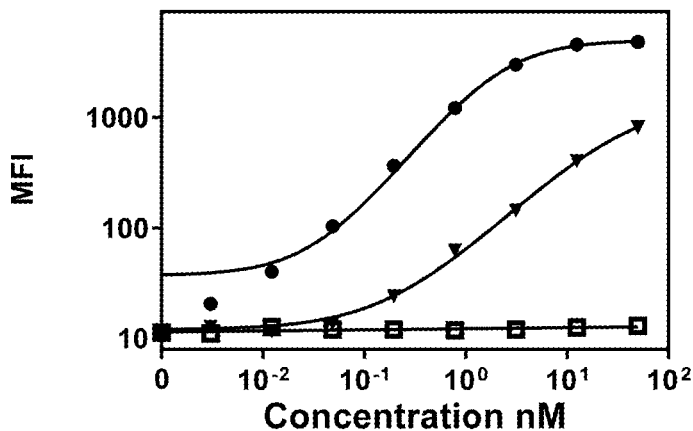
Figure 5D:
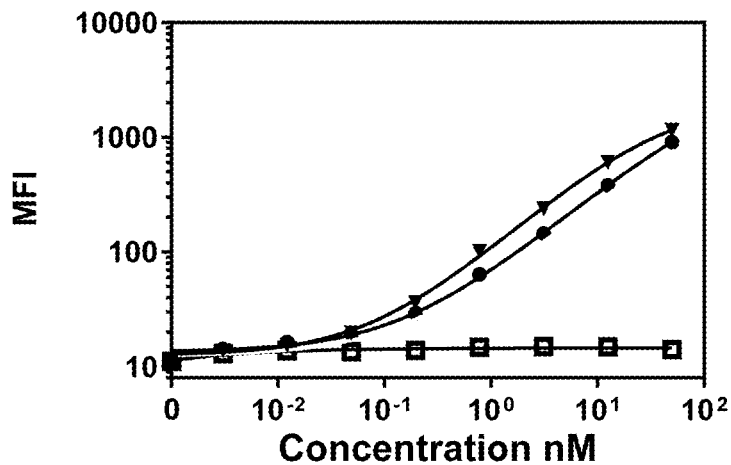

The properties of the B7-H3 mAb 1/CD3 mAb 2/CD8 mAb 1 Tri-Specific Binding Molecule were compared with those of a B7-H3×CD3 DART and a B7-H3×CD3 DART with an Fc Domain. As shown in FIGS. 5A-5B, the B7-H3 mAb 1/CD3 mAb 2/CD8 mAb 1 Tri-Specific Binding Molecule showed similar target cell binding (A498 cells (FIG. 5A); JIMT-1 (FIG. 5B)) compared to the B7-H3×CD3 DART and a B7-H3×CD3 DART with an Fc Domain. However, as shown in FIGS. 5C-5D, the B7-H3 mAb 1/CD3 mAb 2/CD8 mAb 1 Tri-Specific Binding Molecule demonstrated greatly increased binding to CD8+ T cells compared to CD4+ T cells.

Figure 6A:
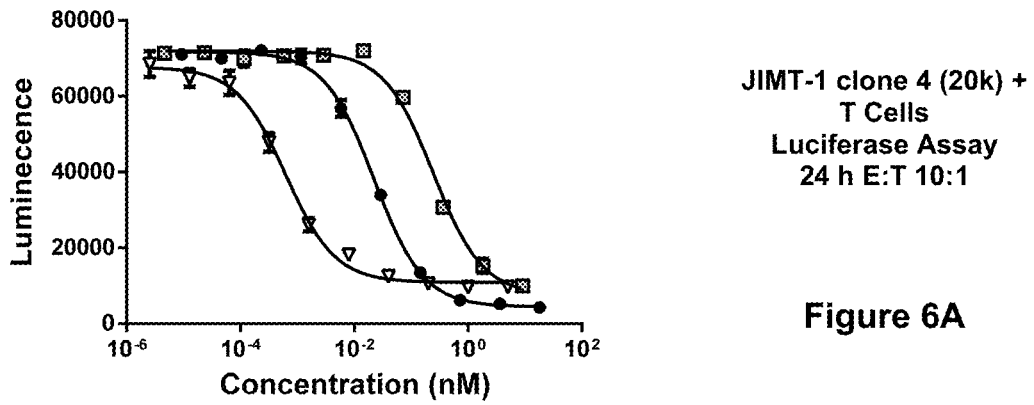
FIGS. 6A-6C demonstrate the ability of the Tri-Specific Binding Molecules of the present invention to mediate the re-directed killing of target cells.
Figure 6B:
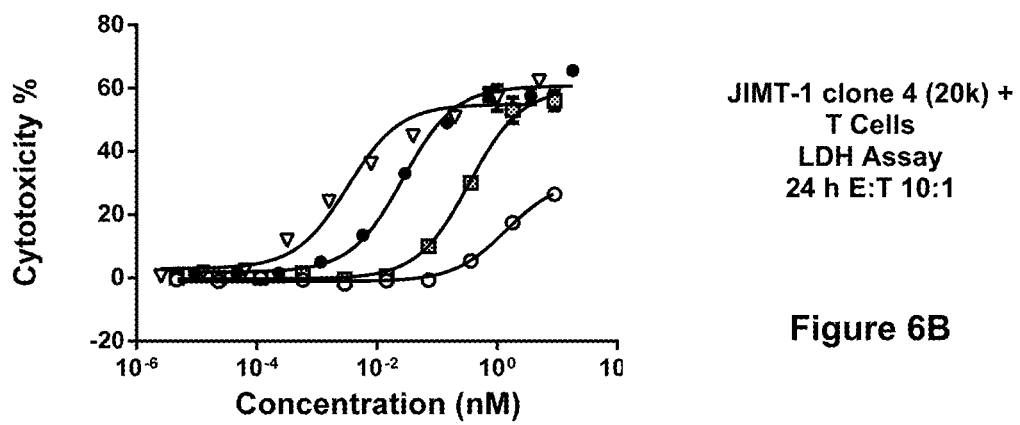
Figure 6C:
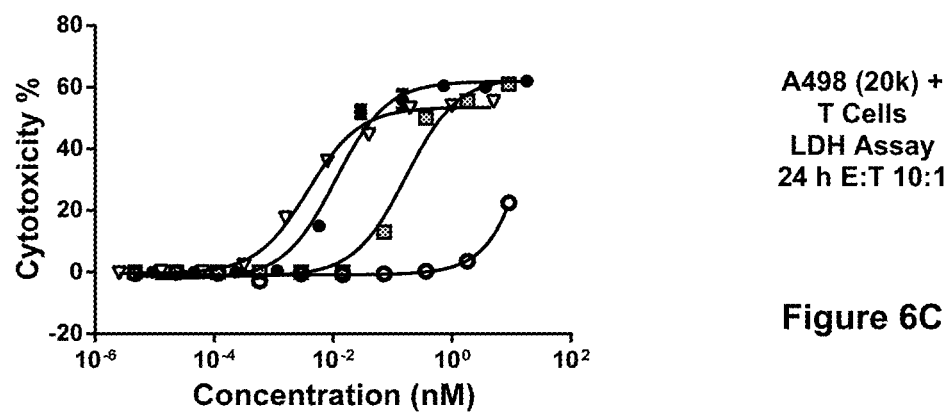
Figures 7A, 7B:
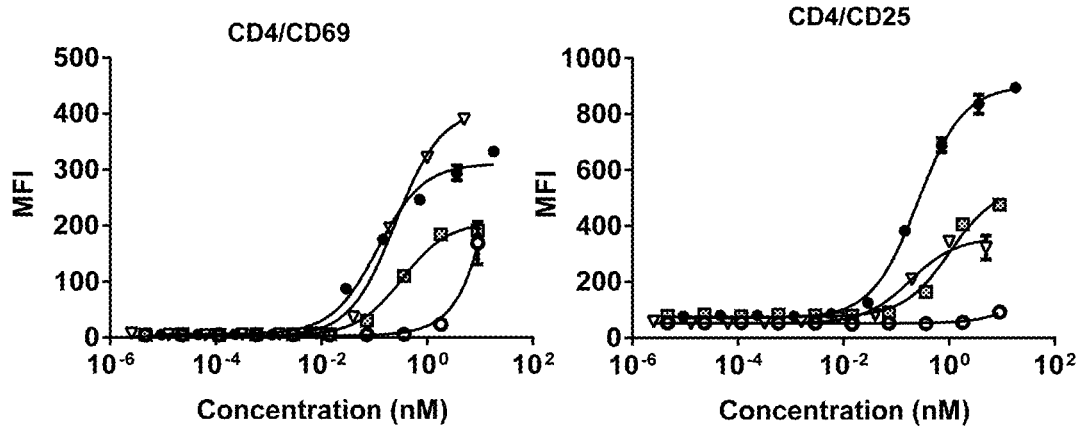
FIGS. 7A-7D demonstrate the ability of the Tri-Specific Binding Molecules of the present invention to mediate T cell activation upon incubation with JIMT-1 cells (FIG. 7A: CD4/CD69 T cells.
Figures 7C, 7D:
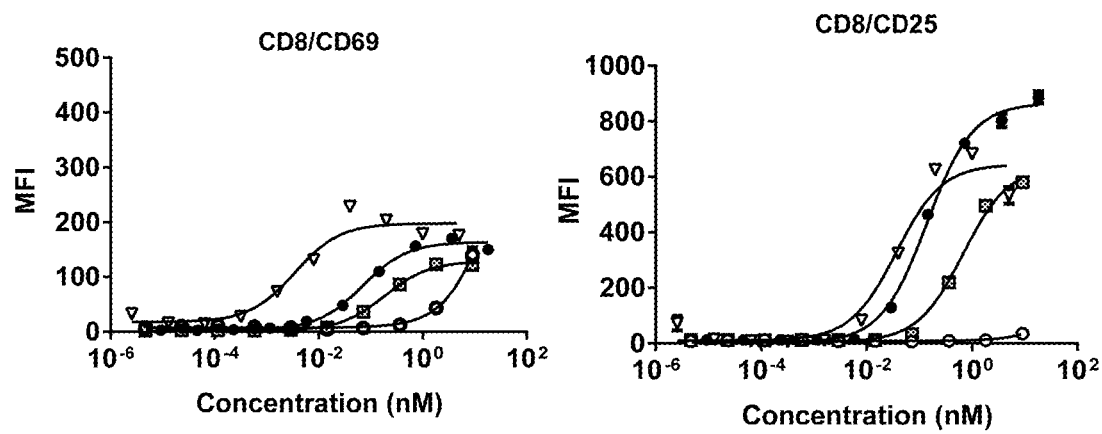
Figure 8A:
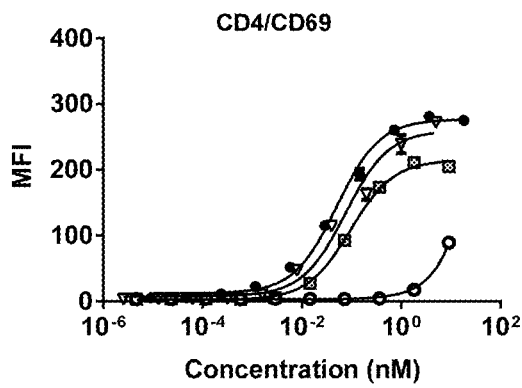
FIGS. 8A-8D demonstrate the ability of the Tri-Specific Binding Molecules of the present invention to mediate T cell activation upon incubation with A498 cells (FIG. 8A: CD4/CD69 T cells.
Figure 8B:
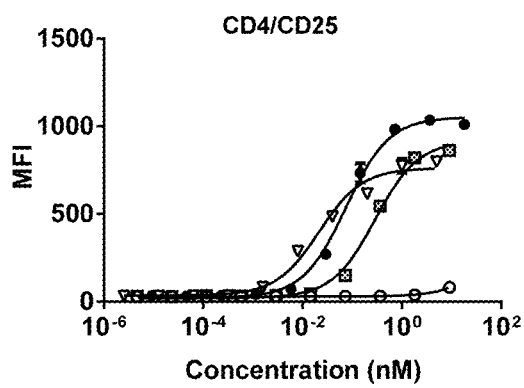
Figure 8C:
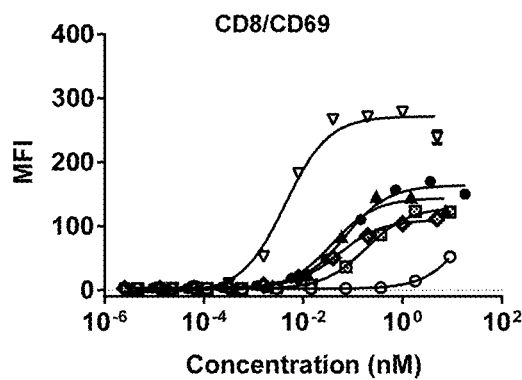
Figure 8D:
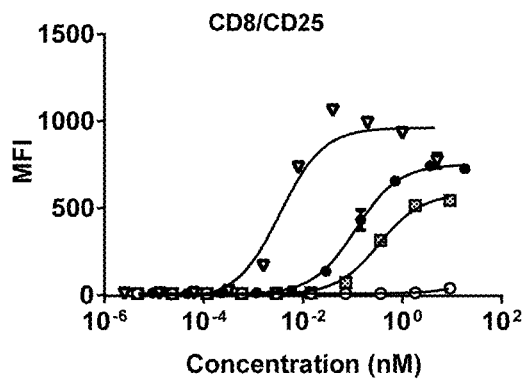

In order to demonstrate the ability of the B7-H3 mAb 1/CD3 mAb 2/CD8 mAb 1 Tri-Specific Binding Molecules of the present invention to mediate the re-directed killing of target cells, such molecules were incubated in the presence of T cells and either JIMT-1 or A498 target cells. JIMT-1 cells are a trastuzumab-resistant carcinoma line (Tanner, M. et al. (2004) "*Characterization Of A Novel Cell Line Established From A Patient With Herceptin-Resistant Breast Cancer,*" Mol. Cancer Ther. 3(12):1585-1592). The A498 cell line is a renal cell carcinoma cell line (Gogh, J. (1978) "*Cultivation, Characterization, And Identification Of Human Tumor Cells With Emphasis On Kidney, Testis, And Bladder Tumors,*" Natl. Cancer Inst. Monogr. 49:5-9). As shown in FIGS. 6A-6C, re-directed killing of the target cells was observed. Unexpectedly, such killing was substantially more potent than that observed for corresponding B7-H3× CD3 DART and a B7-H3×CD3 DART with an Fc Domain. The observed re-directed killing is summarized in Table 6.

TABLE 6

Re-Directed Killing

| | JIMT-1 Cells | | | A498 Cells | |
|---|---|---|---|---|---|
| Binding Molecule Assay | LDH Max Killing (%) | LDH EC50 (pM) | Luciferase EC50 (pM) | LDH Max Killing (%) | LDH EC50 (pM) |
| B7-H3 X CD3 DART™ | 60.72 | 27 | 22 | 61.95 | 11 |
| B7-H3 X CD3 DART™ with Fc Domain | 59.95 | 343 | 245 | 63.2 | 168 |
| B7-H3 mAb 1/CD3 mAb 2/CD8 mAb 1 Tri-Specific Binding Molecule | 54.88 | 0.4 | 0.6 | 53.5 | 4 |

FIGS. 7A-7D show the ability of the B7-H3 mAb 1/CD3 mAb 2/CD8 mAb 1 Tri-Specific Binding Molecules to mediate T cell activation after incubation with JIMT-1 cells. FIGS. 8A-8D show the ability of the B7-H3 mAb 1/CD3 mAb 2/CD8 mAb 1 Tri-Specific Binding Molecules to mediate T cell activation after incubation with A498 cells. In both cases, such activation was unexpectedly superior to the activation observed with comparative B7-H3×CD3 DART™ and a B7-H3×CD3 DART™ with an Fc Domain. Table 7 summarizes the EC50 results.

TABLE 7

EC50 Values of B7-H3 mAb 1/CD3 mAb 2/CD8 mAb 1 Tri-Specific Binding Molecule Compared to DARTs

| Tumor Cells | T Cell Subset | DART™ | DART™ with Fc Domain | Tri-Specific Binding Molecule |
|---|---|---|---|---|
| A498 | CD4/CD69 | 51 | 95 | 75 |
| | CD4/CD25 | 75 | 291 | 22 |
| | CD8/CD69 | 70 | 185 | 4 |
| | CD8/CD25 | 115 | 339 | 4 |
| | CTL | 10 | 48 | 4 |
| JIMT-1 | CD4/CD69 | 116 | 339 | 253 |
| | CD4/CD25 | 257 | 1034 | 185 |
| | CD8/CD69 | 70 | 185 | 3 |
| | CD8/CD25 | 140 | 678 | 37 |
| | CTL | 7 | 68 | 1 |

The expressed B7-H3 mAb 1/CD3 mAb 2/CD8 mAb 1 Tri-Specific Binding Molecule exhibited much greater (13-fold) cytolytic activity using CD8+ effector cells compared to CD4+ effector cells. The B7-H3 mAb 1/CD3 mAb 2/CD8 mAb 1 Tri-Specific Binding Molecule also exhibited greatly increased (85-fold) overall potency using 'pan' T cells as effectors compared to the DART™.

Example 2

Effect of CD8 Binding Domain on Re-Directed Cytotoxicity

In order to assess the effect of CD8 specificity, a second Tri-Specific Binding Molecule specific for the Disease-Associated Antigen B7-H3 was constructed utilizing a different CD8 antibody Variable Domain sequence. The B7-H3 Variable Domain specificities and CD3 Variable Domain specificities were identical to those used to construct the B7-H3 mAb 1/CD3 mAb 2/CD8 mAb 1 Tri-Specific Binding Molecule. The Tri-Specific Binding Molecule is termed B7-H3 mAb 1/CD3 mAb 2/CD8 mAb 2 and was composed of four different polypeptide chains (Table 8).

TABLE 8

| Polypeptide Chain | Domains | Binding Affinity |
|---|---|---|
| 1 | VL(B7-H3 mAb 1)-VH(CD3 mAb 2)-E-Coil-(CH2-CH3) | Light Chain: B7-H3 Heavy Chain: CD3 |
| 2 | VL(CD3 mAb 2)-VH(B7-H3 mAb 1)-K-Coil | Light Chain: CD3 Heavy Chain: B7-H3 |
| 3 | Heavy Chain CD8 mAb 2 | CD8 |
| 4 | Light Chain CD8 mAb 2 | CD8 |

The amino acid sequence of the first polypeptide chain of the B7-H3 mAb 1/CD3 mAb 2/CD8 mAb 2 Tri-Specific Binding Molecule is (SEQ ID NO:63):

```
DIQMTQSPSS LSASVGDRVT ITCRASQDIS NYLNWYQQKP

GKAPKLLIYY TSRLHSGVPS RFSGSGSGTD FTLTISSLQP

EDIATYYCQQ GNTLPPTFGG GTKLEIKGGG SGGGGEVQLV

ESGGGLVQPG GSLRLSCAAS GFTFSTYAMN WVRQAPGKGL

EWVGRIRSKY NNYATYYADS VKDRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLWCLVKGFY PSDIAVEWES

NGQPENNYKT TPPVLDSDGS FFLYSKLTVD KSRWQQGNVF

SCSVMHEALH NHYTQKSLSL SPGK
```

The amino acid sequence of the second polypeptide chain of the B7-H3 mAb 1/CD3 mAb 2/CD8 mAb 2 Tri-Specific Binding Molecule is (SEQ ID NO:64):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSY WMQWVRQAPG

QGLEWMGTIY PGDGDTRYTQ KFKGRVTITA DKSTSTAYME

LSSLRSEDTA VYYCARRGIP RLWYFDVWGQ GTTVTVSSGG

CGGGKVAALK EKVAALKEKV AALKEKVAAL KE
```

The amino acid sequence of the third polypeptide chain of the B7-H3 mAb 1/CD3 mAb 2/CD8 mAb 2 Tri-Specific Binding Molecule is (SEQ ID NO:65):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS

SASTKGPSVF PLAPSSKSTS GGTAALGCLV KDYFPEPVTV
```

-continued

```
SWNSGALTSG VHTFPAVLQS SGLYSLSSVV TVPSSSLGTQ

TYICNVNHKP SNTKVDKRVE PKSCDKTHTC PPCPAPEAAG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRE

EMTKNQVSLS CAVKGFYPSD IAVEWESNGQ PENNYKTTPP

VLDSDGSFFL VSKLTVDKSR WQQGNVFSCS VMHEALHNRY

TQKSLSLSPG K
```

The amino acid sequence of the fourth polypeptide chain of the B7-H3 mAb 1/CD3 mAb 2/CD8 mAb 2 Tri-Specific Binding Molecule is (SEQ ID NO:66):

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

Figure 9A:
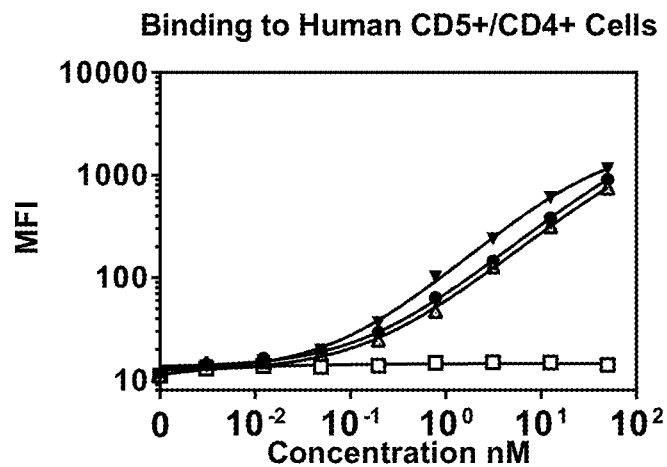
FIGS. 9A-9B show the CD5$^+$ CD4$^+$ gated (FIG. 9A) or CD5$^+$ CD4$^−$ gated (FIG. 9B) cell populations of human PMBC as a function of increasing concentration of B7-H3 mAb 1/CD3 mAb 2/CD8 mAb 1 Tri-Specific Binding Molecules or B7-H3 mAb 1/CD3 mAb 2/CD8 mAb 2 Tri-Specific Binding Molecules. B7-H3×CD3 DARTs™ (with and without Fc Domain) were used as controls.
Figure 9B:
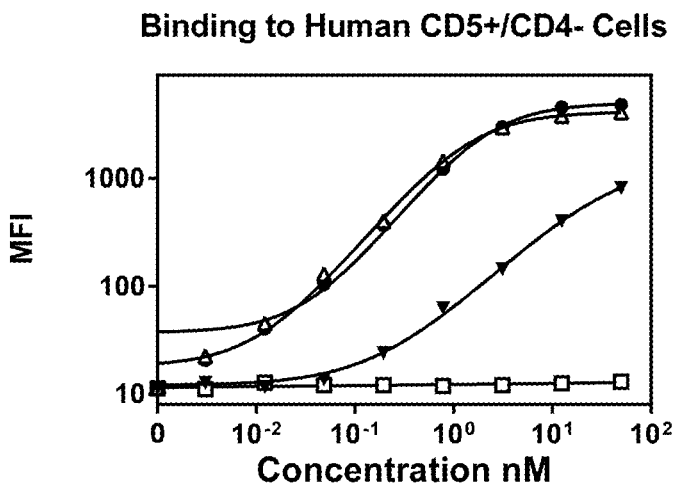

To compare the ability of the B7-H3 mAb 1/CD3 mAb 2/CD8 mAb 1 (construction and sequence described above) or B7-H3 mAb 1/CD3 mAb 2/CD8 mAb 2 Tri-Specific Binding Molecules to bind T cells, human PBMC of healthy donors were purified with Ficoll, wash twice with PBS and re-suspended in FACS buffer contained 10% Human AB serum and incubate at room temperature for 20 minutes, spin down the cell and re-suspended $4 \times 10^6$ cells/mL cells in FACS buffer. 50 µl of serial titrated B7-H3 mAb 1/CD3 mAb 2/CD8 mAb 1 or B7-H3 mAb 1/CD3 mAb 2/CD8 mAb 2 Tri-Specific Binding Molecules or DART™ (B7-H3×CD3 or B7-H3×CD3 with Fc Domain) were added to the wells of a 96-well deep plate. 50 µL ($4 \times 10^6$ cells/mL) of well-mixed cells in FACS buffer containing 0.01% sodium azide were then added into corresponding wells and mixed thoroughly using a pipette. The plate was incubated in the dark for about 45 minutes at 2-8° C. At the end of the incubation, the cells were washed twice by adding 300 µL of FACS buffer to each well, centrifuging the plate at 1,200 rpm for 5 minutes, and discarding the supernatant. The cell pellets were re-suspended in 100 µL mixture of PE-conjugated goat anti-Human Fcγ 1:500 diluted, CD5-APC and CD4-PerCP5.5 in FACS buffer containing 0.01% sodium azide, and incubated in the dark for about 45 minutes at 2-8° C. At the end of the incubation, the cells were washed, re-suspended with FACS buffer, and analyzed with a BD Caliber flow cytometer. Cells were gated to $CD5^+$ $CD4^+$ (FIG. 9A) or $CD5^+$ $CD4^-$ (FIG. 9B). Differential staining was observed on the $CD5^+$ CD4 population comparing to binding molecules that possessed or lacked CD8 specificity.

The cytotoxicity of the B7-H3 mAb 1/CD3 mAb 2/CD8 mAb 1 Tri-Specific Binding Molecule was compared to that of the B7-H3 mAb1/CD3 mAb 2/CD8 mAb 2 Tri-Specific Binding Molecule. Both a luciferase assay and an LDH assay were employed. The results of the two assays were in agreement. The two Tri-Specific Binding Molecules caused equivalent re-directed cytotoxicity in the presence of activating CD8+ T cell or pan T cell populations. The Tri-Specific Binding Molecule having a CD8 mAb 1 Binding Domain exhibited greater re-directed cytotoxicity in the presence of CD8+ cell populations or pan T cells compared to the B7H3×CD3 DART (FIG. 10A-10C).

An increase (60-fold) in EC50 for CD8+ vs. CD4+ effector cells was also observed for the B7-H3 mAb 1/CD3 mAb 2/CD8 mAb 2 Tri-Specific Binding Molecule compared to the B7-H3 mAb 1/CD3 mAb 2/CD8 mAb 1 Tri-Specific Binding Molecule. For the B7-H3 mAb 1/CD3 mAb 2/CD8 mAb 2 Tri-Specific Binding Molecule, increased potency resulting in a decrease in the EC50 of greater that 100-fold was observed when pan T cells were used as effector cells.

Example 3

Effect of Domain Positions on Re-Directed Cytotoxicity

In order to assess the effect of position for a given Binding Domain (CD3, CD8 and Disease-Associate Antigen) within the Tri-Specific Binding Molecule (Site A, Site B and Site C), several additional Tri-Specific Binding Molecules were constructed. Table 9 shows the Tri-Specific Binding Molecules and the location (Site A, Site B and Site C) of the various Binding Domains (CD3, CD8 and Disease-Associated Antigen).

TABLE 9

| Tri-Specific Binding Molecule | Site A | Site B | Site C |
|---|---|---|---|
| B7-H3 mAb 1/CD3 mAb 2/CD8 mAb 1 Tri-Specific Binding Molecule | B7-H3 mAb 1 | CD3 mAb 2 | CD8 mAb 1 |
| CD3 mAb 2/CD8 mAb 1/B7-H3 mAb 1 Tri-Specific Binding Molecule | CD3 mAb 2 | CD8 mAb 1 | B7-H3 mAb 1 |
| B7-H3 mAb 1/CD8 mAb 1/CD3 mAb 2 Tri-Specific Binding Molecule | B7-H3 mAb 1 | CD8 mAb 1 | CD3 mAb 2 |

The construction and sequence of the B7-H3 mAb 1/CD3 mAb 2/CD8 mAb 1 Tri-Specific Binding Molecule was described above. For the additional two Tri-Specific Binding Molecules (CD3 mAb 2/CD8 mAb 1/B7-H3 mAb 1 and B7-H3 mAb 1/CD8 mAb 1/CD3 mAb 2), the B7-H3 Variable Domain specificities, CD3 Variable Domain specificities and CD8 Variable Domain specificities were identical to those used to construct the B7-H3 mAb 1/CD3 mAb 2/CD8 mAb 1 Tri-Specific Binding Molecule. The CD3 mAb 2/CD8 mAb 1/B7-H3 mAb 1 Tri-Specific Binding Molecule was composed of four different polypeptide chains (Table 10).

TABLE 10

| Polypeptide Chain | Domains | Binding Affinity |
|---|---|---|
| 1 | VL(CD3 mAb 2)-VH(CD8 mAb 1)-E-Coil-(CH2-CH3) | Light Chain: CD3 Heavy Chain: CD8 |
| 2 | VL(CD8 mAb 1)-VH(CD3 mAb 2)-K-Coil | Light Chain: CD8 Heavy Chain: CD3 |
| 3 | Heavy Chain B7-H3 mAb 1 | B7-H3 |
| 4 | Light Chain B7-H3 mAb 1 | B7-H3 |

The amino acid sequence of the first polypeptide chain of the CD3 mAb 2/CD8 mAb 1/B7-H3 mAb 1 Tri-Specific Binding Molecule is (SEQ ID NO:67):

```
DVQINQSPSF LAASPGETIT INCRTSRSIS QYLAWYQEKP
GKTNKLLIYS GSTLQSGIPS RFSGSGSGTD FTLTISGLEP
EDFAMYYCQQ HNENPLTFGA GTKLELRGGG SGGGGEVQLV
ESGGGLVQPG GSLRLSCAAS GFTFSTYAMN WVRQAPGKGL
EWVGRIRSKY NNYATYYADS VKGRFTISRD DSKNSLYLQM
NSLKTEDTAV YYCVRHGNFG NSYVSWFAYW GQGTLVTVSS
GGCGGGEVAA LEKEVAALEK EVAALEKEVA ALEKGGGDKT
HTCPPCPAPE AAGGPSVFLF PPKPKDTLMI SRTPEVTCVV
VDVSHEDPEV KFNWYVDGVE VHNAKTKPRE EQYNSTYRVV
SVLTVLHQDW LNGKEYKCKV SNKALPAPIE KTISKAKGQP
REPQVYTLPP SREEMTKNQV SLWCLVKGFY PSDIAVEWES
NGQPENNYKT TPPVLDSDGS FFLYSKLTVD KSRWQQGNVF
SCSVMHEALH NHYTQKSLSL SPGK
```

The amino acid sequence of the second polypeptide chain of the CD3 mAb 2/CD8 mAb 1/B7-H3 mAb 1 Tri-Specific Binding Molecule is (SEQ ID NO:68):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGEV
QLQQSGAELV KPGASVKLSC TASGFNIKDT YIHFVRQRPE
QGLEWIGRID PANDNTLYAS KFQGKATITA DTSSNTAYMH
LCSLTSGDTA VYYCGRGYGY YVFDHWGQGT TLTVSSGGCG
GGKVAALKEK VAALKEKVAA LKEKVAALKE
```

The amino acid sequence of the third polypeptide chain of the CD3 mAb 2/CD8 mAb 1/B7-H3 mAb 1 Tri-Specific Binding Molecule is (SEQ ID NO:69):

```
QVQLVQSGAE VKKPGASVKV SCKASGYTFT SYWMQWVRQA
PGQGLEWMGT IYPGDGDTRY TQKFKGRVTI TADKSTSTAY
MELSSLRSED TAVYYCARRG IPRLWYFDVW GQGTTVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPEAAGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLSC AVKGFYPSDI AVEWESNGQP ENNYKTTPPV
LDSDGSFFLV SKLTVDKSRW QQGNVFSCSV MHEALHNRYT
QKSLSLSPGK
```

The amino acid sequence of the fourth polypeptide chain of the CD3 mAb 2/CD8 mAb 1/B7-H3 mAb 1 Tri-Specific Binding Molecule is (SEQ ID NO:70):

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

The B7-H3 mAb 1/CD8 mAb 1/CD3 mAb 2 Tri-Specific Binding Molecule was composed of four different polypeptide chains (Table 11).

TABLE 11

| Polypeptide Chain | Domains | Binding Affinity |
|---|---|---|
| 1 | VL(B7-H3 mAb 1)-VH(CD8 mAb 1)-E-Coil-(CH2-CH3) | Light Chain: B7-H3 Heavy Chain: CD8 |
| 2 | VL(CD8 mAb 1)-VH(B7-H3 mAb1)-K-Coil | Light Chain: CD8 Heavy Chain: B7-H3 |
| 3 | Heavy Chain CD3 mAb 2 | CD3 |
| 4 | Light Chain CD3 mAb 2 | CD3 |

The amino acid sequence of the first polypeptide chain of the B7-H3 mAb 1/CD8 mAb 1/CD3 mAb 2 Tri-Specific Binding Molecule is (SEQ ID NO:71):

```
DVQINQSPSF LAASPGETIT INCRTSRSIS QYLAWYQEKP
GKTNKLLIYS GSTLQSGIPS RFSGSGSGTD FTLTISGLEP
EDFAMYYCQQ HNENPLTFGA GTKLELRGGG SGGGGQVQLV
QSGAEVKKPG ASVKVSCKAS GYTFTSYWMQ WVRQAPGQGL
EWMGTIYPGD GDTRYTQKFK GRVTITADKS TSTAYMELSS
LRSEDTAVYY CARRGIPRLW YFDVWGQGTT VTVSSGGCGG
GEVAALEKEV AALEKEVAAL EKEVAALEKG GGDKTHTCPP
CPAPEAAGGP SVFLFPPKPK DTLMISRTPE VTCVVVDVSH
EDPEVKFNWY VDGVEVHNAK TKPREEQYNS TYRVVSVLTV
LHQDWLNGKE YKCKVSNKAL PAPIEKTISK AKGQPREPQV
YTLPPSREEM TKNQVSLWCL VKGFYPSDIA VEWESNGQPE
NNYKTTPPVL DSDGSFFLYS KLTVDKSRWQ QGNVFSCSVM
HEALHNHYTQ KSLSLSPGK
```

The amino acid sequence of the second polypeptide chain of the B7-H3 mAb 1/CD8 mAb 1/CD3 mAb 2 Tri-Specific Binding Molecule is (SEQ ID NO:72):

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIKGGG SGGGGEVQLQ
QSGAELVKPG ASVKLSCTAS GFNIKDTYIH FVRQRPEQGL
```

```
EWIGRIDPAN DNTLYASKFQ GKATITADTS SNTAYMHLCS

LTSGDTAVYY CGRGYGYYVF DHWGQGTTLT VSSGGCGGGK

VAALKEKVAA LKEKVAALKE KVAALKE
```

The amino acid sequence of the third polypeptide chain of the B7-H3 mAb 1/CD8 mAb 1/CD3 mAb 2 Tri-Specific Binding Molecule is (SEQ ID NO:73):

```
EVQLVESGGG LVQPGGSLRL SCAASGFTFS TYAMNWVRQA

PGKGLEWVGR IRSKYNNYAT YYADSVKDRF TISRDDSKNS

LYLQMNSLKT EDTAVYYCVR HGNFGNSYVS WFAYWGQGTL

VTVSSASTKG PSVFPLAPSS KSTSGGTAAL GCLVKDYFPE

PVTVSWNSGA LTSGVHTFPA VLQSSGLYSL SSVVTVPSSS

LGTQTYICNV NHKPSNTKVD KRVEPKSCDK THTCPPCPAP

EAAGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLSCAVKGF YPSDIAVEWE SNGQPENNYK

TTPPVLDSDG SFFLVSKLTV DKSRWQQGNV FSCSVMHEAL

HNRYTQKSLS LSPGK
```

The amino acid sequence of the fourth polypeptide chain of the B7-H3 mAb 1/CD8 mAb 1/CD3 mAb 2 Tri-Specific Binding Molecule is (SEQ ID NO:74):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG RTVAAPSVFI

FPPSDEQLKS GTASVVCLLN NFYPREAKVQ WKVDNALQSG

NSQESVTEQD SKDSTYSLSS TLTLSKADYE KHKVYACEVT

HQGLSSPVTK SFNRGEC
```

The results of this investigation are shown in FIGS. 11A-11C, FIGS. 12A-12C, FIGS. 13A-13E, and in Table 26. FIGS. 11A-11C and FIGS. 12A-12C independently demonstrate that placing a CD3 Binding Domain into Site C of the Tri-Specific Binding Molecules reduces the cytotoxicity of the molecule. FIGS. 13A-13E show that this decreased cytotoxicity is observed regardless of whether CD4+, CD8+ or pan T cells were employed.

As shown in FIGS. 14A-14B, placement of the CD3 Binding Domain at Site C, greatly diminished binding to both the CD5+ CD4+ cells (FIG. 14A) and the CD5+ CD4− cells (FIG. 14B). Notably, however, regardless of the placement of the CD3 Binding Domain, all of the Tri-Specific Binding Molecules were capable of mediating re-directed cytotoxicity.

Example 4

Production and Properties of Exemplary Anti-CD3, Anti-CD8, Anti-5T4 Tri-Specific Binding Molecules Additional exemplary Tri-Specific Binding Molecules specific for the Disease-Associated Antigen 5T4 were constructed. The 5T4 mAb 2/CD3 mAb 2/CD8 mAb 1 Tri-Specific Binding Molecule was composed of four different polypeptide chains (Table 12).

TABLE 12

| Polypeptide Chain | Domains | Binding Affinity |
| --- | --- | --- |
| 1 | VL(5T4 mAb 2)-VH(CD3 mAb 2)-E-Coil-(CH2-CH3) | Light Chain: 5T4 Heavy Chain: CD3 |
| 2 | VL(CD3 mAb 2)-VH(5T4 mAb 2)-K-Coil | Light Chain: CD3 Heavy Chain: 5T4 |
| 3 | Heavy Chain CD8 mAb 1 | CD8 |
| 4 | Light Chain CD8 mAb 1 | CD8 |

The amino acid sequence of the first polypeptide chain of the 5T4 mAb 2/CD3 mAb 2/CD8 mAb 1 Tri-Specific Binding Molecule is (SEQ ID NO:75):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IKGGGSGGGG

EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSSGGCGG GEVAALEKEV AALEKEVAAL EKEVAALEKG

GGDKTHTCPP CPAPEAAGGP SVFLFPPKPK DTLMISRTPE

VTCVVVDVSH EDPEVKFNWY VDGVEVHNAK TKPREEQYNS

TYRVVSVLTV LHQDWLNGKE YKCKVSNKAL PAPIEKTISK

AKGQPREPQV YTLPPSREEM TKNQVSLWCL VKGFYPSDIA

VEWESNGQPE NNYKTTPPVL DSDGSFFLYS KLTVDKSRWQ

QGNVFSCSVM HEALHNHYTQ KSLSLSPGK
```

The amino acid sequence of the second polypeptide chain of the 5T4 mAb 2/CD3 mAb 2/CD8 mAb 1 Tri-Specific Binding Molecule is (SEQ ID NO:76):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLQQPGAELV KPGASVKMSC KASGYTFTSY WITWVKQRPG

QGLEWIGDIY PGSGRANYNE KFKSKATLTV DTSSSTAYMQ

LSSLTSEDSA VYNCARYGPL FTTVVDPNSY AMDYWGQGTS

VTVSSGGCGG GKVAALKEKV AALEKVAAL KEKVAALKE
```

The amino acid sequence of the third polypeptide chain of the 5T4 mAb 2/CD3 mAb 2/CD8 mAb 1 Tri-Specific Binding Molecule is (SEQ ID NO:77):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS
```

```
TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The amino acid sequence of the fourth polypeptide chain of the 5T4 mAb 2/CD3 mAb 2/CD8 mAb 1 Tri-Specific Binding Molecule is (SEQ ID NO:78):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The 5T4 mAb 2/CD3 mAb 2/CD8 mAb 2 Tri-Specific Binding Molecule was composed of four different polypeptide chains (Table 13).

TABLE 13

| Polypeptide Chain | Domains | Binding Affinity |
| --- | --- | --- |
| 1 | VL(5T4 mAb 2)-VH(CD3 mAb 2)-E-Coil-(CH2-CH3) | Light Chain: 5T4 Heavy Chain: CD3 |
| 2 | VL(CD3 mAb 2)-VH(5T4 mAb 2)-K-Coil | Light Chain: CD3 Heavy Chain: 5T4 |
| 3 | Heavy Chain CD8 mAb 2 | CD8 |
| 4 | Light Chain CD8 mAb 2 | CD8 |

The amino acid sequence of the first polypeptide chain of the 5T4 mAb 2/CD3 mAb 2/CD8 mAb 2 Tri-Specific Binding Molecule is (SEQ ID NO:79):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IKGGGSGGGG

EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSSGGCGG GEVAALEKEV AALEKEVAAL EKEVAALEKG

GGDKTHTCPP CPAPEAAGGP SVFLFPPKPK DTLMISRTPE

VTCVVVDVSH EDPEVKFNWY VDGVEVHNAK TKPREEQYNS

TYRVVSVLTV LHQDWLNGKE YKCKVSNKAL PAPIEKTISK

AKGQPREPQV YTLPPSREEM TKNQVSLWCL VKGFYPSDIA

VEWESNGQPE NNYKTTPPVL DSDGSFFLYS KLTVDKSRWQ

QGNVFSCSVM HEALHNHYTQ KSLSLSPGK
```

The amino acid sequence of the second polypeptide chain of the 5T4 mAb 2/CD3 mAb 2/CD8 mAb 2 Tri-Specific Binding Molecule is (SEQ ID NO:80):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLQQPGAELV KPGASVKMSC KASGYTFTSY WITWVKQRPG

QGLEWIGDIY PGSGRANYNE KFKSKATLTV DTSSSTAYMQ

LSSLTSEDSA VYNCARYGPL FTTVVDPNSY AMDYWGQGTS

VTVSSGGCGG GKVAALKEKV AALKEKVAAL KEKVAALKE
```

The amino acid sequence of the third polypeptide chain of the 5T4 mAb 2/CD3 mAb 2/CD8 mAb 2 Tri-Specific Binding Molecule is (SEQ ID NO:81):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPEAAG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRE

EMTKNQVSLS CAVKGFYPSD IAVEWESNGQ PENNYKTTPP

VLDSDGSFFL VSKLTVDKSR WQQGNVFSCS VMHEALHNRY

TQKSLSLSPG K
```

The amino acid sequence of the fourth polypeptide chain of the 5T4 mAb 2/CD3 mAb 2/CD8 mAb 2 Tri-Specific Binding Molecule is (SEQ ID NO:82):

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

The 5T4 mAb 2/CD3 mAb 2/CD8 mAb 1 and 5T4 mAb 2/CD3 mAb 2/CD8 mAb 2 Tri-Specific Binding Molecules were expressed and purified as described above. The ability of these two Tri-Specific Binding Molecules to bind to CD5+/CD4+ gated and CD5+/CD4− gated human PBMCs were compared to those of a 5T4×CD3 DART with an Fc Domain. As shown in FIGS. 15A-15B, the 5T4/CD3 mAb 2/CD8 mAb 1 and 5T4/CD3 mAb 2/CD8 mAb 2 Tri-Specific Binding Molecules demonstrated greatly increased binding to CD8+ T cells (FIG. 15B) compared to CD4+ T cells (FIG. 15A).

In order to demonstrate the ability of the 5T4 mAb 2/CD3 mAb 2/CD8 mAb 1 and 5T4 mAb 2/CD3 mAb 2/CD8 mAb 2 Tri-Specific Binding Molecules to mediate the redirected killing of target cells, such molecules were incubated in the presence of T cells and JIMT-1 target cells. As shown in FIGS. 16A-16C, re-directed killing of the target cells was observed. As observed for the B7-H3 Tri-Specific Binding Molecules described above, the killing was substantially more potent than that observed for the corresponding 5T4× CD3 DART containing an Fc Domain. Likewise, as observed for the B7-H3 Tri-Specific Binding Molecules, the use of different CD8 Variable Domains had no effect on the ability of the 5T4 Tri-Specific Binding Molecules to re-direct CD8+ T cells to the target cells. The 5T4 mAb 2/CD3 mAb 2/CD8 mAb 2 Tri-Specific Binding Molecule was also found to be highly active and demonstrated much greater CTL activity using CD8+ vs. CD4+ effector cells (23-fold lower EC50). The 5T4 mAb 2/CD3 mAb 2/CD8 mAb 1 Tri-Specific Binding Molecule was 22-fold more potent using pan T cell effectors compared to a 5T4×CD3 DART™ and the 5T4 mAb 2/CD3 mAb 2/CD8 mAb 2 Tri-Specific Binding Molecule was 25-fold more potent.

Example 5

Properties of Exemplary Anti-CD3, Anti-CD8, Anti-ROR1 Tri-Specific Binding Molecules Additional exemplary Tri-Specific Binding Molecules specific for the Disease-Associated Antigen ROR1 were constructed. The ROR1 mAb 1/CD3 mAb 2/CD8 mAb 1 Tri-Specific Binding Molecule was composed of four different polypeptide chains (Table 14).

TABLE 14

| Polypeptide Chain | Domains | Binding Affinity |
|---|---|---|
| 1 | VL(ROR1 mAb 1)-VH(CD3 mAb 2)-E-Coil-(CH2-CH3) | Light Chain: ROR1 Heavy Chain: CD3 |
| 2 | VL(CD3 mAb 2)-VH(ROR1 mAb 1)-K-Coil | Light Chain: CD3 Heavy Chain: ROR1 |
| 3 | Heavy Chain CD8 mAb 1 | CD8 |
| 4 | Light Chain CD8 mAb 1 | CD8 |

The amino acid sequence of the first polypeptide chain of the ROR1 mAb 1/CD3 mAb 2/CD8 mAb 1 Tri-Specific Binding Molecule is (SEQ ID NO:83):

```
QLVLTQSPSA SASLGSSVKL TCTLSSGHKT DTIDWYQQQP

GKAPRYLMKL EGSGSYNKGS GVPDRFGSGS SSGADRYLTI

SSLQSEDEAD YYCGTDYPGN YLFGGGTQLT VLGGGGSGGG

GEVQLVESGG GLVQPGGSLR LSCAASGFTF STYAMNWVRQ

APGKGLEWVG RIRSKYNNYA TYYADSVKGR FTISRDDSKN

SLYLQMNSLK TEDTAVYYCV RHGNFGNSYV SWFAYWGQGT

LVTVSSGGCG GGEVAALEKE VAALEKEVAA LEKEVAALEK

GGGDKTHTCP PCPAPEAAGG PSVFLFPPKP KDTLMISRTP
```

```
EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

The amino acid sequence of the second polypeptide chain of the ROR1 mAb 1/CD3 mAb 2/CD8 mAb 1 Tri-Specific Binding Molecule is (SEQ ID NO:84):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQE

QLVESGGGLV QPGGSLRLSC AASGFTFSDY YMSWVRQAPG

KGLEWVATIY PSSGKTYYAD SVKGRFTISS DNAKNSLYLQ

MNSLRAEDTA VYYCARDSYA DDAALFDIWG QGTTVTVSSG

GCGGGKVAAL KEKVAALKEK VAALKEKVAA LKE
```

The amino acid sequence of the third polypeptide chain of the ROR1 mAb 1/CD3 mAb 2/CD8 mAb 1 Tri-Specific Binding Molecule is (SEQ ID NO:85):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPG
```

The amino acid sequence of the fourth polypeptide chain of the ROR1 mAb 1/CD3 mAb 2/CD8 mAb 1 Tri-Specific Binding Molecule is (SEQ ID NO:86):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The ROR1 mAb 1/CD3 mAb 2/CD8 mAb 2 Tri-Specific Binding Molecule was composed of four different polypeptide chains (Table 15).

TABLE 15

| Polypeptide Chain | Domains | Binding Affinity |
|---|---|---|
| 1 | VL(ROR1 mAb 1)-VH(CD3 mAb 2)-E-Coil-(CH2-CH3) | Light Chain: ROR1 Heavy Chain: CD3 |
| 2 | VL(CD3 mAb 2)-VH(ROR1 mAb 1)-K-Coil | Light Chain: CD3 Heavy Chain: ROR1 |
| 3 | Heavy Chain CD8 mAb 2 | CD8 |
| 4 | Light Chain CD8 mAb 2 | CD8 |

The amino acid sequence of the first polypeptide chain of the ROR1 mAb 1/CD3 mAb 2/CD8 mAb 2 Tri-Specific Binding Molecule is (SEQ ID NO:87):

```
QLVLTQSPSA SASLGSSVKL TCTLSSGHKT DTIDWYQQQP

GKAPRYLMKL EGSGSYNKGS GVPDRFGSGS SSGADRYLTI

SSLQSEDEAD YYCGTDYPGN YLFGGGTQLT VLGGGGSGGG

GEVQLVESGG GLVQPGGSLR LSCAASGFTF STYAMNWVRQ

APGKGLEWVG RIRSKYNNYA TYYADSVKGR FTISRDDSKN

SLYLQMNSLK TEDTAVYYCV RHGNFGNSYV SWFAYWGQGT

LVTVSSGGCG GGEVAALEKE VAALEKEVAA LEKEVAALEK

GGGDKTHTCP PCPAPEAAGG PSVFLFPPKP KDTLMISRTP

EVTCVVVDVS HEDPEVKFNW YVDGVEVHNA KTKPREEQYN

STYRVVSVLT VLHQDWLNGK EYKCKVSNKA LPAPIEKTIS

KAKGQPREPQ VYTLPPSREE MTKNQVSLWC LVKGFYPSDI

AVEWESNGQP ENNYKTTPPV LDSDGSFFLY SKLTVDKSRW

QQGNVFSCSV MHEALHNHYT QKSLSLSPGK
```

The amino acid sequence of the second polypeptide chain of the ROR1 mAb 1/CD3 mAb 2/CD8 mAb 2 Tri-Specific Binding Molecule is (SEQ ID NO:88):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQE

QLVESGGGLV QPGGSLRLSC AASGFTFSDY YMSWVRQAPG

KGLEWVATIY PSSGKTYYAD SVKGRFTISS DNAKNSLYLQ

MNSLRAEDTA VYYCARDSYA DDAALFDIWG QGTTVTVSSG

GCGGGKVAAL KEKVAALKEK VAALKEKVAA LKE
```

The amino acid sequence of the third polypeptide chain of the ROR1 mAb 1/CD3 mAb 2/CD8 mAb 2 Tri-Specific Binding Molecule is (SEQ ID NO:89):

```
QVQLVESGGG VVQPGRSLRL SCAASGFTFS DFGMNWVRQA

PGKGLEWVAL IYYDGSNKFY ADSVKGRFTI SRDNSKNTLY

LQMNSLRAED TAVYYCAKPH YDGYYHFFDS WGQGTLVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPEAAG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRE

EMTKNQVSLS CAVKGFYPSD IAVEWESNGQ PENNYKTTPP

VLDSDGSFFL VSKLTVDKSR WQQGNVFSCS VMHEALHNRY

TQKSLSLSPG K
```

The amino acid sequence of the fourth polypeptide chain of the ROR1 mAb 1/CD3 mAb 2/CD8 mAb 2 Tri-Specific Binding Molecule is (SEQ ID NO:90):

```
DIQMTQSPSS LSASVGDRVT ITCKGSQDIN NYLAWYQQKP

GKAPKLLIYN TDILHTGVPS RFSGSGSGTD FTFTISSLQP

EDIATYYCYQ YNNGYTFGQG TKVEIKRTVA APSVFIFPPS

DEQLKSGTAS VVCLLNNFYP REAKVQWKVD NALQSGNSQE

SVTEQDSKDS TYSLSSTLTL SKADYEKHKV YACEVTHQGL

SSPVTKSFNR GEC
```

The properties of ROR1 mAb 1/CD3 mAb 2/CD8 mAb 1 and ROR1 mAb 1/CD3 mAb 2/CD8 mAb 2 Tri-Specific Binding Molecules were compared with those of a ROR1× CD3 DART™ containing an Fc Domain. The DART™ and ROR1 mAb 1/CD3 mAb 2/CD8 mAb 1 and ROR1 mAb 1/CD3 mAb 2/CD8 mAb 2 Tri-Specific Binding Molecules were constructed using the Fv sequences from an anti-ROR1 monoclonal antibody, ROR1 mAb 1, that binds to the ROR-1 antigen.

The two ROR1 mAb 1/CD3 mAb 2/CD8 mAb 1 and ROR1 mAb 1/CD3 mAb 2/CD8 mAb 2 Tri-Specific Binding Molecules and DART all were active in CTL assays against JIMT1-luc and A549 target cells. However, the ROR1 mAb 1/CD3 mAb 2/CD8 mAb 1 and ROR1 mAb 1/CD3 mAb 2/CD8 mAb 2 Tri-Specific Binding Molecules exhibited dramatically increased activity with CD8+ T cell and pan T cell effectors.

The ability of the ROR1 mAb 1/CD3 mAb 2/CD8 mAb 1 and ROR1 mAb 1/CD3 mAb 2/CD8 mAb 2 Tri-Specific Binding Molecules to mediate re-directed killing of target cells was measured using both a luciferase assay and an LDH assay. In both cases, re-directed killing was observed. FIGS. 17A-17C demonstrate the re-directed killing of target cells as measured using the luciferase assay. Results are summarized in Table 16.

TABLE 16

| Tri-Specific Binding Molecule | EC50 Effector Cells | | | Ratio | | |
|---|---|---|---|---|---|---|
| | CD4 | CD8 | Pan T | CD4/CD8 | CD4/CD8 | Pan T |
| JIMT-1 LUC Target Cells (Luciferase Assay) | | | | | | |
| ROR1 × CD3 DART ™ | 0.45 | 0.4064 | 0.3931 | 1.1 | 1.0 | 1.0 |
| ROR 1 mAb 1/CD3 inAb 2/CD8 mAb 1 Tri-Specific Binding Molecule | 0.131 | 0.0009 | 0.0015 | 145.3 | 131.3 | 262.1 |
| ROR 1 mAb 1/CD3 mAb 2/CD8 mAb 2 Tri-Specific Binding Molecule | 0.174 | 0.0011 | 0.0016 | 158.0 | 142.7 | 245.7 |
| JIMT-1 LUC Target Cells (LDH Assay) | | | | | | |
| ROR1 × CD3 DART ™ | 0.291 | 0.7761 | 0.7643 | 0.4 | 1.0 | 1.0 |
| ROR 1 mAb 1/CD3 mAb 2/CD8 mAb 1 Tri-Specific Binding Molecule | 0.095 | 0.0017 | 0.0053 | 55.9 | 149.0 | 144.2 |
| ROR 1 mAb 1/CD3 mAb 2/CD8 mAb 2 Tri-Specific Binding Molecule | 0.277 | 0.0021 | 0.0057 | 131.8 | 351.3 | 134.1 |
| A549 | | | | | | |
| ROR1 × CD3 DART ™ | 0.762 | 0.468 | 0.5305 | 1.6 | 1.0 | 1.0 |
| ROR 1 mAb 1/CD3 mAb 2/CD8 mAb 1 Tri-Specific Binding Molecule | 0.879 | 0.0102 | 0.0231 | 86.2 | 53.0 | 23.0 |
| ROR 1 mAb 1/CD3 mAb 2/CD8 mAb 2 Tri-Specific Binding Molecule | 1.257 | 0.009 | 0.0126 | 139.7 | 85.8 | 42.1 |

Example 6

Properties of Exemplary Anti-CD3, Anti-CD8, Anti-Env Tri-Specific Binding Molecules Additional exemplary Tri-Specific Binding Molecules specific for the Disease-Associated Antigen HIV (gp140 antigen) were constructed. The HIV mAb 1/CD3 mAb 2/CD8 mAb 1 Tri-Specific Binding Molecule was composed of four different polypeptide chains (Table 17).

TABLE 17

| Polypeptide Chain | Domains | Binding Affinity |
|---|---|---|
| 1 | VL(HIV mAb 1)-VH(CD3 mAb 2)-E-Coil-(CH2-CH3) | Light Chain: HIV Heavy Chain: CD3 |
| 2 | VL(CD3 mAb 2)-VH(HIV mAb 1)-K-Coil | Light Chain: CD3 Heavy Chain: HIV |
| 3 | Heavy Chain CD8 mAb 1 | CD8 |
| 4 | Light Chain CD8 mAb 1 | CD8 |

The amino acid sequence of the first polypeptide chain of the HIV mAb 1/CD3 mAb 2/CD8 mAb 1 Tri-Specific Binding Molecule is (SEQ ID NO:91):

```
DIVMTQSPDS LAVSPGERAT IHCKSSQTLL YSSNNRHSIA
WYQQRPGQPP KLLLYWASMR LSGVPDRFSG SGSGTDFTLT
INNLQAEDVA IYYCHQYSSH PPTFGHGTRV EIKGGGSGGG
GEVQLVESGG GLVQPGGSLR LSCAASGFTF STYAMNWVRQ
APGKGLEWVG RIRSKYNNYA TYYADSVKGR FTISRDDSKN
SLYLQMNSLK TEDTAVYYCV RHGNFGNSYV SWFAYWGQGT
LVTVSSASTK GEVAACEKEV AALEKEVAAL EKEVAALEKG
GGDKTHTCPP CPAPEAAGGP SVFLFPPKPK DTLMISRTPE
VTCVVVDVSH EDPEVKFNWY VDGVEVHNAK TKPREEQYNS
TYRVVSVLTV LHQDWLNGKE YKCKVSNKAL PAPIEKTISK
AKGQPREPQV YTLPPSREEM TKNQVSLWCL VKGFYPSDIA
VEWESNGQPE NNYKTTPPVL DSDGSFFLYS KLTVDKSRWQ
QGNVFSCSVM HEALHNHYTQ KSLSLSPGK
```

The amino acid sequence of the second polypeptide chain of the HIV mAb 1/CD3 mAb 2/CD8 mAb 1 Tri-Specific Binding Molecule polypeptide is (SEQ ID NO:92):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLVQSGGGVF KPGGSLRLSC EASGFTFTEY YMTWVRQAPG
KGLEWLAYIS KNGEYSKYSP SSNGRFTISR DNAKNSVFLQ
LDRLSADDTA VYYCARADGL TYFSELLQYI FDLWGQGARV
TVSSASTKGK VAACKEKVAA LKEKVAALKE KVAALKE
```

The amino acid sequence of the third polypeptide chain of the HIV mAb 1/CD3 mAb 2/CD8 mAb 1 Tri-Specific Binding Molecule is (SEQ ID NO:93):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPG
```

The amino acid sequence of the fourth polypeptide chain of the HIV mAb 1/CD3 mAb 2/CD8 mAb 1 Tri-Specific Binding Molecule is (SEQ ID NO:94):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The HIV mAb 2/CD3 mAb 2/CD8 mAb 1 Tri-Specific Binding Molecule was composed of four different polypeptide chains (Table 18).

TABLE 18

| Polypeptide Chain | Domains | Binding Affinity |
|---|---|---|
| 1 | VL(HIV mAb 2)-VH(CD3 mAb 2)-E-Coil-(CH2-CH3) | Light Chain: HIV Heavy Chain: CD3 |
| 2 | VL(CD3 mAb 2)-VH(HIV mAb 2)-K-Coil | Light Chain: CD3 Heavy Chain: HIV |
| 3 | Heavy Chain CD8 mAb 1 | CD8 |
| 4 | Light Chain CD8 mAb 1 | CD8 |

The amino acid sequence of the first polypeptide chain of the HIV mAb 2/CD3 mAb 2/CD8 mAb 1 Tri-Specific Binding Molecule is (SEQ ID NO:95):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL GGGSGGGGEV

QLVESGGGLV QPGGSLRLSC AASGFTFSTY AMNWVRQAPG

KGLEWVGRIR SKYNNYATYY ADSVKGRFTI SRDDSKNSLY

LQMNSLKTED TAVYYCVRHG NFGNSYVSWF AYWGQGTLVT

VSSASTKGEV AACEKEVAAL EKEVAALEKE VAALEKGGGD

KTHTCPPCPA PEAAGGPSVF LFPPKPKDTL MISRTPEVTC

VVVDVSHEDP EVKFNWYVDG VEVHNAKTKP REEQYNSTYR

VVSVLTVLHQ DWLNGKEYKC KVSNKALPAP IEKTISKAKG

QPREPQVYTL PPSREEMTKN QVSLWCLVKG FYPSDIAVEW

ESNGQPENNY KTTPPVLDSD GSFFLYSKLT VDKSRWQQGN

VFSCSVMHEA LHNHYTQKSL SLSPGK
```

The amino acid sequence of the second polypeptide chain of the HIV mAb 2/CD3 mAb 2/CD8 mAb 1 Tri-Specific Binding Molecule is (SEQ ID NO:96):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQV

QLQESGPGLV KPSQTLSLSC TVSGGSSSSG AHYWSWIRQY

PGKGLEWIGY IHYSGNTYYN PSLKSRITIS QHTSENQFSL

KLNSVTVADT AVYYCARGTR LRTLRNAFDI WGQGTLVTVS

SASTKGKVAA CKEKVAALKE KVAALKEKVA ALKE
```

The amino acid sequence of the third polypeptide chain of the HIV mAb 2/CD3 mAb 2/CD8 mAb 1 Tri-Specific Binding Molecule is (SEQ ID NO:97):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPG
```

The amino acid sequence of the fourth polypeptide chain of the HIV mAb 2/CD3 mAb 2/CD8 mAb 1 Tri-Specific Binding Molecule is (SEQ ID NO:98):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP
```

```
SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Tri-Specific Binding Molecules were prepared having a Binding Domain capable of binding to the gp140 antigen of Human immunodeficiency Virus (HIV) (i.e., an HIV mAb 1/CD3 mAb 2/CD8 mAb 1 Tri-Specific Binding Molecule and an HIV mAb 2/CD3 mAb 2/CD8 mAb 1 Tri-Specific Binding Molecule).

As a preliminary step, the ability of the HIV mAb 1/CD3 mAb 2/CD8 mAb 1 and HIV mAb 2/CD3 mAb 2/CD8 mAb 1 Tri-Specific Binding Molecules were assessed. Two µg/ml of JR-FL strain gp140 protein in 0.2 M carbonate-bicarbonate buffer (pH 9.4) was coated onto a solid support, and then incubated with the Tri-Specific Binding Molecules (at a starting concentration of 5 µg/ml, followed by 1:2 serial dilutions). At the conclusion of the assay, binding was blocked with phosphate buffered saline (PBS) containing 3% bovine serum albumin (BSA). Binding was detected by ELISA (pico (ThermoScientific-Pierce) using anti-human IgG—that had been conjugated to horseradish peroxidase (HRP). The assay was also used with immobilized human CD3 (2 µg/ml) in order to assess the ability of the molecules to bind to CD3. Both Tri-Specific Binding Molecules were found to be able to bind to the soluble, immobilized gp140 protein (FIG. 18A) and to human CD3 (FIG. 18B). A sandwich ELISA was conducted to demonstrate that the Tri-Specific Binding Molecules were capable of coordinated binding to both gp140 and CD3. For this purpose, 2 µg/ml of the JR-FL strain gp140 proteins in 0.2 M carbonate-bocarbonate buffer (pH 9.4) was coated onto the solid support, and then incubated with the Tri-Specific Binding Molecules (at a starting concentration of 5 µg/ml, followed by 1:2 serial dilutions). Human CD3, labeled with biotin was then added (0.5 µg/ml). Binding was detected by ELISA (pico (ThermoScientific-Pierce) using a streptavidin-HRP conjugate. FIG. 18C shows that the Tri-Specific Binding Molecules were capable of coordinated binding to both gp140 and CD3.

The Tri-Specific Binding Molecules were found to be capable of binding to the surface of cells that express the HIV env protein. To demonstrate this aspect of the invention, HIV env-expressing HEK293/D375 cells under doxycycline induction were incubated with the Tri-Specific Binding Molecules. Detection of binding was performed using biotinylated anti-human Fc antibody and Streptavidin-APC. As shown in FIGS. 19A-19C, both Tri-Specific Binding Molecules were found to be able to bind to the HEK293/D375 cells in contrast to a control Tri-Specific Binding Molecule (FIG. 19C).

In order to demonstrate the ability of such Tri-Specific Binding Molecules to mediate re-directed killing of HIV-infected cells, the ability of such molecules to bind to PBMC was assessed. Human blood was lysed with ACK lysing buffer, washed 2× with PBS and re-suspended in FACS buffer contained 10% Human AB serum and incubated at room temperature for 20 minutes. Thereafter, the cells were pelleted by centrifugation and re-suspended (4×10$^6$ cells/mL) in FACS buffer. 50 µL of serial titrated Tri-Specific Binding Molecules were added into wells of a 96-well deep plate. 50 µL of the cells (4×10$^6$ cells/mL) well-mixed cells in FACS buffer containing 0.01% sodium azide were then added into corresponding wells and mixed thoroughly using a pipette. The plate was incubated in the dark for about 45 minutes at 2-8° C. At the end of incubation, the cells were washed twice by adding 300 µL of FACS buffer to each well, the plate was centrifuged at 1,200 rpm for 5 minutes, and the supernatant was discarded. The cell pellets were re-suspended in 100 µL mixture of goat anti-Human IgG Fcγ-PE, CD5-APC and CD4-PerCP5.5 prepared in FACS buffer containing 0.01% sodium azide, and the cells were incubated in the dark for about 45 minutes at 2-8° C. At the end of the incubation, the cells were washed, re-suspended with FACS buffer, and analyzed with a BD Caliber flow cytometer. As shown in FIGS. 20A-20B, the Tri-Specific Binding Molecules were found to exhibit specific binding to the CD5+/CD4− cell population.

The Tri-Specific Binding Molecules were incubated at 37° C. for 24 hours in the presence of HIV env-expressing Jurkat 522 FY cells and pan T cells in the presence or absence of tetracycline, and cytotoxicity was measured using an LDH assay. As shown in FIGS. 21A-21F, the Tri-Specific Binding Molecules mediated substantial cytotoxicity.

A cytotoxicity analysis was conducted using purified pan T cells and HIV env-expressing Jurkat 522 FY cells and the percent of live cells was measured. The results of this analysis are shown in FIGS. 22A-22B.

An assessment was made of the CTL activity of Tri-Specific Binding Molecules on HIV env-expressing Jurkat 522 FY cells using CD4+, CD8+ or pan T cells. The results of this assessment with respect to the HIV mAb 1/CD3 mAb 2/CD8 mAb 1 Tri-Specific Binding Molecule are shown in FIGS. 23A-23C. The results of this assessment with respect to the HIV mAb 2/CD3 mAb 2/CD8 mAb 1 Tri-Specific Binding Molecule are shown in FIGS. 24A-24C. Table 19 summarizes the results.

TABLE 19

Jurkat Cells 522FY
(% Cytotoxicity Relative to LDH MR from Target Cell w/o Binding Molecule)

| HIV mAb 1, CD 3 mAb 2 DART ™ | | HIV mAb 1/CD3 mAb 2/CD8 mAb 1 Tri-Specific Binding Molecule | | HIV mAb 2, CD3 mAb 2 DART ™ | | HIV mAb 2/CD 3 mAb 2/CD8 mAb 1 Tri-Specific Binding Molecule | |
|---|---|---|---|---|---|---|---|
| $EC_{50}$, nM | $E_{max}$, % | $EC_{50}$, nM | $E_{max}$, % | $EC_{50}$, nM | $E_{max}$, % | $EC_{50}$, nM | $E_{max}$, % |
| CD4 | | | | | | | |
| 0.67 | 13 | 0.36 | 15 | 0.25 | 9 | 0.45 | 8 |

TABLE 19-continued

Jurkat Cells 522FY
(% Cytotoxicity Relative to LDH MR from Target Cell w/o Binding Molecule)

| HIV mAb 1, CD3 mAb 2 DART™ | | HIV mAb 1/CD3 mAb 2/CD8 mAb 1 Tri-Specific Binding Molecule | | HIV mAb 2, CD3 mAb 2 DART™ | | HIV mAb 2/CD 3 mAb 2/CD8 mAb 1 Tri-Specific Binding Molecule | |
|---|---|---|---|---|---|---|---|
| $EC_{50}$, nM | $E_{max}$, % | $EC_{50}$, nM | $E_{max}$, % | $EC_{50}$, nM | $E_{max}$, % | $EC_{50}$, nM | $E_{max}$, % |
| CD8 | | | | | | | |
| 0.20 | 18 | 0.00781 | 37 | 0.052 | 16 | 0.00040 | 27 |
| Pan T | | | | | | | |
| 0.31 | 19 | 0.044 | 38 | 0.26 | 16 | 0.0015 | 23 |

The impact of varying the ratio or target:effector cells was evaluated. Table 20 summarizes the obtained results.

TABLE 20

Jurkat Cells 522FY
(% Cytotoxicity Relative to LDH MR from Target Cell w/o Binding Molecule

| | HIV mAb 1 Binding Domain | | | | HIV mAb 2 Binding Domain | | | |
|---|---|---|---|---|---|---|---|---|
| | E/T = 5:1 | | E/T = 10:1 | | E/T = 5:1 | | E/T = 10:1 | |
| | $EC_{50}$ nM | $E_{max}$ % | $EC_{50}$ nM | $E_{max}$ % | $EC_{50}$ nM | $E_{max}$ % | $EC_{50}$ nM | $E_{max}$ % |
| DART™ | 0.076 | 26 | 0.066 | 27 | 0.00057 | 24 | 0.00061 | 25 |
| DART™ | 0.0092 | 15 | 0.0066 | 15 | 0.0058 | 15 | 0.0054 | 15 |
| Tri-Specific Binding Molecule | 0.00019 | 22 | 0.00029 | 24 | 0.00032 | 25 | 0.00026 | 24 |

An assessment was also made of the CTL activity of Tri-Specific Binding Molecules on HIV env-expressing HEK293 cells using CD4+, CD8+ or pan T cells. The results of this assessment are summarized in Table 21.

TABLE 21

(% Cytotoxicity Relative to LDH MR from Target Cell w/o Tri-Specific Binding Molecule)

| HEK293 D371 Cells | | | | HEK293 D375 Cells | | | |
|---|---|---|---|---|---|---|---|
| HIV mAb 1, CD3 mAb 2 DART™ | | HIV mAb 1/CD3 mAb 2/CD8 mAb 1 Tri-Specific Binding Molecule | | HIV mAb 2, CD3 mAb 2 DART™ | | HIV mAb 2/CD3 mAb 2/CD8 mAb 1 Tri-Specific Binding Molecule | |
| $EC_{50}$, nM | $E_{max}$, % | $EC_{50}$, nM | $E_{max}$, % | $EC_{50}$, nM | $E_{max}$, % | $EC_{50}$, nM | $E_{max}$, % |
| CD4 | | | | | | | |
| 0.45 | 0.64 | 3.16 | 1.12 | 0.15 | 0.14 | 0.84 | 0.18 |
| CD8 | | | | | | | |
| 0.029 | 0.0062 | 1.77 | 0.0043 | 0.018 | 0.0012 | 1.00 | 0.0020 |
| Pan T | | | | | | | |
| 0.082 | 0.025 | 2.06 | N/A | 0.042 | 0.0085 | 1.08 | N/A |

Example 7

Comparison of CD3 Binding Domain Affinity Variants

As noted above, the CD3, CD8 or Disease-Associated Antigen-Binding Domains of the Tri-Specific Binding Molecules of the present invention may be mutated in order to isolate Binding Domains having more desired binding characteristics. The CD3 mAb 2 Binding Domain was subjected to such mutagenesis and two affinity variants (CD3 mAb 2 Low and CD3 mAb 2 Fast) were isolated.

The amino acid sequence of the Variable Light Chain Domain of anti-human CD3 mAb 2 Low is (SEQ ID NO:99):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

The amino acid sequence of the Variable Heavy Chain Domain of anti-human CD3 mAb 2 Low is (SEQ ID NO:100):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVT WFAYWGQGTL

VTVSS
```

The amino acid sequence of the Variable Light Chain Domain of anti-human CD3 mAb 2 Fast is (SEQ ID NO:101):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

The amino acid sequence of the Variable Heavy Chain Domain of anti-human CD3 mAb 2 Fast is (SEQ ID NO: 102):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HKNFGNSYVT WFAYWGQGTL

VTVSS
```

FIGS. 25A-25C show the kinetics of binding for these variants. CD3 mAb 2 Low (FIG. 25A) is a low affinity variant, while CD3 mAb 2 Fast (FIG. 25B) has a faster off rate relative to the wild-type CD3 mAb 2 (FIG. 25C).

In order to assess the effect of CD3 binding characteristics, two CD3 Binding Domain mutants were used. Three Tri-Specific Binding Molecule specific for the Disease-Associated Antigen 5T4 were constructed utilizing a wild-type CD3 mAb 2 Variable Domain sequence, a CD3 mAb 2 Variable Domain sequence with low affinity for CD3 and a CD3 mAb 2 Variable Domain sequence with wild-type affinity but a faster off rate. The 5T4 Variable Domain specificities and CD8 Variable Domain specificities were the same between the three Tri-Specific Binding Molecules. The first Tri-Specific Binding Molecule is termed 5T4 mAb 1/CD3 mAb 2/CD8 mAb 1 and was composed of four different polypeptide chains (Table 22).

TABLE 22

| Polypeptide Chain | Domains | Binding Affinity |
| --- | --- | --- |
| 1 | VL(5T4 mAb 1)-VH(CD3 mAb 2)-E-Coil-(CH2-CH3) | Light Chain: 5T4 Heavy Chain: CD3 |
| 2 | VL(CD3 mAb 2)-VH(5T4 mAb 1)-K-Coil | Light Chain: CD3 Heavy Chain: 5T4 |
| 3 | Heavy Chain CD8 mAb 1 | CD8 |
| 4 | Light Chain CD8 mAb 1 | CD8 |

The amino acid sequence of the first polypeptide chain of the 5T4 mAb 1/CD3 mAb 2/CD8 mAb 1 Tri-Specific Binding Molecule is (SEQ ID NO:103):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVSWFAYW GQGTLVTVSS

GGCGGGEVAA LEKEVAALEK EVAALEKEVA ALEKGGGDKT

HTCPPCPAPE AAGGPSVFLF PPKPKDTLMI SRIPEVICVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLWCLVKGFY PSDIAVEWES

NGQPENNYKT TPPVLDSDGS FFLYSKLTVD KSRWQQGNVF

SCSVMHEALH NHYTQKSLSL SPGK
```

The amino acid sequence of the second polypeptide chain of the 5T4 mAb 1/CD3 mAb 2/CD8 mAb 1 Tri-Specific Binding Molecule is (SEQ ID NO:104):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSF WMHWVRQAPG

QGLEWMGRID PNRGGTEYNE KAKSRVTMTA DKSTSTAYME

LSSLRSEDTA VYYCAGGNPY YPMDYWGQGT TVTVSSGGCG

GGKVAALKEK VAALKEKVAA LKEKVAALKE
```

The amino acid sequence of the third polypeptide chain of the 5T4 mAb 1/CD3 mAb 2/CD8 mAb 1 Tri-Specific Binding Molecule is (SEQ ID NO:105):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS
```

```
TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The amino acid sequence of the fourth polypeptide chain of the 5T4 mAb 1/CD3 mAb 2/CD8 mAb 1 Tri-Specific Binding Molecule is (SEQ ID NO:106):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The second Tri-Specific Binding Molecule is termed 5T4 mAb 1/CD3 mAb 2 Low/CD8 mAb 1 and was composed of four different polypeptide chains (Table 23).

TABLE 23

| Polypeptide Chain | Domains | Binding Affinity |
| --- | --- | --- |
| 1 | VL(5T4 mAb 1)-VH(CD3 mAb 2 Low)-E-coil-(CH2-CH3) | Light Chain: 5T4 Heavy Chain: CD3 |
| 2 | VL(CD3 mAb 2 Low)-VH(5T4 mAb 1)-K-Coil | Light Chain: CD3 Heavy Chain: 5T4 |
| 3 | Heavy Chain CD8 mAb 1 | CD8 |
| 4 | Light Chain CD8 mAb 1 | CD8 |

The amino acid sequence of the first polypeptide chain of the 5T4 mAb 1/CD3 mAb 2 Low/CD8 mAb 1 Tri-Specific Binding Molecule is (SEQ ID NO:107):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHGNFG NSYVTWFAYW GQGTLVTVSS

ASTKGEVAAC EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

The amino acid sequence of the second polypeptide chain of the 5T4 mAb 1/CD3 mAb 2 Low/CD8 mAb 1 Tri-Specific Binding Molecule is (SEQ ID NO:108):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSF WMHWVRQAPG

QGLEWMGRID PNRGGTEYNE KAKSRVTMTA DKSTSTAYME

LSSLRSEDTA VYYCAGGNPY YPMDYWGQGT TVTVSSASTK

GKVAACKEKV AALKEKVAAL KEKVAALKE
```

The amino acid sequence of the third polypeptide chain of the 5T4 mAb 1/CD3 mAb 2 Low/CD8 mAb 1 Tri-Specific Binding Molecule is (SEQ ID NO:109):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The amino acid sequence of the fourth polypeptide chain of the 5T4 mAb 1/CD3 mAb 2 Low/CD8 mAb 1 Tri-Specific Binding Molecule is (SEQ ID NO:110):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

The third Tri-Specific Binding Molecule is termed 5T4 mAb 1/CD3 mAb 2 Fast/CD8 mAb 1 and was composed of four different polypeptide chains (Table 24).

TABLE 24

| Polypeptide Chain | Domains | Binding Affinity |
|---|---|---|
| 1 | VL(5T4 mAb 1)-VH(CD3 mAb 2 Fast)-E-coil-(CH2-CH3) | Light Chain: 5T4 Heavy Chain: CD3 |
| 2 | VL(CD3 mAb 2 Fast)-VH(5T4 mAb 1)-K-Coil | Light Chain: CD3 Heavy Chain: 5T4 |
| 3 | Heavy Chain CD8 mAb 1 | CD8 |
| 4 | Light Chain CD8 mAb 1 | CD8 |

The amino acid sequence of the first polypeptide chain of the 5T4 mAb 1/CD3 mAb 2 Fast/CD8 mAb 1 Tri-Specific Binding Molecule is (SEQ ID NO:111):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIKGGG SGGGGEVQLV

ESGGGLVQPG GSLRLSCAAS GFTFSTYAMN WVRQAPGKGL

EWVGRIRSKY NNYATYYADS VKGRFTISRD DSKNSLYLQM

NSLKTEDTAV YYCVRHKNFG NSYVTWFAYW GQGTLVTVSS

ASTKGEVAAC EKEVAALEKE VAALEKEVAA LEKGGGDKTH

TCPPCPAPEA AGGPSVFLFP PKPKDTLMIS RTPEVTCVVV

DVSHEDPEVK FNWYVDGVEV HNAKTKPREE QYNSTYRVVS

VLTVLHQDWL NGKEYKCKVS NKALPAPIEK TISKAKGQPR

EPQVYTLPPS REEMTKNQVS LWCLVKGFYP SDIAVEWESN

GQPENNYKTT PPVLDSDGSF FLYSKLTVDK SRWQQGNVFS

CSVMHEALHN HYTQKSLSLS PGK
```

The amino acid sequence of the second polypeptide chain of the 5T4 mAb 1/CD3 mAb 2 Fast/CD8 mAb 1 Tri-Specific Binding Molecule is (SEQ ID NO:112):

```
QAVVTQEPSL TVSPGGTVTL TCRSSTGAVT TSNYANWVQQ

KPGQAPRGLI GGINKRAPWT PARFSGSLLG GKAALTITGA

QAEDEADYYC ALWYSNLWVF GGGTKLTVLG GGGSGGGGQV

QLVQSGAEVK KPGASVKVSC KASGYTFTSF WMHWVRQAPG

QGLEWMGRID PNRGGTEYNE KAKSRVTMTA DKSTSTAYME

LSSLRSEDTA VYYCAGGNPY YPMDYWGQGT TVTVSSASTK

GKVAACKEKV AALKEKVAAL KEKVAALKE
```

The amino acid sequence of the third polypeptide chain of the 5T4 mAb 1/CD3 mAb 2 Fast/CD8 mAb 1 Tri-Specific Binding Molecule is (SEQ ID NO:113):

```
EVQLQQSGAE LVKPGASVKL SCTASGFNIK DTYIHFVRQR

PEQGLEWIGR IDPANDNTLY ASKFQGKATI TADTSSNTAY

MHLCSLTSGD TAVYYCGRGY GYYVFDHWGQ GTTLTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLMISRTPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The amino acid sequence of the fourth polypeptide chain of the 5T4 mAb 1/CD3 mAb 2 Fast/CD8 mAb 1 Tri-Specific Binding Molecule is (SEQ ID NO:114):

```
DVQINQSPSF LAASPGETIT INCRTSRSIS QYLAWYQEKP

GKTNKLLIYS GSTLQSGIPS RFSGSGSGTD FTLTISGLEP

EDFAMYYCQQ HNENPLTFGA GTKLELRRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Human PBMC of healthy donors were treated as described above and incubated with the 5T4 mAb 1/CD3 mAb 2/CD8 mAb 1 Tri-Specific Binding Molecule, the 5T4 mAb 1/CD3 mAb 2 Low/CD8 mAb 1 Tri-Specific Binding Molecule and the 5T4 mAb 1/CD3 mAb 2 Fast/CD8 mAb 1 Tri-Specific Binding Molecule. 5T4×CD3 DART™ (with wild-type, Low and Fast CD3 specificities) were used as controls. The 5T4 mAb 1/CD3 mAb 2 Low/CD8 mAb 1 and 5T4 mAb 1/CD3 mAb 2 Fast/CD8 mAb 1 Tri-Specific Binding Molecules contain mutated CD3 Binding Domains that exhibit altered affinity and binding kinetics for CD3.

The Tri-Specific Binding Molecules were found to exhibit weaker binding to the $CD5^+$ $CD4^+$ cells (FIG. 26A), but much stronger binding to the $CD5^+$ $CD4^-$ cells (FIG. 26B) than the DART™ controls.

FIGS. 27A-27C show the effect of the CD3 mAb variants on the cytotoxicity of a 5T4 mAb 1/CD3 mAb 2/CD8 mAb 1 Tri-Specific Binding Molecule using an LDH assay. Similar results were obtained using a luciferase assay and with Tri-Specific Binding Molecules having a B7-H3 Binding Domain in lieu of the 5T4 mAb 1 Binding Domain. The results show that the CD3 mAb 2 Low Tri-Specific Binding Molecule exhibited minimal cytotoxicity, but that the CD3 mAb 2 Fast Tri-Specific Binding Molecule exhibited cytotoxicity with CD8+ T cells and pan T cells to a much greater extent than with CD4+ T cells.

In order to assess the effects of the Tri-Specific Binding Molecules on cytokine profiles, PBMCs from two donors were incubated in the presence of increasing concentrations of the 5T4 mAb 1/CD3 mAb 2/CD8 mAb 1 Tri-Specific Binding Molecule, the 5T4 mAb 1/CD3 mAb 2 Low/CD8 mAb 1 Tri-Specific Binding Molecule and the 5T4 mAb 1/CD3 mAb 2 Fast/CD8 mAb 1 Tri-Specific Binding Molecule for 24 hours. The levels of six cytokines (IFN-γ, TNF-α, IL-10, IL-6, IL-4 and IL-2) were measured. The results are shown in FIGS. 28A-28F (Donor 1) and FIGS. 29A-29F (Donor 2). The results surprisingly show a dramatic decrease in the cytokines released from PBMCs compared to a DART™ that targets only CD3 and is not selective for CD8+ T cells.

The 5T4 mAb 1/CD3 mAb 2/CD8 mAb 1 Tri-Specific Binding Molecule exhibited similar potency to a DART™, 1 pM EC50 compared to 1.3 pM for the DART™, using pan T cells as effectors. The activity of the DART™ may already be maximal for both CD4+ and CD8+ T cells. The Tri-Specific Binding Molecule does shift the activity toward the CD8+ population and away from the CD4+ population which is beneficial in terms of cytokine release, particularly IL-2 and TNFα.

Although the 5T4 mAb 1/CD3 mAb 2 Low/CD8 mAb 1 Tri-Specific Binding Molecule was able to bind CD4+ and CD8+ T cells, its ability to redirect cytolysis of or by those cells was greatly reduced compared to the non-mutated CD3 mAb 2 Binding Domain. The 5T4 mAb 1/CD3 mAb 2 Fast/CD8 mAb 1 Tri-Specific Binding Molecule on the other hand retained CTL activity, particularly with CD8+ T cells compared/relative to CD4+ T cells (75-fold difference in EC50s) compared to the 5T4 mAb 1/CD3 mAb 2/CD8 mAb 1 Tri-Specific Binding Molecule (7-fold difference in EC50s). The EC50 for the 5T4 mAb 1/CD3 mAb 2 Fast/CD8 mAb 1 Tri-Specific Binding Molecule was similar to that of the 5T4 mAb 1/CD3 mAb 2/CD8 mAb 1 Tri-Specific Binding Molecule (2.8 vs 1.3 pM), but the dramatic difference in CD8+ vs CD4+ T cell targeting virtually eliminated the cytokine release that was observed with a 5T4×CD3 DART™ in human PBMC cultures.

Example 8

Summary of EC50 Data of Exemplary Tri-Specific Binding Molecules

In summary, a series of 14 Tri-Specific Binding Molecules were constructed (Table 25), each having two Diabody-Type Binding Domains (Site A and Site B), and one Fab-Type Binding Domain (Sites C):

TABLE 25

| Name | Binding Domain | | |
|---|---|---|---|
| | Site A | Site B | Site C |
| B7-H3 mAb 1/CD3 mAb 2/CD8 mAb 1 | B7-H3 | CD3 | CD8 |
| CD3 mAb 2/CD8 mAb 1/B7-H3 mAb 1 | CD3 | CD8 | B7-H3 |
| B7-H3 mAb 1/CD8 mAb 1/CD3 mAb 2 | B7-H3 | CD8 | CD3 |
| B7-H3 mAb 1/CD3 mAb 2/CD8 mAb 1 | B7-H3 | CD3 | CD8 |
| 5T4 mAb 1/CD3 mAb 2/CD8 mAb 1 | 5T4 | CD3 | CD8 |
| 5T4 mAb 1/CD3 mAb 2 Low/CD8 mAb 1 | 5T4 | CD3 Low | CD8 |
| 5T4 mAb 1/CD3 mAb 2 Fast/CD8 mAb 1 | 5T4 | CD3 Fast | CD8 |
| 5T4 mAb 2/CD3 mAb 2/CD8 mAb 1 | 5T4 | CD3 | CD8 |
| 5T4 mAb 2/CD3 mAb 2/CD8 mAb 2 | 5T4 | CD3 | CD8 |
| Palivizumab/CD3 mAb 2/CD8 mAb 1 | RSV | CD3 | CD8 |
| ROR1 mAb 1/CD3 mAb 2/CD8 mAb 1 | ROR1 | CD3 | CD8 |
| ROR1 mAb 1/CD3 mAb 2/CD8 mAb 2 | ROR1 | CD3 | CD8 |
| HIV mAb 1/CD3 mAb 2/CD8 mAb 1 | HIV | CD3 | CD8 |
| HIV mAb 2/CD3 mAb 2/CD8 mAb 1 | HIV | CD3 | CD8 |

The EC50 data of such Tri-Specific Binding Molecules is summarized in Table 26 (Target cells: JIMT1-luc; Effector: Target Cell Ratio 5:1). In some cases (shown as NR in Table 26), the EC50 could not be calculated from the data because maximal killing was not achieved.

TABLE 26

| Target | Binding Molecule | EC50 nM) | | | to DART | to DART |
|---|---|---|---|---|---|---|
| | | CD8+ | CD4+ | PanT | CD4/CD8 | CD4/CD8 | EC50 w/PanT |
| B7H3 | B7-H3/CD3 mAb 2 DART ™ | 0.5090 | 1.1370 | 0.6943 | 2.2 | 1.0 | 1.0 |
| | B7-H3/CD8 mAb 1 DART ™ | NR | NR | NR | — | — | — |
| | B7-H3 mAb 1/CD3 mAb 2/CD8 mAb 1 Tri-Specific Binding Molecule | 0.0054 | 0.0721 | 0.0082 | 13.3 | 5.9 | 85.1 |
| | B7-H3 mAb 1/CD3 mAb 2/CD8 mAb 2 Tri-Specific Binding Molecule | 0.0051 | 0.3138 | 0.0058 | 61.5 | 27.5 | 119.7 |
| | CD3 mAb 2/CD8 mAb 2/B7-H3 mAb 1 Tri-Specific Binding Molecule | 0.0053 | 0.1055 | 0.0113 | 19.8 | 8.9 | 61.4 |
| | B7-H3 mAb 1/CD8 mAb 2/CD3 mAb 2 Tri-Specific Binding Molecule | 0.4125 | 1.1030 | 0.5347 | 2.7 | 1.2 | 1.3 |
| 5T4 | 5T4 mAb 1/CD3 mAb 2 DART ™ | 0.0012 | 0.0013 | 0.0013 | 1.1 | 1.0 | 1.0 |
| | 5T4 mAb 1/CD3 mAb 2/CD8 mAb 1 Tri-Specific Binding Molecule | 0.0007 | 0.0045 | 0.0009 | 6.8 | 6.4 | 1.5 |
| | 5T4 mAb 1/CD3 mAb 2 Low/CD8 mAb 1 Tri-Specific Binding Molecule | NR | NR | NR | — | — | — |

TABLE 26-continued

| Target | Binding Molecule | EC50 nM) | | | to DART CD4/CD8 | to DART EC50 w/PanT |
|---|---|---|---|---|---|---|
| | | CD8+ | CD4+ | PanT | CD4/CD8 | |
| | 5T4 mAb 1/CD3 mAb 2 Fast/CD8 mAb 1 Tri-Specific Binding Molecule | 0.0021 | 0.1598 | 0.0028 | 74.7 | 70.6 | 0.5 |
| | 5T4 mAb 2/CD3 mAb 2 DART ™ | 0.0362 | 0.0561 | 0.0449 | 1.6 | 1.0 | 1.0 |
| | 5T4 mAb 2/CD3 mAb 2/CD8 mAb 1 Tri-Specific Binding Molecule | 0.0013 | 0.0435 | 0.0020 | 32.7 | 21.1 | 22.1 |
| | 5T4 mAb 2/CD3 mAb 2/CD8 mAb 2 Tri-Specific Binding Molecule | 0.0015 | 0.0336 | 0.0018 | 23.2 | 14.9 | 25.0 |
| RSV | Palivizumab/CD3 mAb 2/CD8 mAb 1 Tri-Specific Binding Molecule | NR | NR | NR | — | — | — |
| ROR1 | ROR1/CD3 mAb 2 DART ™ | 0.7761 | 0.2911 | 0.7643 | 0.4 | 1.0 | 1.0 |
| | ROR1 mAb 1/CD3 mAb 2/CD8 mAb 1 Tri-Specific Binding Molecule | 0.0017 | 0.095 | 0.0053 | 55.9 | 149.0 | 144.2 |
| | ROR1 mAb 1/CD3 mAb 2/CD8 mAb 2 Tri-Specific Binding Molecule | 0.0021 | 0.2767 | 0.0057 | 131.8 | 351.3 | 134.1 |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A multi-chain polypeptide-containing Tri-Specific Binding Molecule that immunospecifically binds to three different epitopes, comprising:
   (I) three different polypeptide chains covalently complexed together;
   (II) an Antigen-Binding Domain I that immunospecifically binds to an Epitope I present on a first antigen, an Antigen-Binding Domain II that immunospecifically binds to an Epitope II present on a second antigen, and an Antigen-Binding Domain III that immunospecifically binds to an Epitope III present on a third antigen; and
   (III) a Fc Domain; wherein:
   (A) a first polypeptide chain comprises, in the N-terminus to C-terminus direction: (VL1 Domain)-(Linker 1)-(VH$_{II}$ Domain)-(Linker 2)-(Heterodimer-Promoting Domain)-(Linker 3)-(CH2-CH3 Domain); or (Cysteine-Containing Domain)-(CH2-CH3 Domain)-(Linker 4)-(V$_L$1 Domain)-(Linker 1)-(VH$_{II}$ Domain)-(Linker 2)-(Heterodimer-Promoting Domain);
   (B) a second polypeptide chain comprises, in the N-terminus to C-terminus direction: (VL$_{II}$ Domain)-(Linker 1)-(VH$_I$ Domain)-(Linker 2)-(Heterodimer-Promoting Domain);
   (C) a third polypeptide chain comprises, in the N-terminus to C-terminus direction: Domain)-(Flexible Linker)-(VH$_{III}$ Domain)-(Cysteine-Containing Domain2)-(CH2-CH3 Domain); or
   (CL Domain)-(VL$_{III}$ Domain)-(Flexible Linker)-(VH$_{III}$ Domain)-(CH1 Domain)-(Cysteine-Containing Domain)-(CH2-CH3 Domain);
   (D) the VL$_I$ Domain is a Light Chain Variable Domain of an immunoglobulin that binds to Epitope I, the VH$_I$ Domain is a Heavy Chain Variable Domain of an immunoglobulin that binds to Epitope I, the VL$_{II}$ Domain is a Light Chain Variable Domain of an immunoglobulin that binds to Epitope II, the VH$_{II}$ Domain is a Heavy Chain Variable Domain of an immunoglobulin that binds to Epitope II, the V$_{III}$ Domain is a Light Chain Variable Domain of an immunoglobulin that binds to Epitope III, and the VH$_{III}$ Domain is a Heavy Chain Variable Domain of an immunoglobulin that binds to Epitope III;
   (E) the VL$_I$ Domain and the VH$_I$ Domain associate to form the Antigen-Binding Domain I, the VL$_{II}$ Domain and the VH$_{II}$ Domain associate to form the Antigen-Binding Domain II, the VL$_{III}$ Domain and the VH$_{III}$ Domain associate to form the Antigen-Binding Domain III, and the CH2-CH3 Domain of the first polypeptide chain and the CH2-CH3 Domain of the third polypeptide chain associate to form the Fc Domain, the Antigen-Binding Domain I and the Antigen-Binding Domain II are Diabody-Type Binding Domains, and the Antigen-Binding Domain Ill is a Non-Diabody-Type Binding Domain;
   (F) the first, second and third antigens are the same antigen, or are independently the same or different from another of the antigens; and
   (G) the Linker 1 comprises the sequence of SEQ ID NO: 1;
   the Linker 2 comprises the sequence of SEQ ID NO: 2 or 131;
   the Linker 3 comprises the sequence of SEQ ID NO: 5 or GGG;
   the Linker 4 comprises the sequence of SEQ ID NO: 15, 16, 131 or 132, or GGC or GGG;
   the CH2-CH3 Domain comprises the sequence of SEQ ID NO: 7 or 8;
   the Cysteine-Containing Domain independently comprises the sequence of SEQ ID NO: 2, 5, 10, 11, 12, 13, 14, 127, 128, 129, 130 or 133;
   the Heterodimer-Promoting Domain on the first polypeptide chain is an E-coil Domain and the Heterodimer-Promoting Domain on the second polypeptide chain is a K-coil Domain, or the Heterodimer-Promoting Domain on the first polypeptide chain is a K-coil Domain and the Heterodimer-Promoting Domain on the second polypeptide chain is an E-coil Domain, the E-coil Domain independently comprises the sequence of SEQ ID NO: 3 or 115, and the K-coil Domain independently comprises the sequence of SEQ ID NO: 4 or 116;
   the CH1 Domain comprises the sequence of SEQ ID NO: 9; and
   the CL Domain comprises the sequence of SEQ ID NO: 13 or 14.

2. The Tri-Specific Binding Molecule of claim 1, wherein:
   the Linker 2 comprises a cysteine residue,
   the E-coil Domain and the K-coil Domain adjacent to the Linker 2 each comprises a cysteine residue, or
   the Linker 2 comprises a cysteine residue and the E-coil Domain or the K-coil Domain adjacent to the Linker 2 comprises a cysteine residue.

3. The Tri-Specific Binding Molecule of claim 2, wherein:
   the E-coil Domain of SEQ ID NO:115 or the K-coil Domain of SEQ ID NO:116 is adjacent to the Linker 2 when the Linker 2 comprises the sequence of SEQ ID NO: 131;
   the E-coil Domain of SEQ ID NO: 3 or the K-coil Domain of SEQ ID NO: 4 is adjacent to the Linker 2 when the Linker 2 comprises the sequence of SEQ ID NO: 2; or
   the E-coil Domain of SEQ ID NO: 115 or the K-coil Domain of SEQ ID NO: 116 is adjacent to the Linker 2 when the Linker 2 comprises the sequence of SEQ ID NO: 2.

4. The Tri-Specific Binding Molecule of claim 1, wherein:
   the CH2-CH3 Domain of the first polypeptide chain is a knob-bearing CH2-CH3 Domain and the CH2-CH3 Domain of the third polypeptide chain is a hole-bearing CH2-CH3 Domain; or
   the CH2-CH3 Domain of the third polypeptide chain is a knob-bearing CH2-CH3 Domain and the CH2-CH3 Domain of the first polypeptide chain is a hole-bearing CH2-CH3 Domain.

5. The Tri-Specific Binding Molecule of claim 4, wherein:
   the knob-bearing CH2-CH3 Domain comprises the sequence of SEQ ID NO: 7, and
   the hole-bearing CH2-CH3 Domain comprises the sequence of SEQ ID NO: 8.

6. The Tri-Specific Binding Molecule of claim 1, wherein the CH2-CH3 Domain of the first polypeptide chain and the third polypeptide chain comprise:
   (A) one substitution selected from the group consisting of: F243L, R292P, Y300L, V305I, and P396L;
   (B) two substitutions selected from the group consisting of:
   (1) F243L and P396L;
   (2) F243L and R292P; and
   (3) R292P and V305I;

(C) three substitutions selected from the group consisting of:
  (1) F243L, R292P and Y300L;
  (2) F243L, R292P and V305I;
  (3) F243L, R292P and P396L; and
  (4) R292P, V305I and P396L;
(D) four substitutions selected from the group consisting of:
  (1) F243L, R292P, Y300L and P396L; and
  (2) F243L, R292P, V305I and P396L; or
(E) five substitutions selected from the group consisting of:
  (1) F243L, R292P, Y300L, V305I and P396L; and
  (2) L235V, F243L, R292P, Y300L and P396L.

7. The Tri-Specific Binding Molecule of claim 1, wherein one of Epitope I, Epitope II or Epitope III is an epitope of:
an effector cell selected from CD2, CD3, CD16, CD19, CD20, CD22, CD32B, CD64, B cell Receptor (BCR), T cell Receptor (TCR), or NKG2D Receptor; or CD8; or
a Disease-Associated Antigen.

8. The Tri-Specific Binding Molecule of claim 7, wherein:
(A) the Epitope I, Epitope II and Epitope III are, respectively, an epitope of CD3, an epitope of CD8 and an epitope of the Disease-Associated Antigen;
(B) the Epitope I, Epitope II and Epitope III are, respectively, an epitope of CD3, an epitope of the Disease-Associated Antigen and an epitope of CD8;
(C) the Epitope I, Epitope II and Epitope III are, respectively, an epitope of CD8, an epitope of CD3, and an epitope of the Disease-Associated Antigen;
(D) the Epitope I, Epitope II and Epitope III are, respectively, an epitope of CD8, an epitope of the Disease-Associated Antigen and an epitope of CD3;
(E) the Epitope I, Epitope II and Epitope III are, respectively, an epitope of the Disease-Associated Antigen, an epitope of CD3, and an epitope of CD8; or
(F) the Epitope I, Epitope II and Epitope III are, respectively, an epitope of the Disease-Associated Antigen, an epitope of CD8, and an epitope of CD3.

9. The Tri-Specific Binding Molecule of claim 8, wherein one of Epitope I, Epitope II or Epitope III is an epitope of CD3 and the Antigen-Binding Domain that immunospecifically binds to the epitope of CD3 comprises the six CDRs of SEQ ID NO: 17 and 18; 19 and 20; 21 and 22; 23 and 25; 24 and 25; 26 and 27; 26 and 28; or 101 and 102; or comprises:
  the light chain variable domain of SEQ ID NO: 17 and the heavy chain variable domain of SEQ ID NO: 18,
  the light chain variable domain of SEQ ID NO: 19 and the heavy chain variable domain of SEQ ID NO: 20,
  the light chain variable domain of SEQ ID NO: 21 and the heavy chain variable domain of SEQ ID NO: 22,
  the light chain variable domain of SEQ ID NO: 23 and the heavy chain variable domain of SEQ ID NO: 25,
  the light chain variable domain of SEQ ID NO: 24 and the heavy chain variable domain of SEQ ID NO: 25,
  the light chain variable domain of SEQ ID NO: 26 and the heavy chain variable domain of SEQ ID NO: 27,
  the light chain variable domain of SEQ ID NO: 26 and the heavy chain variable domain of SEQ ID NO: 28, or
  the light chain variable domain of SEQ ID NO: 101 and the heavy chain variable domain of SEQ ID NO: 102.

10. The Tri-Specific Binding Molecule of claim 8, wherein one of Epitope I, Epitope II or Epitope III is an epitope of CD8 and the Antigen-Binding Domain that immunospecifically binds to the epitope of CD8 comprises the six CDRs of SEQ ID NO: 29 and 30; or 31 and 32; or comprises:
  the light chain variable domain of SEQ ID NO: 29 and the heavy chain variable domain of SEQ ID NO: 30, or
  the light chain variable domain of SEQ ID NO: 31 and the heavy chain variable domain of SEQ ID NO: 32.

11. The Tri-Specific Binding Molecule of claim 8, wherein the Disease-Associated Antigen is:
  a cancer antigen on the surface of a cancer cell; or
  a pathogen antigen on the surface of a pathogen or pathogen-infected cell.

12. The Tri-Specific Binding Molecule of claim 11, wherein the cancer antigen is colon cancer antigen 19.9; gastric cancer mucin antigen 4.2; colorectal carcinoma antigen A33; ADAM-9; AFP oncofetal antigen-alpha-fetoprotein; ALCAM; B7-H3; BAGE; beta-catenin; CA125; Carboxypeptidase M; B1; CD5; CD19; CD20; CD22; CD23; CD25; CD27; CD28; CD30; CD33; CD36; CD40/CD154; CD45; CD56; CD46; CD52; CD79a/CD79b; CD103; CD317; CDK4; CEA carcinoembryonic antigen; CEACAM5 and CEACAM6; CO-43 (blood group Leb) and CO-514 (blood group Lea); CTLA-1 and CTLA-4; Cytokeratin 8; DRS; E1 series (blood group B); EGF-R epidermal growth factor receptor; Ephrin receptors (EphA2); Erb (ErbB1; ErbB3; ErbB4); lung adenocarcinoma antigen F3; antigen FC10.2; GAGE-1; GAGE-2; GD2/GD3/GD49/GM2/GM3; GICA 19-9; gp37 (human leukemia T cell antigen); gp75 (melanoma antigen); gp100; HER-2/neu; human B-lymphoma antigen-CD20; human milk fat globule antigen; human papillomavirus-E6/human papillomavirus-E7; HMW-MAA (high molecular weight melanoma antigen); I antigen (differentiation antigen); I(Ma) as found in gastric adenocarcinomas; Integrin Alpha-V-Beta-6 Integrinβ6 (ITGB6); Interleukin-13 Receptor α2 (IL13Rα2); JAM-3; KID3; KID31; KS 1/4 pan-carcinoma antigen; KSA (17-1A); human lung carcinoma antigens L6 and L20; LEA; LUCA-2; M1:22:25:8, M18, M39; MAGE MAGE-1; MAGE-3; MART; My1, MUC-1; MUM-1; N-acetylglucosaminyltransferase; neoglycoprotein; NS-10; OFA-1 and OFA-2; Oncostatin M (Oncostatin Receptor Beta); ρ15; PSA (prostate specific antigen); PSMA; PEMA (polymorphic epithelial mucin antigen); PIPA; prostatic acid phosphate; R24; ROR1; SSEA-1, SSEA-3 and SSEA-4; sTn; T cell receptor derived peptide; $T_5A_7$; Tissue Antigens 37; TAG-72; TL5 (blood group A); TNF-α receptor; TNF-β receptor; TNF-γ receptor; TRA-1-85 (blood group H); Transferrin Receptor; TSTA tumor-specific transplantation antigen; VEGF-R; Y hapten, $Le^y$; or 5T4.

13. The Tri-Specific Binding Molecule of claim 12, wherein one of Epitope I, Epitope II or Epitope III is an epitope of B7-H3, A33, 5T4 or ROR1 and the Antigen-Binding Domain that immunospecifically binds to the epitope of B7-H3, A33, 5T4 or ROR1 comprises:
  the six CDRs of SEQ ID NO: 39 and 40; 41 and 42; 43 and 44; 45 and 46; 47 and 48; 49 and 50; 51 and 52; 53 and 54; 55 and 56; or 57 and 58; or
  the light chain variable domain of SEQ ID NO: 39 and the heavy chain variable domain of SEQ ID NO: 40,
  the light chain variable domain of SEQ ID NO: 41 and the heavy chain variable domain of SEQ ID NO: 42,
  the light chain variable domain of SEQ ID NO: 43 and the heavy chain variable domain of SEQ ID NO: 44,
  the light chain variable domain of SEQ ID NO: 45 and the heavy chain variable domain of SEQ ID NO: 46,
  the light chain variable domain of SEQ ID NO: 47 and the heavy chain variable domain of SEQ ID NO: 48, the light chain variable domain of SEQ ID NO: 49 and the heavy chain variable domain of SEQ ID NO: 50,
the light chain variable domain of SEQ ID NO: 51 and the heavy chain variable domain of SEQ ID NO: 52,
the light chain variable domain of SEQ ID NO: 53 and the heavy chain variable domain of SEQ ID NO: 54,
the light chain variable domain of SEQ ID NO: 55 and the heavy chain variable domain of SEQ ID NO: 56, or
the light chain variable domain of SEQ ID NO: 57 and the heavy chain variable domain of SEQ ID NO: 58.

14. The Tri-Specific Binding Molecule of claim 11, wherein:
the pathogen is a virus, and/or
the pathogen is human immunodeficiency virus (HIV) or respiratory syncytial virus (RSV), and/or
the pathogen antigen is HIV gp41, HIV gp120 or RSV glycoprotein F.

15. The Tri-Specific Binding Molecule of claim 14, wherein one of Epitope I, Epitope II or Epitope III is an epitope of HIV gp41, HIV gp120 or RSV glycoprotein F and the Antigen-Binding Domain that immunospecifically binds to the epitope of HIV gp41, HIV gp120 or RSV glycoprotein F comprises:
the six CDRs of SEQ ID NO: 33 and 34; 35 and 36; or 37 and 38; or
the light chain variable domain of SEQ ID NO: 33 and the heavy chain variable domain of SEQ ID NO: 34,
the light chain variable domain of SEQ ID NO: 35 and the heavy chain variable domain of SEQ ID NO: 36, or
the light chain variable domain of SEQ ID NO: 37 and the heavy chain variable domain of SEQ ID NO:38.

16. A pharmaceutical composition comprising the Tri-Specific Binding Molecule of claim 1 and a pharmaceutically acceptable carrier, excipient or diluent.

* * * * *